US008362248B2

(12) United States Patent
Jones et al.

(10) Patent No.: US 8,362,248 B2
(45) Date of Patent: Jan. 29, 2013

(54) SUBSTITUTED PYRIDINYL AND PYRIMIDINYL DERIVATIVES AS MODULATORS OF METABOLISM AND THE TREATMENT OF DISORDERS RELATED THERETO

(75) Inventors: Robert M. Jones, San Diego, CA (US); Juerg Lehmann, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 1173 days.

(21) Appl. No.: 11/482,777

(22) Filed: Jul. 6, 2006

(65) Prior Publication Data
US 2007/0167473 A1 Jul. 19, 2007

Related U.S. Application Data

(63) Continuation-in-part of application No. 11/327,896, filed on Jan. 9, 2006, now abandoned.

(60) Provisional application No. 60/642,840, filed on Jan. 10, 2005.

(51) Int. Cl.
C07D 401/14 (2006.01)
A61K 31/506 (2006.01)
A61P 3/10 (2006.01)

(52) U.S. Cl. .................................. 544/319; 514/269
(58) Field of Classification Search .................. 544/319; 514/269
See application file for complete search history.

(56) References Cited

U.S. PATENT DOCUMENTS

| | | |
|---|---|---|
| 3,503,963 A | 3/1970 | Schweizer et al. |
| 3,592,932 A | 7/1971 | Duerr et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,101,541 A | 7/1978 | Petitpierre et al. |
| 4,189,427 A | 2/1980 | Komorowski |
| 4,242,507 A | 12/1980 | Itoh et al. |
| 4,267,174 A | 5/1981 | Berger et al. |
| 4,275,148 A | 6/1981 | Endo et al. |
| 4,397,848 A | 8/1983 | Bosies et al. |
| 4,517,183 A | 5/1985 | Bosies et al. |
| 5,691,364 A | 11/1997 | Buckman et al. |
| 5,849,759 A | 12/1998 | Arnaiz et al. |
| 5,948,786 A | 9/1999 | Fujiwara et al. |
| 5,962,479 A | 10/1999 | Chen |
| 6,008,234 A | 12/1999 | Kochanny et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,414,002 B1 | 7/2002 | Cheng et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,713,508 B2 | 3/2004 | Sahoo et al. |
| 6,787,542 B2 | 9/2004 | Wang et al. |
| 6,844,351 B1 | 1/2005 | Chen |
| 6,849,636 B2 | 2/2005 | Waddell et al. |
| 6,956,047 B1 | 10/2005 | Chen |
| 7,057,046 B2 | 6/2006 | Sher et al. |
| 7,083,933 B1 | 8/2006 | Griffin |
| 7,098,235 B2 | 8/2006 | Sher et al. |
| 7,132,426 B2 | 11/2006 | Jones et al. |
| 7,276,249 B2 | 10/2007 | Ryde et al. |
| 7,417,039 B2 | 8/2008 | Davis |
| 7,763,278 B2 | 7/2010 | Cooper et al. |
| 2002/0058026 A1 | 5/2002 | Hammerly |
| 2003/0224058 A1 | 12/2003 | Ryde et al. |
| 2004/0110241 A1 | 6/2004 | Segal |

(Continued)

FOREIGN PATENT DOCUMENTS

| | | |
|---|---|---|
| AT | 327605 | 6/2006 |
| AU | 492126 | 11/1975 |

(Continued)

OTHER PUBLICATIONS

Christina Rondinone, Expert Opin. Ther. Targets 9(2), 415-418, 2005.*
West, Anthony R., Solid State Chemistry and its Applications, Wiley, New York, 1988, pp. 358 & 365.*
Vippagunta et al., Advanced Drug Delivery Reviews 48: 3-26, 2001.*
Abdalla et al., "Synthesis and reaction of 3-cyano 2-(1H)-pyridones," Pakistan Journal of Scientific and Industrial Research (1977) 20(3):139-149.

(Continued)

Primary Examiner — Venkataraman Balasubramanian
(74) Attorney, Agent, or Firm — Lyle Spruce; Fish & Richardson P.C.

(57) ABSTRACT

The present invention relates to certain substituted pyridinyl and pyrimidinyl derivatives of Formula (Ia) that are modulators of metabolism.

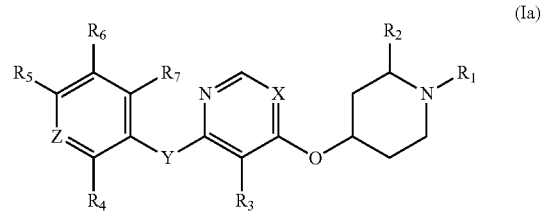

Accordingly, compounds of the present invention are useful in the treatment of metabolic-related disorders and complications thereof, such as, diabetes and obesity.

1 Claim, 5 Drawing Sheets

U.S. PATENT DOCUMENTS

| | | | |
|---|---|---|---|
| 2006/0154866 | A1 | 7/2006 | Chu et al. |
| 2006/0155128 | A1 | 7/2006 | Jones et al. |
| 2007/0167413 | A1 | 7/2007 | Srinivas et al. |
| 2007/0225351 | A1 | 9/2007 | Lippa et al. |

FOREIGN PATENT DOCUMENTS

| | | |
|---|---|---|
| BE | 829845 | 12/1975 |
| BE | 868796 | 1/1979 |
| CH | 560197 | 3/1975 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0 014 976 | 9/1980 |
| EP | 0 055 693 | 7/1982 |
| EP | 0 149 088 | 12/1984 |
| EP | 0 154 190 | 9/1985 |
| EP | 0 191 603 | 8/1986 |
| EP | 0 193 249 | 9/1986 |
| EP | 0 283 261 | 9/1988 |
| EP | 0 324 426 | 7/1989 |
| EP | 0 518 675 | 12/1992 |
| EP | 0 556 889 | 8/1993 |
| EP | 0 565 488 | 10/1993 |
| EP | 0 604 800 | 7/1994 |
| EP | 0 667 343 | 8/1995 |
| EP | 0 801 059 | 10/1997 |
| EP | 0 857 483 | 8/1998 |
| EP | 0 940 387 | 9/1999 |
| EP | 1 074 549 | 2/2001 |
| EP | 1287133 | 3/2003 |
| EP | 1 040 831 | 5/2003 |
| EP | 1 340 749 | 9/2003 |
| EP | 1 475 094 | 11/2004 |
| FR | 1551400 | 12/1968 |
| GB | 935595 | 8/1963 |
| GB | 1311956 | 3/1973 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |
| JP | 2004-269468 | 9/2004 |
| JP | 2004-269469 | 9/2004 |
| NL | 6614961 | 4/1967 |
| NL | 6814810 | 4/1969 |
| SU | 938 559 | 11/1993 |
| WO | WO 94/13677 | 6/1994 |
| WO | WO 95/33750 | 12/1995 |
| WO | WO 96/28427 | 9/1996 |
| WO | WO 96/32383 | 10/1996 |
| WO | WO 96/33994 | 10/1996 |
| WO | WO 96/36613 | 11/1996 |
| WO | WO 97/08152 | 3/1997 |
| WO | WO 97/26252 | 7/1997 |
| WO | WO 97/29109 | 8/1997 |
| WO | WO 97/40832 | 11/1997 |
| WO | WO 97/49706 | 12/1997 |
| WO | WO 98/04528 | 2/1998 |
| WO | WO 98/08846 | 3/1998 |
| WO | WO 98/08847 | 3/1998 |
| WO | WO 98/11094 | 3/1998 |
| WO | WO 98/19998 | 5/1998 |
| WO | WO 98/47874 | 10/1998 |
| WO | WO 98/47903 | 10/1998 |
| WO | WO 99/09026 | 2/1999 |
| WO | WO 99/51599 | 10/1999 |
| WO | WO 00/11003 | 3/2000 |
| WO | WO 00/27825 | 5/2000 |
| WO | WO 00/31068 | 6/2000 |
| WO | WO 00/34241 | 6/2000 |
| WO | WO 00/35875 | 6/2000 |
| WO | WO 00/35886 | 6/2000 |
| WO | 01/60807 | 2/2001 |
| WO | 01/27107 | 4/2001 |
| WO | WO 01/22938 | 4/2001 |
| WO | WO 01/23387 | 4/2001 |
| WO | WO 01/23388 | 4/2001 |
| WO | WO 01/25210 | 4/2001 |
| WO | WO 01/27107 | 4/2001 |
| WO | 01/037831 | 5/2001 |
| WO | 01/46204 | 6/2001 |
| WO | 02/50071 | 6/2001 |
| WO | WO 01/47887 | 7/2001 |
| WO | WO 01/49677 | 7/2001 |
| WO | WO 01/53263 | 7/2001 |
| WO | 01/60870 | 8/2001 |
| WO | WO 01/58900 | 8/2001 |
| WO | WO 01/62233 | 8/2001 |
| WO | 01/76573 | 10/2001 |
| WO | WO 01/85699 | 11/2001 |
| WO | 02/02539 | 1/2002 |
| WO | 02/08188 | 1/2002 |
| WO | WO 02/02549 | 1/2002 |
| WO | WO 02/06237 | 1/2002 |
| WO | WO 02/06274 | 1/2002 |
| WO | 02/24169 | 3/2002 |
| WO | WO 02/19975 | 3/2002 |
| WO | 02/60388 | 4/2002 |
| WO | WO 02/32893 | 4/2002 |
| WO | WO 02/40451 | 5/2002 |
| WO | WO 02/40456 | 5/2002 |
| WO | WO 02/40458 | 5/2002 |
| WO | WO 02/40480 | 5/2002 |
| WO | 02/45652 | 6/2002 |
| WO | WO 02/44362 | 6/2002 |
| WO | 02/064094 | 8/2002 |
| WO | WO 02/59083 | 8/2002 |
| WO | WO 02/070485 | 9/2002 |
| WO | WO 02/072101 | 9/2002 |
| WO | 02/081454 | 10/2002 |
| WO | 02/098864 | 12/2002 |
| WO | 02/102313 | 12/2002 |
| WO | WO 02/98864 | 12/2002 |
| WO | WO 02/98878 | 12/2002 |
| WO | 03/000180 | 1/2003 |
| WO | 03/000181 | 1/2003 |
| WO | 03/004498 | 1/2003 |
| WO | WO 03/000666 | 1/2003 |
| WO | WO 03/002544 | 1/2003 |
| WO | WO 03/004498 | 1/2003 |
| WO | WO 03/026661 | 4/2003 |
| WO | WO 03/032989 | 4/2003 |
| WO | 03/051822 | 6/2003 |
| WO | WO 03/050117 | 6/2003 |
| WO | 03/059378 | 7/2003 |
| WO | 03/061663 | 7/2003 |
| WO | WO 03/057689 | 7/2003 |
| WO | 03/076418 | 9/2003 |
| WO | WO 03/077656 | 9/2003 |
| WO | 02/32408 | 10/2003 |
| WO | 03/080070 | 10/2003 |
| WO | 03/087064 | 10/2003 |
| WO | 03/088962 | 10/2003 |
| WO | WO 03/087064 | 10/2003 |
| WO | WO 03/094845 | 11/2003 |
| WO | 03/103632 | 12/2003 |
| WO | 03/103633 | 12/2003 |
| WO | 03/103640 | 12/2003 |
| WO | 03/104208 | 12/2003 |
| WO | 03/106450 | 12/2003 |
| WO | 2004/000762 | 12/2003 |
| WO | WO 2004/000819 | 12/2003 |
| WO | WO 2004/000843 | 12/2003 |
| WO | 2004/002495 | 1/2004 |

| | | |
|---|---|---|
| WO | 2004/004777 | 1/2004 |
| WO | 2004/004778 | 1/2004 |
| WO | 2004/007468 | 1/2004 |
| WO | WO 2004/009596 | 1/2004 |
| WO | WO 2004/009597 | 1/2004 |
| WO | WO 2004/009602 | 1/2004 |
| WO | 2004/010936 | 2/2004 |
| WO | 2004/010992 | 2/2004 |
| WO | 2004/014871 | 2/2004 |
| WO | 2004/017896 | 3/2004 |
| WO | 2004/019869 | 3/2004 |
| WO | 2004/020408 | 3/2004 |
| WO | 2004/020409 | 3/2004 |
| WO | WO 2004/024943 | 3/2004 |
| WO | 2004/033431 | 4/2004 |
| WO | 2004/033710 | 4/2004 |
| WO | WO 2004/029204 | 4/2004 |
| WO | WO 2004/031189 | 4/2004 |
| WO | WO 2004/035588 | 4/2004 |
| WO | WO 2004/041164 | 5/2004 |
| WO | 2004/056748 | 7/2004 |
| WO | 2004/058174 | 7/2004 |
| WO | 2004/058727 | 7/2004 |
| WO | WO 2004/056825 | 7/2004 |
| WO | WO 2004/056829 | 7/2004 |
| WO | WO 2004/062665 | 7/2004 |
| WO | 2004/065380 | 8/2004 |
| WO | 2004/066963 | 8/2004 |
| WO | WO 2004/065380 | 8/2004 |
| WO | WO 2004/074218 | 9/2004 |
| WO | WO 2004/076413 | 9/2004 |
| WO | 2004/085401 | 10/2004 |
| WO | 2004/098583 | 11/2004 |
| WO | 2004/000819 | 12/2004 |
| WO | 2004/013997 | 12/2004 |
| WO | 2004/110368 | 12/2004 |
| WO | 2004/110375 | 12/2004 |
| WO | WO 2004/111000 | 12/2004 |
| WO | WO 2005/007647 | 1/2005 |
| WO | WO 2005/016894 | 2/2005 |
| WO | WO 2005/020920 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030129 | 4/2005 |
| WO | WO 2005/030751 | 4/2005 |
| WO | WO 2005/033099 | 4/2005 |
| WO | WO 2005/035525 | 4/2005 |
| WO | WO 2005/037215 | 4/2005 |
| WO | WO 2005/040095 | 5/2005 |
| WO | WO 2005/042488 | 5/2005 |
| WO | WO 2005/046603 | 5/2005 |
| WO | WO 2005/047297 | 5/2005 |
| WO | WO 2005/049033 | 6/2005 |
| WO | WO 2005/058315 | 6/2005 |
| WO | WO 2005/058849 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/090348 | 9/2005 |
| WO | WO 2005/100365 | 10/2005 |
| WO | 2005/121121 | 12/2005 |
| WO | WO 2005/117909 | 12/2005 |
| WO | WO 2005/121121 | 12/2005 |
| WO | 2006/034446 | 3/2006 |
| WO | 2006/039325 | 4/2006 |
| WO | WO 2006/040966 | 4/2006 |
| WO | WO 2006/043490 | 4/2006 |
| WO | 2006/052566 | 5/2006 |
| WO | WO 2006/067531 | 6/2006 |
| WO | WO 2006/067532 | 6/2006 |
| WO | 2006/078992 | 7/2006 |
| WO | WO 2006/070208 | 7/2006 |
| WO | 2007/005673 | 1/2007 |
| WO | 2007/039470 | 4/2007 |
| WO | 2007/089335 | 8/2007 |
| WO | 2007/120702 | 10/2007 |

OTHER PUBLICATIONS

Abramovitch et al, "Solution and flash vacuum pyrolysis of some 2,6-disubstituted β-phenethylsulfonyl azides and of β-styrenesulfonyl azide," *J Org Chem* (1985) 50:2066-2073.

Appukkuttan et al., "Transition-Metal-Free Sonogashira-Type Coupling Reactions in Water," *European Journal of Organic Chemistry* (2003) 29:4713-4716.

Arvanitis et al., "Non-peptide corticotropin-releasing hormone antagonists: syntheses and structure-activity relationships of 2-anilinopyrimidines and -triazines.," *J.Med. Chem.* (1999) 42(5)805-18.

Arvanitis et al., "Non-peptide corticotropin-releasing hormone antagonists: syntheses and structure-activity relationships of 2-anilinopyrimidines and -triazines.," *J Med Chem.* (1999) Supporting Material, pp. 1-10.

Arvanitis et al., "CRF Ligands via suzuki and negishi couplings of 3-pyridyl boronic acids or halides with 2-benzyloxy-4-chloro-3-nitropyridine," *Bioorganic & Medicinal Chemistry Letters* (2003) 13(2):289-291.

Arvanitis et al., "Imidazo[4,5-b]pyridines as corticotropin releasing factor receptor ligands," *Bioorganic & Medicinal Ch emistry Letters* (2003) 13(1):125-128.

Arvela et al., "Rapid, Easy Cyanation of Aryl Bromides and Chlorides Using Nickel Salts in Conjunction with Microwave Promotion," *J. Org. Chem.* (2003)68:9122-9125.

Arvela et al., "Rapid cyanation of aryl iodides in water using microwave promotion," *Org. Biomol. Chem.* (2003) 1:1119-1121.

Baindur et al., "Solution-Phase Synthesis of a Library of 3,5,7-Trisubstituted 3H-[1,2,3]triazolo[4,5-1d]pyrimidines," *J. Comb. Chem.* (2003) 5:653-659.

Bakkestuen et al., "Regioselective N-9 arylation of purines employing arylboronic acids in the presence of Cu(II)," *Tetrahedron Letters* (2003) 44:3359-3362.

Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," *Tetrahedron* (2002) 58:7607-7611.

Barta et al., "Synthesis and activity of selective MMP inhibitors with an aryl backbone," *Bioorg & Med Chem Ltrs* (2000) 10(24):2815-2817.

Baskin et al., "A mild, convenient synthesis of sulfinic acid salts and sulfonamides from alkyl and aryl halides," *Tetrahedron Letters* (2002) 43:8979-8483.

Baskin et al., "An Efficient Copper Catalyst for the Formation of Sulfones from Sulfinic Acid Salts and Aryl Iodides," *Org. Lett.* (2002) 4(25):4423-4425.

Baskin et al., "An Efficient Copper Catalyst for the Formation of Sulfones from Sulfinic Acid Salts and Aryl Iodides," *Org. Lett.* (2002) 4(25):4423-4425, Supporting Material #1.

Baskin et al., "An Efficient Copper Catalyst for the Formation of Sulfones from Sulfinic Acid Salts and Aryl Iodides," *Org. Lett.* (2002) 4(25):4423-4425, Supporting Material #2.

Bedford et al., "Nonquaternary cholinesterase reactivators. 3. 3(5)-Substituted 1,2,4-oxadiazol-5(3)-aldoximes and 1,2,4-oxadiazole-5(3)-thiocarbohydroximates as reactivators of organophosphonate-inhibited eel and human acetylcholinesterase in vitro," *J Med Chem* (1986) 29(11):2174-2183.

Beller et al., "Base-catalyzed amination of olefins: an example of an environmentally friendly synthesis of amines," *Chemosphere* (2001) 43(1):21-26.

Biagi et al., "4,5,6-trisubstituted 2-phenylpyrimidines and their affinity towards A1 adenosine receptors," *Farmaco* (1997) 52(1):61-65.

Betti, et al., "Novel 3-Aralkyl-7-(amino-substituted)-1,2,3-triazole[4,5-d]pyrimidines with High Affinity toward A1 Adenoside Receptors," *J. Med. Chem.* (1998) 41:668-673.

Boldt et al., "Synthesis of 2,4-diaminopyridines," *Angewandte Chemie International Edition* (1970) 9(5):377.

Bomika et al., Translation of "Certain reactions of nucleophilic substitution in the 2-chloro-3-cyanopyridine series," *Khimiya Geterotsiklicheskikh Soedinenii* (1976) (8):1085-1088 (Translated pp. 896-899).

Boschelli et al., "1,3,4-Oxadiazole, 1,3,4-thiadiazole, and 1,2,4-triazole analogs of the fenamates: in vitro inhibition of cyclooxygenase and 5-lipoxygenase activities," *J Med Chem* (1993) 36:1802-1810.

Boswell et al., "Synthesis of some N-carboxylic acid derivatives of 3-phenoxypyrrolidines, 4-phenoxypiperidines, and 3-phenoxynortropanes with muscle relaxant and anticonvulsant activities," *J Med Chem* (1974) 17(9):1000-1008.

Brancati et al., "Body Weight Patterns From 20 to 49 Years of Age and Subsequent Risk for Diabetes Mellitus: The Johns Hopkins Precursors Study," *Arch Intern Med.* (1999)159:957-963.

Bromidge et al., "Design of [R-(Z)]-(+)-alpha-(methoxyimino)-1-azabicyclo[2.2.2]octane-3-acetonitri le (SB 202026), a functionally selective azabicyclic muscarinic M1 agonist incorporating the N-methoxy imidoyl nitrite group as a novel ester bioisostere," *J Med Chem* (1997) 40(26):4265-4280.

Muci et al., "Practical Palladium Catalysts for C-N and C-O Bond Formation," *Topics in Current Chemistry* (2002) 219:131-209.

Buehler et al., "Physiologically active compounds. VI. Cyclic amino thiolesters of substituted chloroacetic, benzilic and glycolic acids," *J Med Chem* (1965) 8:643-647.

Bulger et al., "An investigation into the alkylation of 1,2,4-triazole," *Tetrahedron Letters* (2000) 41:1297-1301.

Chan et al., "Isoquinoline-6-Carboxamides as Potent and Selective Anti-Human Cytomegalovirus (HCMV)Inhibitors," *Bioorganic & Medicinal Chemistry Letters* (1999) 9:2583-2586.

Chen et. al., "Optimization of 3-phyenylpyrazolo[1,5-alpha]pyrimidines as potent corticotrophin-releasing factor-1 antagonists with adequate lipophilicity and water solubility," *Bioorganic & Medicinal Chemistry Letters* (2004) 14:3669-3673.

Chen et al., "Design and Synthesis of a Series of Non-Peptide High-Affinity Human Corticotropin-Releasing Factor 1 Receptor Antagonists," *J. Med. Chem.* (1996) 39:4358-4360.

Chen et al., "Free Radical Method for the Synthesis of Spiro-Piperidinyl Heterocycles," *Tetrahedron Letters* (1996) 37(30)5233-5234.

Chorvat et al., "Synthesis, Corticotropin-Releasing Factor Receptor Binding Affinity, and Pharmacokinetic Properties of Triazolo-, Imidazo-, and Pyrrolopyrimidines and -pyridines," *J. Med. Chem.* (1999) 42:833-848.

Clark et al., "Synthesis and Analgesic Activity of 1,3-Dihydro-3-(Substituted phenyl)imidazo[4,5-*b*]pyridine-2-ones and 3-(Substituted phenyl)-1,2,3-triazolo(4,5-*b*]pyridines," *J. Med. Chem.* (1978) 21(9):965-978.

Cocuzza et al., "Use of the Suzuki Reaction for the Synthesis of Aryl-Substituted Heterocycles as Corticotropin-Releasing Hormone (CRH) Antagonists," *Bioorganic &Medicinal Chemistry Letters* (1999) 9:1063-1066.

Cohen et al., "The Preparation and Properties of 6-Halomethylpurines," *Div. of Nucleoprotein Chemistry, Sloan-Kettering Institute for Cancer Research, and Sloan Kettering Div. Grad. School of Med. Sci., Cornell Uiv. Med. College* (1962) 27:3545-3549.

Colandrea et al., "Synthesis and regioselective alkylation of 1,6- and 1,7-naphythridines," *Tetrahedron Letters* (2000) 41:8053-8057.

Collier et al., "Radiosynthesis and in-vivo evaluation of the pseudopeptide δ-opioid antagonist [$^{125}$I]-ITIPP(Ψ)," *J. Labeled Compd. Radiopharm.*, (1999) 42(Suppl. I):S264-S266.

Cossey et al., "Amide-acid chloride adducts. VI. Pyridines and pyridinium salts from cyanoacetamides," *Australian Journal of Chemistry* (1976) 29(5):1039-1050.

Cryan et al., "Behavioral characterization of the novel GABAB receptor-positive modulator GS39783 (N,N'-dicyclopentyl-2-methylsulfanyl-5-nitropyrimidine-4,6-diamine): Anxiolytic-like activity without side effects associated with baclofen or benzodiazepines," *Journal of Pharmacology and Experimental Therapeutics* (2004) 310(3):952-963.

Dai et al., "The first general method for palladium-catalyzed Negishi cross-coupling of aryl and vinyl chlorides: use of commercially available Pd(P(*t*-Bu)$_3$)$_2$ as a catalyst," *J Am Chem Soc* (2001) 123(12):2719-2724.

Desimoni et al., "Polynuclear Isoxazole Types-I—Isoxazolo[4,5-d]Pyrimidines," *Tetrahedron* (1967) 23:675-680.

Devita et al., "Identification and initial structure-activity relationships of a novel non-peptide quinolone GnRH receptor antagonist," *Bioorg & Med Chem Ltrs* (1999) 9(17):2615-2620.

Di Braccio et al., "Synthesis and preliminary pharmacological examination of 2,4-disubstituted N,N-dialkyl-1,8-naphthyridine-3-carboxamides," *Farmaco* (1989) 44(9):865-881.

Dzierba et al., "Synthesis, Structure-Activity Relationships, and in Vivo Properties of 3,4-Dihydro-1H-pyrido[2,3-*b*]pyrazin-2-ones as Corticotropin-Releasing Factor-1 Receptor Antagonists," *Journal of Medicinal Chemistry* (2004) 47(23):5783-5790.

Eicher et al., "Reaction of triafulvenes with isonitriles. A simple synthesis of diphenyl-substituted functionalized cyclobutene derivatives and related products," *Synthesis* (1987) (7):619-626.

Escher et al., "Cyclopentylamine Substituted Triazolo[4,5-*D*]Pyrimidine: Implications for Binding to the Adenosine Receptor," *Tetrahedron Letters* (1991) 32(29):3583-3584.

Gangloff et al., "Synthesis of 3,5-disubstituted-1,2,4-oxadiazoles using tetrabutylammonium fluoride as a mild and efficient catalyst," *Tetrahedron Letters* (2001)42:1441-1443.

Gilligan et al., "Corticotropin-releasing factor antagonists: Recent advances and exciting prospects for the treatment of human diseases," *Current Opinion in Drug Discovery & Development* (2004) 7(4):487-497.

Gilligan, et al., "Corticotropin Releasing Factor (CRF) Receptor Modulators" Progress and Opportunities for New Therapeutic Agents, *J. Med. Chem.* (2000) 43(9):1641-1660.

Goldner et al, "Die Darstellung 2,9-; 2,6,9- und 6,9-substituierter Purine," *Journal fuer Praktische Chemie (Leipzig)* (1961)12:242-252.

Giner-Sorolla et al., "The Synthesis and Properties of 6-Mercaptomethylpurine and Derivatives," *Cornell University Medical College* (1965) 8:667-672.

Gomtsyan et al., "Design, synthesis, and structure-activity relationship of 6-alkynylpyrimidines as potent adenosine kinase inhibitors," *J Med Chem.* (2002) 45(17):3639-3648.

Hamada et al., "An improved synthesis of arylsulfonyl chlorides from arylhalides," *Synthesis* (1986) pp. 852-854.

He et al., "4-(1,3-Dimethozyprop-2-ylamino)-27-dimethyl-8-(2,4-dichlorophenyl)-pyrazolo[1,5-*a*]-1,3,5-triazine: A Potent, Orally Bioavailable CRF1 Receptor Antagonist," *J. Med. Chem.*(2000) 43:449-456.

Hecht et al., "On the "activation" of cytokins," *J of Biological Chemistry* (1975) 250(18):7343-7351.

Hersperger et al., "Palladium-Catalyzed Cross-Coupling Rtions for the Synthesis of 6,8-Disubstituted 1,7-Naphthyridines: A Novel Class of Potent and Selective Phosphodiesterase Type 4D Inhibitors," *J. Med. Chem.* (2000) 43:675-682.

Higuchi et al., "Pro-drugs as novel delivery systems," *A.C.S. Symposium Series*, vol. 14 (1987).

Hill et al., "Environmental contributions to the obesity epidemic," *Science* (1998) 280(5368):1371-4.

Hocek et al., "An Efficient Synthesis of 2-Substituted 6-Methylpurine Bases and Nucleosides by Fe- or Pd-Catalyzed C ross-Coupling Reactions of 2,6-Dichloropurines," *J. Org. Chem.* (2003) 68:5773-5776.

Huang et al., "Synthesis and Antiplatelet Activity of Phenyl Quinolones," *Bioorganic & Medicinal Chemistry* (1998) 6:1657-1662.

Berge et al., "Pharmaceutical Salts," *Journal of Pharmaceutical Sciences* (1977) 66(1):1-19.

Jia, et al., "Design, Synthesis and Biological Activity of Novel Non-Amidine Factor Xa Inhibitors. Part 1: P1 Structure-Activity Relationships of the Substituted 1-(2-Naphtyl)-1*H*-pyrazole-5-carboxylamides," *Bioorganic & Medicinal Chemistry Letters* (2002) 12:1651-1655.

Jogie et al., "Unusual protein-binding specificity and capacity of aza-arenophilic gels," *Journal of Molecular Recognition* (1998) 11:261-262.

Kawase et al., "α-trifluoromethylated acyloins induce apoptosis in human oral tumor cell lines," *Bioorg & Med Chem Ltrs* (1999) 9(21):3113-3118.

Kelly et al, "A Synthesis of Aaptamine," *Tetrahedron* (1985) 41(15):3033-3066.

Kelley et al., "Benzodiazepine receptor binding activity of 8-substituted-9-(3-substituted-benzyl)-6-(dimethylamino)-9*H*-purines," *J Med Chem* (1990) 33(1):196-202.

Kempson et al., "Fused pyrimidine based inhibitors of phosphodiesterase 7 (PDE7): synthesis and initial structure-activity relationships," *Bioorganic & Medicinal Chemistry Letters* (2005) 15:1829-1833.

Khattab et al., "Quinolines with heteroatom substituents in position 2 and 4. Nucleophilic substitution of 2,4-dichloro-3-phenylquinolines," *ACH—Models in Chemistry* (1994) 131(3-4)521-527.

Kloetzer et al., "Chlorierende formylierungsreaklionen an pyrimidinen," *Monatshefte fuer Chemie*, (1965) 96(5):1567-1572.

Kotian et al., "Synthesis, ligand binding, and quantitative structure-activity relationship study of 3β-(4'-substituted phenyl)-2β-heterocyclic tropanes evidence for an electrostatic interaction at the 2β-position," *J Med Chem* (1996) 39(14):2753-2763.

Krauze et al., "Derivatives of 3-cyano-6-phenyl-4-(3'-pyridyl)-pyridine-2(1H)-thione and their neurotropic activity," *European Journal of Medicinal Chemistry* (1999) 34(4):301-310.

Krauze et al; "Synthesis of 3-oxoisothiazolo[5,4-b]pyridines," *Khimiya Geterotsiklicheskikh Soedinenii* (1982) (4):508-512.

Kumegai et al., "Synthesis, SAR and biological activities of CRH1 Receptor: Novel 3- or 4-carbamoyl-1,2,5,6-tetrahydropyridinopyrrolopyrimidine derivative," 4$^{th}$ ACS National Meeting, Aug. 18-22, 2002, Boston, MA. Poster #259.

Lai et al., "A one-pot method for the efficient conversion of aryl- and acyl-substituted methyl alcohols into chlorides," *Synthetic Communications* (2003) 33(10):1727-1732.

Lanier et al., "Small molecule corticotrophin-releasing factor antagonists," *Expert Opinion* (2002) 12(11):1619-1630.

Leadbeater et al., "First Examples of Transition-Metal Free Sonogashira—Type Couplings," *Organic Letters* (2003) 5(21):3919-3922.

Leadbeater et al., "Transition-metal free sonogashira—type couplings," *Department of Chemistry, King's College London*, Supplementary Information, pp. S1-S4.

Lee et al., "Synthesis and biological evaluation of clitocine analogues as adenosine kinase inhibitors," *Bioorg & Med Chem Ltrs* (2001) 11(18):2419-2422.

Leese et al., "Potential antipurines. II. Synthesis of 6- and 9-substituted purines and 8-azapurines," *Journal of the Chemical Society* (1958) 4107-4110.

Le Bas et al., "Radioiodinated analogs of EP 00652218 for the exploration of the tachykinin NK1 receptor by spect," *J. Labeled Compd. Radiopharm.* (2001) 44:S280-S282.

Le Stunff et al., "Early changes in postprandial insulin secretion, not in insulin sensitivity, characterize juvenile obesity," Diabetes (1989) 43:696-702.

Lin, et al., "Synthesis and Antitumor Activity of Halogen-Substituted 4-(3,3-Dimethyl-1-triazeno)quinolines," *J. Med. Chem.* (1978) 21(3):268-272.

Litvak et al., "Polynucleotides and Their Components in the Processes of Aromatic Nucleophilic Substitution: II.1 Nucleophilic Modification of 3',5'-Bis-O-(α,β,α',β'-tetrafluoropyrid-γ-yl)thymidine," *Russian Journal of Bioorganic Chemistry* (2004) 30(4):337-343.

Litvinov et al., "Naphthyridines. Structure, physicochemical properties and general methods of synthesis," *Russian Chemical Reviews* (2000) 69(3):201-220.

Loupy et al., "Easy and efficient SNAr Reactions on halopyridines in solvent free conditions," *Heterocycles* (1991) 32(10):1947-1952.

Luo et al., "Microwave-assisted synthesis of aminopyrimidines," *Tetrahedron Letters* (2002) 43:5739-5742.

Groger "Moderne methoden der Suzuki-kreuzkupplung: die langerwarteten universellen synthesevarianten mit arylchloriden," *J Prakt Chem* (2000) 342(4):334-339.

Ma, et al. "Mild Method for Ullmann Coupling Reaction of Amines and Aryl Halides," *Organic Letters* (2003) 5(14):2453-2455.

Macchia et al., "New N-n-propyl-substituted 3-aryl- and 3-cyclohexylpiperidines as partial agonists at the D4 dopamine receptor," *J Med Chem* (2003) 46(1):161-168.

Mackman et al., "2-(2-Hydroxy-3-alkoxyphenyl)-1*H*-benzimidazole-5-carboxamidine derivatives as potent and selective urokinase-type plasminogen activator inhibitors," *Bioorganic & Medicinal Chemistry Letters* (2002) 12(15):2019-2022.

Majeed, et al, "Stannylation Reactions and Cross-Couplings in Pyrimidines," *Tetrahedron* (1989) 45(4):993-1006.

Matsui et al., "Highly potent inhibitors of TNF-α production. Part II: metabolic stabilization of a newly found chemical lead and conformational analysis of an active diastereoisomer," *Bioorg Med Chem.* (2002) 10(12):3787-805.

Matsuno et al., "Potent and selective inhibitors of platelet-derived growth factor receptor phosphorylation. 3. Replacement of quinazoline moiety and improvement of metabolic polymorphism of 4-[4-(*N*-substituted (thio)carbamoyl)-1-piperazinyl]-6,7-dimethoxyquinazoline derivatives," *J Med Chem* (2003) 46(23):4910-4925.

Mesguiche et al., "4-Alkoxy-2,6-diaminopyrimidine derivatives: inhibitors of cyclin dependent kinases 1 and 2," *Bioorganic & Medicinal Chemistry Letters* (2003) 13(2):217-222.

Metzger et al.; "Einstufensynthese von 2,4-Bis(*sec*-alkylamino-6-halogen-3-pyridincarbonitrilen)," *Liebigs Annalen der Chemie* (1980) (6):946-953.

Mittelbach et al., "Syntheses with nitriles. 60. Preparation of 4-amino-5-cyano-6-phenylpyrimidines from 2-amino-1,1-dicyano-2-phenylethene," *Journal of Heterocyclic Chemistry* (1980) 17(7):1385-1387.

Miyashita et al., "Preparation of Heterarenecarbonitriles by Reaction of Haloheteroarenes with Potassium Cyanide Atalyzied by Sodium *p*-Toluenesulfinate," *Heterocycles* (1994) 39(1):345-350.

Mohan et al., "Solid-phase synthesis of N-substituted amidinophenoxy pyridines as factor Xa inhibitors," *Bioorganic & Medicinal Chemistry Letters* (1998) 8(14):1877-1882.

Mombereau et al., "Genetic and Pharmacological Evidence of a Role for GABAB Receptors in the Modulation of Anxiety- and Antidepressant-Like Behavior," *Neuropsychopharmacology* (2004) 29(6):1050-1062.

Mongin et al., "Advances in the directed metallation of azines and diazines (pyridines, pyrimidines, pyrazines, pyridazines, quinolines, benzodiazines and carbolines). Part 1: Metallation of pyridines, quinolines and carbolines," *Tetrahedron* (2001) 57(19):4059-4090.

Montgomery et al., "Isonucleosides. 1. Preparation of methyl 2-deoxy-2-(purin-9-yl)arabinofuranosides and methyl 3-deoxy-3-(purin-9-yl)xylofuranosides," *Journal of Organic Chemistry* (1975) 40(13):1923-1927.

Morimoto et al., "Potent and selective ET-A antagonists. 1. Syntheses and structure-activity relationships of *N*-(6-(2-(aryloxy)ethoxy)-4-pyrimidinyl)sulfonamide derivatives," *J Med Chem* (2001) 44(21):3355-3368.

Moschitskii et al., Translation of "Reaction of 2,3,5,6-tetrachloro-4-pyridyl-vinyl sulfone with nuleophilic agents," *Khimiya Geterotsiklicheskikh Soedinenii* (1972) pp. 1634-1637, (Translated pp. 1482-1485).

Muller et al., "7-Deaza-2-phenyladenines: Structure-Activity Relationships of Potent A1 Selective adenosine Receptor Antagonists," *J. Med. Chem.* (1990) 33:2822-2828.

Nakazato et al., "Synthesis, SAR and biological activities of CRH1 Receptor: Novel 3- or 4-carbamoyl-1,2,5,6-tetrahydropyridinoquinoline derivative," 24$^{th}$ ACS National Meeting, Aug. 18-22, 2002, Boston, MA. Poster #258.

Nakazato et al., "Design, synthesis and structure-affinity relationships of 4-methylidenepiperidine and 4-aryl-1,2,3,6-tetrahydropyridine derivatives as corticotropin-releasing facton receptor antagonists," *Bioorganic & Medicinal Chemistry* (2000) 8(5):1183-1193.

Nesi et al., "New Difunctionalized 4-Nitroisoxazoles from Alpha-Nitroacetophenone Oxime," *Heterocycles* (1985) 23(6):1465-1469.

Nicewonger et al., "Microwave-assisted acylation of 7-amino-5-aryl-6-cyanopyrido[2,3-d]pyrimidines," *Molecular Diversity* (2003) 7(2-4):247-252.

Norman et al., "Structure -activity relationships of a series of pyrrolo(3,2-d) pyrimidine derivatives and related compounds as neuropeptide Y5 receptor antagonists" *J. Med. Chem.* (2000) 43(22):4288-4312.

Norman et al., "Structure—activity relationships of a series of pyrrolo(3,2-*d*) pyrimidine derivatives and related compounds as neuropeptide Y5 receptor antagonists" *J. Med. Chem.* (2000) 43(22):4288-4312, JM000269T, Supplemental Material, pp. 1-11.

Olesen et al., "The use of bioisosteric groups in lead optimization," *Current Opinion in Drug Discovery & Development* (2001) 4(4):471-478.
Parlow et al., "Design, synthesis, and crystal structure of selective 2-pyridone tissue factor VIIa inhibitors," *J Med Chem* (2003) 46(22):4696-4701.
Paulsen et al., "Darstellung von Bausteinen zur Synthese carbocyclischer furanose-analoga," *Chemische Berichte* (1981) 114(1):346-358.
Pederson, "The impact of obesity on the pathogenesis of non-insulin-dependent diabetes mellitus: a review of current hypotheses," *Diab. Metab. Rev.*, (1989) 5(6):495-509.
Perry et al., "Prospective study of risk factors for development of non-insulin dependent diabetes in middle aged British men," *BMJ* (1995) 310(6979):560-4.
Phillips et al., "Discovery of N-[2-[5-[Amino(imino)methyl]-2-hydroxyphenoxyl]-3,5-difluoro-6-[3-(4,5-dihydro-1-methyl-1H-imidazol-2-yl)phenoxy]pyridine-4-yl]-N-methylglycine(ZK-807834): A Potent, Selective, and Orally Active Inhibitor of the Blood Coagulation Enzyme Factor Xa," *J. Med. Chem.* (1998) 41(19)3557-3562.
Pomorski "Synthesis of Acids, Derivatives of 4-Hydroxy-1,5-Naphthyridine," *Roczniki Chemii, Ann. Soc. Chim. Polonorum* (1974) 48:321-325.
Potenza et al., "A rapid quantitative bioassay for evaluating the effects of ligands upon receptors that modulate cAMP levels in a melanophore cell line," *Pigment Cell Res.* (1992) 5(6):372-8.
Prasad, et al., "Convenient Methods for the Reduction of Amides, Nitriles, Carboxylic Esters, Acids and Hydroboration of Alkenes Using NaBH$_4$/I$_2$System," *Tetrahedron* (1992) 48(22):4623-4628.
Press et al., "Synthesis and SAR of 6-Substituted Purine Derivatives as Novel Selective Positive Inotropes," *J. Med. Chem.* (1992) 35(24):4509-4515.
Quintela et al., "6-Dimethylaino 1H-Pyrazolo[3,4-d]pyrimidine Derivatives as New Inhibitors of Inflammatory Mediators in Intact Cells," *Bioorganic &Medicinal Chemistry* (2003) 11:863-868.
Quintela et al., "Pyrazolopyrimidines: synthesis, effect on histamine release from rat peritoneal mast cells and cytotoxic activity," *Eur. J. Med. Chem.* (2001) 36:321-332.
Ram et al., "Chemotherapeutic agents. Part XXII. Synthesis of π-deficient pyrimidines as leishmanicides," *Indian Journal of Chemistry, Section B* (1991) 30B(10):962-965.
Reed et al., "In-vivo and in-vitro models of type 2 diabetes in pharmaceutical drug discovery," *Diabetes Obes Metab*, (1999) 1(2):75-86.
Rehwald et al.; "Syntheses of thieno(2,3-d)pyrimiclines and aminopyrimidines from 2-alkoxy-5-cyano-4-thioxopyrimidine intermediates," *Heterocycles* (1998) 48(6):1157-1167.
*Remington's Pharmaceutical Sciences*, 17$^{th}$ Ed., (1985), Mack Publishing Company, Easton, PA, p. 1418-1419.
*Remington's Pharmaceutical Sciences*, 16$^{th}$ Ed., (1980), Mack Publishing Company, Easton, PA.
Rewcastle, et al., "Tyrosine Kinase Inhibitors. 10. Isomeric 4-[(3-Bromophenyl)amino]pyrido[d]pyrimidines are Potent ATP Binding Site Inhibitors of the Tyrosine Kinase Function of the Epidermal Growth Factor Receptor," *J. Med. Chem.* (1996)39:1823-1835.
Raffel et al., "Diabetes Mellitus," *Principles and Practice of Medical Genetics*, 3$^{rd}$ Ed. 1:1401-1440 (1996).
Roberts et al., "Peroxy-acid oxidation of N,N-disubstituted aminotetrafluoro-, amino-3-chlorotrifluoro-, and amino-3,5-dichlorodifluoro-pyridines," *Journal of the Chemical Society [Section] C: Organic* (1969) (11):1485-1491.
Roberts at al., "Polychloroaromatic compounds. I. Oxidation of pentachloropyridine and its N,N-disubstituted amino derivatives with peroxyacids," *Journal of the Chemical Society [Section]C: Organic* (1968) (12):1537-1541.
Robins, et al., "Potential Purine Antagonists. IV. Synthesis of Some 9-Methyl-6-substituted-purines," (1957) 79:490-494.
Robev et al., "4-Cyclopropylamino- and 4-cyclobutylamino derivatives of some aryl-substituted 5-cyanopyrimidines," *Doklady Bolgarskoi Akademii Nauk* (1981) 34(12):1677-1680.
Roche, *Bioreversible Carriers in Drug Design, ed.*, American Pharmaceutical Association and Pergamon Press (1987).

Rotwein et al., "Polymorphism in the 5' flanking region of the human insulin gene: a genetic marker for non-insulin-dependent diabetes," *N Engl J Med.* (1983) 308(2):65-71.
Showell et al.,"Tetrahydropyridyloxadiazoles: semirigid muscarinic ligands," *J Med Chem* (1991) 34(3):1086-1094.
Silhar et al., "Facile and Efficient Synthesis of 6-(Hydroxymethyl)purines," *Org. Lett.* (2004) 6(19):3225-3228.
Smith et al., "Effects of positive allosteric modulators of the GABAB receptor on cocaine self-administration in rats," *Psychopharmacology* (2004) 173(1-2):105-111.
Silvestri et al., "Novel indolyl aryl sulfones active against HIV-1 carrying NNRTI resistance mutations: synthesis and SAR studies," *J Med Chem* (2003) 46(12):2482-2493.
Steensma et al., "A novel method for the synthesis of aryl sulfones," *Tetrahedron Ltrs* (2001) 42:2281-2283.
Sternfeld et al., "Synthesis and serotonergic activity of 3-[2-(pyrrolidin-1-yl)ethyl]indoles: potent agonists for the h5-HT1D receptor with high selectivity over the h5-HT1B receptor," *J Med Chem* (1999) 42(4):677-690.
Strupczewski et al, "Synthesis and neuroleptic activity of 3-(1-substituted-4-piperidinyl)-1,2-benzisoxazoles," *J Med Chem* (1985) 28(6):761-769.
Suami et al., "Nucleoside analogs. I. Synthesis of 1,3-dihydroxy-2-(6-substituted-9-purinyl)cyclohexane," *Journal of Heterocyclic Chemistry* (1969) 6(5):663-665.
Sugimoto et al., "Preparation of Nitrogen-Containing π—Deficient Heteroaromatic Grignard Reagents: Oxidative Magnesiation of Nitrogen-Containing π-Deficient Halgenoheteroaromatics Using Active Magnesium," *J. Org. Chem.* (2003) 68:2054-2057.
Sugimoto et al., "Lithiation of 1H-Pyrazolo[3,4-d]pyrimidine Derivative Using Lithium Alkanetellurolate," *Tetrahedron Letters* (1999) 40:2139-2140.
Terashima et al., "Inhibition of human O6-alkylguanine-DNA alkyltransferase and potentiation of the cytotoxicity of chloroethylnitrosourea by 4(6)-(benzyloxy)-2,6(4)-diamino-5-(nitro or nitroso)pyrimidine derivatives and analogues," *J Med Chem* (1998) 41(4):503-508.
Thompson et al., "N$^6$,9-Disubstituted Adenines: Potent, Selective Antagonists at the A1 Adenosine Receptor," *J. Med. Chem.* (1991) 34:2877-2882.
Thompson et al., "Synthesis and evaluation of 6-(dibromomethyl)-5-nitropyrimidines as potential antitumor agents," *J Med Chem* (1997) 40(5):766-770.
Turck et al., "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines," *Tetrahedron* (2001) 57(21):4489-4505.
Urgaonkar et al., "Pd/P(i-BuNCH$_2$CH$_2$)3N: an efficient catalyst for Suzuki cross-coupling of aryl bromides and chlorides with arylboronic acids," *Tetrahedron Letters* (2002) 43(49):8921-8924.
Urwyler et al., "N,N—Dicyclopentyl-2-methylsulfanyl-5-nitro-pyrimidine-4,6-diamine (GS39783) and structurally related compounds: Novel allosteric enhancers of γ-aminobutyric acidB receptor function," *Journal of Pharmacology and Experimental Therapeutics* (2003) 307(1):322-330.
Vaughan et al., "The Reformatsky Reaction. I. Zinc and Ethyl Alpha-Bromoisobutyrate," *Dept. of Chem., The Univ. of Michigan*, Ann Arbor, MI., (1964) 30:1790-1795.
Vice,et al "Concise Formation of 4-Benzyl Piperidines and Related Derivatives Using a Suzuki Protocol," *J. Org. Chem.* (2001) 66:2487-2492.
Vice,et al., "Concise Formation of 4-Benzyl Piperidines and Related Derivatives Using a Suzuki Protocol," *J. Org. Chem.* (2001) 66:2487-2492, Supporting Information, pp. S1-S32.
Wang at at, "Improving the oral efficacy of CNS drug candidates: discovery of highly orally efficacious piperidinyl piperidine M2 muscarinic receptor antagonists," *J Med Chem* (2002) 45(25):5415-5418.
Wells et al., "Regioselective nucleophilic substitutions of fluorobenzene derivatives," *Tetrahedron Letters* (1996) 37(36):6439-6442.

Werbel et al., "Synthesis and antimalarial effects of 5,6-dichioro-2-[(4-[[ [4—(diethylamino) 1-methylbutyl]amino [[-6-methyl-2-pyrimidinyl)amino] benzimidazole and related benzimidazoles and 1,H-Imidazo[4,5-b]pyridines," *J. Het. Chem* (1973) vol. 10, 363-382.

Wilson et al., "Microwave-assisted synthesis of 2-aminoquinolines," *Tetrahedron Letters* (2002) 43(4)581-583.

Wolfe et al., "Scope and limitations of the Pd/BINAP-catalyzed amination of aryl bromides," *J Org Chem* (2000) 65(4):1144-1157.

Wolfe et al., "Simple, efficient catalyst system for the palladium-catalyzed amination of aryl chlorides, bromides, and triflates," *J Org Chem* (2000) 65(4):1158-1174.

Wolter et al., "Copper-Catalyzed Coupling of Aryl Iodides with Aliphatic Alcohols," *Organic Letters* (2002) 4(6)973-976.

Wolter et al., "Copper-Catalyzed Coupling of Aryl Iodides with Aliphatic Alcohols," *Organic Letters* (2002) 4(6):973-976, Supporting Information, pp. S1-S16.

Wu et al., "One-Pot Two-Step Microwave-Assisted Reaction in Constructing 4,5-Disubstituted Pyrazolopyrimidines," *Org. Lett.*, (2003) 5(20):3587-3590.

Yarovenko et al., "New method for the preparation of 5-amino-1,2,4-oxadiazoles," *Bull Acad Sci, USSR Div Chem Sci*, (1991) 40:1924.

Yoon et al., "Reaction of Diisobutylaluminum Hydride with Selected Organic Compounds Containing Representative Functional Groups," *J. Org. Chem.* (1985) 50:2443-2450.

Zamponi et al, "Unique structure-activity relationship for 4-isoxazolyl-1,4-dihydropyridines," *J Med Chem* (2003) 46:87-96.

Zamponi et al., "Unique structure-activity relationship for 4-isoxazolyl-1,4-dihydropyridines," *J Med Chem* (2003), Supporting Information., pp. 1-31.

Zhang, et al., "Preparation of 1-(Tri-n-Butylstannyl) Furanoid Glycals and Their Use in Palladium-Mediated Coupling Reactions," *Tetrahedron Letters* (1993) 34(10):1571-1574.

Zhu et al., Synthesis and mode of action of (125)I- and (3)H-labeled thieno[2,3-c]pyridine antagonists of cell adhesion molecule expression, *J Org Chem.* (2002) 67(3):943-8.

Accession No. 2003:2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1.

Accession No. 2003:2415906 CHEMCATS, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8.

Accession No. 2003:2416398 CHEMCATS, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2.

Accession No. 2003:2417080 CHEMCATS, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6.

Cover Sheet and 54 Compounds—CAS Registry file (23 pp.).

Cover Sheet and 18 Compounds—CAS Registry file (9 pp.).

Cover Sheet and 2534 Compounds—CAS Registry and ChemCats files (817pp.).

Cover Sheet and 1185 Compounds—CAS Registry and ChemCats Files (391pp.).

23 Compounds—ChemCats File (11pp.).

Greene et al., *Protective Groups in Organic Synthesis*, 3rd Ed., John Wiley & Sons, New York (1999).

Remington, *The Science and Practice of Pharmacy*, 20th Ed., Lippincott Williams & Wilkins (2000).

Oae, *Organic Chemistry of Sulfur*, Ed., Plenum Press: New York (1977).

Abstract #107, p. 56, *Toward Understanding Islet Biology*, Jan. 21, 2003—Jan. 26, 2003, Keystone, Colorado.

Abstract #112, p. 42, *Diabetes Mellitus: Molecular Mechanisms, Genetics and New Therapies*, Jan. 27-Feb. 2, 2005, Keystone, Colorado.

Abstract #228, p. 54, *Diabetes Mellitus: Molecular Mechanisms, Genetics and New Therapies*, Jan. 27-Feb. 2, 2005, Keystone, Colorado.

Abstract #117 & Poster, *Diabetes: Molecular Genetics, Signaling Pathways and Integrated Physiology*, Jan. 14-19, 2007, Keystone, Colorado.

Abstract #230 & Poster, *Diabetes: Molecular Genetics, Signaling Pathways and Integrated Physiology*, Jan. 14-19, 2007, Keystone, Colorado.

Chu et al., "A role for β-cell-expressed G protein-coupled receptor 119 in glycemic control by enhancing glucose-dependent insulin release," Endocrinology (2007) 148:2601-2609.

Fyfe et al., Diabetes (2007) 56(Supplement I):A142 (Abstract #532-P).

Overton et al., "Deorphanization of a G protein-coupled receptor for oleoylethanolamide and its use in the discovery of small-molecule hypophagic agents," Cell Metabolism (2006) 3:167-175.

Soga et al., "Lysophosphatidylcholine enhances glucose-dependent insulin secretion via an orphan G-protein-coupled receptor," Biochem Biophys Res Commit (2005) 326:744-751.

Chu et al., "A role for intestinal endocrine cell-expressed GPR119 in glycemic control by enhancing GLP-1 and GIP release", Arena Pharmaceuticals pre-publication document.

Hocek et al., "An efficient synthesis of 2-substituted 6-methylpurine bases and nucleosides by Fe- or Pd-catalyzed cross-coupling reactions of 2,6-dichloropurines", *Journal of Organic Chemistry*, 68:5773-6 (2003).

Lin et al., "Synthesis and antitumor activity of halogen-substituted 4-(3,3-dimethyl-1-triazeno)quinolines", *Journal of Medicinal Chemistry*, 21(3):268-72 (1978).

Litvinov et al., "Naphthyridines. Structure, physicochemical properties and general methods of synthesis", *Russian Chemical Reviews*, 69(3):201-220 (2000).

Ulrich, J., Ch. 4, "Crystallization," *Kirk-Othmer Encyclopedia of Chemical Technology*, John Wiley & Sons, Inc., (2002), on-line post.

Peterson, M.L., et al. *J. Pharm. Pharmaceut. Sci.* (www.cspsCanada.org), 9(3): 317-326 (2006) pp. 317-326.

Guillory et al., *Polymorphism in Pharmaceutical Solids*, ed. H.G. Brittain, Marcel Dekker, Inc., New York, pp. 202-209 (1999).

Non-Final Office Action mailed Apr. 6, 2007 in connection with U.S. Appl. No. 10/888,747.

Amendment and Response in Reply to Office Action of Apr. 6, 2007 filed Jul. 5, 2007 in connection with U.S. Appl. No. 10/888,747.

Non-Final Office Action mailed Oct. 19, 2007 in connection with U.S. Appl. No. 10/888,747.

Amendment in Reply to Action of Oct. 19, 2007 in connection with U.S. Appl. No. 10/888,747.

Final Office Action mailed Apr. 21, 2008 in connection with U.S. Appl. No. 10/888,747.

Interview Summary mailed Jun. 17, 2008 in connection with U.S. Appl. No. 10/888,747.

Amendment in Reply to Action of Apr. 21, 2008 in connection with U.S. Appl. No. 10/888,747.

International Search Report in connection with WO 2006/083491 (Int. App. No. PCT/US2006/000567).

Written Opinion of the International Searching Authority in connection with WO 2006/083491 (Int. App. No. PCT/US2006/000567).

International Search Report in connection with WO 2005/007647 (Int. App. No. PCT/US2004/022327).

Written Opinion of the International Searching Authority in connection with WO 2005/007647 (Int. App. No. PCT/US2004/022327).

Atwal, et al.; Synthesis and Biological Activity of 5-aryl-4-(5-methyl-1H-imidazol-4-yl)piperidin-l-yl)pyrimidine Analogs as Potent, Highly Selective, and Orally Bioavailable NHE-1 Inhibitors; Bioorganic & Medicinal Chemistry Letters (2006), 16(18), 4796-4799.

Wang, et al.; Amino-Substituted Heterocycles as Isosteres of Trans-Cinnamides: Design and Synthesis of Heterocyclic Biaryl Sulfides as Potent Antagonists of LFA-1/ICAM-1 Binding; Bioorganic & Medicinal Chemistry Letters, 15(1), 195-201 (2005).

Nakamura, et al.; Effect of Cerivastatin on Endothelial Dysfunction and Aortic CD36 Expression in Diabetic Hyperlipidemic Rats; Hypertension Research; 27(8) 589-598; (2004).

Cheng; Rosuvastatin in the Management of Hyperlipidemia; Clinical Therapeutics; 26(9), 1368-1387 (2004).

Chen, et al.; Inhibitory Effect of Candesartan and Rousuvastatin on CD40 and MPs Expression in Apo-E Knockout Mice: Novel Insights into the Role of RAS and Dyslipidemia in Atherogenesis; Journal of Cardiovascular Pharmacology; 44(4), 446-452 (2004).

De Denus, et al.; Dyslipidemias and HMG-CoA Reductase Inhibitor Prescription in Heart Transplant Recipients; Annals of Pharmacotherapy, 28 (7/8), 1136-1141 (2004).

Crouse, et al.; Measuring Effects on Intima Media Thickness: An Evaluation of Rosuvastatin in Subclinical Atherosclerosis—The Rationale and Methodology of the METEOR Study; Cardiovascular Drugs and Therapy, 18(3), 231-238 (2004).

Dugue, et al., Detection and Incidence of Muscular Adverse Drug Reactions: A prospective Analysis from Laboratory Signals; European Journal of clinical Pharmacology, 60(4), 285-292 (2004).

Chapman, et al.; Non-High-Density Lipoprotein Cholesterol as a Risk Factor: Addressing Risk Associated with Apolipoprotein B-Containing Lipoproteins; European Heart Journal Supplements, 6(Suppl. A), A43-A48 (2004).

Kanstrup, et al., Quality of Lipid-Lowering Therapy in Patients with Ischaemic Heart disease: A Register-Based Study in 3477 Patients; Journal of Internal Medicine, 255(3), 367-372 (2004).

Roberts; Two More Drugs for Dyslipidemia; American Journal of Cardiology; 93(6), 8martin09-811 (2004).

Martin, et al.; Metabolism, Excretion, and Pharmacokinetics of Rosuvastatin in Healthy Adult Male Volunteers; Clinical Therapeutics, 25(11), 2822-2835 (2003).

Martin, et al.; Absolute Oral Bioavailability of Rosuvastatin in Healthy White Adult Male Volunteers; Clinical Therapeutics, 25(10), 2553-2563 (2003).

Winkelmann, et al.; Haplotypes of the Cholesteryl Ester Transfer Protein Gene Predict Lipid-Modifying Response to Statin Therapy; Germany Pharmacogenomics Journal, 3(5), 284-296 (2003).

Martin, et al.; A Double-Blind, Randomized, Incomplete Crossover Trial to Assess the Dose Proportionality of Rosuvastatin in Healthy Volunteers; Clinical Therapeutics, 25(8), 2215-2224 (2003).

Brewer; Benefit-Risk Assessment of Rosuvastatin 10 to 40 Milligrams; American Journal of Cardioloty, 92(4B), 23K-29K (2003).

Schuster; Rosuvastatin—A Highly Effective New 3-hydroxy-3-methylglutaryl Coenzyme A Reductase Inhibitor: Review of clinical Trial Data at 10-40 mg doses in Dyslipidemic Patients; Cardiology, 99(3), 126-139 (2003).

Holdgate, et al., Molecular Mechanism for Inhibition of 3-hydroxy-3-methylglutaryl CoA (HMG-CoA) Reductase by Rosuvastatin; Biochemical Society Transactions, 31(3), 528-531 (2003).

Capuzzi, et al.; Beneficial Effects of Rosuvastatin Alone and in Combination with a Combined Hyperlipidemia and Low High-Density Lipoprotein Cholesterol Levels; American Journal of Cardiology, 91(11), 1304-1310 (2003).

Fellstrom, et al; Why Do We Need a Statin Trial in Hemodialysis Patients?; Kidney International Supplement, 84, S204-S206 (2003).

Pelat, et al.; Rosuvastatin Decreases Caveolin-1 and Improves Nitric Oxide-Dependent Heart Rate and Blood Pressure Variability in Apolipoprotein E-/- Mice in Vivo; Circulation, 107(19), 2480-2486 (2003).

Nezasa, et al.; Uptake of Rosuvastatin by Isolated Rat Hepatocytes: Comparison with Pravastatin; Xenobiotica, 33(4), 379-388 (2003).

Clark; Treating Dyslipidemia with Statins: The Risk-Benefit Profile; American Heart Journal, 145(3), 387-396 (2003).

Martin, et al.; An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers; Clinical Therapeutics, 25(2), 459-471 (2003).

Olsson, et al.; Rosuvastatin: A Highly Effective New HMG-CoA Reductase Inhibotor; Cardiovascular Drug Reviews, 20(4), 303-328 (2002).

Cheng-Lai; Rosuvastatin: A New HMG-CoA Reductase Inhibitor for the Treatment of Hypercholesterolemia; Heart Disease, 5(1), 72-78 (2003).

Stein; Management of Dyslipidemia in the High-Risk Patient; American Heart Journal, 144(6, Suppl.), S43-S50 (2002).

Carswell, et al.; Rosuvastatin; Drugs, 62(14), 2075-2085 (2002).

Ural, et al.; Treatment with Cervistatin in Primary Mixed Hyperlipidemia Induces Changes in Platelet Aggregation and Coagulation System Components; International Journal of Hematology, 76(3) 279-283 (2002).

Garcia, et al.; Effects of Cerivastatin in Dyslipemia and Other Cardiovascular Risk Factors after Renal Transplantation; Transplantation Proceedings, 34(1), 401-402 (2002).

Bayes, et al.; Apolipoprotein E alleles, Dyslipemia, and Kidney Transplantation; Transplantation Proceedings, 34(1), 373 (2002).

Breuer; Hypertriglyceridemia: A Review of Clinical Relevance and Treatment Options: Focus on Cerivastatin; Current Medical Research and Opinion, 17(1), 60-73 (2001).

Deighan, et al.; Comparative Effects of Cerivastatin and Fenofibrate on the Atherogenic Lipoprotein Phenotype in Proteinuric Renal Disease; Journal of the American Society of Nephrology, 12(2), 341-348 (2001).

Keane et al.; The CHORUS (Cerivastatin in Heart Outcomes in Renal Disease: Understanding Survival) Protocol: A Double-Blind, Placebo-Controlled Trial in Patients with ESRD; American Journal of Kidney Diseases, 37(1, Suppl. 2), S48-S53 (2001).

Lechleitner; Dyslipidaemia and Renal Disease—Pathophysiology and Lipid Lowering Therapy in Patients with Impaired Renal Function; Journal of Clinical and Basic Cardiology, 3(1), 3-6 (2000).

Muck, et al.; Lack of Pharmacolinetic Drud-Drug Interaction Between Orlistat and Cerivastatin; Clinical Drug Investigation, 19(1), 71-73 (2000).

Tuomilehto, et al.; A Review of the Efficacy of Rosuvastatin in Patients with Type 2 Diabetes; International Journal of Clinical Practice, Supplement, 143, 30-40 (2004).

Capuzzi, et al.; Rosuvastatin Alone or With Extended-Release Niacin: A New Therapeutic Option for Patients with Combined Hyperlipidemia; Preventive Cardiology, 7(4), 176-181 (2004).

Semple, et al.; Discovery of the First Potent and Orally Efficacious Agonist of the Orphan G-Protein Coupled Receptor 119; Journal of Medical Chemistry; 51; 5172-5175 (2008).

Pei, et al.; Discovery and Structure-Adctivity Relationships of Piperidinone- and Pipe Constrained Phenethylamines as Novel, Potent, and Selective Dipeptidyl Peptidase IV Inhibitors; Journal of Medical Chemistry; 50; 1983-1987 (2007).

Shepherd, et al., Safety of rosuvastatin, Dept. of Vascular Biochemistry, University of Glasgow, Glasgow, UK, American Journal of Cardiology, 94(7):882-888 (2004), ISSN: 0002-9419.

Davidson; Rosuvastatin: A Highly Efficacious Statin for the Treatment of Dyslipidemia, Expert Opinion on Investigational Drugs, 11(3), 455 (2002).

Bailey, et al.; Interactions Between Grapefruit Juice and Cardiovascular Drugs; American Journal of Cardiovascular Drug; 4(5), 281-297 (2004).

Scott, et al.; Rosuvastatin: A Review of Its Use in the Management of Dyslipidemia; American Journal of Cardiovascular Drugs, 4(2), 117-138 (2004).

Rosenson, Rosuvastatin: a new inhibitor of HMG-CoA reductase for the treatment of dyslipidemia, Expert Review of Cardiovascular Therapy, 1(4):495-505 (2003).

Cheng-Lai, Cerivastatin, Heart Disease (2):93-99 (2000).

Olsson, Statins: how far have we come? A review of rosuvastatin, International Journal of Clinical Practice, Supplement, 137, 15-25 (2003).

* cited by examiner

SEQUENCE LISTING

<160> NUMBER OF SEQ ID NOS: 7

<210> SEQ ID NO 1
<211> LENGTH: 1191
<212> TYPE: DNA
<213> ORGANISM: Homo sapien

<400> SEQUENCE: 1

```
atgtacccat acgacgtccc agactacgct ggaagcttgg aatcatcttt ctcatttgga      60
gtgatccttg ctgtcctggc ctccctcatc attgctacta acacactagt ggctgtggct     120
gtgctgctgt tgatccacaa gaatgatggt gtcagtctct gcttcacctt gaatctggct     180
gtggctgaca ccttgattgg tgtggccatc tctggcctac tcacagacca gctctccagc     240
ccttctcggc ccacacagaa gacccgtgcg agcctgcgga tggcatttgt cacttcctcc     300
gcagctgcct ctgtcctcac ggtcatgctg atcacctttg acaggtacct tgccatcaag     360
cagcccttcc gctacttgaa gatcatgagt gggttcgtgg ccggggcctg cattgccggg     420
ctgtggttag tgtcttacct cattggcttc ctcccactcg gaatccccat gttccagcag     480
actgcctaca aagggcagtg cagcttcttt gctgtatttc accctcactt cgtgctgacc     540
ctctcctgcg ttggcttctt cccagccatg ctcctctttg tcttcttcta ctgcgacatg     600
ctcaagattg cctccatgca cagccagcag attcgaaaga tggaacatgc aggagccatg     660
gctggaggtt atcgatcccc acggactccc agcgacttca aagctctccg tactgtgtct     720
gttctcattg ggagctttgc tctatcctgg accccttcc ttatcactgg cattgtgcag     780
gtggcctgcc aggagtgtca cctctaccta gtgctggaac ggtacctgtg gctgctcggc     840
gtgggcaact ccctgctcaa cccactcatc tatgcctatt ggcagaagga ggtgcgactg     900
cagctctacc acatggccct aggagtgaag aaggtgctca cctcattcct cctctttctc     960
tcggccagga attgtggccc agagaggccc agggaaagtt cctgtcacat cgtcactatc    1020
tccagctcag agtttgatgg cgaattcgga tccaagggca attctgcaga tatccagcac    1080
agtggcggcc gctcgagtct agagggcccg cggttcgaag gtaagcctat ccctaaccct    1140
ctcctcggtc tcgattctac gcgtaccggt catcatcacc atcaccattg a              1191
```

```
<210> SEQ ID NO 2
<211> LENGTH: 396
<212> TYPE: PRT
<213> ORGANISM: Homo sapien

<400> SEQUENCE: 2

Met Tyr Pro Tyr Asp Val Pro Asp Tyr Ala Gly Ser Leu Glu Ser Ser
1               5                   10                  15

Phe Ser Phe Gly Val Ile Leu Ala Val Leu Ala Ser Leu Ile Ile Ala
                20                  25                  30

Thr Asn Thr Leu Val Ala Val Ala Val Leu Leu Leu Ile His Lys Asn
            35                  40                  45

Asp Gly Val Ser Leu Cys Phe Thr Leu Asn Leu Ala Val Ala Asp Thr
        50                  55                  60

Leu Ile Gly Val Ala Ile Ser Gly Leu Leu Thr Asp Gln Leu Ser Ser
65                  70                  75                  80

Pro Ser Arg Pro Thr Gln Lys Thr Leu Cys Ser Leu Arg Met Ala Phe
                85                  90                  95

Val Thr Ser Ser Ala Ala Ala Ser Val Leu Thr Val Met Leu Ile Thr
                100                 105                 110

Phe Asp Arg Tyr Leu Ala Ile Lys Gln Pro Phe Arg Tyr Leu Lys Ile
            115                 120                 125

Met Ser Gly Phe Val Ala Gly Ala Cys Ile Ala Gly Leu Trp Leu Val
        130                 135                 140

Ser Tyr Leu Ile Gly Phe Leu Pro Leu Gly Ile Pro Met Phe Gln Gln
145                 150                 155                 160

Thr Ala Tyr Lys Gly Gln Cys Ser Phe Phe Ala Val Phe His Pro His
                165                 170                 175

Phe Val Leu Thr Leu Ser Cys Val Gly Phe Phe Pro Ala Met Leu Leu
                180                 185                 190

Phe Val Phe Phe Tyr Cys Asp Met Leu Lys Ile Ala Ser Met His Ser
            195                 200                 205

Gln Gln Ile Arg Lys Met Glu His Ala Gly Ala Met Ala Gly Gly Tyr
        210                 215                 220

Arg Ser Pro Arg Thr Pro Ser Asp Phe Lys Ala Leu Arg Thr Val Ser
225                 230                 235                 240

Val Leu Ile Gly Ser Phe Ala Leu Ser Trp Thr Pro Phe Leu Ile Thr
                245                 250                 255

Gly Ile Val Gln Val Ala Cys Gln Glu Cys His Leu Tyr Leu Val Leu
                260                 265                 270

Glu Arg Tyr Leu Trp Leu Leu Gly Val Gly Asn Ser Leu Leu Asn Pro
            275                 280                 285

Leu Ile Tyr Ala Tyr Trp Gln Lys Glu Val Arg Leu Gln Leu Tyr His
        290                 295                 300

Met Ala Leu Gly Val Lys Lys Val Leu Thr Ser Phe Leu Leu Phe Leu
305                 310                 315                 320

Ser Ala Arg Asn Cys Gly Pro Glu Arg Pro Arg Glu Ser Ser Cys His
                325                 330                 335

Ile Val Thr Ile Ser Ser Ser Glu Phe Asp Gly Glu Phe Gly Ser Lys
            340                 345                 350

Gly Asn Ser Ala Asp Ile Gln His Ser Gly Gly Arg Ser Ser Leu Glu
        355                 360                 365

Gly Pro Arg Phe Glu Gly Lys Pro Ile Pro Asn Pro Leu Leu Gly Leu
    370                 375                 380
```

```
Asp Ser Thr Arg Thr Gly His His His His His His
385                 390                 395
```

<210> SEQ ID NO 3
<211> LENGTH: 24
<212> TYPE: DNA
<213> ORGANISM: Artificial
<220> FEATURE:
<223> OTHER INFORMATION: Homo sapien Primer

<400> SEQUENCE: 3
cattgccggg ctgtggttag tgtc                                            24

<210> SEQ ID NO 4
<211> LENGTH: 24
<212> TYPE: DNA
<213> ORGANISM: Artificial
<220> FEATURE:
<223> OTHER INFORMATION: Homo sapien Primer

<400> SEQUENCE: 4
ggcatagatg agtgggttga gcag                                            24

<210> SEQ ID NO 5
<211> LENGTH: 22
<212> TYPE: DNA
<213> ORGANISM: Artificial
<220> FEATURE:
<223> OTHER INFORMATION: Rat Primer

<400> SEQUENCE: 5
catgggccct gcaccttctt tg                                              22

<210> SEQ ID NO 6
<211> LENGTH: 24
<212> TYPE: DNA
<213> ORGANISM: Artificial
<220> FEATURE:
<223> OTHER INFORMATION: Rat Primer

<400> SEQUENCE: 6
gctccggatg gctgatgata gtga                                            24

<210> SEQ ID NO 7
<211> LENGTH: 23
<212> TYPE: PRT
<213> ORGANISM: Artificial
<220> FEATURE:
<223> OTHER INFORMATION: Rat Peptide

<400> SEQUENCE: 7

```
Arg Gly Pro Glu Arg Thr Arg Glu Ser Ala Tyr His Ile Val Thr Ile
1               5                   10                  15

Ser His Pro Glu Leu Asp Gly
            20
```

SUBSTITUTED PYRIDINYL AND PYRIMIDINYL DERIVATIVES AS MODULATORS OF METABOLISM AND THE TREATMENT OF DISORDERS RELATED THERETO

RELATED APPLICATIONS

This application is a continuation-in-part of U.S. patent application Ser. No. 11/327,896 filed Jan. 9, 2006 now abandoned, which claims the benefit of U.S. Provisional Patent Application, Ser. No. 60/642,840, filed Jan. 10, 2005, each incorporated by reference in their entirety.

FIELD OF THE INVENTION

The present invention relates to certain substituted pyridinyl and pyrimidinyl derivatives that are modulators of glucose metabolism. Accordingly, compounds of the present invention are useful in the treatment of metabolic-related disorders and complications thereof, such as, diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

People with IDDM, which accounts for about 5% to 10% of those who have diabetes, don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. *N. Engl. J. Med.* 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically inapparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentery lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. *Diabetes* 43, 696-702 (1989)). However, after several decades, β cell function deteriorates and non-insulin-dependent diabetes develops in about 20% of the obese population (Pederson, P. *Diab. Metab. Rev.* 5, 505-509 (1989)) and (Brancati, F. L., et al., *Arch. Intern. Med.* 159, 957-963 (1999)). Given its high prevalence in modem societies, obesity has thus become the leading risk factor for NIDDM (Hill, J. O., et al., *Science* 280, 1371-1374 (1998)). However, the factors which predispose a fraction of patients to alteration of insulin secretion in response to fat accumulation remain unknown.

Whether someone is classified as overweight or obese is generally determined on the basis of their body mass index BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$ (see TABLE below). There are problems with this definition in that it does not take into account the proportion of body mass that is muscle in relation to fat (adipose tissue). To account for this, obesity can also be defined on the basis of body fat content: greater than 25% and 30% in males and females, respectively.

| CLASSIFICATION OF WEIGHT BY BODY MASS INDEX (BMI) | |
|---|---|
| BMI | CLASSIFICATION |
| <18.5 | Underweight |
| 18.5–24.9 | Normal |
| 25.0–29.9 | Overweight |
| 30.0–34.9 | Obesity (Class I) |
| 35.0–39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL™) and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/ noradrenaline reuptake inhibitor) can increase blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn after reports of preliminary evidence of heart valve abnormalities associated with their use. Accordingly, there is a need for the development of a safer anti-obesity agent.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

SUMMARY OF THE INVENTION

The present invention is drawn to compounds which bind to and modulate the activity of a GPCR, referred to herein as RUP3, and uses thereof. The term RUP3 as used herein includes the human sequences found in GeneBank accession number AY288416, naturally-occurring allelic variants, mammalian orthologs, and recombinant mutants thereof. A preferred human RUP3 for use in screening and testing of the compounds of the invention is provided in the nucleotide sequence of Seq. ID. No:1 and the corresponding amino acid sequence in Seq. ID. No:2.

One aspect of the present invention encompasses certain substituted pyridinyl and pyrimidinyl derivatives as shown in Formula (Ia):

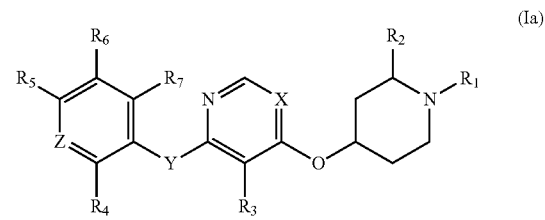

or a pharmaceutically acceptable salt, solvate or hydrate thereof;
wherein:
X is N or CR$_8$ wherein R$_8$ is H or halogen;
Y is NH or O;
Z is CH or N;
R$_1$ is carbo-C$_{1-6}$-alkoxy, oxadiazolyl or pyrimidinyl wherein said carbo-C$_{1-6}$-alkoxy, oxadiazolyl and pyrimidinyl are each optionally substituted with 1 or 2 substituents selected independently from the group consisting of C$_{1-4}$ alkyl, C$_{1-4}$ alkoxy and C$_{3-5}$ cycloalkyl;
R$_2$ is H or C$_{1-4}$ alkyl;
R$_3$ is C$_{1-4}$ alkoxy, O—C$_{2-4}$-alkynyl or hydroxyl;
R$_4$ is selected from the group consisting of H, C$_{1-4}$ alkoxy, C$_{1-4}$ alkyl, C$_{2-4}$ alkynyl and halogen;
R$_5$ is selected from the group consisting of C$_{1-4}$ acylsulfonamide, C$_{1-4}$ alkoxy, C$_{1-4}$ alkyl, C$_{1-4}$ alkylamino, C$_{1-4}$ alkylsulfonyl, C$_{1-4}$ alkylthio, cyano, heterocyclyl, di-C$_{1-4}$-dialkylamino and sulfonamide, wherein said C$_{1-4}$ alkoxy, C$_{1-4}$ alkyl, C$_{1-4}$ alkylamino, C$_{1-4}$ alkylsulfonyl, C$_{1-4}$ alkylthio, di-C$_{1-4}$-dialkylamino and heterocyclyl are each optionally substituted with 1 or 2 substituents selected independently from the group consisting of C$_{2-4}$ alkynyl, C$_{1-4}$ alkoxy, C$_{1-4}$ alkylcarboxamide, C$_{1-4}$ alkylsulfonyl, C$_{3-5}$ cycloalkyl, C$_{3-5}$ cycloalkyloxy, di-C$_{1-4}$-alkylcarboxamide, hydroxyl and phosphonooxy, wherein said C$_{1-4}$ alkylcarboxamide is optionally substituted with hydroxyl; or $R_5$ is a group of Formula (A):

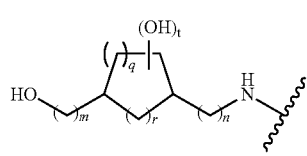

wherein "m", "n" and "q" are each independently 0, 1, 2 or 3; "r" is 0, 1 or 2; and "t" is 0 or 1;
$R_6$ is H or halogen; and
$R_7$ is H or $C_{1-4}$ alkyl.

One aspect of the present invention pertains to compounds of the following Formula:

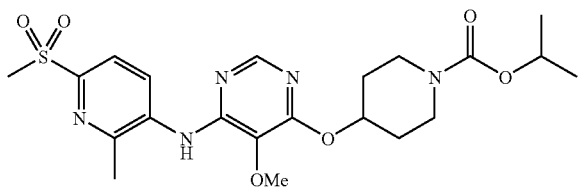 [SMILES: COc1c(Nc2ccc(S(C)(=O)=O)nc2C)ncnc1OC1CCN(C(=O)OC(C)C)CC1]

and pharmaceutically acceptable salts, solvates, and hydrates thereof.

One aspect of the present invention pertains to pharmaceutical compositions comprising at least one compound of the present invention and a pharmaceutically acceptable carrier.

One aspect of the present invention pertains to methods for the treatment of a metabolic-related disorder in an individual comprising administering to the individual in need of such treatment a therapeutically effective amount of a compound of the present invention or a pharmaceutical composition thereof.

One aspect of the present invention pertains to methods of decreasing food intake of an individual comprising administering to the individual in need thereof a therapeutically effective amount of a compound of the present invention or pharmaceutical composition thereof.

One aspect of the present invention pertains to methods of inducing satiety in an individual comprising administering to the individual in need thereof a therapeutically effective amount of a compound of the present invention or pharmaceutical composition thereof.

One aspect of the present invention pertains to methods of controlling or decreasing weight gain of an individual comprising administering to the individual in need thereof a therapeutically effective amount of a compound of the present invention or pharmaceutical composition thereof.

One aspect of the present invention pertains to methods of modulating a RUP3 receptor in an individual comprising contacting the receptor with a compound of the present invention. In some embodiments, the compound is an agonist for the RUP3 receptor. In some embodiments, the modulation of the RUP3 receptor is the treatment of a metabolic-related disorder.

Some embodiments of the present invention include a method of modulating a RUP3 receptor in an individual comprising contacting the receptor with a compound of the present invention wherein the modulation of the RUP3 receptor reduces food intake of the individual.

Some embodiments of the present invention include a method of modulating a RUP3 receptor in an individual comprising contacting the receptor with a compound of the present invention wherein the modulation of the RUP3 receptor induces satiety in the individual.

Some embodiments of the present invention include a method of modulating a RUP3 receptor in an individual comprising contacting the receptor with a compound of the present invention wherein the modulation of the RUP3 receptor controls or reduces weight gain of the individual.

One aspect of the present invention pertains to use of a compound of the present invention for production of a medicament for use in the treatment of a metabolic-related disorder.

One aspect of the present invention pertains to use of a compound of the present invention for production of a medicament for use in decreasing food intake in an individual.

One aspect of the present invention pertains to use of a compound of the present invention for production of a medicament for use of inducing satiety in an individual.

One aspect of the present invention pertains to use of a compound of the present invention for production of a medicament for use in controlling or decreasing weight gain in an individual.

One aspect of the present invention pertains to a compound of the present invention for use in a method of treatment of the human or animal body by therapy.

One aspect of the present invention pertains to a compound of the present invention for use in a method of treatment of a metabolic-related disorder of the human or animal body by therapy.

In some embodiments the individual is a mammal. In some embodiments the mammal is a human.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

In some embodiments, the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertryglicieridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X.

One aspect of the present invention pertains to a method of producing a pharmaceutical composition comprising admixing at least one compound, as described herein, and a pharmaceutically acceptable carrier.

Applicant reserves the right to exclude any one or more of the compounds from any of the embodiments of the invention. Applicant additionally reserves the right to exclude any disease, condition or disorder from any of the embodiments of the invention.

DETAILED DESCRIPTION OF THE INVENTION

Definitions

Figure 1:
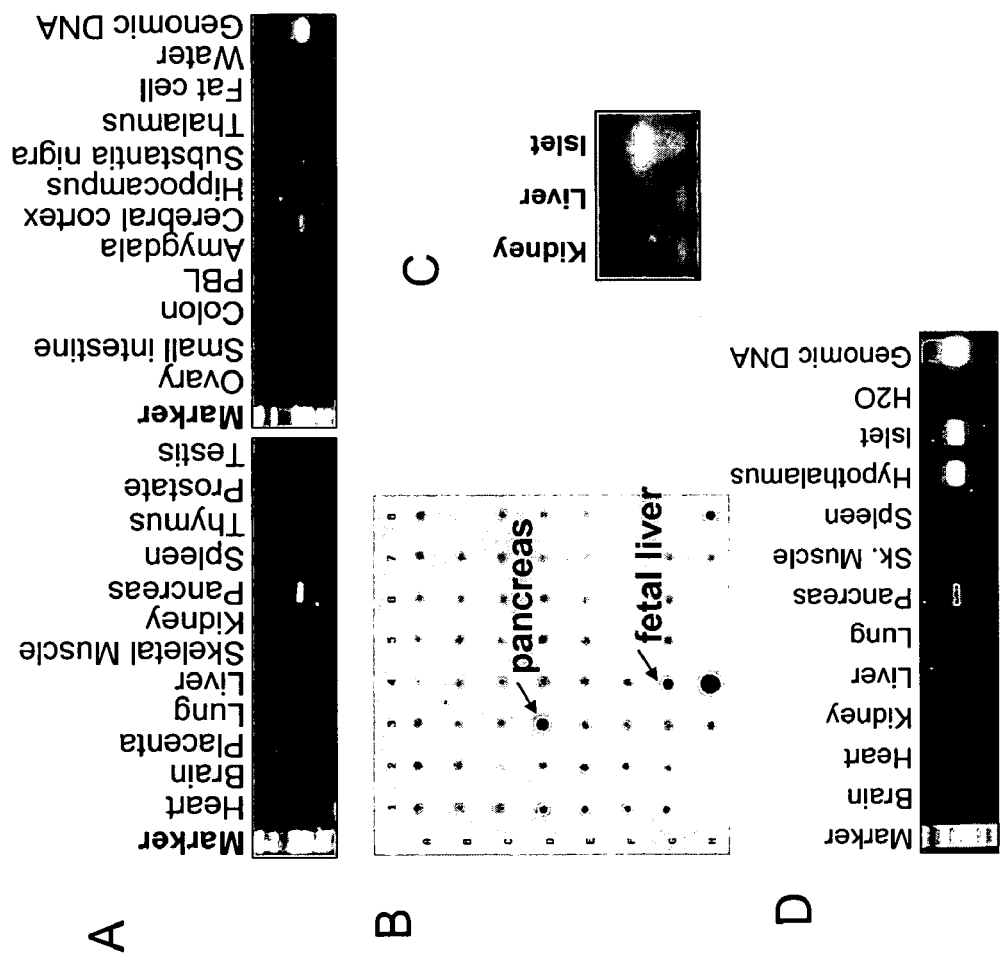
FIG. 1A shows RT-PCR analysis of RUP3 expression in human tissues. A total of twenty-two (22) human tissues were analyzed.
FIG. 1B shows the cDNA Dot-Blot analysis of RUP 3 expression in human tissues.
FIG. 1C shows analysis of RUP3 by RT-PCR with isolated human pancreatic islets of Langerhans.
FIG. 1D shows analysis of RUP3 expression with cDNAs of rat origin by RT-PCR.

The scientific literature that has evolved around receptors has adopted a number of terms to refer to ligands having various effects on receptors. For clarity and consistency, the following definitions will be used throughout this patent document.

AGONISTS shall mean moieties that interact and activate the receptor, such as the RUP3 receptor and initiates a physiological or pharmacological response characteristic of that receptor. For example, when moieties activate the intracellular response upon binding to the receptor, or enhance GTP binding to membranes.

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

The term "$C_{1-4}$ acyl" refers to a $C_{1-6}$ alkyl radical attached directly to the carbon of a carbonyl group wherein the definition for alkyl is as described herein; some examples include, but not limited to, acetyl, propionyl, n-butanoyl, iso-butanoyl, sec-butanoyl, t-butanoyl (also referred to as pivaloyl) and the like.

The term "$C_{1-4}$ acylsulfonamide" refers to a $C_{1-4}$ acyl attached directly to the nitrogen of the sulfonamide, wherein the definitions for $C_{1-4}$ acyl and sulfonamide have the same meaning as described herein, and a $C_{1-4}$ acylsulfonamide group can be represented by the following formula:

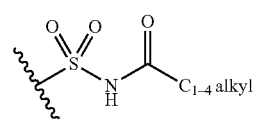

Some embodiments of the present invention are when acylsulfonamide is a $C_{1-3}$ acylsulfonamide, some embodiments are $C_{1-2}$ acylsulfonamide and some embodiments are $C_1$ acylsulfonamide. Examples of an acylsulfonamide group include, but not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, and the like.

The term "$C_{1-4}$ alkoxy" refers to an alkyl radical, as defined herein, attached directly to an oxygen atom (i.e., —O—$C_{1-4}$ alkyl). Examples include methoxy, ethoxy, n-propoxy, iso-propoxy, n-butoxy, t-butoxy, iso-butoxy, sec-butoxy and the like.

The term "$C_{1-4}$ alkyl" refers to a straight or branched carbon radical containing 1 to 4 carbons, some embodiments are 1 to 3 carbons, some embodiments are 1 to 2 carbons. Examples of an alkyl include, but not limited to, methyl, ethyl, n-propyl, iso-propyl, n-butyl, iso-butyl, t-butyl, sec-butyl, and the like.

The term "$C_{1-4}$ alkylamino" refers to one alkyl radical attached directly to an amino radical (—HN—$C_{1-4}$ alkyl) wherein the alkyl radical has the same meaning as described herein. Some examples include, but not limited to, methylamino (i.e., —HNCH$_3$), ethylamino, n-propylamino, iso-propylamino, n-butylamino, sec-butylamino, iso-butylamino, t-butylamino, and the like.

The term "$C_{1-4}$ alkylcarboxamide" or "$C_{1-4}$ alkylcarboxamido" refers to a single $C_{1-4}$ alkyl group attached to the nitrogen of an amide group, wherein alkyl has the same definition as described herein. The $C_{1-4}$ alkylcarboxamido may be represented by the following:

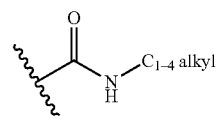

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-4}$ alkylsulfonyl" refers to a alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" refers to a alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{2-4}$ alkynyl" refers to a radical containing 2 to 4 carbons and at least one carbon-carbon triple bond (—C≡C—), some embodiments are 2 to 3 carbons, and some embodiments have 2 carbons (—C≡CH). Examples of a $C_{2-4}$ alkynyl include, but not limited to, ethynyl, 1-propynyl, 2-propynyl, 1-butynyl, 2-butynyl, 3-butynyl, and the like. The term $C_{2-4}$ alkynyl includes di- and tri-ynes.

The term "amino" refers to the group —NH$_2$.

The term "carbo-$C_{1-6}$-alkoxy" refers to an alkoxy group attached directly to the carbon of a carbonyl and can be represented by the formula —C(=O)O—$C_{1-6}$-alkyl, wherein the $C_{1-6}$ alkyl group is as defined herein. In some embodiments, the carbo-$C_{1-6}$-alkoxy group is further bonded to a nitrogen atom and together form a carbamate group (e.g., NC(=O)O—$C_{1-6}$-alkyl). Examples of the carbo-$C_{1-6}$-alkoxy group include, but not limited to, methoxycarbonyl, ethoxycarbonyl, propoxycarbonyl, iso-propoxycarbonyl, butoxycarbonyl, sec-butoxycarbonyl, iso-butoxycarbonyl, t-butoxycarbonyl, n-pentoxycarbonyl, iso-pentoxycarbonyl, t-pentoxycarbonyl, neo-pentoxycarbonyl, n-hexyloxycarbonyl, and the like.

The term "cyano" refers to the group —CN.

The term "$C_{3-5}$ cycloalkyl" refers to a saturated ring radical containing 3 to 5 carbons; some embodiments contain 3 to 4 carbons; some embodiments contain 3 carbons. Examples include cyclopropyl, cyclobutyl, cyclopentyl, and the like.

The term "$C_{3-5}$-cycloalkoxy" refers to a cycloalkyl, as defined herein, attached directly to an oxygen atom (i.e., —O—$C_{3-5}$ cycloalkyl). Examples include, but not limited to, cyclopropoxy, cyclobutoxy, cyclopentoxy, and the like.

The term "di-$C_{1-4}$-dialkylamino" refers to an amino group substituted with two of the same or different $C_{1-4}$ alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like.

The term "di-$C_{1-4}$-alkylcarboxamide" or "di-$C_{1-4}$-alkylcarboxamido" refers to two $C_{1-4}$ alkyl radicals, that are the same or different, attached to an amide group, wherein alkyl has the same definition as described herein. A di-$C_{1-4}$-alkylcarboxamido can be represented by the following group:

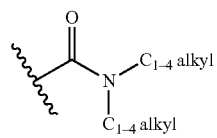

wherein $C_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "halogen" or "halo" refers to a fluoro, chloro, bromo or iodo group.

The term "heterocyclyl" refers to a non-aromatic carbon ring (i.e., cycloalkyl or cycloalkenyl) wherein one, two or three ring carbons are replaced by a heteroatom selected from, but not limited to, the group consisting of —O—, —S—, —S(=O)—, —S(=O)$_2$—, and —NH—, and the ring carbon atoms are optionally substituted with oxo or thiooxo thus forming a carbonyl or thiocarbonyl group respectively. The heterocyclic group can be a 3, 4, 5 or 6-member containing ring. Examples of a heterocyclic group, include but not limited to, aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "hydroxyl" refers to the group —OH.

The term "oxadiazolyl" refers to the group represented by the following formulae:

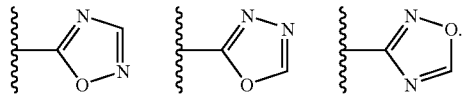

The term "oxo" refers generally to a double bonded oxygen; typically "oxo" is a substitution on a carbon and together form a carbonyl group.

The term "phosphonooxy" refers to a group of the formula —OP(O)(OH)$_2$ and can be represented by the following chemical structure:

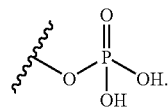

The term "pyrimidinyl" refers to the group represented by the following formulae:

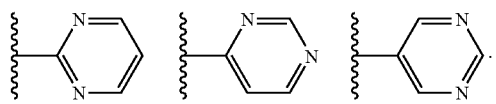

The term "sulfonamide" refers to the group —S(=O)$_2$NH$_2$.

COMPOSITION shall mean a material comprising at least two compounds or two components; for example, and without limitation, a Pharmaceutical Composition is a Composition comprising a compound of the present invention and a pharmaceutically acceptable carrier.

COMPOUND EFFICACY shall mean a measurement of the ability of a compound to inhibit or stimulate receptor functionality, as opposed to receptor binding affinity.

CONTACT or CONTACTING shall mean bringing the indicated moieties together, whether in an in vitro system or an in vivo system. Thus, "contacting" a RUP3 receptor with a compound of the invention includes the administration of a compound of the present invention to an individual, for example a human, having a RUP3 receptor, as well as, for example, introducing a compound of the invention into a sample containing a cellular or more purified preparation containing a RUP3 receptor.

IN NEED OF TREATMENT as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual is ill, or will be ill, as the result of a disease, condition or disorder that is treatable by the compounds of the invention. The term "treatment" also refers in the alternative to "prophylaxis." Therefore, in general, "in need of treatment" refers to the judgment of the caregiver that the individual is already ill, accordingly, the compounds of the present invention are used to alleviate, inhibit or ameliorate the disease, condition or disorder. Furthermore, the phrase also refers, in the alternative, to the judgment made by the caregiver that the individual will become ill. In this context, the compounds of the invention are used in a protective or preventive manner.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient, whereby the composition is amenable to investigation or treatment of a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Present Invention:

One aspect of the present invention encompasses certain substituted pyridinyl and pyrimidinyl derivatives as shown in Formula (Ia):

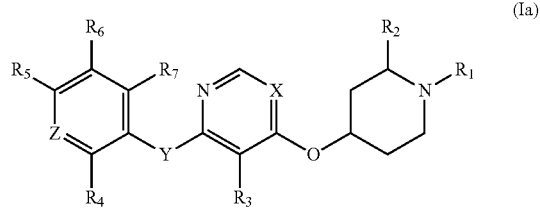

or a pharmaceutically acceptable salt, hydrate or solvate thereof; wherein X, Y, Z, $R_1$, $R_2$, $R_3$, $R_4$, $R_5$, $R_6$ and $R_7$ have the same definitions as described herein, supra and infra.

One aspect of the present invention pertains to compounds of the following Formula:

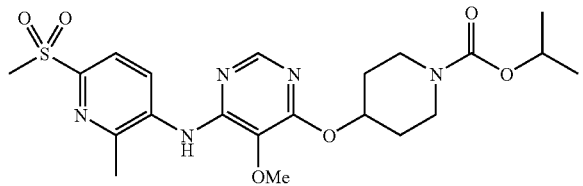 [SMILES: COc1c(Nc2ccc(S(C)(=O)=O)nc2C)ncnc1OC1CCN(C(=O)OC(C)C)CC1]

and pharmaceutically acceptable salts, solvates, and hydrates thereof.

The compound, 4-[6-(6-Methanesulfonyl-2-methyl-pyridin-3-ylamino)-5-methoxy-pyrimidin-4-yloxy]-piperidine-1-carboxylic acid isopropyl ester (Compound 84), is a potent agonist of the RUP3 receptor and is able to lower blood glucose in the oGTT model. Further, 4-[6-(6-Methanesulfonyl-2-methyl-pyridin-3-ylamino)-5-methoxy-pyrimidin-4-yloxy]-piperidine-1-carboxylic acid isopropyl ester also demonstrates linear dose escalation pharmacokinetics.

The compound 4-[6-(6-Methanesulfonyl-2-methyl-pyridin-3-ylamino)-5-methoxy-pyrimidin-4-yloxy]-piperidine- 1-carboxylic acid isopropyl ester also exhibits improved characteristics in regard to cytochrome P450 enzymes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R_1$, $R_2$, $R_3$, $R_4$, $R_5$, $R_6$, $R_7$, X, Y, and Z) contained within the generic chemical formulae described herein [e.g. (Ia), (IIa), (IIc), (IIe), (IIg), etc.] are specifically embraced by the present invention just as if they were explicitly disclosed, to the extent that such combinations embrace compounds that result in stable compounds (ie., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcomination of uses and medical indications were explicitly disclosed herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

It is understood and appreciated that compounds of the invention may have one or more chiral centers, and therefore can exist as enantiomers and/or diastereomers. The invention is understood to extend to and embrace all such enantiomers, diastereomers and mixtures thereof, including, but not limited to, racemates. Accordingly, some embodiments of the present invention pertain to compounds that are R enantiomers. Further, some embodiments of the present invention pertain to compounds that are S enantiomers. When more than one chiral center is present, for example two chiral centers then, some embodiments of the present invention are compounds that are RS or SR enantiomers. In further embodiments, compounds of the present invention are RR or SS enantiomers. It is understood that compounds of Formula (Ia) and formulae used throughout this disclosure are intended to represent all individual enantiomers and mixtures thereof, unless stated or shown otherwise.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

Some embodiments of the present invention pertain to compounds wherein X is N.

Some embodiments of the present invention pertain to compounds wherein X is $CR_8$. In some embodiments, $R_8$ is H or F.

Some embodiments of the present invention pertain to compounds wherein Y is NH.

Some embodiments of the present invention pertain to compounds wherein Y is O.

Some embodiments of the present invention pertain to compounds wherein Z is CH.

Some embodiments of the present invention pertain to compounds wherein Z is N.

Some embodiments of the present invention pertain to compounds wherein $R_1$ is carbo-$C_{1-6}$-alkoxy optionally substituted with $C_{3-5}$ cycloalkyl.

Some embodiments of the present invention pertain to compounds wherein $R_1$ is selected form the group consisting of $C(O)OCH_2CH_3$, $C(O)OCH(CH_3)_2$, $C(O)OCH(CH_3)(CH_2CH_3)$, $C(O)OCH_2$-cyclopropyl, $C(O)OCH(CH_3)$(cyclopropyl), and $C(O)OCH(CH_2CH_3)_2$.

Some embodiments of the present invention pertain to compounds wherein $R_1$ is selected form the group consisting of $C(O)OCH_2CH_3$, $C(O)OCH(CH_3)_2$, $C(O)OCH(CH_3)(CH_2CH_3)$, $C(O)OCH_2$-cyclopropyl and $C(O)OCH(CH_3)$(cyclopropyl); these can be represented by the respective formulae:

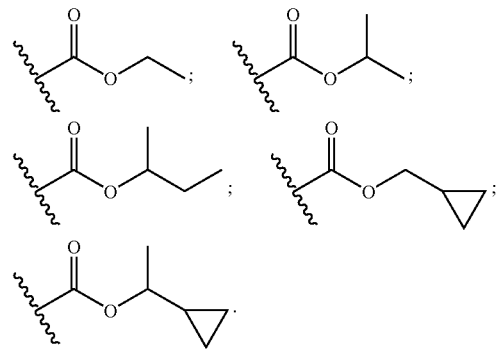

Some embodiments of the present invention pertain to compounds wherein $R_1$ is oxadiazolyl optionally substituted with one $C_{1-4}$ alkyl group.

Some embodiments of the present invention pertain to compounds wherein $R_1$ is 5-isopropyl-[1,2,4]oxadiazol-3-yl.

Some embodiments of the present invention pertain to compounds wherein $R_1$ is pyrimidinyl optionally substituted with one $C_{1-4}$ alkoxy group.

Some embodiments of the present invention pertain to compounds wherein $R_1$ is 5-methoxy-pyrimidin-2-yl.

Some embodiments of the present invention pertain to compounds wherein $R_2$ is H.

Some embodiments of the present invention pertain to compounds wherein $R_2$ is $CH_3$.

Some embodiments of the present invention pertain to compounds wherein $R_3$ is $C_{1-4}$ alkoxy.

Some embodiments of the present invention pertain to compounds wherein $R_3$ is $OCH_3$ or $OCH_2CH_3$.

Some embodiments of the present invention pertain to compounds wherein $R_3$ is $OCH_3$.

Some embodiments of the present invention pertain to compounds wherein $R_3$ is OH or O—C≡CH.

Some embodiments of the present invention pertain to compounds wherein $R_4$ is selected from the group consisting of H, $OCH_3$, $CH_3$, $CH_2CH_3$, F, Cl and C≡CH.

Some embodiments of the present invention pertain to compounds wherein $R_4$ is $CH_3$.

Some embodiments of the present invention pertain to compounds wherein $R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$, $S(O)_2NH_2$, $CH_3$, $SCH_2CH_2CH_3$, $S(O)_2CH_2CH_2CH_3$, $SCH_2CH_3$, $SCH(CH_3)_2$, $S(O)_2CH(CH_3)_2$, and $CH_2OH$.

Some embodiments of the present invention pertain to compounds wherein $R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$ and $S(O)_2NH_2$.

Some embodiments of the present invention pertain to compounds wherein $R_5$ is selected from the group consisting of $OCH_2CH_2CH_2OH$, $S(O)_2CH_3$, $CH_2CH_2S(O)_2CH_3$, $NHCH_2CH_2OH$, cyano, $CH_2CH_2OH$, $CH_2CH_2CH(CH_3)OH$, $CH_2CH_2OP(O)(OH)_2$, $S(O)_2NHC(O)CH_2CH_3$, $CH_2CH_2CH_2OH$, $S(O)_2CH_2CH_3$, $NHCH_2CH(OH)CH_2OH$, amino, $NHCH_2CH_3$, $NHCH(CH_3)_2$ and $NHCH(CH_3)CH_2CH_3$.

Some embodiments of the present invention pertain to compounds wherein $R_5$ is a group other than —$CH_2$—$R_{10}$, wherein $R_{10}$ is selected from the group consisting of $C_{1-4}$ alkylcarboxamide, $C_{1-4}$ alkylsulfonyl, di-$C_{1-4}$-alkylcarboxamide, and phosphonooxy. In some embodiments, $R_5$ is a group other than —$CH_2$—$R_{10}$, wherein $R_{10}$ is $C_{1-4}$ alkylcarboxamide. In some embodiments, $R_5$ is a group other than —$CH_2$—$R_{10}$, wherein $R_{10}$ is $C_{1-4}$ alkylsulfonyl. In some embodiments, $R_5$ is a group other than —$CH_2$—$R_{10}$, wherein $R_{10}$ is di-$C_{1-4}$-alkylcarboxamide. In some embodiments, $R_5$ is a group other than —$CH_2$—$R_{10}$, wherein $R_{10}$ is phosphonooxy.

Some embodiments of the present invention pertain to compounds wherein $R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$ and $S(O)_2NH_2$.

Some embodiments of the present invention pertain to compounds wherein $R_5$ is a group of Formula (A):

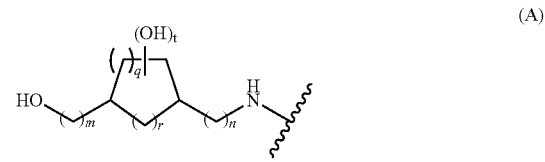

wherein "m", "n" and "q" are each independently 0, 1, 2 or 3; "r" is 0, 1 or 2; and "t" is 0 or 1. In some embodiments, "m" and "n" are each independently 0 or 1. In some embodiments, "q" is 0 or 1 and "r" is 1 or 2. In some embodiments, "t" is 1. In some embodiments, "t" is 0.

Some embodiments of the present invention pertain to compounds wherein $R_5$ is a group of Formula (B):

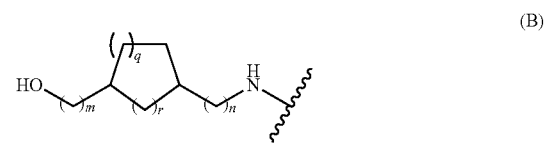

wherein "m", "n", "q" and "r" are as described herein, supra and infra.

Some embodiments of the present invention pertain to compounds wherein $R_5$ is selected from the group consisting of:

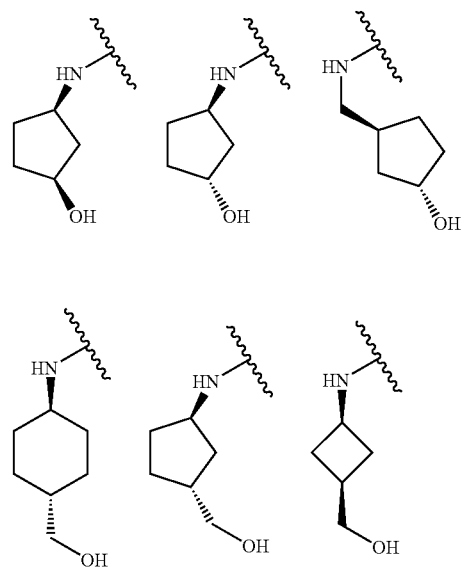

Some embodiments of the present invention pertain to compounds wherein $R_6$ is H.

Some embodiments of the present invention pertain to compounds wherein $R_6$ is F.

Some embodiments of the present invention pertain to compounds wherein $R_7$ is H.

Some embodiments of the present invention pertain to compounds wherein $R_7$ is $CH_3$.

Some embodiments of the present invention pertain to compounds having Formula (IIa):

(IIa)

or a pharmaceutically acceptable salt, solvate or hydrate thereof;
wherein:
Y is NH or O;
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$ and $S(O)_2NH_2$;
$R_6$ is H or F; and
$R_7$ is H or $CH_3$.

Some embodiments of the present invention pertain to compounds having Formula (IIa):

(IIa)

or a pharmaceutically acceptable salt, solvate or hydrate thereof;
wherein:
Y is NH or O;
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_2OH$, $S(O)_2CH_3$, $CH_2CH_2S(O)_2CH_3$, $NHCH_2CH_2OH$, cyano, $CH_2CH_2OH$, $CH_2CH_2CH(CH_3)OH$, $CH_2CH_2OP(O)(OH)_2$, $S(O)_2NHC(O)CH_2CH_3$, $CH_2CH_2CH_2OH$, $S(O)_2CH_2CH_3$, $NHCH_2CH(OH)CH_2OH$ and $S(O)_2NH_2$;
$R_6$ is H or F; and
$R_7$ is H or $CH_3$.

Some embodiments of the present invention pertain to compounds having Formula (IIc):

(IIc)

or a pharmaceutically acceptable salt, solvate or hydrate thereof;
wherein:
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$ and $S(O)_2NH_2$;
$R_6$ is H or F; and
$R_7$ is H or $CH_3$.

Some embodiments of the present invention pertain to compounds having Formula (IIc):

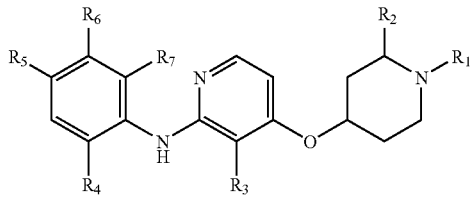

(IIc)

or a pharmaceutically acceptable salt, solvate or hydrate thereof;
wherein:
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_2OH$, $S(O)_2CH_3$, $CH_2CH_2S(O)_2CH_3$, $NHCH_2CH_2OH$, cyano, $CH_2CH_2OH$, $CH_2CH_2CH(CH_3)OH$, $CH_2CH_2OP(O)(OH)_2$, $S(O)_2NHC(O)CH_2CH_3$, $CH_2CH_2CH_2OH$, $S(O)_2CH_2CH_3$, $NHCH_2CH(OH)CH_2OH$ and $S(O)_2NH_2$;
$R_6$ is H or F; and
$R_7$ is H or $CH_3$.

Some embodiments of the present invention pertain to compounds having Formula (IIe):

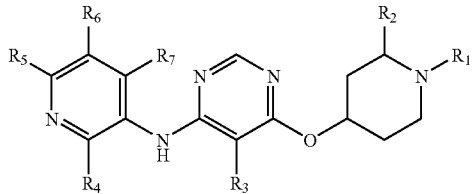

(IIe)

or a pharmaceutically acceptable salt, solvate or hydrate thereof;
wherein:
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP(O)(OH)_2$, $S(O)_2CH_2CH_3$, $NHCH_2CH(OH)CH_2OH$, $S(O)_2CH_2CH_2OH$, $OCH_2CH_2OP(O)(OH)_2$, $OCH_2CH_2CH_2OP(O)(OH)_2$ and $S(O)_2NH_2$;

$R_6$ is H or F; and
$R_7$ is H or $CH_3$.

Some embodiments of the present invention pertain to compounds having Formula (IIe):

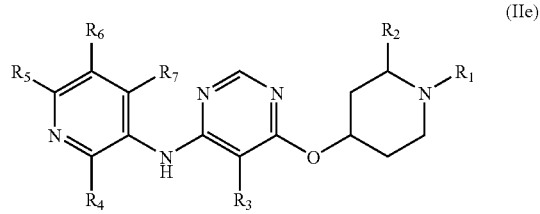

(IIe)

or a pharmaceutically acceptable salt, solvate or hydrate thereof;
wherein:
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_2OH$, $S(O)_2CH_3$, $CH_2CH_2S(O)_2CH_3$, $NHCH_2CH_2OH$, cyano, $CH_2CH_2OH$, $CH_2CH_2CH(CH_3)OH$, $CH_2CH_2OP(O)(OH)_2$, $S(O)_2NHC(O)CH_2CH_3$, $CH_2CH_2CH_2OH$, $S(O)_2CH_2CH_3$, $NHCH_2CH(OH)CH_2OH$ and $S(O)_2NH_2$;
$R_6$ is H or F; and
$R_7$ is H or $CH_3$.

Some embodiments of the present invention pertain to compounds having Formula (IIg):

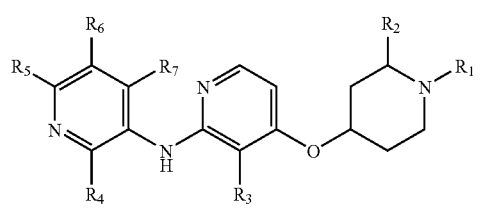

(IIg)

or a pharmaceutically acceptable salt, solvate or hydrate thereof;
wherein:
$R_1$ is carbo-$C_{1-6}$-alkoxy optionally substituted with $C_{3-5}$ cycloalkyl;
$R_2$ is H or $CH_3$;
$R_3$ is $C_{1-4}$ alkoxy;
$R_4$ is selected from the group consisting of H, $OCH_3$, $CH_3$, $CH_2CH_3$, F and Cl;
$R_5$ is selected from the group consisting of $OCH_2CH_2CH_3$, $OCH_2CH_2CH_2OH$, $S(O)_2CH_3$, $CH_2CH_2S(O)_2CH_3$, $NHCH_2CH_2OH$, cyano, $CH_2CH_2OCH_3$, $CH_2CH_2OH$, $CH_2CH_2CH(CH_3)OH$, $CH_2CH_2OP(O)(OH)_2$, $S(O)_2NHC(O)CH_2CH_3$, $CH_2CH_2O$-cyclopropyl, $NHCH_2CH_2OCH_3$, $OCH_2CH_2S(O)_2CH_3$, $NHCH_2CH(CH_3)OH$, $CH_2CH_2CH_2OH$, $CH_2CH_2CH_2OP(O)(OH)_2$, $NHCH_2CH(CH_3)S(O)_2CH_3$, $N(CH_3)CH_2CH(CH_3)S(O)_2CH_3$, 3-methanesulfonyl-pyrrolidin-1-yl, 3-methanesulfonyl-piperidin-1-yl, $CH_2C(O)N(CH_3)_2$, 3-methanesulfonyl-azetidin-1-yl, $CH_2C(O)NHCH_2CH_2OH$, $SCH_2CH_2OH$, $S(O)_2CH_2CH_2OP$ (O)(OH)$_2$, S(O)$_2$CH$_2$CH$_3$, NHCH$_2$CH(OH)CH$_2$OH, S(O)$_2$CH$_2$CH$_2$OH, OCH$_2$CH$_2$OP(O)(OH)$_2$, OCH$_2$CH$_2$CH$_2$OP(O)(OH)$_2$ and S(O)$_2$NH$_2$;

R$_6$ is H or F; and
R$_7$ is H or CH$_3$.

Some embodiments of the present invention pertain to compounds having Formula (IIg):

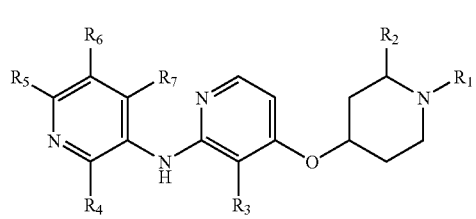

(IIg)

or a pharmaceutically acceptable salt, solvate or hydrate thereof;
wherein:
R$_1$ is carbo-C$_{1-6}$-alkoxy optionally substituted with C$_{3-5}$ cycloalkyl;
R$_2$ is H or CH$_3$;
R$_3$ is C$_{1-4}$ alkoxy;
R$_4$ is selected from the group consisting of H, OCH$_3$, CH$_3$, CH$_2$CH$_3$, F and Cl;
R$_5$ is selected from the group consisting of OCH$_2$CH$_2$CH$_2$OH, S(O)$_2$CH$_3$, CH$_2$CH$_2$S(O)$_2$CH$_3$, NHCH$_2$CH$_2$OH, cyano, CH$_2$CH$_2$OH, CH$_2$CH$_2$CH(CH$_3$)OH, CH$_2$CH$_2$OP(O)(OH)$_2$, S(O)$_2$NHC(O)CH$_2$CH$_3$, CH$_2$CH$_2$CH$_2$OH, S(O)$_2$CH$_2$CH$_3$, NHCH$_2$CH(OH)CH$_2$OH and S(O)$_2$NH$_2$;

R$_6$ is H or F; and
R$_7$ is H or CH$_3$.

Some embodiments of the present invention pertain to compounds having Formula (IIi):

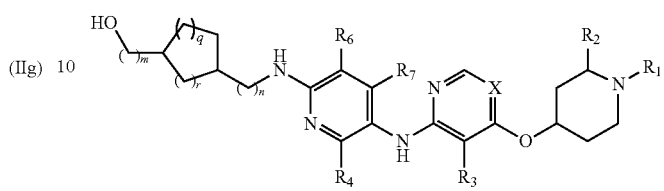

(IIi)

or a pharmaceutically acceptable salt, solvate or hydrate thereof;
wherein:
"m" and "n" are each independently 0 or 1;
"q" is 0 or 1;
"r" is 1 or 2;
X is N;
R$_1$ is carbo-C$_{1-6}$-alkoxy optionally substituted with C$_{3-5}$ cycloalkyl;
R$_2$ is H or CH$_3$;
R$_3$ is C$_{1-4}$ alkoxy;
R$_4$ is selected from the group consisting of H, OCH$_3$, CH$_3$, CH$_2$CH$_3$, F and Cl;
R$_6$ is H or F; and
R$_7$ is H or CH$_3$.

Some embodiments of the present invention include every combination of one or more compounds selected from the following group in Table A:

TABLE A

| Cmpd No. | Structure | Chemical Name |
|---|---|---|
| 1 | 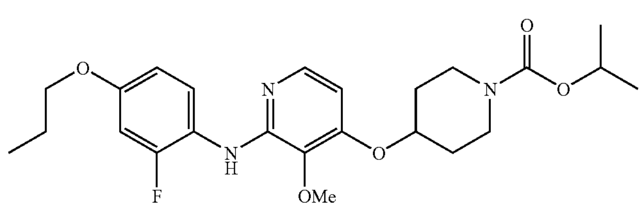 [SMILES: CCCOc1ccc(Nc2nccc(OC3CCN(C(=O)OC(C)C)CC3)c2OC)c(F)c1] | 4-[2-(2-Fluoro-4-propoxy-phenylamino)-3-methoxy-pyridin-4-yloxy]-piperidine-1-carboxylic acid isopropyl ester |
| 2 | 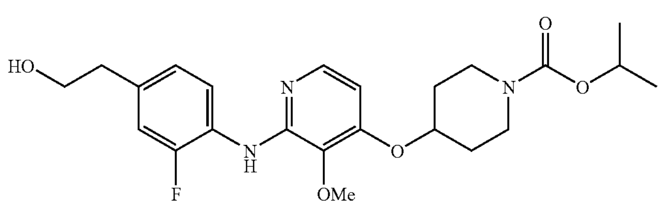 [SMILES: COc1c(OC2CCN(C(=O)OC(C)C)CC2)ccnc1Nc1ccc(CCO)cc1F] | 4-{2-[2-Fluoro-4-(2-hydroxy-ethyl)-phenylamino]-3-methoxy-pyridin-4-yloxy}-piperidine-1-carboxylic acid isopropyl ester |
| 3 | 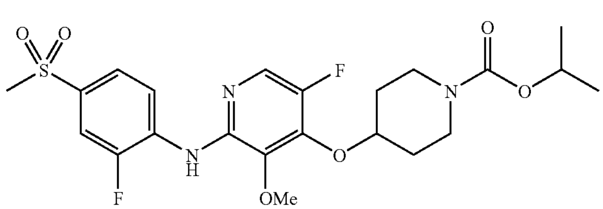 [SMILES: COc1c(Nc2ccc(S(C)(=O)=O)cc2F)ncc(F)c1OC1CCN(C(=O)OC(C)C)CC1] | 4-[5-Fluoro-2-(2-fluoro-4-methanesulfonyl-phenylamino)-3-methoxy-pyridin-4-yloxy]-piperidine-1-carboxylic acid isopropyl ester |

TABLE A-continued

| Cmpd No. | Structure | Chemical Name |
|---|---|---|
| 4 | 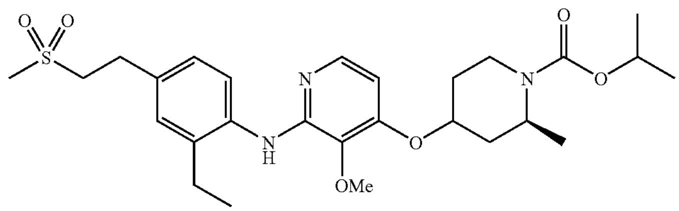 [SMILES: CCc1cc(CCS(C)(=O)=O)ccc1Nc1nccc(OC2CCN(C(=O)OC(C)C)[C@@H](C)C2)c1OC] | (S)-4-{2-[2-Ethyl-4-(2-methanesulfonyl-ethyl)-phenylamino]-3-methoxy-pyridin-4-yloxy}-2-methyl-piperidine-1-carboxylic acid isopropyl ester |
| 5 | 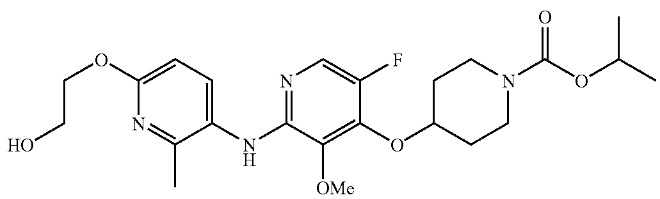 [SMILES: COc1c(Nc2ccc(OCCO)nc2C)ncc(F)c1OC1CCN(C(=O)OC(C)C)CC1] | 4-{5-Fluoro-2-[6-(2-hydroxy-ethoxy)-2-methyl-pyridin-3-ylamino]-3-methoxy-pyridin-4-yloxy}-piperidine-1-carboxylic acid isopropyl ester |
| 6 | 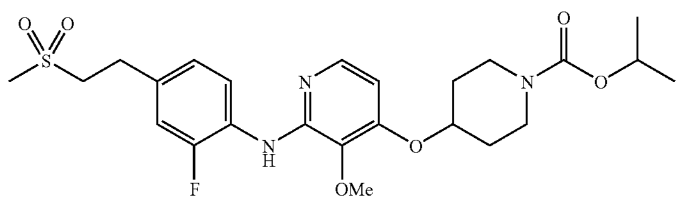 [SMILES: COc1c(OC2CCN(C(=O)OC(C)C)CC2)ccnc1Nc1ccc(CCS(C)(=O)=O)cc1F] | 4-{2-[2-Fluoro-4-(2-methanesulfonyl-ethyl)-phenylamino]-3-methoxy-pyridin-4-yloxy}-piperidine-1-carboxylic acid isopropyl ester |
| 7 | 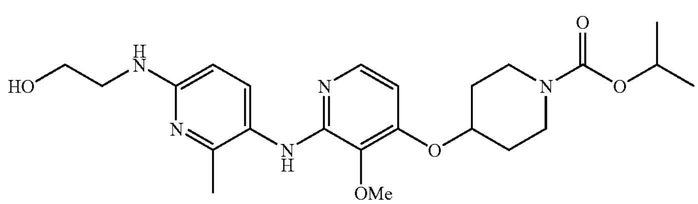 [SMILES: COc1c(OC2CCN(C(=O)OC(C)C)CC2)ccnc1Nc1ccc(NCCO)nc1C] | 4-{2-[6-(2-Hydroxy-ethylamino)-2-methyl-pyridin-3-ylamino]-3-methoxy-pyridin-4-yloxy}-piperidine-1-carboxylic acid isopropyl ester |
| 8 | 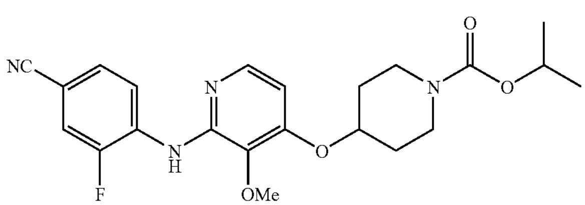 | 4-[2-(4-Cyano-2-fluoro-phenylamino)-3-methoxy-pyridin-4-yloxy]-piperidine-1-carboxylic acid isopropyl ester |
| 9 | 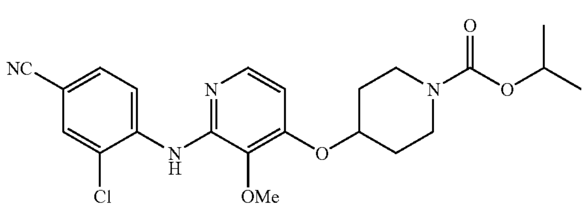 | 4-[2-(2-Chloro-4-cyano-phenylamino)-3-methoxy-pyridin-4-yloxy]-piperidine-1-carboxylic acid isopropyl ester |
| 10 | 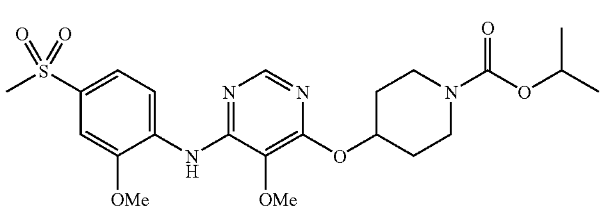 [SMILES: COc1cc(S(C)(=O)=O)ccc1Nc1ncnc(OC2CCN(C(=O)OC(C)C)CC2)c1OC] | 4-[6-(4-Methanesulfonyl-2-methoxy-phenylamino)-5-methoxy-pyrimidin-4-yloxy]-piperidine-1-carboxylic acid isopropyl ester |

TABLE A-continued

| Cmpd No. | Structure | Chemical Name |
|---|---|---|
| 11 | 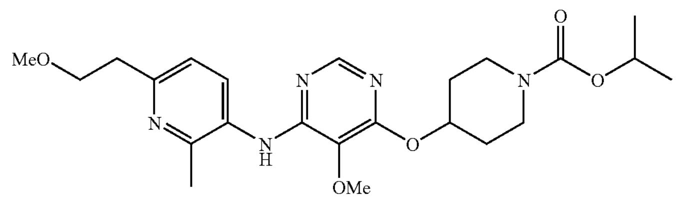 [SMILES: COCCc1ccc(Nc2ncnc(OC3CCN(C(=O)OC(C)C)CC3)c2OC)c(C)n1] | 4-{5-Methoxy-6-[6-(2-methoxy-ethyl)-2-methyl-pyridin-3-ylamino]-pyrimidin-4-yloxy}-piperidine-1-carboxylic acid isopropyl ester |
| 12 | 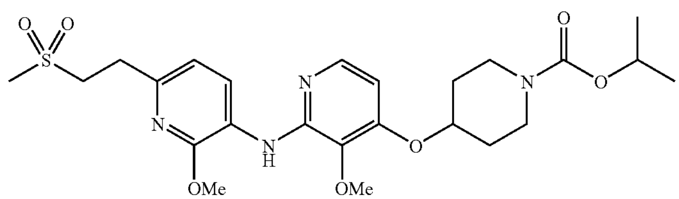 [SMILES: COc1nc(CCS(C)(=O)=O)ccc1Nc1nccc(OC2CCN(C(=O)OC(C)C)CC2)c1OC] | 4-{2-[6-(2-Methanesulfonyl-ethyl)-2-methoxy-pyridin-3-ylamino]-3-methoxy-pyridin-4-yloxy}-piperidine-1-carboxylic acid isopropyl ester |
| 13 | 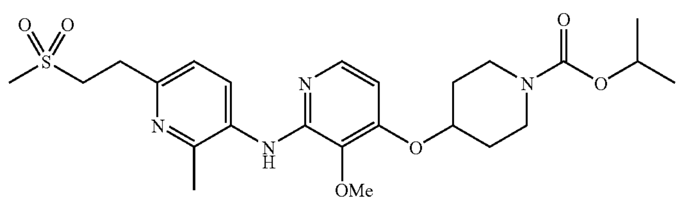 [SMILES: COc1c(OC2CCN(C(=O)OC(C)C)CC2)ccnc1Nc1ccc(CCS(C)(=O)=O)nc1C] | 4-{2-[6-(2-Methanesulfonyl-ethyl)-2-methyl-pyridin-3-ylamino]-3-methoxy-pyridin-4-yloxy}-piperidine-1-carboxylic acid isopropyl ester |
| 14 | 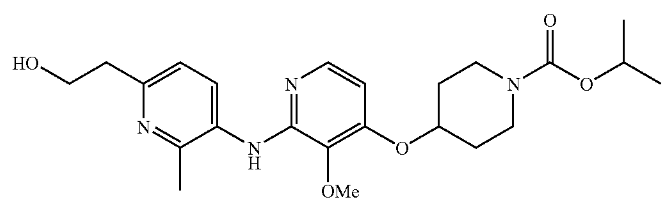 [SMILES: COc1c(OC2CCN(C(=O)OC(C)C)CC2)ccnc1Nc1ccc(CCO)nc1C] | 4-{2-[6-(2-Hydroxy-ethyl)-2-methyl-pyridin-3-ylamino]-3-methoxy-pyridin-4-yloxy}-piperidine-1-carboxylic acid isopropyl ester |
| 15 | 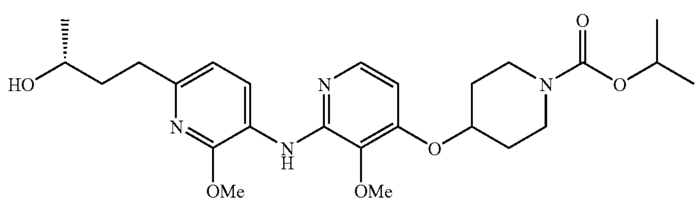 [SMILES: COc1nc(CC[C@@H](C)O)ccc1Nc1nccc(OC2CCN(C(=O)OC(C)C)CC2)c1OC] | (R)-4-{2-[6-(3-Hydroxy-butyl)-2-methoxy-pyridin-3-ylamino]-3-methoxy-pyridin-4-yloxy}-piperidine-1-carboxylic acid isopropyl ester |
| 16 | 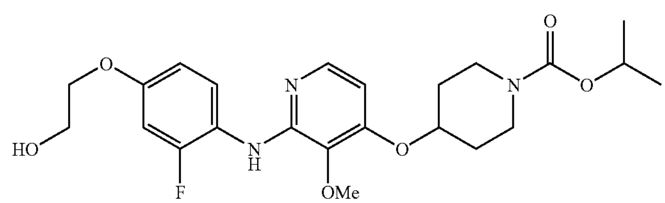 [SMILES: COc1c(OC2CCN(C(=O)OC(C)C)CC2)ccnc1Nc1ccc(OCCO)cc1F] | 4-{2-[2-Fluoro-4-(2-hydroxy-ethoxy)-phenylamino]-3-methoxy-pyridin-4-yloxy}-piperidine-1-carboxylic acid isopropyl ester |
| 17 | 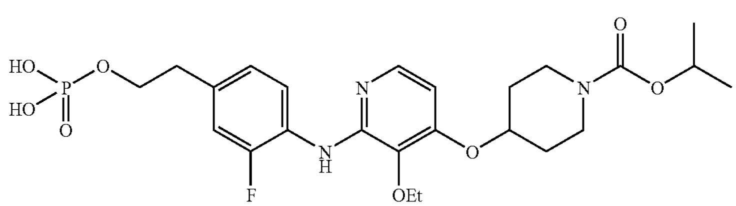 [SMILES: CCOc1c(OC2CCN(C(=O)OC(C)C)CC2)ccnc1Nc1ccc(CCOP(=O)(O)O)cc1F] | 4-{3-Ethoxy-2-[2-fluoro-4-(2-phosphonooxy-ethyl)-phenylamino]-pyridin-4-yloxy}-piperidine-1-carboxylic acid isopropyl ester |

TABLE A-continued

| Cmpd No. | Structure | Chemical Name |
|---|---|---|
| 18 | 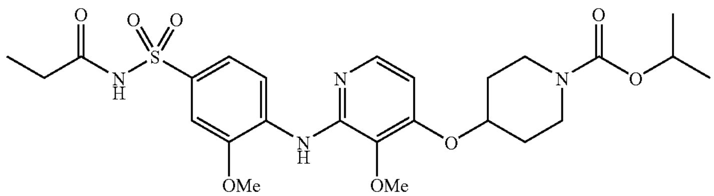 [SMILES: CCC(=O)NS(=O)(=O)c1ccc(Nc2nccc(OC3CCN(C(=O)OC(C)C)CC3)c2OC)c(OC)c1] | 4-[3-Methoxy-2-(2-methoxy-4-propionylsulfamoyl-phenylamino)-pyridin-4-yloxy]-piperidine-1-carboxylic acid isopropyl ester |
| 19 | 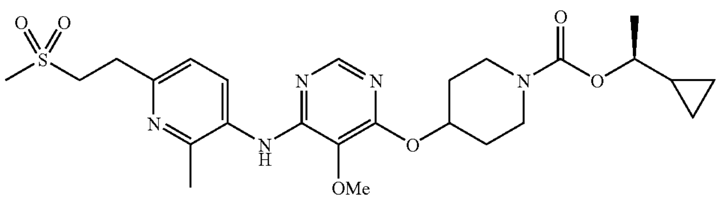 [SMILES: COc1c(Nc2ccc(CCS(C)(=O)=O)nc2C)ncnc1OC1CCN(C(=O)O[C@@H](C)C2CC2)CC1] | (S)-4-{6-[6-(2-Methanesulfonyl-ethyl)-2-methyl-pyridin-3-ylamino]-5-methoxy-pyrimidin-4-yloxy}-piperidine-1-carboxylic acid 1-cyclopropyl-ethyl ester |
| 20 | 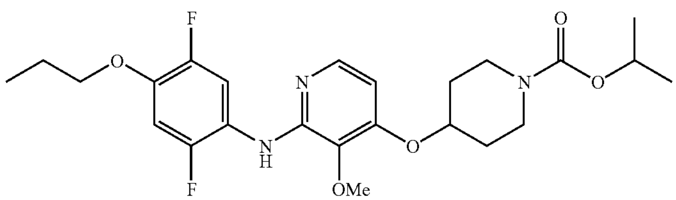 [SMILES: CCCOc1cc(F)c(Nc2nccc(OC3CCN(C(=O)OC(C)C)CC3)c2OC)cc1F] | 4-[2-(2,5-Difluoro-4-propoxy-phenylamino)-3-methoxy-pyridin-4-yloxy]-piperidine-1-carboxylic acid isopropyl ester |
| 21 | 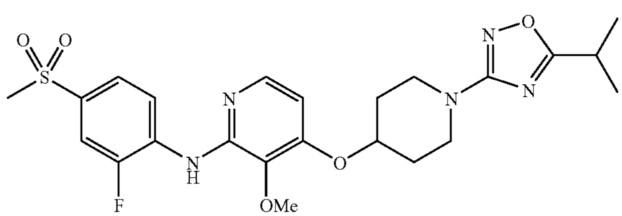 [SMILES: COc1c(OC2CCN(c3noc(C(C)C)n3)CC2)ccnc1Nc1ccc(S(C)(=O)=O)cc1F] | (2-Fluoro-4-methanesulfonyl-phenyl)-{4-[1-(5-isopropyl-[1,2,4]oxadiazol-3-yl)-piperidin-4-yloxy]-3-methoxy-pyridin-2-yl}-amine |
| 22 | 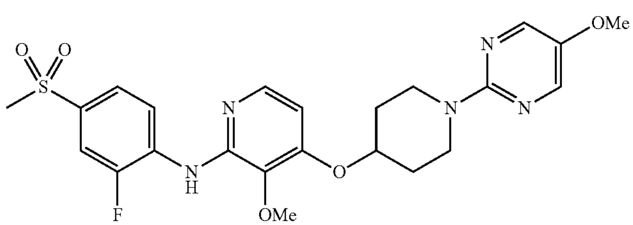 [SMILES: COc1cnc(N2CCC(Oc3ccnc(Nc4ccc(S(C)(=O)=O)cc4F)c3OC)CC2)nc1] | (2-Fluoro-4-methanesulfonyl-phenyl)-{3-methoxy-4-[1-(5-methoxy-pyrimidin-2-yl)-piperidin-4-yloxy]-pyridin-2-yl}-amine |
| 23 | 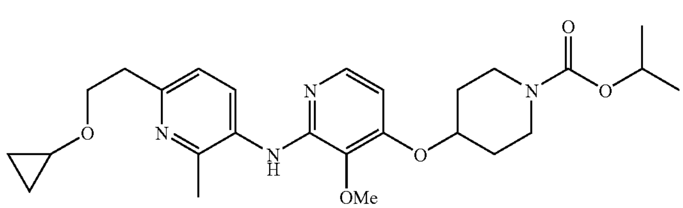 [SMILES: COc1c(OC2CCN(C(=O)OC(C)C)CC2)ccnc1Nc1ccc(CCOC2CC2)nc1C] | 4-{2-[6-(2-Cyclopropoxy-ethyl)-2-methyl-pyridin-3-ylamino]-3-methoxy-pyridin-4-yloxy}-piperidine-1-carboxylic acid isopropyl ester |
| 24 | 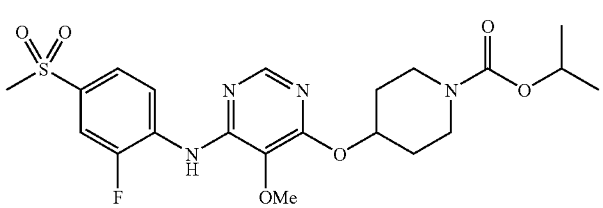 [SMILES: COc1c(Nc2ccc(S(C)(=O)=O)cc2F)ncnc1OC1CCN(C(=O)OC(C)C)CC1] | 4-[6-(2-Fluoro-4-methanesulfonyl-phenylamino)-5-methoxy-pyrimidin-4-yloxy]-piperidine-1-carboxylic acid isopropyl ester |

| Cmpd No. | Structure | Chemical Name |
| --- | --- | --- |
| 25 | 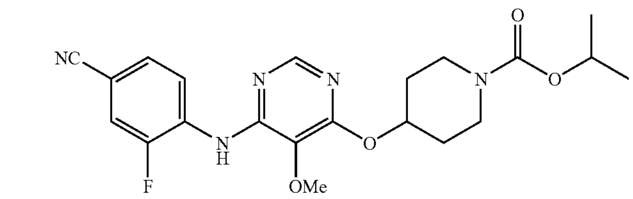 | 4-[6-(4-Cyano-2-fluoro-phenylamino)-5-methoxy-pyrimidin-4-yloxy]-piperidine-1-carboxylic acid isopropyl ester |
| 26 | 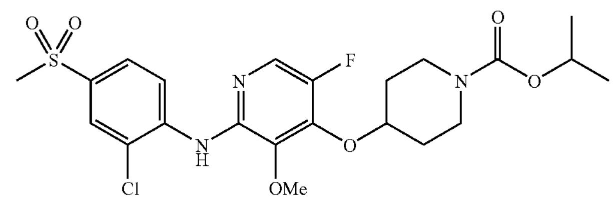 [SMILES: COc1c(Nc2ccc(S(C)(=O)=O)cc2Cl)ncc(F)c1OC1CCN(C(=O)OC(C)C)CC1] | 4-[2-(2-Chloro-4-methanesulfonyl-phenylamino)-5-fluoro-3-methoxy-pyridin-4-yloxy]-piperidine-1-carboxylic acid isopropyl ester |
| 27 | 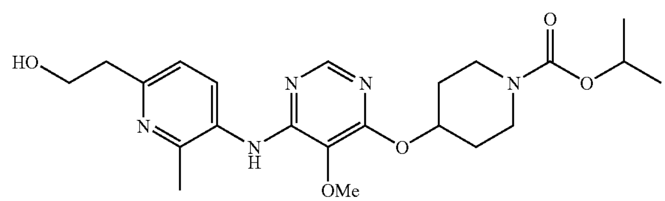 | 4-{6-[6-(2-Hydroxy-ethyl)-2-methyl-pyridin-3-ylamino]-5-methoxy-pyrimidin-4-yloxy}-piperidine-1-carboxylic acid isopropyl ester |
| 28 | 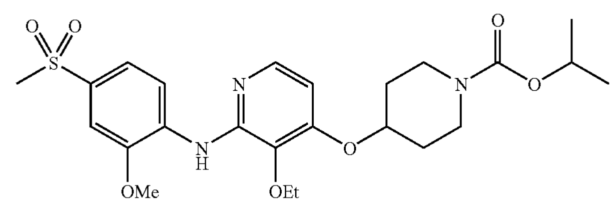 [SMILES: CCOc1c(OC2CCN(C(=O)OC(C)C)CC2)ccnc1Nc1ccc(S(C)(=O)=O)cc1OC] | 4-[3-Ethoxy-2-(4-methanesulfonyl-2-methoxy-phenylamino)-pyridin-4-yloxy]-piperidine-1-carboxylic acid isopropyl ester |
| 29 | 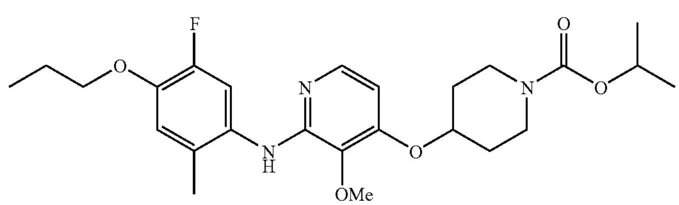 | 4-[2-(5-Fluoro-2-methyl-4-propoxy-phenylamino)-3-methoxy-pyridin-4-yloxy]-piperidine-1-carboxylic acid isopropyl ester |
| 30 | 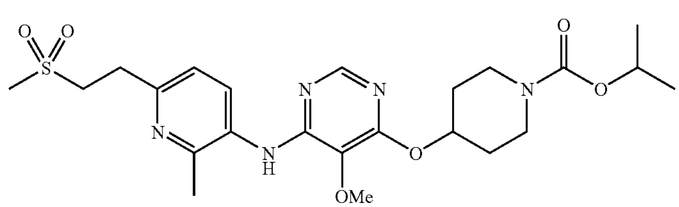 [SMILES: COc1c(Nc2ccc(CCS(C)(=O)=O)nc2C)ncnc1OC1CCN(C(=O)OC(C)C)CC1] | 4-{6-[6-(2-Methanesulfonyl-ethyl)-2-methyl-pyridin-3-ylamino]-5-methoxy-pyrimidin-4-yloxy}-piperidine-1-carboxylic acid isopropyl ester |
| 31 | 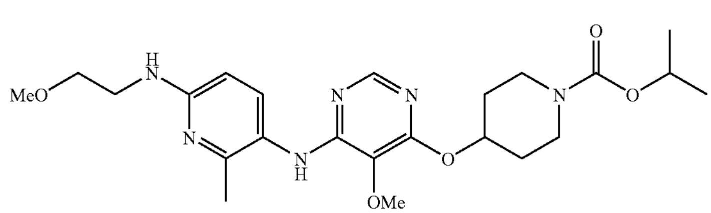 [SMILES: COCCNc1ccc(Nc2ncnc(OC3CCN(C(=O)OC(C)C)CC3)c2OC)c(C)n1] | 4-{5-Methoxy-6-[6-(2-methoxy-ethylamino)-2-methyl-pyridin-3-ylamino]-pyrimidin-4-yloxy}-piperidine-1-carboxylic acid isopropyl ester |

TABLE A-continued

| Cmpd No. | Structure | Chemical Name |
|---|---|---|
| 32 | 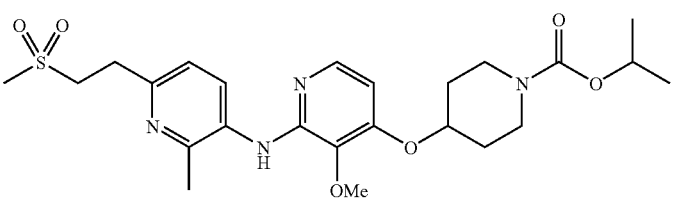 [SMILES: COc1c(OC2CCN(C(=O)OC(C)C)CC2)ccnc1Nc1ccc(CCS(C)(=O)=O)nc1C] | 4-{2-[6-(2-Methanesulfonyl-ethyl)-2-methyl-pyridin-3-ylamino]-3-methoxy-pyridin-4-yloxy}-piperidine-1-carboxylic acid isopropyl ester |
| 33 | 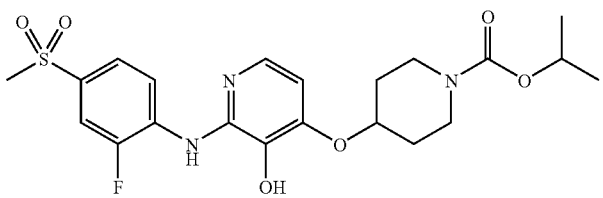 [SMILES: CC(C)OC(=O)N1CCC(Oc2ccnc(Nc3ccc(S(C)(=O)=O)cc3F)c2O)CC1] | 4-[2-(2-Fluoro-4-methanesulfonyl-phenylamino)-3-hydroxy-pyridin-4-yloxy]-piperidine-1-carboxylic acid isopropyl ester |
| 34 | 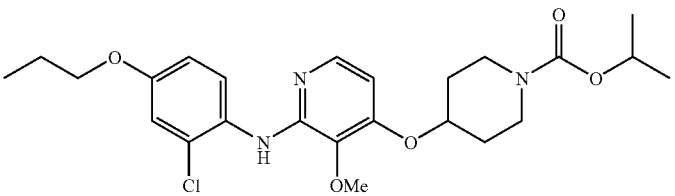 [SMILES: CCCOc1ccc(Nc2nccc(OC3CCN(C(=O)OC(C)C)CC3)c2OC)c(Cl)c1] | 4-[2-(2-Chloro-4-propoxy-phenylamino)-3-methoxy-pyridin-4-yloxy]-piperidine-1-carboxylic acid isopropyl ester |
| 35 | 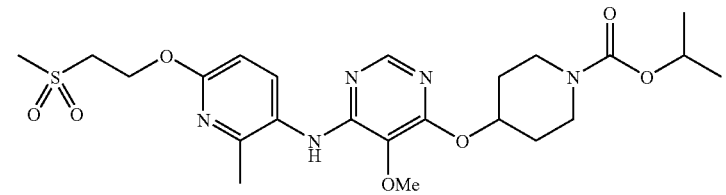 [SMILES: COc1c(Nc2ccc(OCCS(C)(=O)=O)nc2C)ncnc1OC1CCN(C(=O)OC(C)C)CC1] | 4-{6-[6-(2-Methanesulfonyl-ethoxy)-2-methyl-pyridin-3-ylamino]-5-methoxy-pyrimidin-4-yloxy}-piperidine-1-carboxylic acid isopropyl ester |
| 36 | 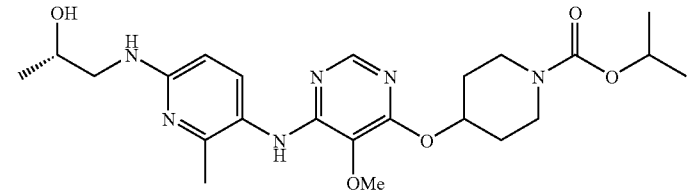 [SMILES: COc1c(Nc2ccc(NC[C@H](C)O)nc2C)ncnc1OC1CCN(C(=O)OC(C)C)CC1] | (S)-4-{6-[6-(2-Hydroxy-propylamino)-2-methyl-pyridin-3-ylamino]-5-methoxy-pyrimidin-4-yloxy}-piperidine-1-carboxylic acid isopropyl ester |
| 37 | 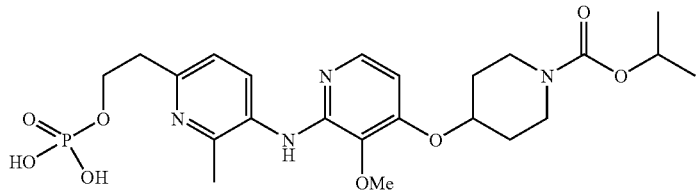 [SMILES: COc1c(OC2CCN(C(=O)OC(C)C)CC2)ccnc1Nc1ccc(CCOP(=O)(O)O)nc1C] | 4-{3-Methoxy-2-[2-methyl-6-(2-phosphonooxy-ethyl)-pyridin-3-ylamino]-pyridin-4-yloxy}-piperidine-1-carboxylic acid isopropyl ester |
| 38 | 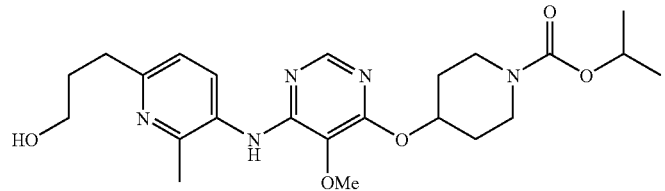 [SMILES: COc1c(Nc2ccc(CCCO)nc2C)ncnc1OC1CCN(C(=O)OC(C)C)CC1] | 4-{6-[6-(3-Hydroxy-propyl)-2-methyl-pyridin-3-ylamino]-5-methoxy-pyrimidin-4-yloxy}-piperidine-1-carboxylic acid isopropyl ester |

TABLE A-continued

| Cmpd No. | Structure | Chemical Name |
|---|---|---|
| 39 | 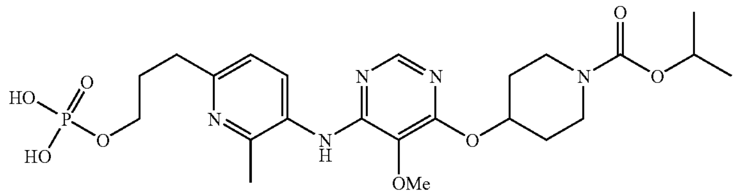 [SMILES: COc1c(Nc2ccc(CCCOP(=O)(O)O)nc2C)ncnc1OC1CCN(C(=O)OC(C)C)CC1] | 4-{5-Methoxy-6-[2-methyl-6-(3-phosphonooxy-propyl)-pyridin-3-ylamino]-pyrimidin-4-yloxy}-piperidine-1-carboxylic acid isopropyl ester |
| 40 | 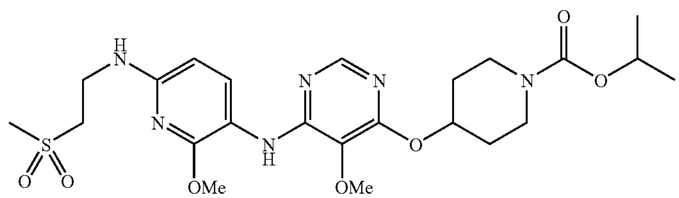 [SMILES: COc1nc(NCCS(C)(=O)=O)ccc1Nc1ncnc(OC2CCN(C(=O)OC(C)C)CC2)c1OC] | 4-{6-[6-(2-Methanesulfonyl-ethylamino)-2-methoxy-pyridin-3-ylamino]-5-methoxy-pyrimidin-4-yloxy}-piperidine-1-carboxylic acid isopropyl ester |
| 41 | 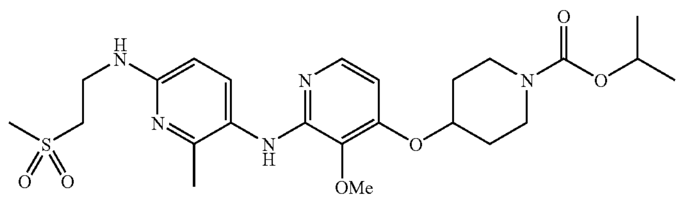 [SMILES: COc1c(OC2CCN(C(=O)OC(C)C)CC2)ccnc1Nc1ccc(NCCS(C)(=O)=O)nc1C] | 4-{2-[6-(2-Methanesulfonyl-ethylamino)-2-methyl-pyridin-3-ylamino]-3-methoxy-pyridin-4-yloxy}-piperidine-1-carboxylic acid isopropyl ester |
| 42 | 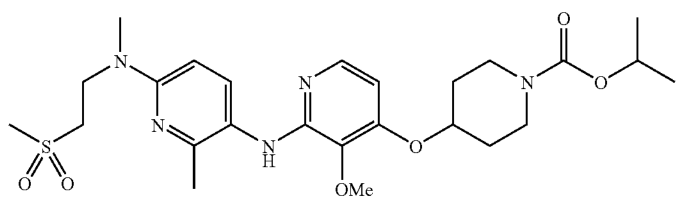 [SMILES: COc1c(OC2CCN(C(=O)OC(C)C)CC2)ccnc1Nc1ccc(N(C)CCS(C)(=O)=O)nc1C] | 4-(2-{6-[(2-Methanesulfonyl-ethyl)-methyl-amino]-2-methyl-pyridin-3-ylamino}-3-methoxy-pyridin-4-yloxy)-piperidine-1-carboxylic acid isopropyl ester |
| 43 | 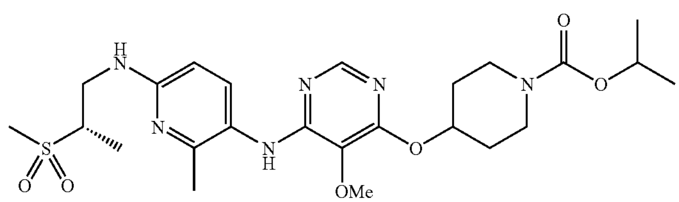 [SMILES: COc1c(Nc2ccc(NC[C@H](C)S(C)(=O)=O)nc2C)ncnc1OC1CCN(C(=O)OC(C)C)CC1] | (S)-4-{6-[6-(2-Methanesulfonyl-propylamino)-2-methyl-pyridin-3-ylamino]-5-methoxy-pyrimidin-4-yloxy}-piperidine-1-carboxylic acid isopropyl ester |
| 44 | 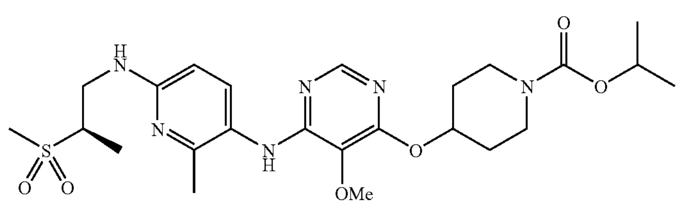 [SMILES: COc1c(Nc2ccc(NC[C@@H](C)S(C)(=O)=O)nc2C)ncnc1OC1CCN(C(=O)OC(C)C)CC1] | (R)-4-{6-[6-(2-Methanesulfonyl-propylamino)-2-methyl-pyridin-3-ylamino]-5-methoxy-pyrimidin-4-yloxy}-piperidine-1-carboxylic acid isopropyl ester |
| 45 | 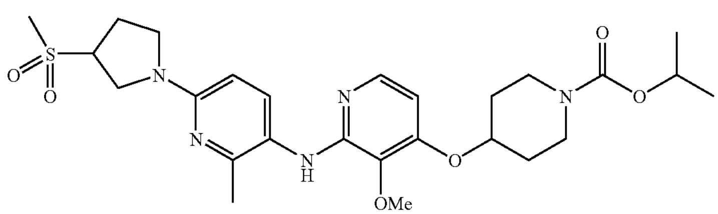 [SMILES: COc1c(OC2CCN(C(=O)OC(C)C)CC2)ccnc1Nc1ccc(N2CCC(S(C)(=O)=O)C2)nc1C] | 4-{2-[6-(3-Methanesulfonyl-pyrrolidin-1-yl)-2-methyl-pyridin-3-ylamino]-3-methoxy-pyridin-4-yloxy}-piperidine-1-carboxylic acid isopropyl ester |

TABLE A-continued

| Cmpd No. | Structure | Chemical Name |
|---|---|---|
| 46 | 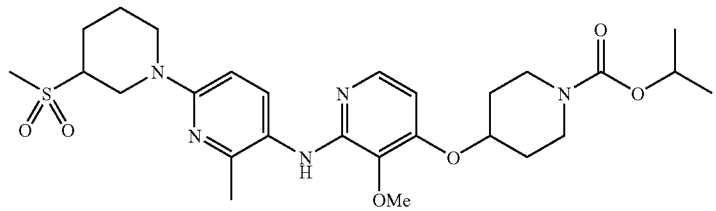 [SMILES: COc1c(OC2CCN(C(=O)OC(C)C)CC2)ccnc1Nc1ccc(N2CCCC(S(C)(=O)=O)C2)nc1C] | 4-[2-(3-Methanesulfonyl-6'-methyl-3,4,5,6-tetrahydro-2H-[1,2']bipyridinyl-5'-ylamino)-3-methoxy-pyridin-4-yloxy]-piperidine-1-carboxylic acid isopropyl ester |
| 47 | 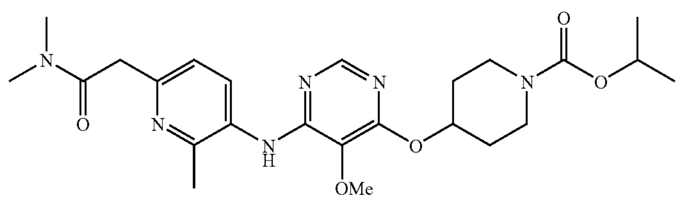 [SMILES: COc1c(Nc2ccc(CC(=O)N(C)C)nc2C)ncnc1OC1CCN(C(=O)OC(C)C)CC1] | 4-[6-(6-Dimethylcarbamoylmethyl-2-methyl-pyridin-3-ylamino)-5-methoxy-pyrimidin-4-yloxy]-piperidine-1-carboxylic acid isopropyl ester |
| 48 | 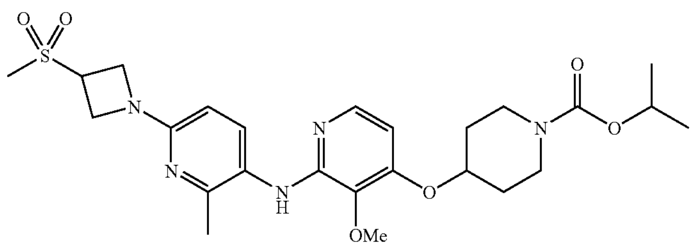 [SMILES: COc1c(OC2CCN(C(=O)OC(C)C)CC2)ccnc1Nc1ccc(N2CC(S(C)(=O)=O)C2)nc1C] | 4-{2-[6-(3-Methanesulfonyl-azetidin-1-yl)-2-methyl-pyridin-3-ylamino]-3-methoxy-pyridin-4-yloxy}-piperidine-1-carboxylic acid isopropyl ester |
| 49 | 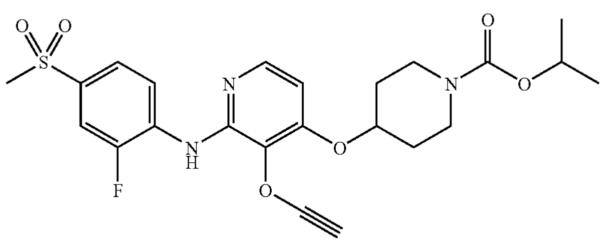 [SMILES: C#COc1c(OC2CCN(C(=O)OC(C)C)CC2)ccnc1Nc1ccc(S(C)(=O)=O)cc1F] | 4-[3-Ethynyloxy-2-(2-fluoro-4-methanesulfonyl-phenylamino)-pyridin-4-yloxy]-piperidine-1-carboxylic acid isopropyl ester |
| 50 | 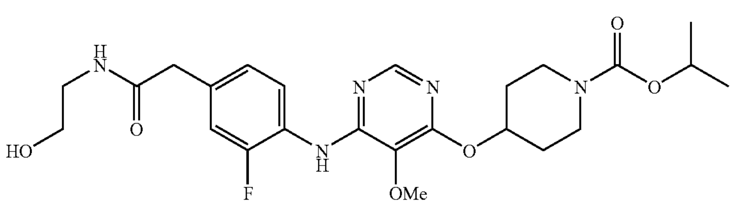 [SMILES: COc1c(Nc2ccc(CC(=O)NCCO)cc2F)ncnc1OC1CCN(C(=O)OC(C)C)CC1] | 4-(6-{2-Fluoro-4-[(2-hydroxy-ethylcarbamoyl)-methyl]-phenylamino}-5-methoxy-pyrimidin-4-yloxy)-piperidine-1-carboxylic acid isopropyl ester |
| 51 | 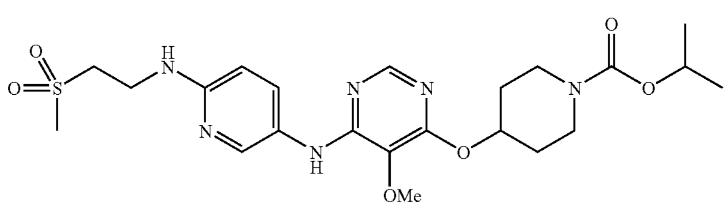 [SMILES: COc1c(Nc2ccc(NCCS(C)(=O)=O)nc2)ncnc1OC1CCN(C(=O)OC(C)C)CC1] | 4-{6-[6-(2-Methanesulfonyl-ethylamino)-pyridin-3-ylamino]-5-methoxy-pyrimidin-4-yloxy}-piperidine-1-carboxylic acid isopropyl ester |
| 52 | 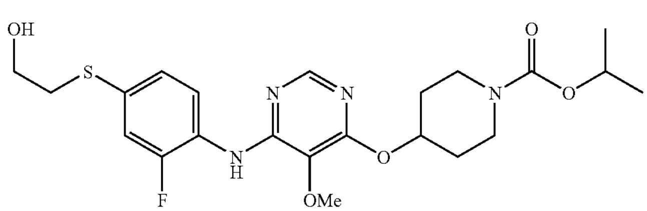 [SMILES: COc1c(Nc2ccc(SCCO)cc2F)ncnc1OC1CCN(C(=O)OC(C)C)CC1] | 4-{6-[2-Fluoro-4-(2-hydroxy-ethylsulfanyl)-phenylamino]-5-methoxy-pyrimidin-4-yloxy}-piperidine-1-carboxylic acid isopropyl ester |

TABLE A-continued

| Cmpd No. | Structure | Chemical Name |
|---|---|---|
| 53 | 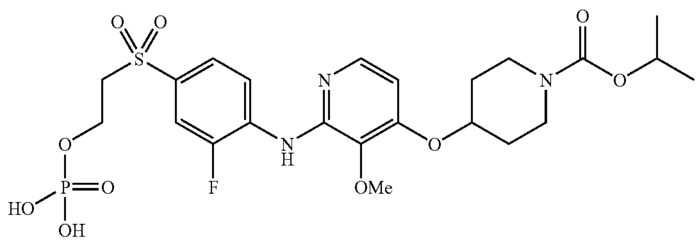 [SMILES: COc1c(OC2CCN(C(=O)OC(C)C)CC2)ccnc1Nc1ccc(S(=O)(=O)CCOP(=O)(O)O)cc1F] | 4-{2-[2-Fluoro-4-(2-phosphonooxy-ethanesulfonyl)-phenylamino]-3-methoxy-pyridin-4-yloxy}-piperidine-1-carboxylic acid isopropyl ester |
| 54 | 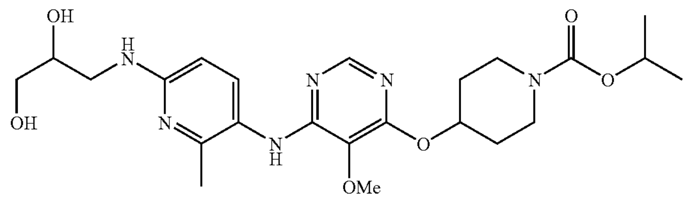 [SMILES: COc1c(Nc2ccc(NCC(O)CO)nc2C)ncnc1OC1CCN(C(=O)OC(C)C)CC1] | 4-{6-[6-(2,3-Dihydroxy-propylamino)-2-methyl-pyridin-3-ylamino]-5-methoxy-pyrimidin-4-yloxy}-piperidine-1-carboxylic acid isopropyl ester |
| 55 | 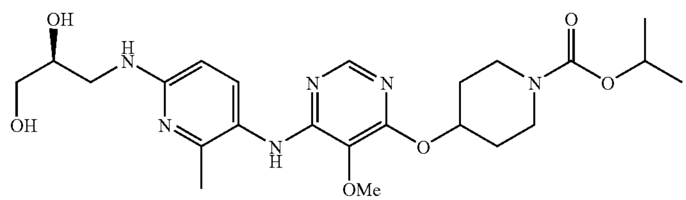 [SMILES: COc1c(Nc2ccc(NC[C@H](O)CO)nc2C)ncnc1OC1CCN(C(=O)OC(C)C)CC1] | (S)-4-{6-[6-(2,3-Dihydroxy-propylamino)-2-methyl-pyridin-3-ylamino]-5-methoxy-pyrimidin-4-yloxy}-piperidine-1-carboxylic acid isopropyl ester |
| 56 | 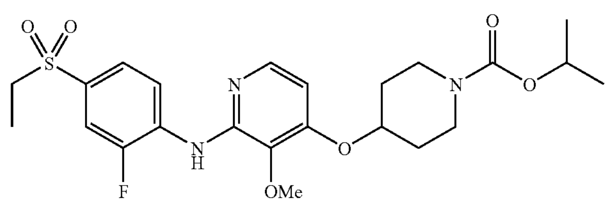 [SMILES: CCS(=O)(=O)c1ccc(Nc2nccc(OC3CCN(C(=O)OC(C)C)CC3)c2OC)c(F)c1] | 4-[2-(4-Ethanesulfonyl-2-fluoro-phenylamino)-3-methoxy-pyridin-4-yloxy]-piperidine-1-carboxylic acid sec-butyl ester |
| 57 | 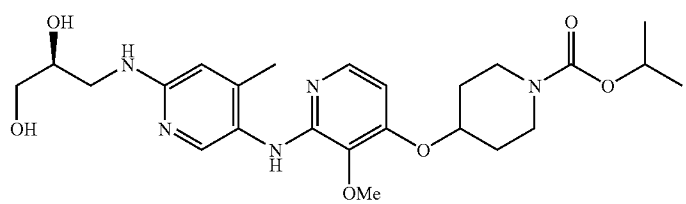 [SMILES: COc1c(OC2CCN(C(=O)OC(C)C)CC2)ccnc1Nc1cnc(NC[C@H](O)CO)cc1C] | 4-{2-[6-(2,3-Dihydroxy-propylamino)-4-methyl-pyridin-3-ylamino]-3-methoxy-pyridin-4-yloxy}-piperidine-1-carboxylic acid isopropyl ester |
| 58 | 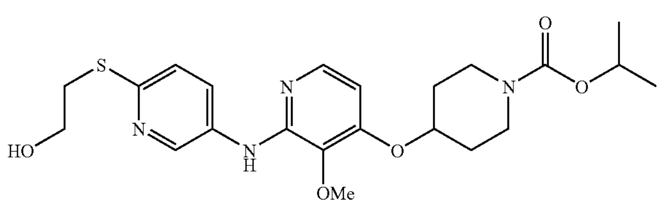 [SMILES: COc1c(OC2CCN(C(=O)OC(C)C)CC2)ccnc1Nc1ccc(SCCO)nc1] | 4-{2-[6-(2-Hydroxy-ethylsulfanyl)-pyridin-3-ylamino]-3-methoxy-pyridin-4-yloxy}-piperidine-1-carboxylic acid isopropyl ester |
| 59 | 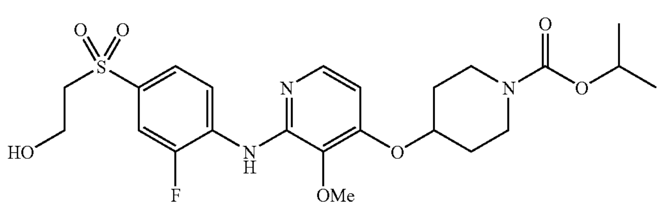 [SMILES: COc1c(OC2CCN(C(=O)OC(C)C)CC2)ccnc1Nc1ccc(S(=O)(=O)CCO)cc1F] | 4-{2-[2-Fluoro-4-(2-hydroxy-ethanesulfonyl)-phenylamino]-3-methoxy-pyridin-4-yloxy}-piperidine-1-carboxylic acid isopropyl ester |

TABLE A-continued

| Cmpd No. | Structure | Chemical Name |
|---|---|---|
| 60 | 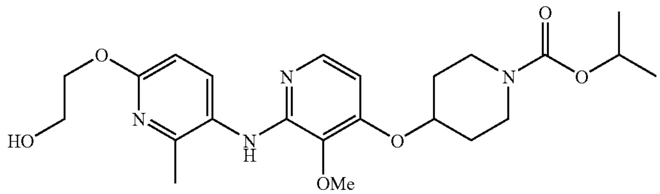 | 4-{2-[6-(2-Hydroxy-ethoxy)-2-methyl-pyridin-3-ylamino]-3-methoxy-pyridin-4-yloxy}-piperidine-1-carboxylic acid isopropyl ester |
| 61 | 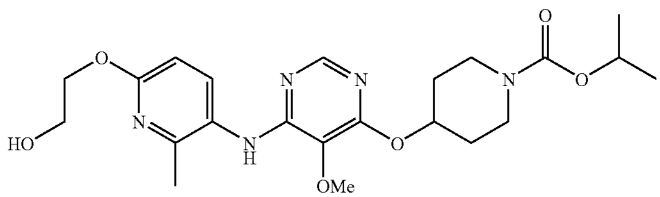 | 4-{6-[6-(2-Hydroxy-ethoxy)-2-methyl-pyridin-3-ylamino]-5-methoxy-pyrimidin-4-yloxy}-piperidine-1-carboxylic acid isopropyl ester |
| 62 | 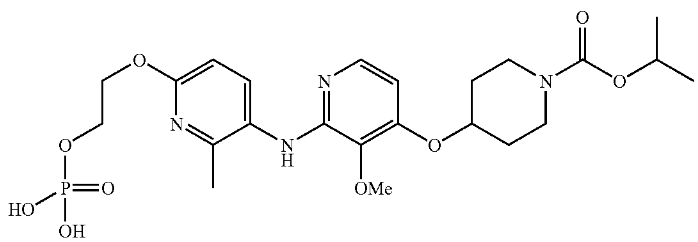 [SMILES: COc1c(OC2CCN(C(=O)OC(C)C)CC2)ccnc1Nc1ccc(OCCOP(=O)(O)O)nc1C] | 4-{3-Methoxy-2-[2-methyl-6-(2-phosphonooxy-ethoxy)-pyridin-3-ylamino]-pyridin-4-yloxy}-piperidine-1-carboxylic acid isopropyl ester |
| 63 | 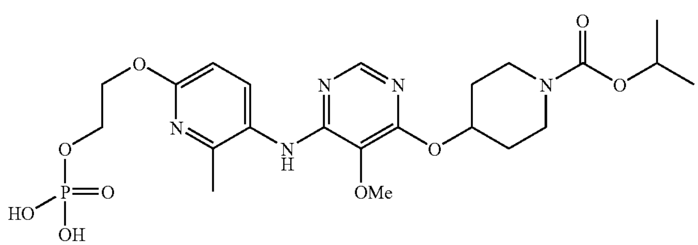 [SMILES: COc1c(Nc2ccc(OCCOP(=O)(O)O)nc2C)ncnc1OC1CCN(C(=O)OC(C)C)CC1] | 4-{5-Methoxy-6-[2-methyl-6-(2-phosphonooxy-ethoxy)-pyridin-3-ylamino]-pyrimidin-4-yloxy}-piperidine-1-carboxylic acid isopropyl ester |
| 64 | 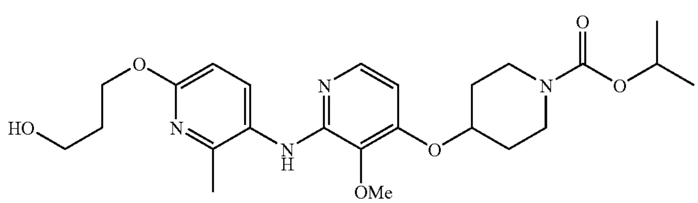 [SMILES: COc1c(OC2CCN(C(=O)OC(C)C)CC2)ccnc1Nc1ccc(OCCCO)nc1C] | 4-{2-[6-(3-Hydroxy-propoxy)-2-methyl-pyridin-3-ylamino]-3-methoxy-pyridin-4-yloxy}-piperidine-1-carboxylic acid isopropyl ester |
| 65 | 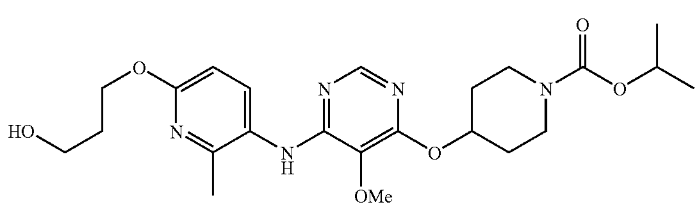 [SMILES: COc1c(Nc2ccc(OCCCO)nc2C)ncnc1OC1CCN(C(=O)OC(C)C)CC1] | 4-{6-[6-(3-Hydroxy-propoxy)-2-methyl-pyridin-3-ylamino]-5-methoxy-pyrimidin-4-yloxy}-piperidine-1-carboxylic acid isopropyl ester |
| 66 | 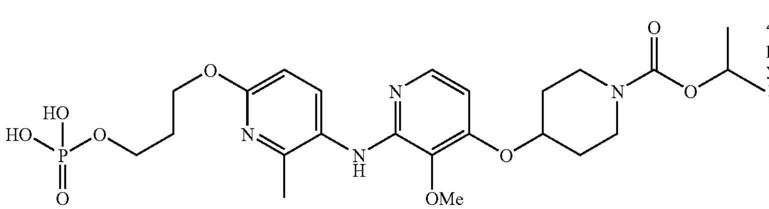 [SMILES: COc1c(OC2CCN(C(=O)OC(C)C)CC2)ccnc1Nc1ccc(OCCCOP(=O)(O)O)nc1C] | 4-{3-Methoxy-2-[2-methyl-6-(3-phosphonooxy-propoxy)-pyridin-3-ylamino]-pyridin-4-yloxy}-piperidine-1-carboxylic acid isopropyl ester |

TABLE A-continued

| Cmpd No. | Structure | Chemical Name |
|---|---|---|
| 67 | 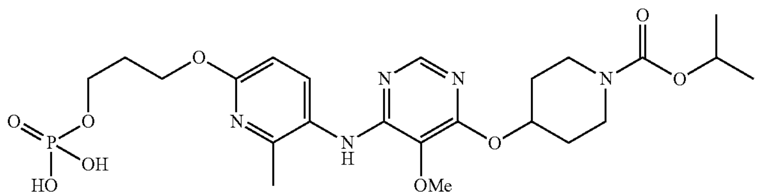 [SMILES: COc1c(Nc2ccc(OCCCOP(=O)(O)O)nc2C)ncnc1OC1CCN(C(=O)OC(C)C)CC1] | 4-{5-Methoxy-6-[2-methyl-6-(3-phosphonooxy-propoxy)-pyridin-3-ylamino]-pyrimidin-4-yloxy}-piperidine-1-carboxylic acid isopropyl ester |
| 68 | 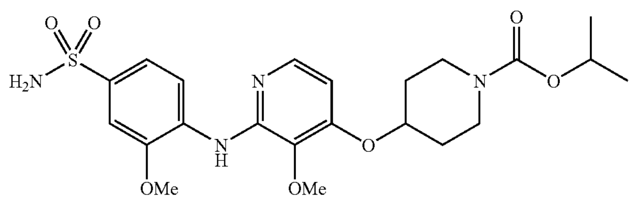 [SMILES: COc1cc(S(N)(=O)=O)ccc1Nc1nccc(OC2CCN(C(=O)OC(C)C)CC2)c1OC] | 4-[3-Methoxy-2-(2-methoxy-4-sulfamoyl-phenylamino)-pyridin-4-yloxy]-piperidine-1-carboxylic acid isopropyl ester |
| 69 | 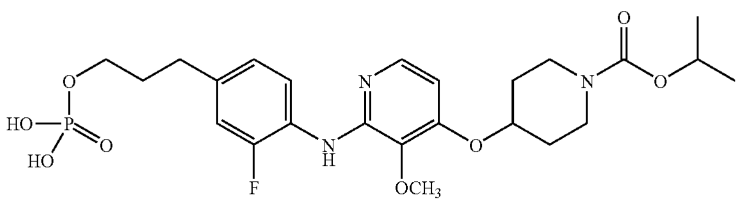 [SMILES: COc1c(OC2CCN(C(=O)OC(C)C)CC2)ccnc1Nc1ccc(CCCOP(=O)(O)O)cc1F] | 4-{2-[2-Fluoro-4-(3-phosphonooxy-propyl)-phenylamino]-3-methoxy-pyridin-4-yloxy}-piperidine-1-carboxylic acid isopropyl ester |
| 70 | 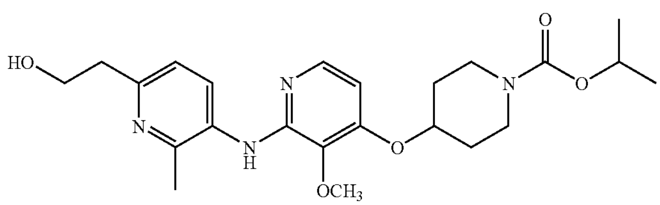 [SMILES: COc1c(OC2CCN(C(=O)OC(C)C)CC2)ccnc1Nc1ccc(CCO)nc1C] | 4-{2-[6-(2-Hydroxy-ethyl)-2-methyl-pyridin-3-ylamino]-3-methoxy-pyridin-4-yloxy}-piperidine-1-carboxylic acid isopropyl ester |
| 71 | 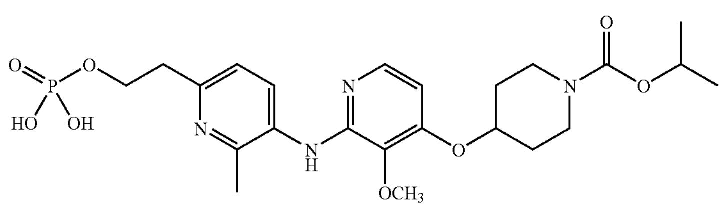 [SMILES: COc1c(OC2CCN(C(=O)OC(C)C)CC2)ccnc1Nc1ccc(CCOP(=O)(O)O)nc1C] | 4-{3-Methoxy-2-[2-methyl-6-(2-phosphonooxy-ethyl)-pyridin-3-ylamino]-pyridin-4-yloxy}-piperidine-1-carboxylic acid isopropyl ester |
| 72 | 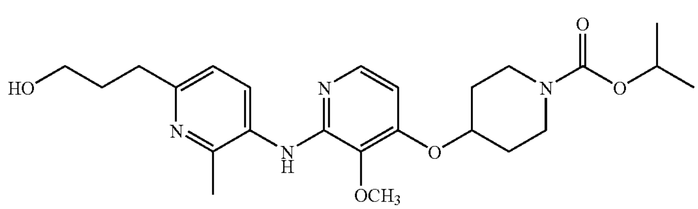 | 4-{2-[6-(3-Hydroxy-propyl)-2-methyl-pyridin-3-ylamino]-3-methoxy-pyridin-4-yloxy}-piperidine-1-carboxylic acid isopropyl ester |
| 73 | 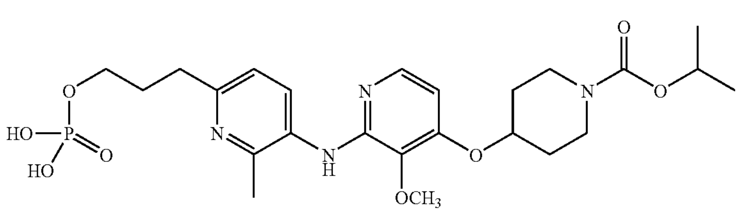 [SMILES: COc1c(OC2CCN(C(=O)OC(C)C)CC2)ccnc1Nc1ccc(CCCOP(=O)(O)O)nc1C] | 4-{3-Methoxy-2-[2-methyl-6-(3-phosphonooxy-propyl)-pyridin-3-ylamino]-pyridin-4-yloxy}-piperidine-1-carboxylic acid isopropyl ester |

TABLE A-continued

| Cmpd No. | Structure | Chemical Name |
|---|---|---|
| 74 | 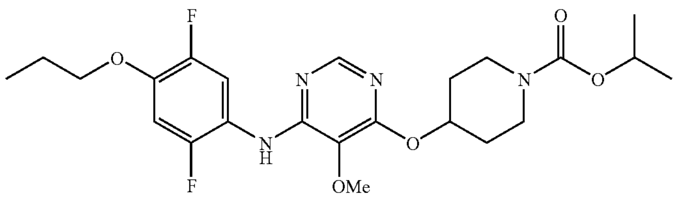 | 4-[6-(2,5-Difluoro-4-propoxy-phenylamino)-5-methoxy-pyrimidin-4-yloxy]-piperidine-1-carboxylic acid isopropyl ester |
| 75 | 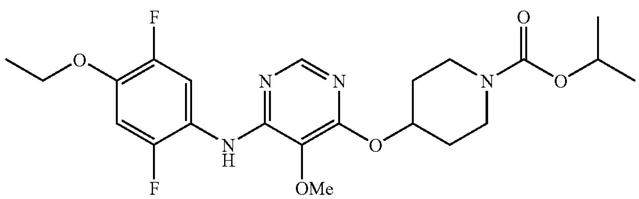 [SMILES: CCOc1cc(F)c(Nc2ncnc(OC3CCN(C(=O)OC(C)C)CC3)c2OC)cc1F] | 4-[6-(4-Ethoxy-2,5-difluoro-phenylamino)-5-methoxy-pyrimidin-4-yloxy]-piperidine-1-carboxylic acid isopropyl ester |
| 76 | 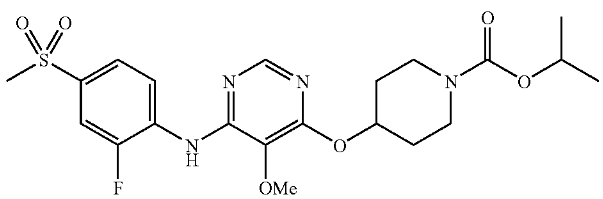 [SMILES: COc1c(Nc2ccc(S(C)(=O)=O)cc2F)ncnc1OC1CCN(C(=O)OC(C)C)CC1] | 4-[6-(2-Fluoro-4-methanesulfonyl-phenoxy)-5-methoxy-pyrimidin-4-yloxy]-piperidine-1-carboxylic acid isopropyl ester |
| 77 | 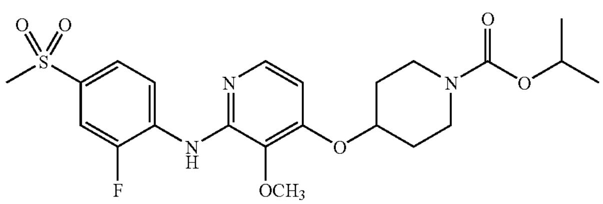 [SMILES: COc1c(OC2CCN(C(=O)OC(C)C)CC2)ccnc1Nc1ccc(S(C)(=O)=O)cc1F] | 4-[2-(2-Fluoro-4-methanesulfonyl-phenylamino)-3-methoxy-pyridin-4-yloxy]-piperidine-1-carboxylic acid isopropyl ester |
| 78 | 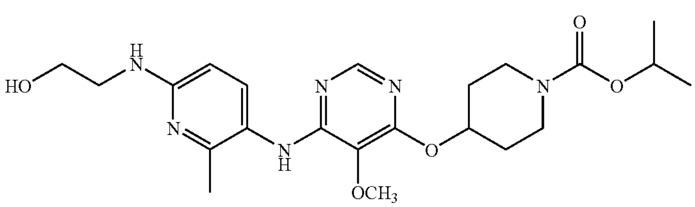 [SMILES: COc1c(Nc2ccc(NCCO)nc2C)ncnc1OC1CCN(C(=O)OC(C)C)CC1] | 4-{6-[6-(2-Hydroxy-ethylamino)-2-methyl-pyridin-3-ylamino]-5-methoxy-pyrimidin-4-yloxy}-piperidine-1-carboxylic acid isopropyl ester |
| 79 | 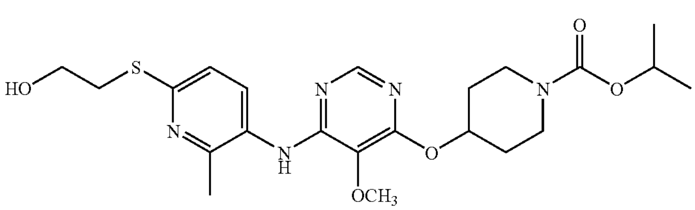 [SMILES: COc1c(Nc2ccc(SCCO)nc2C)ncnc1OC1CCN(C(=O)OC(C)C)CC1] | 4-{6-[6-(2-Hydroxy-ethylsulfanyl)-2-methyl-pyridin-3-ylamino]-5-methoxy-pyrimidin-4-yloxy}-piperidine-1-carboxylic acid isopropyl ester |
| 80 | 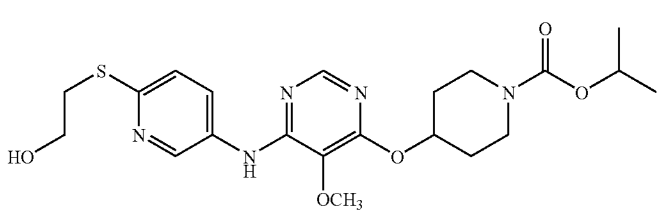 [SMILES: COc1c(Nc2ccc(SCCO)nc2)ncnc1OC1CCN(C(=O)OC(C)C)CC1] | 4-{6-[6-(2-Hydroxy-ethylsulfanyl)-pyridin-3-ylamino]-5-methoxy-pyrimidin-4-yloxy}-piperidine-1-carboxylic acid isopropyl ester |

TABLE A-continued

| Cmpd No. | Structure | Chemical Name |
| --- | --- | --- |
| 81 | 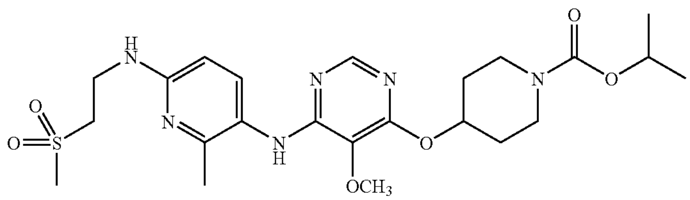 [SMILES: COc1c(Nc2ccc(NCCS(C)(=O)=O)nc2C)ncnc1OC1CCN(C(=O)OC(C)C)CC1] | 4-{6-[6-(2-Methanesulfonyl-ethylamino)-2-methyl-pyridin-3-ylamino]-5-methoxy-pyrimidin-4-yloxy}-piperidine-1-carboxylic acid isopropyl ester |
| 82 | 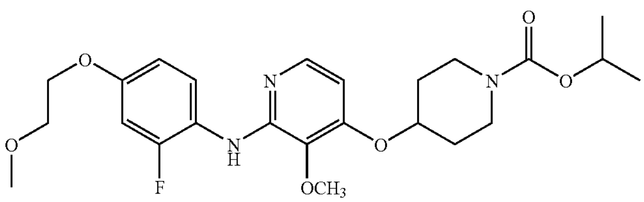 [SMILES: COCCOc1ccc(Nc2nccc(OC3CCN(C(=O)OC(C)C)CC3)c2OC)c(F)c1] | 4-{2-[2-Fluoro-4-(2-methoxy-ethoxy)-phenylamino]-3-methoxy-pyridin-4-yloxy}-piperidine-1-carboxylic acid isopropyl ester |
| 83 | 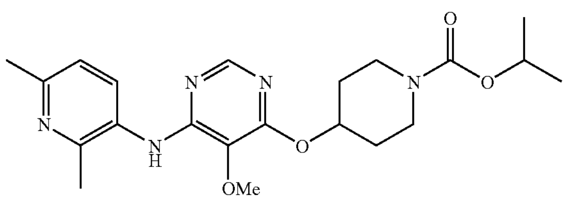 [SMILES: COc1c(Nc2ccc(C)nc2C)ncnc1OC1CCN(C(=O)OC(C)C)CC1] | 4-[6-(2,6-Dimethyl-pyridin-3-ylamino)-5-methoxy-pyrimidin-4-yloxy]-piperidine-1-carboxylic acid isopropyl ester |
| 84 | 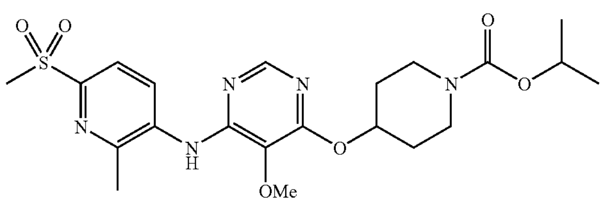 | 4-[6-(6-Methanesulfonyl-2-methyl-pyridin-3-ylamino)-5-methoxy-pyrimidin-4-yloxy]-piperidine-1-carboxylic acid isopropyl ester |
| 85 | 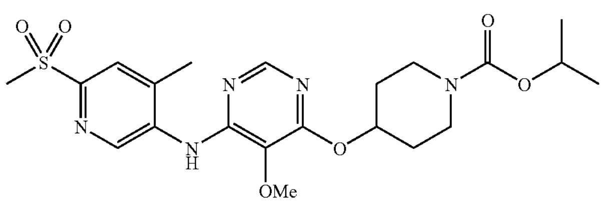 | 4-[6-(6-Methanesulfonyl-4-methyl-pyridin-3-ylamino)-5-methoxy-pyrimidin-4-yloxy]-piperidine-1-carboxylic acid isopropyl ester |
| 86 | 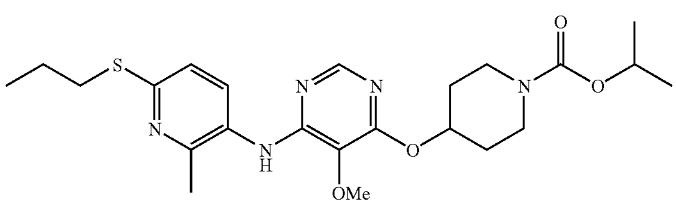 [SMILES: CCCSc1ccc(Nc2ncnc(OC3CCN(C(=O)OC(C)C)CC3)c2OC)c(C)n1] | 4-[5-Methoxy-6-(2-methyl-6-propylsulfanyl-pyridin-3-ylamino)-pyrimidin-4-yloxy]-piperidine-1-carboxylic acid isopropyl ester |
| 87 | 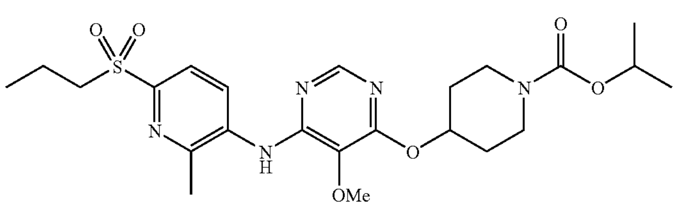 [SMILES: CCCS(=O)(=O)c1ccc(Nc2ncnc(OC3CCN(C(=O)OC(C)C)CC3)c2OC)c(C)n1] | 4-{5-Methoxy-6-[2-methyl-6-(propane-1-sulfonyl)-pyridin-3-ylamino]-pyrimidin-4-yloxy}-piperidine-1-carboxylic acid isopropyl ester |

TABLE A-continued

| Cmpd No. | Structure | Chemical Name |
|---|---|---|
| 88 | 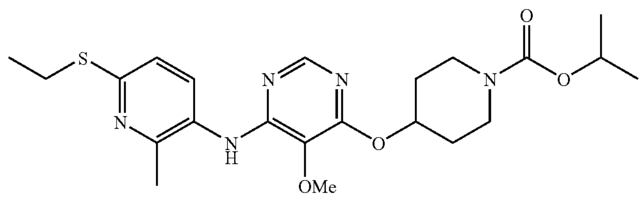 [SMILES: CCSc1ccc(Nc2ncnc(OC3CCN(C(=O)OC(C)C)CC3)c2OC)c(C)n1] | 4-[6-(6-Ethylsulfanyl-2-methyl-pyridin-3-ylamino)-5-methoxy-pyrimidin-4-yloxy]-piperidine-1-carboxylic acid isopropyl ester |
| 89 | 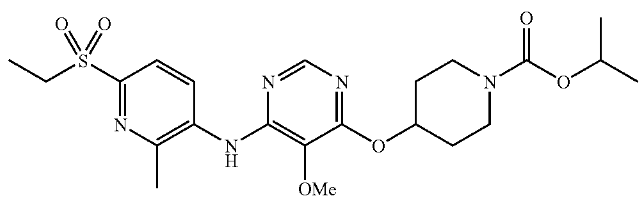 [SMILES: CCS(=O)(=O)c1ccc(Nc2ncnc(OC3CCN(C(=O)OC(C)C)CC3)c2OC)c(C)n1] | 4-[6-(6-Ethanesulfonyl-2-methyl-pyridin-3-ylamino)-5-methoxy-pyrimidin-4-yloxy]-piperidine-1-carboxylic acid isopropyl ester |
| 90 | 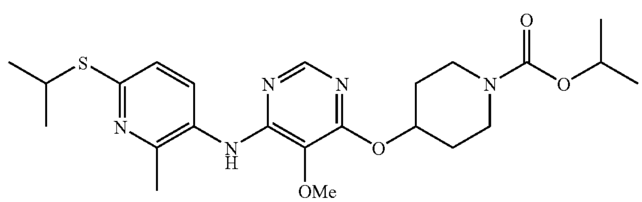 [SMILES: COc1c(Nc2ccc(SC(C)C)nc2C)ncnc1OC1CCN(C(=O)OC(C)C)CC1] | 4-[6-(6-Isopropylsulfanyl-2-methyl-pyridin-3-ylamino)-5-methoxy-pyrimidin-4-yloxy]-piperidine-1-carboxylic acid isopropyl ester |
| 91 | 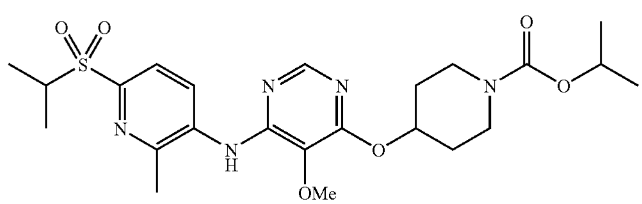 [SMILES: COc1c(Nc2ccc(S(=O)(=O)C(C)C)nc2C)ncnc1OC1CCN(C(=O)OC(C)C)CC1] | 4-{5-Methoxy-6-[2-methyl-6-(propane-2-sulfonyl)-pyridin-3-ylamino]-pyrimidin-4-yloxy}-piperidine-1-carboxylic acid isopropyl ester |
| 92 | 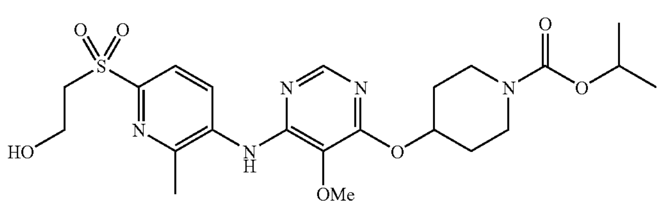 [SMILES: COc1c(Nc2ccc(S(=O)(=O)CCO)nc2C)ncnc1OC1CCN(C(=O)OC(C)C)CC1] | 4-{6-[6-(2-Hydroxy-ethanesulfonyl)-2-methyl-pyridin-3-ylamino]-5-methoxy-pyrimidin-4-yloxy}-piperidine-1-carboxylic acid isopropyl ester |
| 93 | 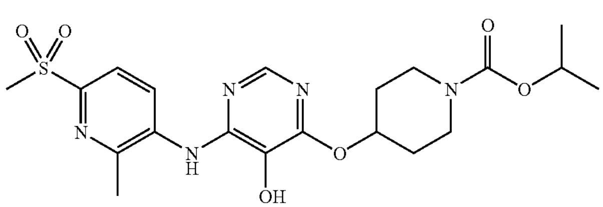 [SMILES: Cc1nc(S(C)(=O)=O)ccc1Nc1ncnc(OC2CCN(C(=O)OC(C)C)CC2)c1O] | 4-[5-Hydroxy-6-(6-methanesulfonyl-2-methyl-pyridin-3-ylamino)-pyrimidin-4-yloxy]-piperidine-1-carboxylic acid isopropyl ester |
| 94 | 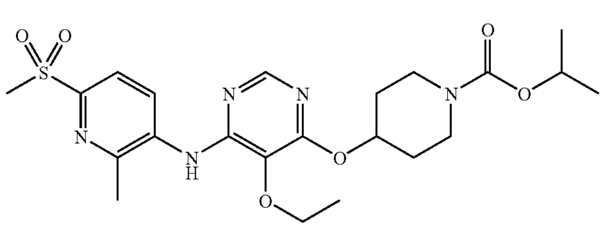 [SMILES: CCOc1c(Nc2ccc(S(C)(=O)=O)nc2C)ncnc1OC1CCN(C(=O)OC(C)C)CC1] | 4-[5-Ethoxy-6-(6-methanesulfonyl-2-methyl-pyridin-3-ylamino)-pyrimidin-4-yloxy]-piperidine-1-carboxylic acid isopropyl ester |

TABLE A-continued

| Cmpd No. | Structure | Chemical Name |
|---|---|---|
| 95 | 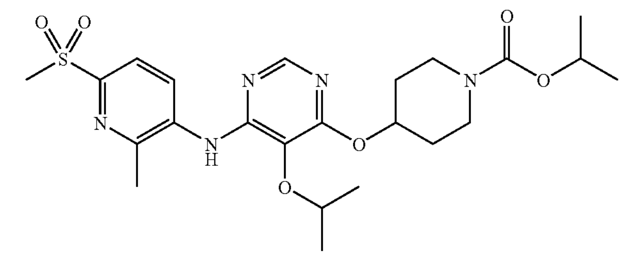 [SMILES: Cc1nc(S(C)(=O)=O)ccc1Nc1ncnc(OC2CCN(C(=O)OC(C)C)CC2)c1OC(C)C] | 4-[5-Isopropoxy-6-(6-methanesulfonyl-2-methyl-pyridin-3-ylamino)-pyrimidin-4-yloxy]-piperidine-1-carboxylic acid isopropyl ester |
| 96 | 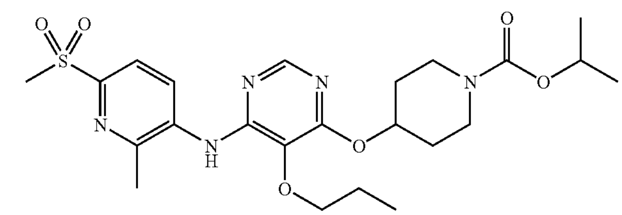 [SMILES: CCCOc1c(Nc2ccc(S(C)(=O)=O)nc2C)ncnc1OC1CCN(C(=O)OC(C)C)CC1] | 4-[6-(6-Methanesulfonyl-2-methyl-pyridin-3-ylamino)-5-propoxy-pyrimidin-4-yloxyl]-piperidine-1-carboxylic acid isopropyl ester |
| 97 | 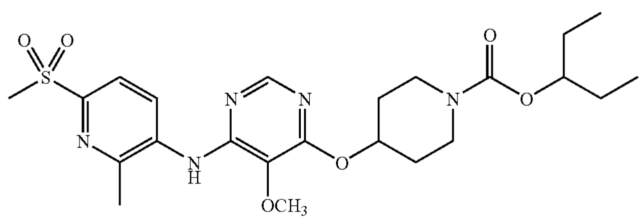 [SMILES: CCC(CC)OC(=O)N1CCC(Oc2ncnc(Nc3ccc(S(C)(=O)=O)nc3C)c2OC)CC1] | 4-[6-(6-Methanesulfonyl-2-methyl-pyridin-3-ylamino)-5-methoxy-pyrimidin-4-yloxy]-piperidine-1-carboxylic acid 1-ethyl-propyl ester |
| 98 | 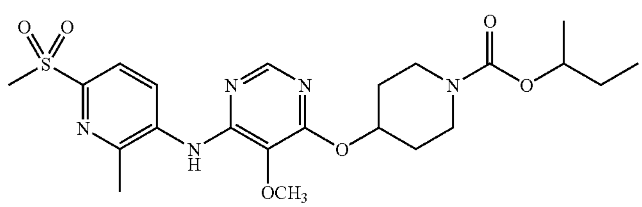 [SMILES: CCC(C)OC(=O)N1CCC(Oc2ncnc(Nc3ccc(S(C)(=O)=O)nc3C)c2OC)CC1] | 4-[6-(6-Methanesulfonyl-2-methyl-pyridin-3-ylamino)-5-methoxy-pyrimidin-4-yloxy]-piperidine-1-carboxylic acid sec-butyl ester |
| 99 | 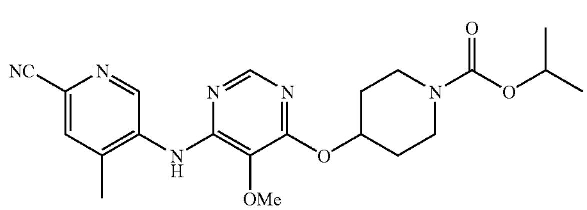 | 4-[6-(6-Cyano-4-methyl-pyridin-3-ylamino)-5-methoxy-pyrimidin-4-yloxy]-piperidine-1-carboxylic acid isopropyl ester |
| 100 | 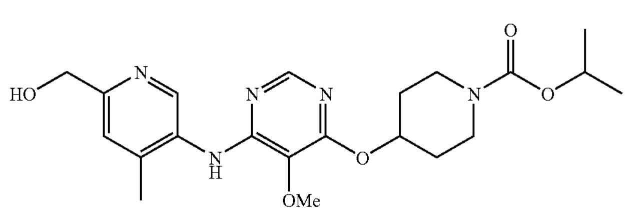 [SMILES: COc1c(Nc2cnc(CO)cc2C)ncnc1OC1CCN(C(=O)OC(C)C)CC1] | 4-[6-(6-Hydroxymethyl-4-methyl-pyridin-3-ylamino)-5-methoxy-pyrimidin-4-yloxy]-piperidine-1-carboxylic acid isopropyl ester |

TABLE A-continued

| Cmpd No. | Structure | Chemical Name |
|---|---|---|
| 101 | 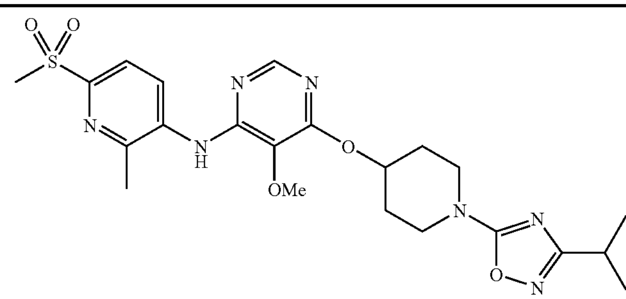 | {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine |
| 102 | 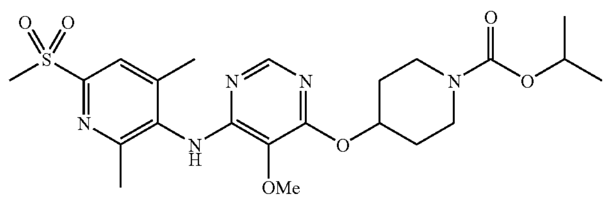 [SMILES: COc1c(Nc2c(C)cc(S(C)(=O)=O)nc2C)ncnc1OC1CCN(C(=O)OC(C)C)CC1] | 4-[6-(6-Methanesulfonyl-2,4-dimethyl-pyridin-3-ylamino)-5-methoxy-pyrimidin-4-yloxy]-piperidine-1-carboxylic acid isopropyl ester |
| 103 | 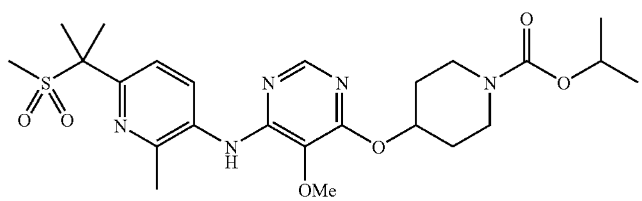 [SMILES: COc1c(Nc2ccc(C(C)(C)S(C)(=O)=O)nc2C)ncnc1OC1CCN(C(=O)OC(C)C)CC1] | 4-{6-[6-(1-Methanesulfonyl-1-methyl-ethyl)-2-methyl-pyridin-3-ylamino]-5-methoxy-pyrimidin-4-yloxy}-piperidine-1-carboxylic acid isopropyl ester |

Additionally, compounds of the present invention, including those illustrated in TABLE A, encompass all pharmaceutically acceptable salts, solvates, and particularly hydrates, thereof.

General Synthetic Methods

The de novo biosynthesis of pyrimidine nucleotides provides essential precursors for multiple growth-related events in higher eukaryotes. Assembled from ATP, bicarbonate and glutamine, the uracil and cytosine nucleotides are fuel for the synthesis of RNA, DNA, phospholipids, UDP sugars and glycogen. Over the past 2 decades considerable progress has been made in elucidating the mechanisms by which cellular pyrmidines are modulated to meet the needs of the cell. These studies point to increasing evidence for cooperation between key cell signaling pathways and basic elements of cellular metabolism, and suggest that these events have the potential to determine distinct cellular fates, including growth, differentiation and death.

As a result of their profound biological significance in higher eukaryotes and utilization of the pyrimidine core in a number of marketed drugs (Scheme 1) and other medicinally relevant compounds, pyrimidines and pyridines play pivotal roles as chemotypes in drug discovery campaigns. As a direct consequence of this there is a wealth of scientific literature describing synthetic construction, as well as chemical modification and elaboration of these classes of heterocycles.

Scheme 1

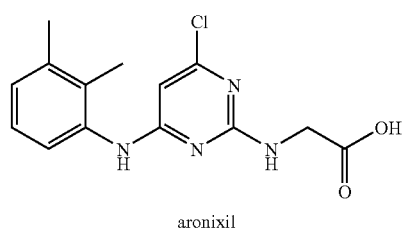

aronixil

[1]

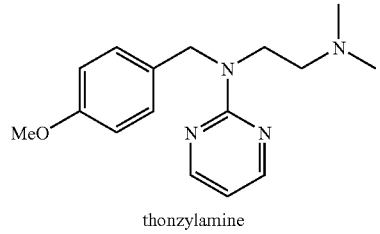

thonzylamine

[2]

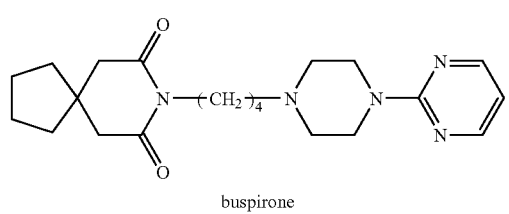

buspirone

[3]

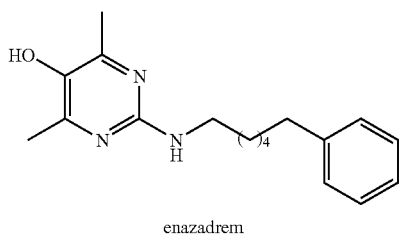

enazadrem

The novel substituted pyridine and pyrimidine derivatives of the current invention can prepared according to a variety of synthetic manipulations, all of which would be familiar to one skilled in the art of synthetic organic chemistry. Certain methods for the preparation of compounds of the present invention include, but are not limited to, those described in Schemes 2-9 as set forth in this section of the specification.

Common dichloro-substituted intermediate 8, used as a starting point for the synthesis of compounds of the present invention can be prepared as depicted in Scheme 2a. This is accomplished in two steps from a di-$C_{1-6}$-alkylmalonate, one particularly useful di-$C_{1-6}$-alkylmalonate is diethyl malonate 5. Cyclization to the 4,6-dihydroxypyrimidine 7 is achieved by reacting 5 with formamidine in the presence of an alkali metal alkoxide, by mixing the malonate and all or part of the formamidine with the alkoxide or with the alkoxide and the rest of the formamide. Alternative reagents such as dimethylmalonate, sodium methoxide, formamide, in low molecular weight alcoholic solvents, including methanol, ethanol, 2-propanol and the like, may be utilized in the synthesis by heating at a temperature range between about 80 to about 100° C. for about 30 mins to about 90 mins followed by a mineral acid work up. Preparation of dihydroxypyrimidines can also be achieved using microorganisms such as *Rhodococcus* (see for reference WO97008152 A1).

One intermediate used in the preparation of compounds of the present invention is Intermediate 8a. Chlorination of the 4 and 6 ring positions to produce Intermediate 8a maybe carried out by reacting 7 with a chlorinating reagent, such as, phosgene, POCl$_3$ (for reference see A. Gomtsyan et al., J. Med. Chem. 2002, 45, 3639-3648), thionyl chloride, oxalyl chloride and by mixtures of the above reagents including PCl$_3$/POCl$_3$ at elevated reaction temperatures. The preparation of Intermediate 8a is illustrated in Scheme 2a below:

Scheme 2a

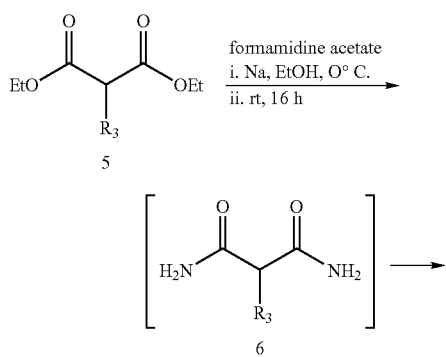

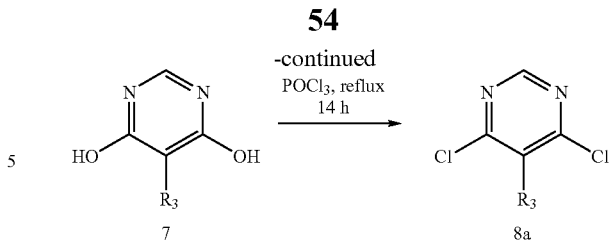

Another intermediate that can be used in the preparation of compounds of the present invention is Intermediate 8b. The preparation of Intermediate 8b can be prepared as illustrated in Scheme 2b. Nitration of 2-chloro-3-hydroxy pyridine provides 2-chloro-4-nitro-pyridin-3-ol. The hydroxyl can be protected with a suitable group for use during the remaining steps of the scheme or the hydroxyl group can be alkylated, for example, methylated using TMS diazomethane to give 2-chloro-3-methoxy-4-nitro-pyridine. Nucleophilic substitution of the nitro group with a 4-hydroxyl piperidine can provide Intermediate 8b. Using similar steps, general Intermediate 8c can be prepared.

Scheme 2b

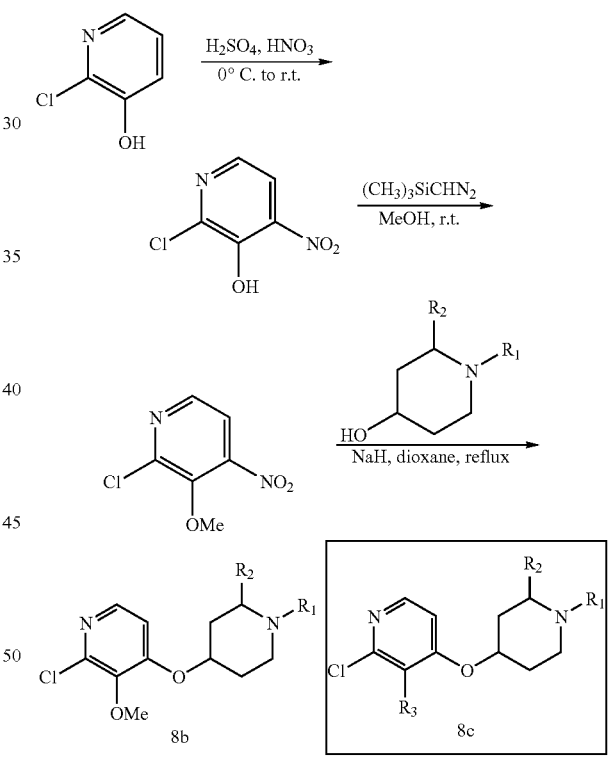

Conventional thermal aromatic substitution reactions of amines and alcohols with halogenated pyrimidines have been well documented (see for example A. G. Arvanitis et al., J. Medicinal Chemistry, 1999, 42, 805-818 and references therein). Nucleophilic aromatic (SN$_{Ar}$) substitution reactions of electron deficient halogenated pyrimidines are usually rapid and high yielding. However, in certain cases, such as electron rich or neutral halogenated heterocycles, successful substitution is afforded by prolonged heating. To facilitate rapid entry into many of the compounds of the invention microwave synthesis was utilized (Schemes 3 and 4). The Smith synthesizer from Personal Chemistry is a commercially available focussed field heating instrument that provides safer and more uniform conditions for performing the base catalysed substitution reactions depicted in Scheme. Bases employed for such conversions include tertiary amines such as triethylamine, Hunig's base (i.e. diisopropyl-ethylamine), N-methylmorpholine and the like. Alternatively, one skilled in the art can employ alkali metal hydrides, alkali metal carbonates (such as, $Li_2CO_3$, $Na_2CO_3$, $K_2CO_3$ and the like), an alkali metal hydrogencarbonate (such as, $LiHCO_3$, $NaHCO_3$, $KHCO_3$ and the like). Suitable solvents include ethereal solvent such as tetrahydrofuran, 1,4-dioxane, and the like. Reaction times to access typical intermediates, such as Intermediate 10, can range from about 300 s to about 3000 s and when conventional thermal methods are employed about 20 mins to about 120 mins.

transition metal catalyst selected from, but not limited to, $Pd_2(dba)_3$, $Pd(OAc)_2$, CuI, $Cu(OTf)_2$, $Ni(COD)_2$, $Ni(acac)_2$ in a suitable anhydrous solvent (such as, THF, 1,4-dioxane, and the like) with as strong alkali metal alkoxide base (such as, $NaO^tBu$, $KO^tBu$ and the like). A suitable ligand employed in this step can be selected from BINAP, $P(o-tolyl)_3$, $tBu_3P$, DPPF, $P[N(^iBu)CH_2CH_3]_3N$ and the like when the catalyst is a palladium derived complex.

Alternatively, for "Ullman-type" aryl aminations catalyzed by copper derived complexes, the base employed may be selected from an alkali metal carbonate in an aprotic polar solvent (such as N,N-dimethylacetamide, DMF, DMSO, and the like) with L-proline, N-methylglycine or diethylsalicyclamide as the ligand (for reference see D. Ma, Organic Lett., 2003, 5, 14, 2453-2455).

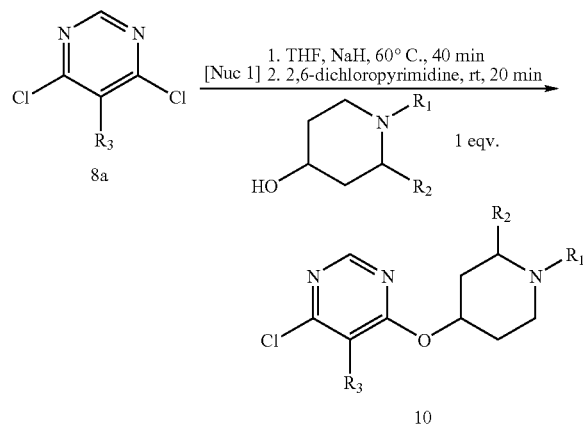

Scheme 3

Methods for conversion of intermediate monosubstituted pyridine and pyrimidine 10 are illustrated in Scheme 4. One method includes using palladium catalysed aminations. This synthetic strategy has emerged as a powerful tool for synthesis of substituted aryl and heteroaryl anilines in recent times (for reference see S. L. Buchwald., Top. Curr. Chem., 2002, 219, 131 and references therein). Addition reactions can be conducted using a suitably substituted amine (Intermediate 16) or alcohol (Intermediate 17) in the presence of a palladium or alternative

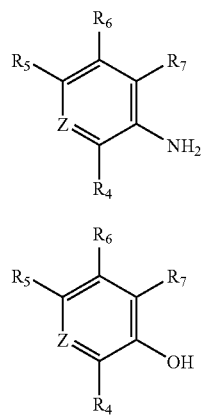

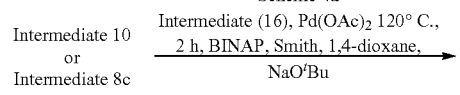

Scheme 4-Addition of Nuc 2

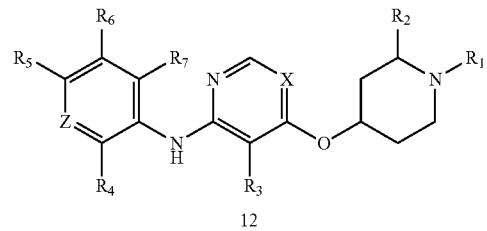

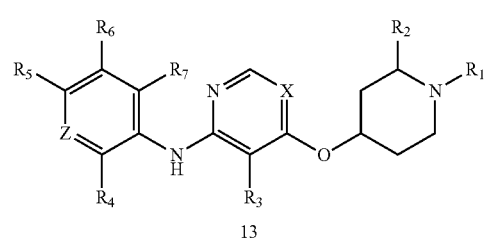

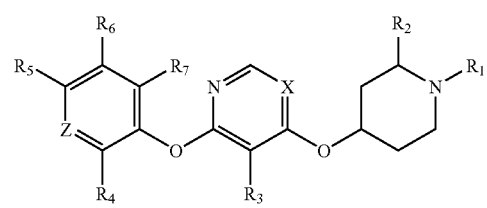

-continued

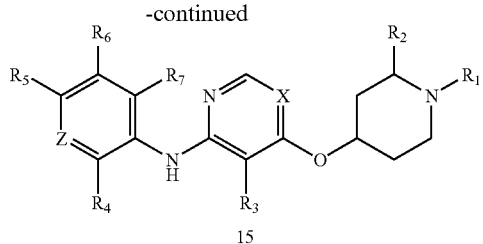

15

Compounds of general Formulae 12 to 15 may also be obtained by reversing the order of the reaction steps (i.e. introduction of Nuc 2 followed by Nuc 1), wherein the initial step comprises of introduction of either Intermediate 16 or 17 by using base in $^i$PrOH followed by addition of 4N HCl in dioxane followed by addition of the substituted 4-hydroxyl piperdinyl.

As illustrated in Scheme 5, a similar transition metal catalyzed couplings can also be utilized to obtain molecules of general Formula 21a (Scheme 5a) wherein the Intermediate 20 (Hal=Br, I and the like) is modified to give analogs with alkyl amino substituents (i.e., $NR_aR_b$, wherein $R_a$ and $R_b$ are each independently H, $C_{1-6}$ alkyl or a $C_{1-4}$ alkyl optionally substituted as described herein, or $R_a$ and $R_b$ together with the nitrogen form a heterocyclic ring, such as pyrrolidine, piperdine, and the like). Alternatively, the linker atom can be oxygen by utilizing the CuI catalyzed method for aromatic C—O formation described by Buchwald (see for reference S. L. Buchwald; Organic Lett., 2002, 4, 6, 973-976) by utilizing, for example, 10 mol % CuI, 20 mol % 1,10-phenanthroline, 2 equivalents of $Cs_2CO_3$, at 110° C. for 18 h, with an iodo substitution in Intermediate 20 (Scheme 5b).

Alternatively, compounds of Formulae 21a and 21b can also be prepared as illustrated in Scheme 5c.

Scheme 5c

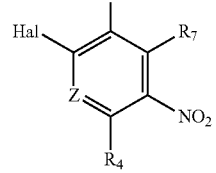

This method is particularly useful for when $R_3$ is an alkoxy group. A variety of alcohol, amine and thiol compounds can be introduced resulting in the $R_5$ group to provide Intermediates 21c, 21d and 21e. Intermediates 21c, 21d and 21e can subsequently be reduced to the corresponding amines and Scheme 5

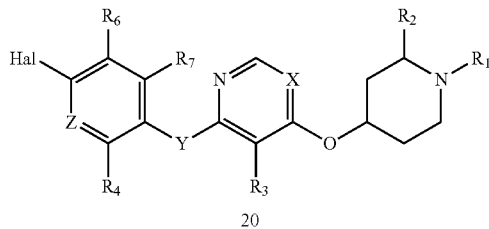

20

Scheme 5a
$R_aR_bNH$, CuI, $K_2CO_3$,
L-proline, DMSO,
Smith, 9 h, 80° C.

Scheme 5b
$R_aOH$, CuI, $K_2CO_3$,
1,10-phenanthroline,
$Cs_2CO_3$, Smith, 18 h, 110° C.

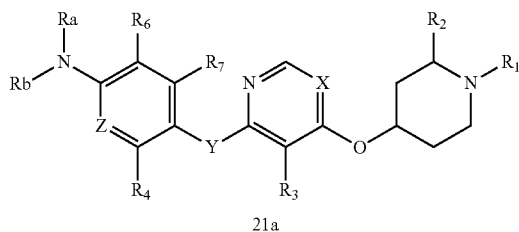

21a

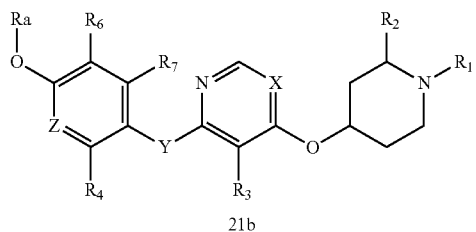

21b finally coupled to provide compounds of the present invention. Coupling methods include those described in Scheme 4a to 4d, supra.

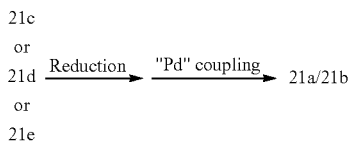

A particular substitution for Intermediates 12, 13, 14, and 15 is wherein $R_1$=C(O)O—$C_{1-6}$ alkyl wherein the alkyl is optionally substituted as described herein. Urethanes of this type can be prepared directly from intermediates depicted in Schemes 3 and 4 when $R_1$=H. In certain reactions, use of a suitable nitrogen protecting group (such as, $^tBoc$, Cbz, Moz, Alloc, Fmoc and the like) may be necessary during further chemical modification of the core. Deprotection can be achieved using standard reagents familiar to one skilled in the art (these might include TFA, mineral acid, Palladium/hydrogen gas and the like in an alcoholic or ethereal solvent system chosen from methanol, ethanol, tert-butanol, THF, 1,4-dioxane, and the like). On occasion wherein the target molecule contains 2 protecting groups, an orthogonal protection strategy may be adopted. The deprotected secondary amine ($R_1$=H) can subsequently be modified accordingly.

Schemes 6 and 7 illustrate such chemistries wherein generation of a carbamate can be executed using an appropriate reaction in the presence of a base, for example, a tertiary amine base such as TEA, DIEA and the like, in an inert solvent system.

As illustrated in Scheme 6, Urethane 23 can be obtained by a urethane reaction using $R_cOC(O)$-halide (wherein $R_c$ is $C_{1-6}$ alkyl optionally substituted as described herein, and halide is chloro, bromo, or iodo, particularly useful is chloro) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, poly-4-vinylpyridine), and the like).

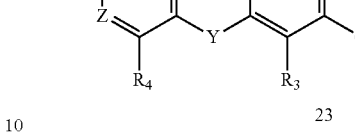

The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about −20° C. to 120° C. preferably about 0° C. to 100° C.

Scheme 7 illustrates the synthesis of aryl/hetero-alkyl sulfones 26 which are used as aryl building blocks in Scheme 4 of the present invention. The common methods for preparing these sulfones include the oxidation of sulfides using an oxidizing agent (i.e., $H_2O_2$) or the sulfonylation of arenes using aryl sulfonyl halides or aryl sulfonic acids in the presence of a strong acid catalyst (see for general reference: the Organic Chemistry of Sulfur; Oae S., Ed.; Plenum Press: New York, 1977). Optimal conversion to the optionally 2,5-disubstituted arene 26 was achieved thermally wherein Hal is preferably iodo using 5 mol % $(CuOTf)_2PhH$ and 10 mol % N,N'-dimethylethylenediamine in DMSO by the method of Wang et al (see for reference Wang Z.; Baskin J. M., Org. Lett., 2002, 4, 25, 4423-4425). In some embodiments, $R_4$ and $R_6$ are each independently H, halogen, or $C_{1-6}$ alkyl; $R_7$ is H; Hal=Br, I; and Y=O or NH.

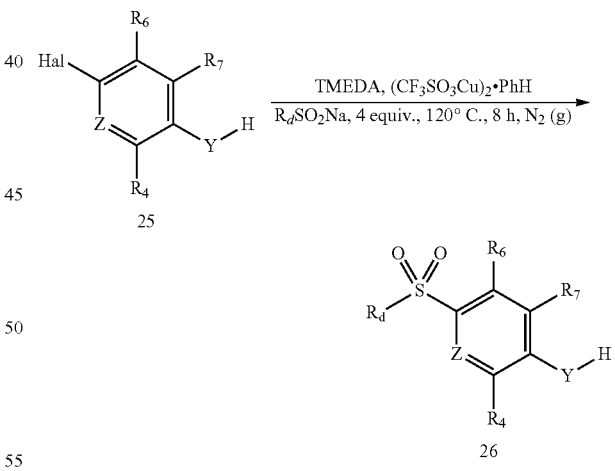

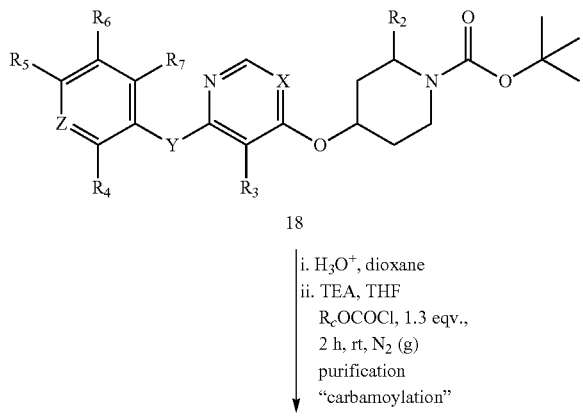

Alternative standard organic synthetic methods may be used to introduce alternate substituents in to the Ar component. In one example wherein the linker atom is Y=NH, the manipulation maybe carried out by protecting the aniline amino functionality using standard FmocCl and CbzCl protection deprotection steps familiar to one skilled in the art (Scheme 8, wherein $R_4$, $R_6$ and $R_7$ have the same meaning as described herein) and subsequently using the deprotected aniline in subsequent steps such as those depicted in Scheme 4. In some embodiments of the invention $R_4$ is halogen, and $R_6$ is H or halogen.

Scheme 8

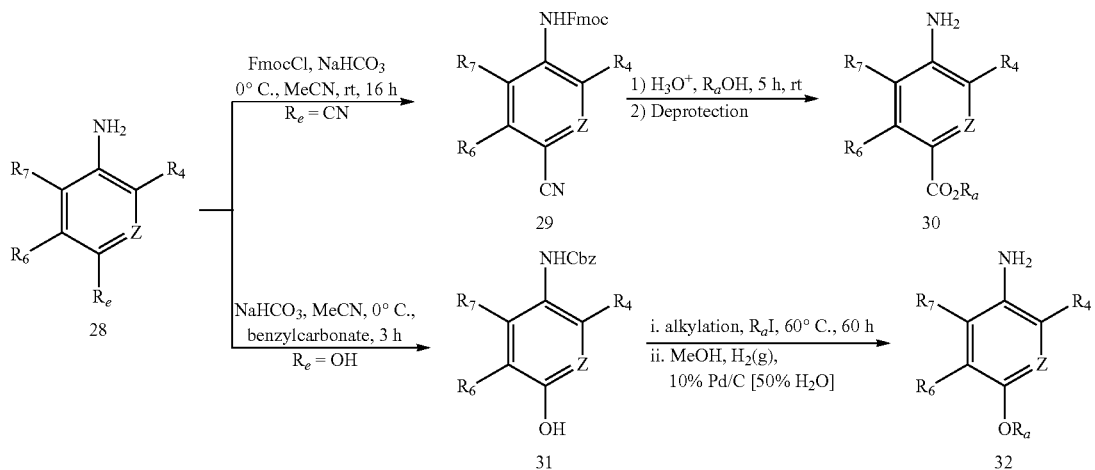

Synthesis of the 3,5-oxadiazolyl variant is depicted in Scheme 9. Zinc(II)chloride catalysed coupling of amidoxime 34 with 4-hydroxypiperidine, CNBr derived 36 yielded building block 37 after acidic workup, which was subsequently utilized in reaction sequences depicted as illustrated in Scheme 3.

Scheme 9

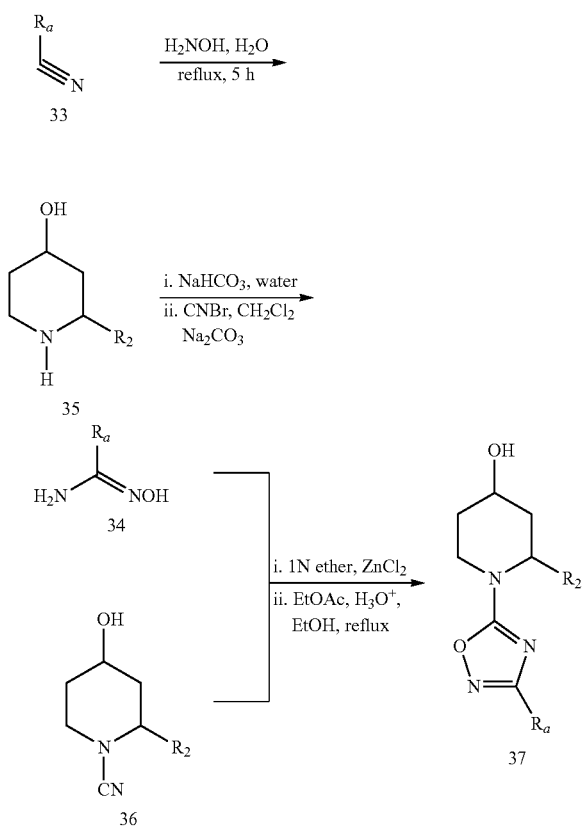

Protecting groups may be required for various functionality or functionalities during the synthesis of some of the compounds of the invention. Accordingly, representative protecting groups that are suitable for a wide variety of synthetic transformations are disclosed in Greene and Wuts, *Protective Groups in Organic Synthesis,* 3rd edition, John Wiley & Sons, New York, 1999, the disclosure of which is incorporated herein by reference in its entirety.

The present invention also encompasses diastereomers as well as optical isomers, e.g. mixtures of enantiomers including racemic mixtures, as well as individual enantiomers and diastereomers, which arise as a consequence of structural asymmetry in certain compounds of the present invention. Separation of the individual isomers or selective synthesis of the individual isomers is accomplished by application of various methods which are well known to practitioners in the art.

Indications and Methods of Treatment

In addition to the foregoing beneficial uses for compounds of the present invention disclosed herein, compounds of the invention are useful in the treatment of additional diseases. Without limitation, these include the following.

The most significant pathologies in Type II diabetes are impaired insulin signaling at its target tissues ("insulin resistance") and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling-systems which function in this manner are well-characterized and include the gut peptides GLP1, GIP and PACAP. These hormones act via their cognate G-protein coupled receptor to stimulate the production of cAMP in pancreatic β-cells. The increased cAMP does not appear to result in stimulation of insulin release during the fasting or preprandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including RUP3, would also stimulate the release of endogenous insulin and consequently promote normoglycemia in Type II diabetes.

It is also established that increased cAMP, for example as a result of GLP1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRS, including RUP3, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In some embodiments of the present invention the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

One aspect of the present invention pertains to methods for treatment of a metabolic-related disorder in an individual comprising administering to the individual in need of such treatment a therapeutically effective amount of a compound as described herein or a pharmaceutical composition thereof. In some embodiments the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments the metabolic-related disorder is type II diabetes. In some embodiments the metabolic-related disorder is hyperglycemia. In some embodiments the metabolic-related disorder is hyperlipidemia. In some embodiments the metabolic-related disorder is hypertriglyceridemia. In some embodiments the metabolic-related disorder is type I diabetes. In some embodiments the metabolic-related disorder is dyslipidemia. In some embodiments the metabolic-related disorder is syndrome X. In some embodiments the individual is a mammal. In some embodiments the mammal is a human.

One aspect of the present invention pertains to methods of decreasing food intake of an individual comprising administering to the individual in need thereof a therapeutically effective amount of a compound of the present invention or pharmaceutical composition thereof. In some embodiments the individual is a mammal. In some embodiments the mammal is a human.

One aspect of the present invention pertains to methods of inducing satiety in an individual comprising administering to the individual in need of such treatment a therapeutically effective amount of a compound of the present invention or pharmaceutical composition thereof. In some embodiments the individual is a mammal. In some embodiments the mammal is a human.

One aspect of the present invention pertains to methods of controlling or decreasing weight gain of an individual comprising administering to the individual in need of such treatment a therapeutically effective amount of a compound of the present invention or pharmaceutical composition thereof. In some embodiments the individual is a mammal. In some embodiments the mammal is a human.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to methods of modulating a RUP3 receptor in an individual comprising contacting the receptor with a compound of the invention. In some embodiments, the compound is an agonist. In some embodiments, the compound is an inverse agonist. In some embodiments, the compound is an antagonist. In some embodiments, the modulation of the RUP3 receptor is treatment of a metabolic-related disorder and complications thereof. In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X. In some embodiments, the individual is a mammal. In some embodiments, the mammal is a human.

Some embodiments of the present invention include a method of modulating a RUP3 receptor in an individual comprising contacting the receptor with a compound of the present invention wherein the modulation of the RUP3 receptor reduces food intake of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor induces satiety in the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor controls or reduces weight gain of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

One aspect of the present invention pertains to use of a compound as described herein, for production of a medicament for use in treatment of a metabolic-related disorder. In some embodiments, the metabolic-related disorder is type II diabetes, inadequate glucose tolerance, insulin resistance, hyperglycemia, hyperlipidemia, hypertriglyceridemia, hypercholesterolemia, dyslipidemia or syndrome X.

One aspect of the present invention pertains to use of a compound as described herein, for production of a medicament for use in decreasing food intake of an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use of inducing satiety in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use in controlling or decreasing weight gain in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to a compound, as described herein, for use in a method of treatment of the human or animal body by therapy.

One aspect of the present invention pertains to a compound, as described herein, for use in a method of treatment of a metabolic-related disorder of the human or animal body by therapy.

Pharmaceutical Compositions and Salts

A further aspect of the present invention pertains to pharmaceutical compositions comprising one or more compounds of Formula (Ia) or any formula disclosed herein, and one or more pharmaceutically acceptable carriers. Some embodiments of the present invention pertain to pharmaceutical compositions comprising a compound of Formula (Ia) and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention, including pharmaceutically acceptable salts and solvates thereof, can be used as active ingredients in pharmaceutical compositions, specifically as RUP3 receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodent diabetes model as described in Example 5, infra (as well as other animal models known in the art, such as those reported by Reed and Scribner in Diabetes, Obesity and Metabolism, 1, 1999, 75-86). In some circumstances, these extrapolations may merely be based on the weight of the animal in the respective model in comparison to another, such as a mammal, preferably a human, however, more often, these extrapolations are not simply based on weights, but rather incorporate a variety of factors. Representative factors include, but not limited to, the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct product of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

In addition, compounds according to the invention may optionally exist as pharmaceutically acceptable basic addition salts. For example, these salts can be prepared in situ during the final isolation and purification of the compounds of the invention, or separately by reacting an acidic moiety, such as a carboxylic acid, with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

In some embodiments the pharmaceutical agents is selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

It is noted that when the RUP3 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as RUP3 receptor modulators, for the treatment of obesity in domestic animals (e.g., cats and dogs), and RUP3 receptor modulators in other domestic animals where no disease or disorder is evident (e.g., food-oriented animals such as cows, chickens, fish, etc.). Those of ordinary skill in the art are readily credited with understanding the utility of such compounds in such settings.

Combination Therapy

In the context of the present invention, a compound as described herein or pharmaceutical composition thereof can be utilized for modulating the activity of RUP3 receptor mediated diseases, conditions and/or disorders as described herein. Examples of modulating the activity of RUP3 receptor mediated diseases include the treatment of metabolic related disorders. Metabolic related disorders includes, but not limited to, hyperlipidemia, type 1 diabetes, type 2 diabetes mellitus, and conditions associated therewith, such as, but not limited to coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance. In some embodiments, metabolic related disorders include type I diabetes, type II diabetes, inadequate glucose tolerance, insulin resistance, hyperglycemia, hyperlipidemia, hypertriglyceridemia, hypercholesterolemia, dyslipidemia and syndrome X. Other examples of modulating the activity of RUP3 receptor mediated diseases include the treatment of obesity and/or overweight by decreasing food intake, inducing satiation (i.e., the feeling of fullness), controlling weight gain, decreasing body weight and/or affecting metabolism such that the recipient loses weight and/or maintains weight.

While the compounds of the invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of prophylaxis and/or treatment of a metabolic related disorder or a weight related disorder, such as obesity, comprising administering to an individual in need of prophylaxis and/or treatment a therapeutically effective amount of a compound of the present invention in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of metabolic related disorders and/or concomitant diseases thereof. For example, but not limited to, congestive heart failure, type I diabetes, type II diabetes, inadequate glucose tolerance, insulin resistance, hyperglycemia, hyperlipidemia, hypertriglyceridemia, hypercholesterolemia, dyslipidemia, syndrome X, retinopathy, nephropathy and neuropathy. Treatment of one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists, adiponectin and the like. In accordance to one aspect of the present invention, a compound of the present can be used in combination with a pharmaceutical agent or agents belonging to one or more of the classes of drugs cited herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic related disorders.

Some embodiments of the present invention include methods of treatment of a disease, disorder, condition or complication thereof as described herein, comprising administering to an individual in need of such treatment a therapeutically effective amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, methods of the present invention include compounds of the present invention and the pharmaceutical agents are administered separately. In further embodiments, compounds of the present invention and the pharmaceutical agents are administered together.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing HbA1c. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the Fibrates. Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Suitable pharmaceutical agents that can be used in conjunction with compounds of the present invention include the squalene synthesis inhibitors. Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

Suitable pharmaceutical agents that can be used in conjunction with compounds of the present invention include, but not limited to, amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds), insulin signalling pathway modulators, like inhibitors of protein tyrosine phosphatases (PTPases), non-small mol. mimetic compds. and inhibitors of glutamine-fructose-6-phosphate amidotransferase (GFAT), compds. influencing a dysregulated hepatic glucose prodn., like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK), pyruvate dehydrogenase kinase (PDHK) inhibitors, insulin sensitivity enhancers, insulin secretion enhancers, inhibitors of gastric emptying, $\alpha_2$-adrenergic antagonists and retinoid X receptor (RXR) agonists.

Suitable pharmaceutical agents that can be used in conjunction with compounds of the present invention include inhibitors of dipeptidyl peptidase IV (DPP-IV). Examples of DPP-IV inhibitors include valine-pyrrolidide, 3-(L-Isoleucyl)thiazolidine, 1-[2-[5-cyanopyridin-2-yl)amino]ethylamino]acetyl-2-cyano-(S)-pyrrolidine (NVP-DPP728), 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one (MK-0431), (1-[[3-hydroxy-1-adamantyl)amino] acetyl]-2-cyano-(S)-pyrrolidine (LAF237), (1S,3S,5S)-2-[2 (S)-Amino-2-(3-hydroxyadamantan-1-yl)acetyl]-2-azabicyclo[3.1.0]hexane-3-carbonitrile (BMS477118), [1-[2 (S)-Amino-3-methylbutyryl]pyrrolidin-2(R)-yl]boronic acid (PT-100), GSK-823093, PSN-9301, T-6666, SYR-322, SYR-619 and DPP-IV inhibitors known in the art. Exemplary DPP-IV inhibitors known in the art include but are not limited to those disclosed in the following International Applications: WO 2005/075426, WO 2005/072530, WO 2005/063750, WO 2005/058849, WO 2005/047297, WO 2005/042488, WO 2005/040095, WO 2005/033099, WO 2005/030751, WO 2005/030127, WO 2005/026148, WO 2005/025554, WO 2005/023762, WO 2005/020920, WO 03/04498, WO 00/34241, WO 98/19998 and WO 97/40832. In some embodiments, the DPP-IV inhibitor is a selective DPP-IV inhibitor, having selectivity for DPP-IV over closely related peptidases, such as one or more of post-proline-cleaving enzyme (PPCE), dipeptidyl peptidase II (DPP-II), dipeptidyl peptidase 8 (DPP-8) and dipeptidyl peptidase 9 (DPP-9).

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds of the present invention are administered as a combination therapy with another active compound the therapeutic agents can be formulated as a separate pharmaceutical compositions given at the same time or at different times, or the therapeutic agents can be given as a single composition.

Other Utilities

Another object of the present invention relates to radio-labeled compounds as described herein that would be useful not only in radio-imaging but also in assays, both in vitro and in vivo, for localizing and quantitating the RUP3 receptor in tissue samples, including human, and for identifying RUP3 receptor ligands by inhibition binding of a radio-labeled compound. It is a further object of this invention to develop novel RUP3 receptor assays of which comprise such radio-labeled compounds.

The present invention embraces isotopically-labeled compounds of Formula (Ia) and any subgenera herein, such as but not limited to, Formula (Ia) through Formula (IIi). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro RUP3 receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of present invention that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3H$]—This procedure is rather inexpensive and requires precursors containing reducible functional groups such as aldehydes, ketones, lactones, esters, and the like.

C. Reduction with Lithium Aluminum Hydride [$^3H$]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3H$]—This procedure is usually employed to prepare O-methyl or N-methyl ($^3H$) products by treating appropriate precursors with high specific activity methyl iodide ($^3H$). This method in general allows for higher specific activity, such as for example, about 70-90 Ci/mmol.

Synthetic methods for incorporating activity levels of $^{125}I$ into target molecules include:

A. Sandmeyer and like reactions—This procedure transforms an aryl or heteroaryl amine into a diazonium salt, such as a tetrafluoroborate salt, and subsequently to $^{125}I$ labeled compound using Na$^{125}I$. A represented procedure was reported by Zhu, D.-G. and co-workers in J. Org. Chem. 2002, 67, 943-948.

B. Ortho $^{125}I$odination of phenols—This procedure allows for the incorporation of $^{125}I$ at the ortho position of a phenol as reported by Collier, T. L. and co-workers in J. Labeled Compd Radiopharm. 1999, 42, S264-S266.

C. Aryl and heteroaryl bromide exchange with $^{125}I$—This method is generally a two step process. The first step is the conversion of the aryl or heteroaryl bromide to the corresponding tri-alkyltin intermediate using for example, a Pd catalyzed reaction [i.e. Pd(Ph₃P)4] or through an aryl or heteroaryl lithium, in the presence of a tri-alkyltinhalide or hexaalkylditin [e.g., (CH₃)₃SnSn(CH₃)₃]. A represented procedure was reported by Bas, M.-D. and co-workers in J. Labeled Compd Radiopharm. 2001, 44, S280-S282.

A radio-labeled RUP3 receptor compound of present invention can be used in a screening assay to identify/evaluate compounds. In general terms, a newly synthesized or identified compound (i.e., test compound) can be evaluated for its ability to reduce binding of the "radio-labeled compound" of the present invention to the RUP3 receptor. Accordingly, the ability of a test compound to compete with the "radio-labeled compound" of the present invention for the binding to the RUP3 receptor directly correlates to its binding affinity.

The labeled compounds of the present invention bind to the RUP3 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM, and in still yet another embodiment the labeled inhibitor has an IC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

The examples are provided to further define the invention without, however, limiting the invention to the specifics of these examples.

Example 1

96-Well Cyclic AMP Membrane Assay for RUP3

Materials:
1) Adenlyl cyclase Activation Flashplate Assay kit from Perkin Elmer—96 wells (SMP004B) and $^{125}$I tracer (NEX 130) which comes with the kit. Keep in refrigerator, in a box, and do not expose the Flashplates to light.
2) Phosphocreatine—Sigma P-7936
3) Creatine Phosphokinase—Sigma C-3755
4) GTP—Sigma G-8877
5) ATP—Sigma A-2383
6) IBMX—Sigma I-7018
7) Hepes—1M solution in distilled water—Gibco #15630080
8) MgCl₂—Sigma M-1028-1M Solution
9) NaCl—Sigma—S6546-5M Solution
10) Bradford Protein Assay Kit—Biorad #5000001
11) Proclin 300—Sigma #4-8126
Binding Buffer—filter through 45-micron Nalgene filter and keep in refrigerator. All buffers and membranes should be kept cold (in ice bucket) while performing assay.
20 mM Hepes, pH7.4
1 mM MgCl₂
100 mM NaCl 2× Regeneration Buffer (make in binding buffer):
20 mM Phosphocreatine (1.02 gm/200 ml binding buffer)
20 units Creatine phosphokinase (4 mg/200 ml)
20 uM GTP (make up 10.46 mg/ml in binding buffer and add 200 ul/200 ml)
0.2 mM ATP (22.04 mg/200 ml)
100 mM IBMX (44.4 mg IBMX dissolved in 1 ml 100% DMSO first and then add the entire amount to 200 ml of buffer).
Regeneration buffer can be aliquotted into 40-45 ml portions (in 50 ml sterile tubes) and kept frozen for up to 2 months. Simply put the tube in a beaker with room temperature water to thaw out the regeneration buffer on the day of the assay.

A. Assay Procedure
1) Pipet 50 ul regeneration buffer in all 96 wells using Matrix 1250 8-channel pipettor.
2) Pipet 5 ul DMSO in columns 1 and columns 11 and 12.
3) Pipet 50 ul cAMP standards in columns 11 and 12 in this format: 50 pmole/well for row A, 25 pmole/well for row B, 12.5 pmole/well for row C, 5 picomole/well for row D, 2.5 pmole/well for row E, 1.25 pmole/well for row F, 0.5 pmole/well for row G, and 0 pmole/well (buffer only) for row H.
4) Pipet 5 ul compounds from each well of a compound dilution plate, for IC50s, using the following dilution scheme:
Well H: 400 uM compound (final concentration of compound in reaction mix=5/100×400 uM=20uM
Well G: 1:10 dilution of Well H (i.e. 5 ul compound from well H+45 ul 100% DMSO) (final concentration=2 uM)
Well F: 1:10 dilution of well G (final concentration=0.2 uM)
Well E: 1:10 dilution of well F (final concentration=0.02 uM)
Well D: 1:10 dilution of well E (final concentration=0.002 uM)
Well C: 1:10 dilution of well D (final concentration=0.0002 uM
Well B: 1:10 dilution of well C (final concentration=0.00002 uM)
Well A: 1:10 dilution of well B (final concentration=0.000002 uM)
IC$_{50}$s or EC$_{50}$s are done in triplicate. One Flashplate can therefore be set up to handle 3 compounds. (i.e., columns 2, 3, and 4 are for compound #1, columns 5, 6, and 7 are for compound #2, and columns 8, 9, and 10 are for compound #3.)
5) Add 50 ul of RUP3 membranes to all wells in Columns 2 to 10. (Prior to the start of the assay, the frozen membrane pellets for both RUP3 and CMV (cells transfected with an expression plasmid containing no RUP3 sequences), are suspended in binding buffer, usually 1 ml binding buffer for 1 plate of membranes. The membranes are kept in ice all the time, and a polytron (Brinkmann polytron, model #PT-3100) is used (setting 6-7, for 15-20 seconds) to obtain a homogeneous membrane suspension.) Protein concentration is determined by Bradford protein assay kit using instructions given in the kit, using the standard supplied with the kit as a reference. The protein concentration of the membranes is adjusted with binding buffer, so that 50 ul membranes=15 ug protein (i.e. 0.3 mg/ml protein).
6) In column 1, Wells A, B, C, and D, add 50 ul RUP3 membranes. To wells E, F, G, and H, add 50 ul CMV membranes, (CMV membranes being of the same protein concentration as the RUP3 membranes).
7) Incubate 1 hour at room temperature with agitation on a rotating platform shaker. Cover with foil while shaking.

8) After 1 hour, add (to all 96 wells), 100 ul of the $^{125}$I tracer in detection buffer supplied with the Flashplate kit plus proclin, made up in the following manner:
Pipet per 10 ml per Flashplate: 100 ml of detection buffer+1 ml $^{125}$I+0.2 ml of Proclin (the proclin helps to stop the production of cAMP). Make a smaller quantity of detection buffer mix if you have fewer plates.
9) Shake the plates on a rotating platform shaker for 2 hours, covering the plates with lead sheeting.
10) Seal the plates with the plastic film sealers provided with the Flashplate kit.
11) Count the plates using a TRILUX 1450 Microbeta Counter. See the door of the counter to determine which counting protocol to use.
12) Data is analyzed on the Arena Database according to the RUP3 non-fusion, $IC_{50}$ $EC_{50}$ for 96-well cAMP membrane assay, and the compound numbers and the concentrations of compounds must be entered by the user.

B. Membrane Cyclase Criteria
1) Signal to Noise:
An acceptable signal-to-noise ratio for RUP3 can vary from 4 to 6. The raw cpms are approximately 1800 to 2500 for RUP3 and 3500-4500 for CMV. The cpm (or ultimately pmoles of cAMP/well) cannot be outside the standard curve, and should not approach well A of the standard curve (50 pmole/well) and well H (no cAMP). Generally, the pmoles of cAMP produced by RUP3 receptor are around 11 to 13 pmole/well (for 15 ug/well protein), and for CMV are between 2 to 3 pmole/well (for 15 ug protein/well).
2) Standard curve:
The slope should be linear and the error bars for duplicates should be very small. The receptor and CMV controls cannot be off scale of the standard curve, as described above. If the receptor controls are off the high end of the standard curve, i.e. 50 pmole/well or higher, one must repeat the experiment using less protein. However, such a case has not been observed with transiently transfected RUP3 membranes (10 ug DNA/15 cm plate, using 60 ul Lipofectamine, and preparing membranes after 24 hour of transfection.)
3) The $IC_{50}$ or $EC_{50}$ curve should be at 100% (+ or −20%) of control RUP3 membranes at the top, and should go down to 0 (or up to 20%) at the bottom. The standard error of the triplicate determinations should be + or −10%.

C. Stimulation of cAMP in HIT-T15 Cells
HIT-T15 (ATCC CRL#1777) is an immortalized hamster insulin-producing cell line. These cells express RUP3 and therefore can be used to assess the ability of RUP3 ligands to stimulate or inhibit cAMP accumulation via its endogenously expressed receptor. In this assay, cells are grown to 80% confluence and then distributed into a 96-well Flashplate (50,000 cells/well) for detection of cAMP via a "cAMP Flashplate Assay" (NEN, Cat # SMP004). Briefly, cells are placed into anti-cAMP antibody-coated wells that contain either vehicle, the test ligand(s) at a concentration of interest, or 1 uM forskolin. The latter is a direct activator of adenylyl cyclase and serves as a positive control for stimulation of cAMP in HIT-T15 cells. All conditions are tested in triplicate. After a 1 hour incubation to allow for stimulation of cAMP, a Detection Mix containing $^{125}$I-cAMP is added to each well and the plate is allowed to incubate for another 1 hour. The wells are then aspirated to remove unbound $^{125}$I-cAMP. Bound $^{125}$I-cAMP is detected using a Wallac Microbeta Counter. The amount of cAMP in each sample is determined by comparison to a standard curve, obtained by placing known concentrations of cAMP in some wells on the plate.

D. Stimulation of Insulin Secretion in HIT-T15 Cells
It is known that stimulation of cAMP in HIT-T15 cells causes an increase in insulin secretion when the glucose concentration in the culture media is changed from 3 mM to 15 mM. Thus, RUP3 ligands can also be tested for their ability to stimulate glucose-dependent insulin secretion (GSIS) in HIT-T15 cells. In this assay, 30,000 cells/well in a 12-well plate are incubated in culture media containing 3 mM glucose and no serum for 2 hours. The media is then changed; wells receive media containing either 3 mM or 15 mM glucose, and in both cases the media contains either vehicle (DMSO) or RUP3 ligand at a concentration of interest. Some wells receive media containing 1 uM forskolin as a positive control. All conditions are tested in triplicate. Cells are incubated for 30 minutes, and the amount of insulin secreted into the media is determined by ELISA, using a kit from either Peninsula Laboratories (Cat # ELIS-7536) or Crystal Chem Inc. (Cat #90060).

E. Stimulation of Insulin Secretion in Isolated Rat Islets
As with HIT-T15 cells, it is known that stimulation of cAMP in isolated rat islets causes an increase in insulin secretion when the glucose concentration in the culture media is changed from 60 mg/dl to 300 mg/dl. RUP3 is an endogenously expressed GPCR in the insulin-producing cells of rat islets. Thus, RUP3 ligands can also be tested for their ability to stimulate GSIS in rat islet cultures. This assay is performed as follows:

A. Select 75-150 islet equivalents (IEQ) for each assay condition using a dissecting microscope. Incubate overnight in low-glucose culture medium. (Optional.)
B. Divide the islets evenly into triplicate samples of 25-40 islet equivalents per sample. Transfer to 40 gm mesh sterile cell strainers in wells of a 6-well plate with 5 ml of low (60 mg/dl) glucose Krebs-Ringers Buffer (KRB) assay medium.
C. Incubate 30 minutes (1 hour if overnight step skipped) at 37° C. and 5% $CO_2$. Save the supernatants if a positive control for the RIA is desired.
D. Move strainers with islets to new wells with 5 ml/well low glucose KRB. This is the second pre-incubation and serves to remove residual or carryover insulin from the culture medium. Incubate 30 minutes.
E. Move strainers to next wells (Low 1) with 4 or 5 ml low glucose KRB. Incubate @ 37° C. for 30 minutes. Collect supernatants into low-binding polypropylene tubes pre-labelled for identification and keep cold.
F. Move strainers to high glucose wells (300 mg/dl, which is equivalent to 16.7 mM). Incubate and collect supernatants as before. Rinse islets in their strainers in low-glucose to remove residual insulin. If the rinse if to be collected for analysis, use one rinse well for each condition (i.e. set of triplicates.)
G. Move strainers to final wells with low-glucose assay medium (Low 2). Incubate and collect supernatants as before.
H. Keeping cold, centrifuge supernatants at 1800 rpm for 5 minutes @ 4-8° C. to remove small islets/islet pieces that escape the 40 mm mesh. Remove all but lower 0.5-1 ml and distribute in duplicate to pre-labelled low-binding tubes. Freeze and store at <−20° C. until insulin concentrations can be determined.
I. Insulin determinations are done as above, or by Linco Labs as a custom service, using their rat insulin RIA (Cat. # RI-13K).

Example 2

A. RT-PCR Analysis of RUP3 Expression in Human Tissues (FIG. 1A).

RT-PCR was applied to determine the tissue distribution of RUP3. Oligonucleotides used for PCR had the following sequences:

```
ZC47: 5'-CATTGCCGGGCTGTGGTTAGTGTC-3'
(forward primer), (SEQ ID NO: 3);

ZC48: 5'-GGCATAGATGAGTGGGTTGAGCAG-3'
(reverse primer), (SEQ ID NO: 4);
``` and the human multiple tissue cDNA panels (MTC, Clontech) were used as templates (1 ng cDNA per PCR amplification). Twenty-two (22) human tissues were analyzed. PCR was performed using Platinum PCR SuperMix (Life Technologies, Inc.; manufacture instructions were followed) in a 50 µl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 466 base-pair DNA fragment representing RUP3 was specifically amplified from cDNA of pancreas origin. Low expression was also evident in subregions of brain.

B. cDNA Dot-Blot Analysis of RUP3 Expression in Human Tissues (FIG. 1B).

Results from RT-PCR analysis were further confirmed in cDNA dot-blot analysis. In this assay, a dot-blot membrane containing cDNA from 50 human tissues (Clontech) was hybridized with a $^{32}$P-radiolabelled DNA probe having sequences derived from human RUP3. Hybridyzation signals were seen in pancreas and fetal liver, suggesting these tissues express RUP3. No significant expression was detected in other tissues analyzed.

C. Analysis of RUP3 by RT-PCR with Isolated Human Pancreatic Islets of Langerhans (FIG. 1C).

Further analysis of RUP3 by RT-PCR with isolated human pancreatic islets of Langerhans showed robust expression of RUP3 in islet cells but not in control samples.

D. Analysis of RUP3 Expression with cDNAs of Rat Origin by RT-PCR (FIG. 1D).

RUP3 expression was further analyzed with cDNAs of rat origin by RT-PCR technique. Tissue cDNAs used for this assay were obtained from Clontech except those for hypothalamus and islets, which were prepared in house. Concentrations of each cDNA sample were normalized via a control RT-PCR analysis of the house-keeping gene GAPDH before assaying for RUP3 expression. Oligonucleotides used for PCR had the following sequences:

```
rat RUP3 ("rRUP3") forward:
5'-CATGGGCCCTGCACCTTCTTTG-3'   (SEQ ID NO: 5);

rRUP3 reverse:
5'-GCTCCGGATGGCTGATGATAGTGA-3' (SEQ ID NO: 6).
```

PCR was performed using Platinum PCR SuperMix (Life Technologies, Inc.; manufacture instructions were followed) in a 50 µl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 547 base-pair DNA fragment representing rat RUP3 was specifically amplified from cDNA of pancreas origin, revealing a similar expression profile with human. Of particular note, robust expression was seen in isolated islets and hypothalamus.

Example 3

Figure 2:
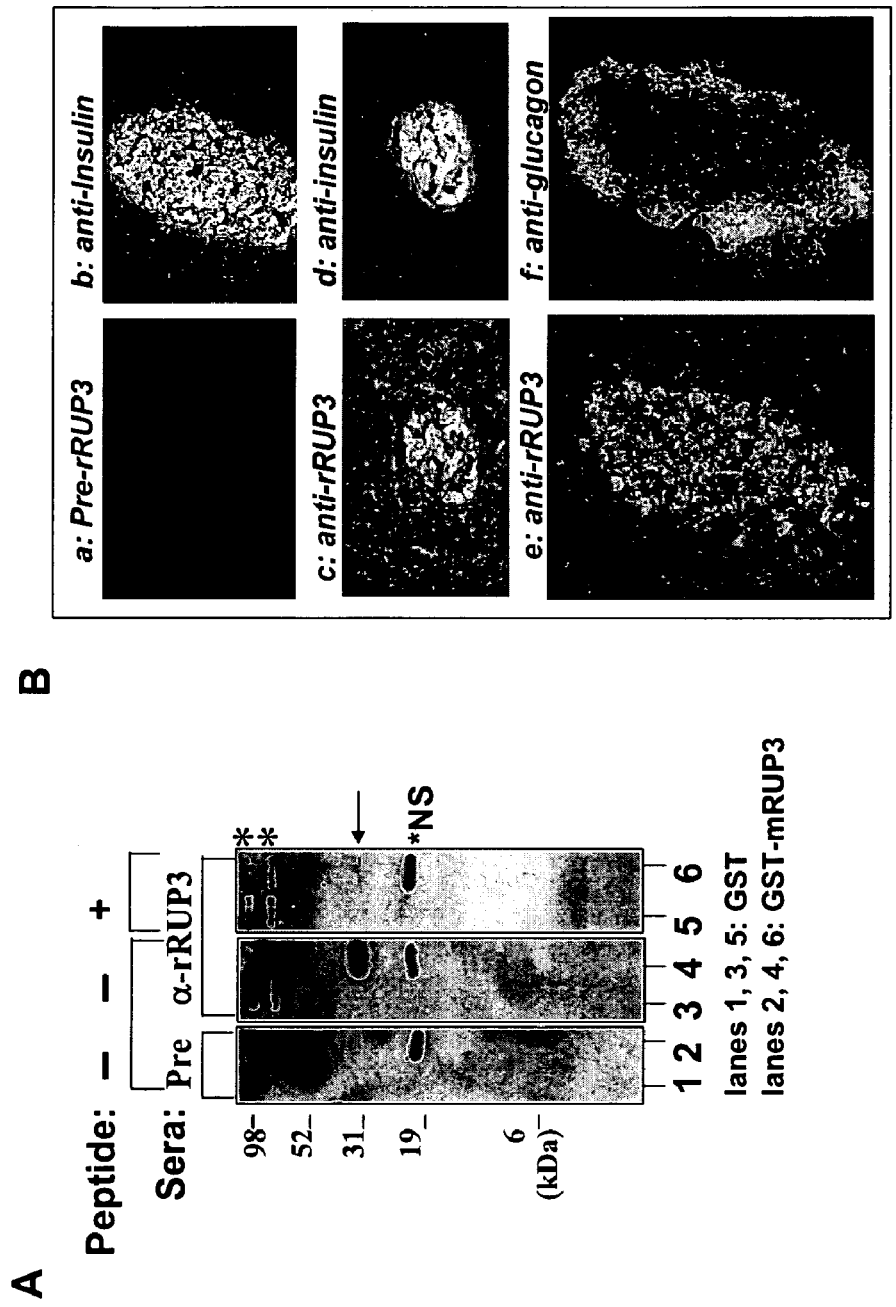
FIG. 2A shows a polyclonal anti-RUP3 antibody prepared in Rabbits.
FIG. 2B shows the expression of RUP3 in insulin-producing β cells of pancreatic islets.

RUP3 Protein Expression is Restricted to β Cell Lineage of Pancreatic Islets (FIG. 2)

A. A polyclonal anti-RUP3 antibody was prepared in rabbits (FIG. 2A).

Rabbits were immunized with an antigenic peptide with sequence derived from rat RUP3 ("rRUP3"). The peptide sequence was RGPERTRESAYHIVTISHPELDG and shared 100% identity with mouse RUP3 in the corresponding region. A cysteine residue was incorporated at the N-terminal end of this antigenic peptide to facilitate KLH crosslinking before injecting into rabbits. The resulting antisera ("anti-rRUP3") and the corresponding preimmune sera ("pre-rRUP3") were tested for immune reactivity to mouse RUP3 in immunobloting assays (lanes 1 though 4). In this assay, the GST-RUP3 fusion protein was readily recognized by the anti-rRUP3 antisera (lane 4), but not by the preimmune sera (lane 2). The immunoreactive signal could be efficiently eliminated when the immunobloting assay was performed in the presence of excess antigenic peptide (lane 6).

B. RUP3 expression in insulin-producing β cells of pancreatic islets (FIG. 2B). Rat pancreas was perfused with 4% paraformaldehyde (PFA) in PBS and embedded in OCT embedding medium. Ten micron sections were prepared, fixed on glass slides, and immunostained with either pre-rRUP3 (FIG. 2B, panel a) or with anti-rRUP3 antisera (FIG. 2B, panels c and e) followed by secondary staining with donkey anti-rabbit IgG conjugated to the fluorochrome Cy-3. Each section was also co-immunostained with a monoclonal anti-insulin antibody (Santa Cruz, FIG. 2B, panels b and d) in primary staining followed by a secondary staining with donkey anti-mouse IgG conjugated with FITC, or with a goat anti-glucagon antibody (Santa Cruz, FIG. 2B, panel f) and donkey anti-goat IgG coupled to FITC. Immunofluorescent signals were examined under a fluorescent microscope. RUP3 was found expressed in insulin producing cells (panels c and d), but not in glucagons producing cells (panels e and f). These data demonstrated that RUP3 is expressed in β cells but not in β cells of the rat pancreatic islets. Analogous results were obtained when mouse pancreatic sections were investigated for RUP3 expression.

Example 4

Figure 3:
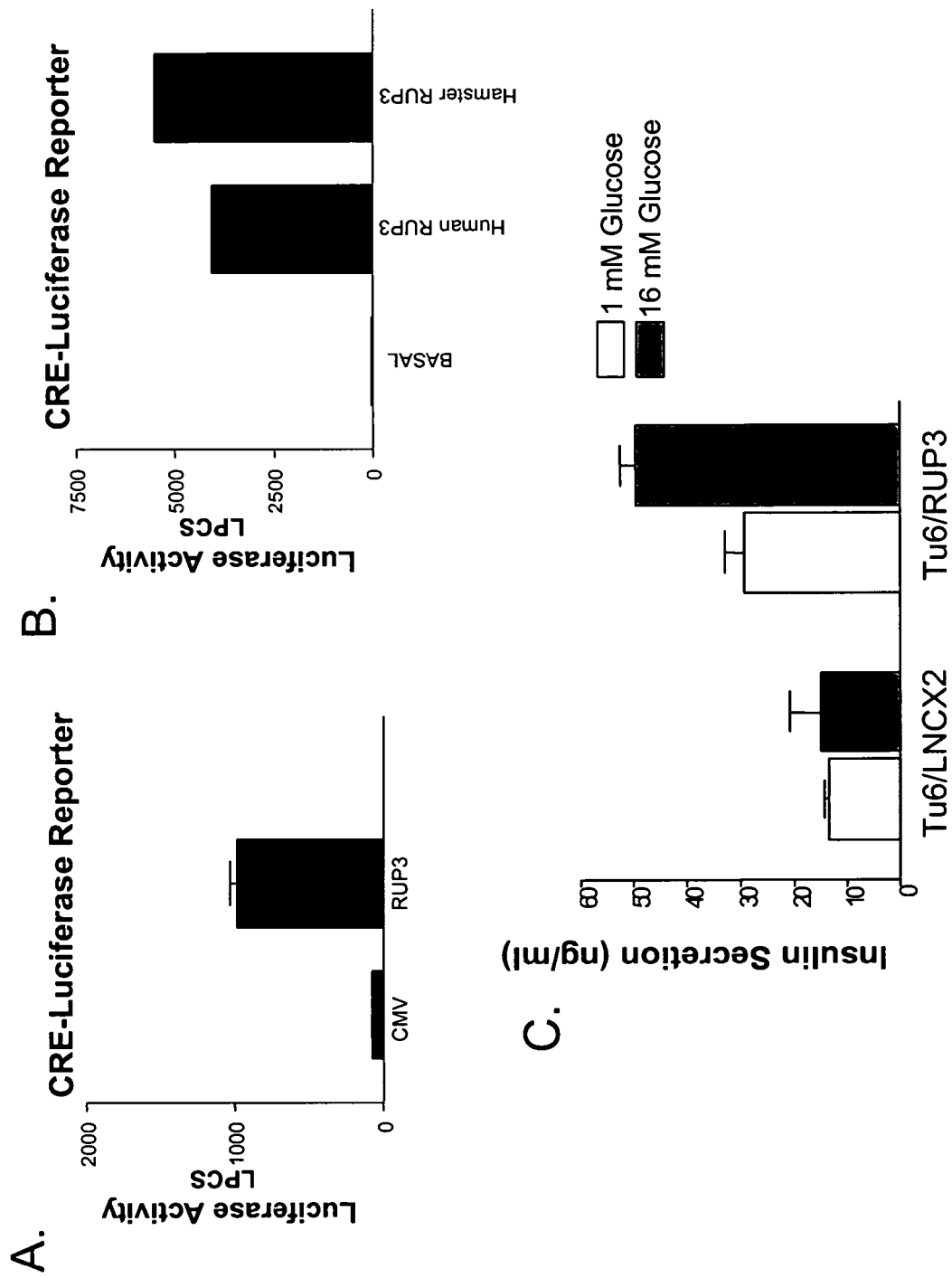
FIG. 3 shows in vitro functional activities of RUP3.
Figure 4:
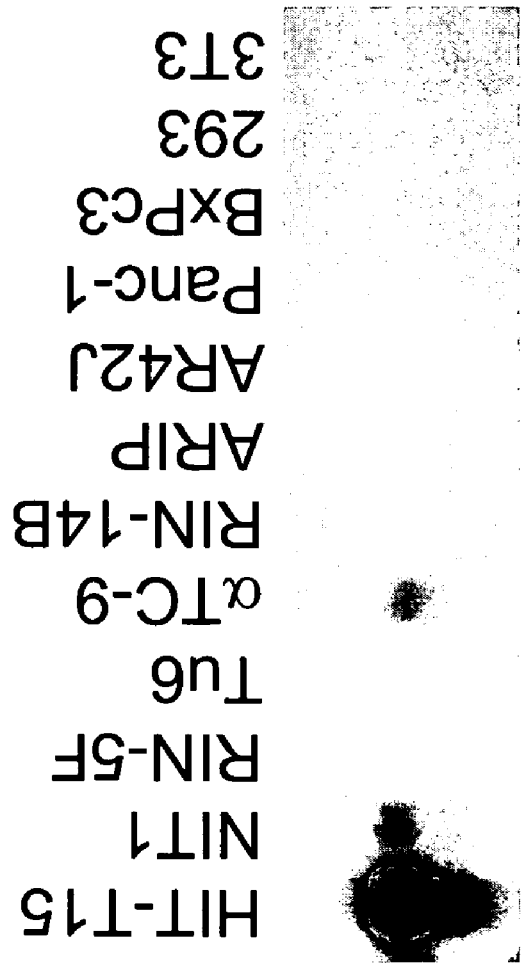
FIG. 4 shows a RUP3 RNA blot.

Functional Activities of RUP3 In Vitro (FIG. 3)

It was established that RUP3 stimulates the production of cAMP by cotransfection of 293 cells with: (1) a CRE-Luciferase reporter, wherein the ability to stimulate the production of firefly luciferase depends on increased cAMP in cells, and (2) an expression plasmid encoding the human form of RUP3 (FIG. 3A). Note that cells co-transfected with an expression plasmid containing no RUP3 sequences ("CMV" in FIG. 3A) produce very little luciferase activity, whereas cells transfected with an expression plasmid encoding RUP3 ("RUP3" in FIG. 3A) have at least a 10-fold increase in luciferase activity. This indicates that RUP3 stimulates the production of cAMP when introduced into 293 cells. This property of RUP3 is conserved across species, because hamster RUP3 stimulates luciferase activity when introduced into 293 cells in a manner analogous to that described for human RUP3 (FIG. 3B).

It is established that, when cAMP is increased in insulin-producing cells of the pancreas, these cells exhibit an enhanced ability to secrete insulin when glucose concentrations rise. To test whether RUP3 might impart enhanced glucose-dependent insulin release, retrovirus containing human RUP3 was used to generate Tu6 cells that express high levels of RUP3. Tu6 cells produce insulin, but do not express appreciable levels of RUP3 and do not normally exhibit an increase in insulin release when increased glucose is present in the culture media. As shown in FIG. 3C, Tu6 cells transduced with a control virus that contains no receptor are still able to produce insulin, but do not show an increase in insulin secretion when the concentration of glucose in the culture media is shifted from 1 mM to 16 mM. By contrast, Tu6 cells transduced with RUP3-containing retrovirus display significant glucose-dependent insulin secretion (FIG. 3C).

Example 5

In Vivo Effects of RUP3 Agonists on Glucose Homeostasis in Mice

A. Oral Glucose tolerance test (oGTT)

Male C57bl/6J mice at approximately 8 weeks of age were fasted for 18 hours and randomly grouped (n=5) to receive a RUP3 agonist at 1, 3 or 10 mg/Kg. Compounds were delivered orally via a gavage needle (p.o., volume 10 mL/Kg). At time 0, levels of blood glucose were assessed using a glucometer (Elite XL, Bayer), and mice were administered either vehicle (20% hydroxypropyl-beta-cyclodextrin) or test compound. Thirty minutes after administration of test compound, levels of blood glucose were again assessed, and mice were administered dextrose orally at a dose of 3 g/Kg. Blood glucose measurements were then taken 20 min, 40 min, 60 min and 120 min after this time. Table 2 shows the mean percentage inhibition of glucose excursion for each dose of test compound, averaged across the five animals in each treatment group. These results demonstrated that the RUP3 agonists, including Compound 75, lowered blood glucose in a dose-dependent manner in mice after challenged with glucose.

TABLE 2

Mean % Inhibition of Glucose Excursion

| | Dose | |
|---|---|---|
| Compound | 3 mg/Kg | 10 mg/Kg |
| 75 | 22 | 34 |

The data from the oGTT alos demonstrated that, 4-[6-(6-Methanesulfonyl-2-methyl-pyridin-3-ylamino)-5-methoxy-pyrimidin-4-yloxy]-piperidine-1-carboxylic acid isopropyl ester (Compound 84), was able to lower blood glucose in two separate experiments (Experiment 1, 38% reduction in AUC/30 mpk, and Experiment 2, 84% reduction in AUC/30 mpk).

Example 6

Generation of Tu6/RUP3 Stable Lines

To produce Tu6 cells that express RUP3 at high levels, a retrovirus bearing an expression cassette for RUP3 was generated. Briefly, RUP3 coding sequence was cloned into the retroviral vector pLNCX2 (Clontech, Cat #6102-1). The amphotropic packaging cell line PT-67 (Clontech, K1060-D) was then transfected with either the parental vector pLNCX2 or pLNCX2/RUP3 using Lipofectamine and stable lines were established using guidelines provided by the PT-67 vendor. Retrovirus-containing supernatant was obtained by collecting media from the resultant stables according to the manufacturer's directions. Tu6 cells, in a 10 cm dish, were then infected with retrovirus by incubating in a solution of 1 ml viral supernatant/9 ml culture media containing 40 ug/ml polybrene for 24 hours. The medium was then changed to culture media containing 300 ug/ml G418. G418-resistant clones were ultimately created by virtue of the neomycin-resistance gene cassette present in the pLNCX2 vector, thus indicating the successful integration of retrovirus into the Tu6 genome. The expression of RUP3 in the Tu6/RUP3 G418-resistant colonies was confirmed by Northern blot.

Example 7

Insulin Secretion, Tu6 Stables

To measure insulin secretion from rodent insulin-producing cell lines, cells were first cultured overnight in serum-free, glucose-deficient media. The following morning, the cells were then placed in the same media supplemented with either 1 mM or 16 mM glucose. After an incubation of 4 hours, the media was collected and analyzed for insulin content using a Rat Insulin Enzyme-Immunoassay (EIA) System (Amersham Pharmacia Biotech, Cat. #RPN 2567). Typically, the assay was performed using multiple dilutions of sample media in order to ensure that the sample measurements fell within the boundaries of the standard curve (generated using known amounts of insulin), as recommended by the manufacturer.

Example 8

Receptor Binding Assay

In addition to the methods described herein, another means for evaluating a test compound is by determining binding affinities to the RUP3 receptor. This type of assay generally requires a radiolabelled ligand to the RUP3 receptor. Absent the use of known ligands for the RUP3 receptor and radiolabels thereof, compounds of Formula (Ia) can be labelled with a radioisotope and used in an assay for evaluating the affinity of a test compound to the RUP3 receptor.

A radiolabelled RUP3 compound of Formula (Ia) can be used in a screening assay to identify/evaluate compounds. In general terms, a newly synthesized or identified compound (i.e., test compound) can be evaluated for its ability to reduce binding of the "radiolabelled compound of Formula (Ia)" to the RUP3 receptor. Accordingly, the ability to compete with the "radio-labelled compound of Formula (Ia)" or Radiolabelled RUP3 Ligand for the binding to the RUP3 receptor directly correlates to its binding affinity of the test compound to the RUP3 receptor.

Assay Protocol for Determining Receptor Binding for RUP3:

A. RUP3 Receptor Preparation 293 cells (human kidney, ATCC), transiently transfected with 10 ug human RUP3 receptor and 60 ul Lipofectamine (per 15-cm dish), were grown in the dish for 24 hours (75% confluency) with a media change and removed with 10 ml/dish of Hepes-EDTA buffer (20 mM Hepes+10 mM EDTA, pH 7.4). The cells were then centrifuged in a Beckman Coulter centrifuge for 20 minutes, 17,000 rpm (JA-25.50 rotor). Subsequently, the pellet was resuspended in 20 mM Hepes+1 mM EDTA, pH 7.4 and homogenized with a 50-ml Dounce homogenizer and again centrifuged. After removing the supernatant, the pellets were stored at −80° C. until used in binding assay. When used in the assay, membranes were thawed on ice for 20 minutes and then 10 mL of incubation buffer (20 mM Hepes, 1 mM $MgCl_2$, 100 mM NaCl, pH 7.4) added. The membranes were then vortexed to resuspend the crude membrane pellet and homogenized with a Brinkmann PT-3100 Polytron homogenizer for 15 seconds at setting 6. The concentration of membrane protein was determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of Radiolabelled RUP3 Ligand. For nonspecific binding, 50 ul of assay buffer is added instead of 100 ul and an additional 50 ul of 10 uM cold RUP3 is added before 50 ul of Radiolabelled RUP3 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For compound competition studies, instead of adding 100 ul of assay buffer, 100 ul of appropriately diluted test compound is added to appropriate wells followed by addition of 50 ul of Radiolabelled RUP3 Ligand.

C. Calculations

The test compounds are initially assayed at 1 and 0.1 μM and then at a range of concentrations chosen such that the middle dose would cause about 50% inhibition of a Radio-RUP3 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_D)$$

where [L] is the concentration of a Radio-RUP3 Ligand used in the assay and $K_D$ is the dissociation constant of a Radio-RUP3 Ligand determined independently under the same binding conditions.

Chemistry Examples

Syntheses of Compounds of the Present Invention

The compounds of the invention and their synthesis are further illustrated by the following examples. The following examples are provided to further define the invention without, however, limiting the invention to the particulars of these examples. The compounds described herein, supra and infra, are named according to the CS Chem Draw Ultra Version 7.0.1. In certain instances common names are used and it is understood that these common names would be recognized by those skilled in the art.

Chemistry: Proton nuclear magnetic resonance ($^1$H NMR) spectra were recorded on a Varian Mercury Vx-400 equipped with a 4 nucleus auto switchable probe and z-gradient or a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, t=triplet, q=quartet, m=multiplet, br=broad. Microwave irradiations were carried out using the Emyrs Synthesizer (Personal Chemistry). Thin-layer chromatography (TLC) was performed on silica gel 60 $F_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. 2) Mac: HPLC-pumps: LC-8A VP, Shimadzu Inc; HPLC system controller: SCL-10A VP, Shimadzu Inc. UV-Detector: SPD-10A VP, Shimadzu Inc; Autosampler: 215 Liquid Handler, Gilson Inc; Mass spectrometer: API 150EX with Turbo Ion Spray source, AB/MDS Sciex Software: Masschrom 1.5.2.

Example 9

Example 9.1

Preparation of 4-[6-(2,5-difluoro-4-propoxy-phenylamino)-5-methoxy-pyrimidin-4-yloxy]-piperidine-1-carboxylic acid isopropyl ester (Compound 74)

Step A: Preparation of 4-(6-chloro-5-methoxy-pyrimidin-4-yloxy)-piperidine-1-carboxylic acid isopropyl ester To a solution of 4-hydroxy-piperidine-1-carboxylic acid isopropyl ester (3.15 g, 17 mmol) and 4,6-dichloro-5-methoxy-pyrimidine (3.00 mg, 17 mmol) in 15 ml of THF, IM potassium-t-butoxide in THF (18.4 ml, 18.4 mmol) was added dropwise at 0° C. After 45 min, the crude mixture was extracted with $CH_2Cl_2$ and brine. Organic phase was dried over $MgSO_4$, filtered, and concentrated. The residue was purified by column chromatography on silica gel with hexane/ethyl acetate (3:1→1:1 v/v) to provide 4-(6-chloro-5-methoxy-pyrimidin-4-yloxy)-piperidine-1-carboxylic acid isopropyl ester as a solid (4.7 g, 85%). $^1$HNMR ($CDCl_3$, 400 MHz) δ 1.24-1.28 (d, 6H), 1.80-1.84 (m, 2H), 2.00-2.05 (m, 2H), 3.37-3.44 (m, 2H), 3.77-3.81 (m, 2H), 3.91 (s, 3H), 4.92-4.95 (m, 1H), 5.38-5.40 (m, 1H), 8.27 (s, 1H). Exact mass calculated for $C_{14}H_{20}ClN_3O_4$ 329.11. found 330.1 ($MH^+$).

Step B: Preparation of 2,5-difluoro-4-nitro-phenol

A solution of 2,5-difluorophenol (5 g, 38.4 mmol) in acetic acid (10 mL) was added slowly to a mixture of concentrated nitric acid (10 mL) and acetic acid (10 mL) cooled in an acetonitrile/dry ice bath in a manner that temperature did not exceed −18° C. After everything was added, solution was kept at −30° C. for 30 minutes, stirred at −13° C. for 30 minutes, and then at 0° C. for 1 hour. Solution was transferred into a separatory funnel, diluted with methylene chloride, and extracted three times with water. Organic phase was dried over magnesium sulfate, filtered, and concentrated. Residue was purified by column chromatography on $SiO_2$ (hexane/ acetyl acetate 1:1) to give 2,5-difluoro-4-nitro-phenol as a yellow solid (1.74 g, 26%). $^1$HNMR (MeOD, 400 MHz) δ 7.97-7.93 (m, 1H), 6.95-6.91 (m, 1H), 6.17 (s, 1H).

Step C: Preparation of
1,4-difluoro-2-nitro-5-propoxy-benzene

To a solution of 2,5-difluoro-4-nitro-phenol (1.71 g, 9.77 mmol) in acetonitrile (20 mL), potassium carbonate (2.7 g, 19.5 mmol) and 1-iodopropane (1.14 mL, 11.7 mmol) were added. After stirring at 60° C. for 15 hours, mixture was concentrated and extracted with methylene chloride and 2M NaOH solution. Organic phases were dried over magnesium sulfate, filtered, and concentrated to give 1,4-difluoro-2-nitro-5-propoxy-benzene as a yellow solid (0.995 g, 47%). $^1$HNMR ($CDCl_3$, 400 MHz) δ 7.92-7.88 (m, 1H), 6.83-6.78 (m, 1H), 4.08-4.05 (t, J=6.5 Hz, 2H), 1.95-1.86 (m, 2H), 1.10-1.06 (t, J=7.4 Hz, 2H).

Step D: Preparation of
2,5-difluoro-4-propoxy-phenylamine

To a solution of 1,4-difluoro-2-nitro-5-propoxy-benzene (0.99 g, 4.59 mmol) in acetic acid (10 mL), zinc dust (1.5 g, 22.9 mmol) were added. After 30 minutes, more acetic acid (10 mL) and zinc dust were added (1.5 g, 22.9 mmol). Zinc was filtered off, residue was concentrated and purified by HPLC to give 2,5-difluoro-4-propoxy-phenylamine as a purple solid (TFA salt, 401 mg, 29%). $^1$HNMR ($CDCl_3$, 400 MHz) δ 6.99-7.87 (m, 2H), 3.93-3.90 (t, J=6.4, 2H), 1.79-1.71 (m, 2H), 1.01-0.98 (t, J=7.4 Hz, 2H). Exact mass calculated for $C_9H_{11}F_2NO$ 187.08 found 188.1 (MH$^+$).

Step E: Preparation of 4-[6-(2,5-difluoro-4-propoxy-phenylamino)-5-methoxy-pyrimidin-4-yloxy]-piperidine-1-carboxylic acid isopropyl ester (Compound 74)

A mixture of 4-(6-chloro-5-methoxy-pyrimidin-4-yloxy)-piperidine-1-carboxylic acid isopropyl ester (528 mg, 1.6 mmol), palladium acetate (29.4 mg, 0.13 mmol), biphenyl-2-yl-di-tert-butyl-phosphane (19.5 mg, 0.065 mmol), sodium tert-butoxide (315 mg, 3.28 mmol), and 2,5-difluoro-4-propoxy-phenylamine (TFA salt, 395 mg, 1.31 mmol) in 15 mL dioxane was heated under microwave irradiation at 120° C. After 2 hours, more palladium acetate (29.4 mg, 0.13 mmol) was added and mixture was heated under microwave irradiation at 120° C. for 18 hours. Mixture was purified by HPLC to give 4-[6-(2,5-difluoro-4-propoxy-phenylamino)-5-methoxy-pyrimidin-4-yloxy]-piperidine-1-carboxylic acid isopropyl ester (Compound 74) as a tan solid (TFA salt, 217 mg, 32%). $^1$HNMR (MeOD, 400 MHz) δ 8.06-8.05 (d, J=2.0 Hz, 1H), 7.41-7.36 (m, 1H), 7.09-7.04 (m, 1H), 5.41-5.39 (m, 1H), 4.87-4.81 (m, 1H), 4.01-3.98 (t, J=6.4 Hz, 2H), 3.92 (s, 3H), 3.74-3.71 (m, 2H), 3.55-3.52 (m, 2H), 2.00-1.97 (m, 2H), 1.81-1.77 (m, 4H), 1.21-1.19 (d, J=5.5 Hz, 6H), 1.04-1.00 (t, 5.5 Hz, 3H). Exact mass calculated for $C_{23}H_{30}F_2N_4O_5$ 480.22. found 481.2 (MH$^+$).

Example 9.2

Preparation of 4-[6-(4-ethoxy-2,5-difluoro-phenylamino)-5-methoxy-pyrimidin-4-yloxy]-piperidine-1-carboxylic acid isopropyl ester (Compound 75)

Step A: Preparation of
1-ethoxy-2,5-difluoro-4-nitro-benzene

To a solution of 2,5-difluoro-4-nitro-phenol (4.86 g, 28.2 mmol) in acetonitrile (50 mL), potassium carbonate (4.7 g, 34 mmol) and bromoethane (4.21 mL, 56.4 mmol) were added. After stirring at 70° C. for 3.5 hours, iodoethane (2.73, 33.8 mmol) was added and mixture was stirred at 80° C. After 20 hours, mixture was concentrated and extracted with methylene chloride and 2M NaOH solution. Organic phases were dried over magnesium sulfate, filtered, and concentrated to give 1-ethoxy-2,5-difluoro-4-nitro-benzene as a yellow solid (5.05 g, 88%). $^1$HNMR ($CDCl_3$, 400 MHz) δ 7.92-7.88 (m, 1H), 6.82-6.78 (m, 1H), 4.21-4.16 (q, 1H), 4.13-4.07 (q, J=7.0 Hz, 2H), 1.54-1.51 (t, J=7.0 Hz, 3H).

Step B: Preparation of
4-ethoxy-2,5-difluoro-phenylamine

A mixture of 1-ethoxy-2,5-difluoro-4-nitro-benzene (1.00 g, 4.92 mmol) and palladium on carbon (10%, 50% water, 307 mg) in ethanol (20 mL) were shaken in a hydrogenator under $H_2$ atmosphere at 45 psi. After 30 minutes, solids were filtered off, washed with ethanol, and filtrate was concentrated to give 4-ethoxy-2,5-difluoro-phenylamine as a red solid (835 mg, 98%). $^1$HNMR ($CDCl_3$, 400 MHz) δ 6.72-6.67 (m, 1H), 6.58-6.53 (m, 1H), 4.03-3.97 (q, J=7.0 Hz, 2H), 3.50 (s br, 2H), 1.41-1.37 (t, J=7.0 Hz, 3H). Exact mass calculated for $C_8H_9F_2NO$ 173.07 found 174.2 (MH$^+$).

Step C: Preparation of 4-[6-(4-ethoxy-2,5-difluoro-phenylamino)-5-methoxy-pyrimidin-4-yloxy]-piperidine-1-carboxylic acid isopropyl ester (Compound 75)

A mixture of 4-(6-chloro-5-methoxy-pyrimidin-4-yloxy)-piperidine-1-carboxylic acid isopropyl ester (6.71 g, 20.3 mmol), palladium acetate (460 mg, 2.05 mmol), biphenyl-2-yl-di-tert-butyl-phosphane (77.0 mg, 0.26 mmol), sodium tert-butoxide (2.7 g, 28.1 mmol) and 4-ethoxy-2,5-difluoro-phenylamine (3.26 g, 18.8 mmol) in 100 mL toluene was heated under reflux for 17 hours. Mixture was purified by HPLC to give 4-[6-(4-ethoxy-2,5-difluoro-phenylamino)-5-methoxy-pyrimidin-4-yloxy]-piperidine-1-carboxylic acid isopropyl ester (Compound 75) as a tanned solid (TFA salt, 1.36 g, 14%). $^1$HNMR ($CDCl_3$, 400 MHz) δ 8.25 (s, 1H), 7.47-7.41 (m, 1H), 6.81-6.76 (m, 1H), 5.52-5.48 (m, 1H), 4.98-4.88 (m, 1H), 4.13-4.07 (q, J=7.0 Hz, 2H), 3.84-3.76 (m, 2H), 3.68 (s, 3H), 3.40-3.33 (m, 2H), 2.09-2.04 (m, 2H), 1.85-1.77 (m, 2H), 1.49-1.46 (t, J=7.0 Hz, 3H), 1.10-1.09 (d, J=6.3 Hz, 6H). Exact mass calculated for $C_{22}H_{28}F_2N_4O_5$ 466.48. found 467.5 (MH$^+$).

Example 9.3

Preparation of 4-[2-(2,5-Difluoro-4-propoxy-phenylamino)-3-methoxy-pyridin-4-yloxy]-piperidine-1-carboxylic acid isopropyl ester (Compound 20)

Step A: Preparation of 2-chloro-4-nitro-pyridin-3-ol

A solution of 2-chloro-3-pyridinol (11.3 g, 87.2 mmol) in concentrated sulfuric acid (25 mL) was cooled in an ice-bath and a 1:1 mixture of nitric acid and sulfuric acid (25 mL) was added slowly. After everything was added, solution was stirred at 0° C. for 1 hour and then at room temperature for another hour. Mixture was diluted with water and extracted with methylene chloride. Organic phases were dried over magnesium sulfate, filtered, and concentrated. Residue was purified by column chromatography on silica gel (ethyl acetate/hexane 2:1→3:1) to give 2-chloro-4-nitro-pyridin-3-ol as a tanned solid (3.58 g, 24%). $^1$HNMR (CDCl$_3$, 400 MHz) δ 10.5 (s, 2H), 8.14-8.13 (d, J=5.5 Hz, 1H), 7.88-7.87 (d, J=5.5 Hz, 1H).

Step B: Preparation of
2-chloro-3-methoxy-4-nitro-pyridine

To a solution of 2-chloro-4-nitro-pyridin-3-ol (1.05 g, 6.02 mmol) in acetonitrile (45 mL) and methanol (5 mL), trimethylsilyldiazomethane (2M in hexane, 3.9 mL, 7.8 mmol) were added slowly. After 30 minutes, mixture was concentrated and residue was purified by column chromatography on silica gel (hexane/ethyl acetate 5:1) to give 2-chloro-3-methoxy-4-nitro-pyridine as a white solid (0.77 g, 68%). $^1$HNMR (CDCl$_3$, 400 MHz) δ 8.35-8.34 (d, J=5.1 Hz, 1H), 7.58-7.56 (d, J=5.2 Hz, 1H), 4.08 (s, 3H).

Step C: Preparation of 4-(2-chloro-3-methoxy-pyridin-4-yloxy)-piperidine-1-carboxylic acid isopropyl ester To a solution of 2-chloro-3-methoxy-4-nitro-pyridine (102.3 mg, 0.543 mmol) and 4-hydroxy-piperidine-1-carboxylic acid isopropyl ester (110 mg, 0.587 mmol) in dioxane (3 mL), sodium hydride (60% dispersion, 32 mg, 0.8 mmol) were added. After stirring at 100° C. for 1 hour, mixture was purified by HPLC to give 4-(2-chloro-3-methoxy-pyridin-4-yloxy)-piperidine-1-carboxylic acid isopropyl ester as a white solid (42.0 mg, 24%). $^1$HNMR (CDCl$_3$, 400 MHz) δ 8.16-8.15 (d, J=5.4 Hz, 1H), 6.92-6.90 (d, J=5.8 Hz), 4.97-4.91 (m, 1H), 4.72-4.68 (m, 1H), 3.91 (s, 3H), 3.75-3.68 (m, 2H), 3.75-3.68 (m, 2H), 3.55 (m, 2H), 2.02-1.85 (m, 4H), 1.27-1.26 (d, J=6.2 Hz, 6H). Exact mass calculated for C$_{15}$H$_{21}$ClN$_2$O$_4$ 328.12. found 329.2 (MH$^+$).

Step D: Preparation of 4-[2-(2,5-difluoro-4-propoxy-phenylamino)-3-methoxy-pyridin-4-yloxy]-piperidine-1-carboxylic acid isopropyl ester (Compound 20)

A mixture of 4-(2-chloro-3-methoxy-pyridin-4-yloxy)-piperidine-1-carboxylic acid isopropyl ester (42 mg, 0.128 mmol), palladium acetate (30 mg, 0.13 mmol), 2,8,9-triisobutyl-2,5,8,9-tetraaza-1-phospha-bicyclo[3.3.3]undecane (4.4 μl, 0.013 mmol), sodium tert-butoxide (31 mg, 0.32 mmol), and 2,5-difluoro-4-propoxy-phenylamine (30 mg, 0.13 mmol) in toluene (0.5 mL) was heated under microwave irradiation at 120° C. for 1 hour. Mixture was purified by HPLC to give 4-[2-(2,5-difluoro-4-propoxy-phenylamino)-3-methoxy-pyridin-4-yloxy]-piperidine-1-carboxylic acid isopropyl ester (Compound 20) as a tanned solid (TFA salt, 35.4 mg, 47%). $^1$HNMR (MeOD, 400 MHz) δ 7.52-7.50 (d, J=7.4 Hz, 1H), 7.23-7.18 (m, 1H), 7.12-7.08 (m, 1H), 6.98-6.96 (m, 1H), 4.88-4.77 (m, 2H), 4.00-3.97 (m, 2H), 3.90 (s, 3H), 3.72-3.67 (m, 2H), 3.41-3.37 (m, 2H), 2.00-1.96 (m, 2H), 1.82-1.75 (m, 4H), 1.19-1.17 (d, J=6.1 Hz, 6H), 1.01-0.98 (t, J=7.4 Hz, 3H). Exact mass calculated for C$_{24}$H$_{31}$F$_2$N$_3$O$_5$ 479.22. found 479.7 (MH$^+$).

Example 9.4

Preparation of 4-[6-(4-methanesulfonyl-2-methoxy-phenylamino)-5-methoxy-pyrimidin-4-yloxy]-piperidine-1-carboxylic acid isopropyl ester (Compound 10)

Step A: Preparation of 4-[6-(4-bromo-2-methoxy-phenylamino)-5-methoxy-pyrimidin-4-yloxy]-piperidine-1-carboxylic acid isopropyl ester A mixture of 4-(6-chloro-5-methoxy-pyrimidin-4-yloxy)-piperidine-1-carboxylic acid isopropyl ester (521 mg, 1.58 mmol), palladium acetate (75 mg, 0.33 mmol), biphenyl-2-yl-di-tert-butyl-phosphane (51 mg, 0.17 mmol), sodium tert-butoxide (380 mg, 3.95 mmol), and 4-bromo-2-methoxy-phenylamine (HCl salt, 377 mg, 1.58 mmol) in 15 mL dioxane was heated under microwave irradiation at 120° C. After 3 hours, mixture was purified by HPLC to give 4-[6-(4-bromo-2-methoxy-phenylamino)-5-methoxy-pyrimidin-4-yloxy]-piperidine-1-carboxylic acid isopropyl ester as a tanned solid (TFA salt, 124 mg, 13%). $^1$HNMR (MeOD, 400 MHz) δ 8.05-8.04 (d, J=2.2 Hz, 1H), 7.93-7.91 (d, J=8.5 Hz, 1H), 7.21-7.20 (d, J=2.0 Hz, 1H), 7.12-7.09 (m, 1H), 5.37-5.34 (m, 1H), 4.89-4.79 (m, 1H), 3.94 (s, 3H), 3.86 (s, 3H), 3.74-3.70 (m, 2H), 3.42-3.38 (m, 2H), 2.01-1.98 (m, 2H), 1.78-1.74 (m, 2H), 1.22-1.21 (d, J=6.2 Hz, 6H). Exact mass calculated for C$_{21}$H$_{27}$BrN$_4$O$_5$ 494.12. found 495.1 (MH$^+$).

Step B: Preparation of 4-[6-(4-methanesulfonyl-2-methoxy-phenylamino)-5-methoxy-pyrimidin-4-yloxy]-piperidine-1-carboxylic acid isopropyl ester (Compound 10)

A mixture of 4-[6-(4-bromo-2-methoxy-phenylamino)-5-methoxy-pyrimidin-4-yloxy]-piperidine-1-carboxylic acid isopropyl ester (TFA salt, 112 mg, 0.184 mmol), sodium methansulfinate (51 mg, 0.425 mmol), copper (I) trifluoromethane sulfonate benzene complex (92 mg, 0.16 mmol), and N,N-dimethylethylendiamine (60 μl, 0.56 mmol) in DMSO (4.5 mL) were heated under microwave irradiation at 160° C. for 30 minutes. Mixture was purified by HPLC to give 4-[6-(4-methanesulfonyl-2-methoxy-phenylamino)-5-methoxy-pyrimidin-4-yloxy]-piperidine-1-carboxylic acid isopropyl ester (Compound 10) as a white solid (TFA salt, 45.7 mg, 41%). $^1$HNMR (MeOD, 400 MHz) δ 8.75-8.73 (m, 1H), 8.13-8.12 (d, 2.2 Hz, 1H), 7.53-7.47 (m, 2H), 5.37-5.33 (m, 1H), 4.85-4.80 (m, 1H), 4.00 (s, 3H), 3.91 (s, 3H), 3.75-3.70 (m, 2H), 3.42-3.37 (m, 2H), 3.08 (s, 3H), 2.02-1.97 (m, 2H), 1.78-1.73 (m, 2H), 1.22-1.21 (d, J=6.2 Hz, 6H). Exact mass calculated for C$_{22}$H$_{30}$N$_4$O$_7$S 494.18 found 495.5 (MH$^+$).

Example 9.5

Preparation of 4-[6-(2-fluoro-4-methanesulfonyl-phenylamino)-5-methoxy-pyrimidin-4-yloxy]-piperidine-1-carboxylic acid isopropyl ester (Compound 24)

A mixture of 4-(6-chloro-5-methoxy-pyrimidin-4-yloxy)-piperidine-1-carboxylic acid isopropyl ester (2.494 g, 7.56 mmol), 2-fluoro-4-(methylsulfonyl)-aniline (1.4315 g, 7.56 mmol), palladium acetate (169.9 mg, 0.756 mmol), 2,8,9-triisobutyl-2,5,8,9-tetraaza-1-phospha-bicyclo[3.3.3]undecane (26.8 μL, 0.0756 mmol) and sodium tert-butoxide (1.475 g, 15.3 mmol) in dioxane (30 mL) was heated under microwave irradiation at 120° C. for 2 hours. The crude mixture was purified by HPLC and recrystalized with EtOH to provide compound 4-[6-(2-fluoro-4-methanesulfonyl-phenylamino)-5-methoxy-pyrimidin-4-yloxy]-piperidine-1-carboxylic acid isopropyl ester (Compound 24) as a solid (TFA salt, 513 mg, 11.3%). $^1$HNMR (DMSO-$d_6$, 400 MHz) δ 1.19-1.20 (d, 6H), 1.65-1.70 (m, 2H), 1.94-1.99 (m, 2H), 3.26 (s, 3H), 3.31-3.35 (m, 2H), 3.63-3.69 (m, 2H), 3.85 (s, 3H), 4.77-4.80 (m, 1H), 5.29-5.31 (m, 1H), 7.73-7.75 (m, 1H), 7.80-7.83 (m, 1H), 8.06-8.11 (m, 2H), 8.79 (s, 1H). Exact mass calculated for $C_{21}H_{27}FN_4O_6S$ 482.16 found 483.3 (MH$^+$).

Example 9.6

Preparation of 4-[6-(2-fluoro-4-methanesulfonyl-phenoxy)-5-methoxy-pyrimidin-4-yloxy]-piperidine-1-carboxylic acid isopropyl ester (Compound 76)

Step A: Preparation of 4-(6-chloro-5-methoxy-pyrimidin-4-yloxy)-piperidine-1-carboxylic acid isopropyl ester A mixture of 4-(6-chloro-5-methoxy-pyrimidin-4-yloxy)-piperidine-1-carboxylic acid isopropyl ester (2.19 g, 6.7 mmol), potassium carbonate (1.84 g, 13.3 mmol), and 4-bromo-2-fluorophenol (1.65 g, 8.65 mmol) in 32 ml DMA was heated at 160° C. for 5 hours. The mixture was extracted with AcOEt and brine. Organic phase was dried over MgSO$_4$, filtered and concentrated. The residue was purified by HPLC to give 4-[6-(4-bromo-2-fluoro-phenoxy)-5-methoxy-pyrimidin-4-yloxy]-piperidine-1-carboxylic acid isopropyl ester as an oil (1.12 g, 35%). Exact mass calculated for $C_{20}H_{23}BrFN_3O_5$ 483.08. found 484.4 (MH$^+$).

Step B: Preparation of 4-[6-(2-fluoro-4-methanesulfonyl-phenoxy)-5-methoxy-pyrimidin-4-yloxy]-piperidine-1-carboxylic acid isopropyl ester (Compound 76)

A mixture of 4-[6-(4-bromo-2-fluoro-phenoxy)-5-methoxy-pyrimidin-4-yloxy]-piperidine-1-carboxylic acid isopropyl ester (0.543 g, 1.21 mmol), sodium methane sulfinate (774.2 mg, 7.58 mmol), and N,N'-dimethyl-ethylene diamine (50.31 μL, 0.44 mmol) and copper (I) trifluoromethane sulfonate benzene complex (384.9 mg, 0.759 mmol) in 20 mL DMSO was heated in microwave for 7 minutes at 120° C. The mixture was purified by HPLC to give compound 4-[6-(2-fluoro-4-methanesulfonyl-phenoxy)-5-methoxy-pyrimidin-4-yloxy]-piperidine-1-carboxylic acid isopropyl ester (Compound 76) as an oil (242.7 mg, 42%). $^1$HNMR (DMSO-$d_6$, 400 MHz) δ 1.19-1.21 (d, 6H), 1.68-1.72 (m, 2H), 1.97-2.02 (m, 2H), 3.30-3.33 (m, 2H), 3.33 (s, 3H), 3.65-3.71 (m, 2H), 3.90 (s, 3H), 4.78-4.81 (m, 1H), 5.28-5.37 (m, 1H), 7.69-7.73 (m, 1H), 7.84-7.87 (m, 1H), 8.00-8.03 (m, 1H), 8.16 (s, 1H). Exact mass calculated for $C_{21}H_{26}FN_3O_7S$ 483.15 found 484.2 (MH$^+$).

Example 9.7

Preparation of 4-[2-(2-fluoro-4-methanesulfonyl-phenylamino)-3-methoxy-pyridin-4-yloxy]-piperidine-1-carboxylic acid isopropyl ester (Compound 77)

A mixture of compound 4-(2-chloro-3-methoxy-pyridin-4-yloxy)-piperidine-1-carboxylic acid isopropyl ester (TFA salt, 57 mg, 0.13 mmol), 2-fluoro-4-(methylsulfonyl)-aniline (49 mg, 0.26 mmol), palladium acetate (29 mg, 0.13 mmol), 2,8,9-triisobutyl-2,5,8,9-tetraaza-1-phospha-bicyclo[3.3.3]undecane (11.5 μt, 0.033 mmol), and sodium tert-butoxide (24 mg, 0.25 mmol) in 2 mL of dioxane was purged with argon and heated under microwave irradiation at 120° C. for 2 hours. The crude mixture was purified by HPLC to provide 4-[2-(2-fluoro-4-methanesulfonyl-phenylamino)-3-methoxy-pyridin-4-yloxy]-piperidine-1-carboxylic acid isopropyl ester (Compound 77) as an oil (TFA salt, 50 mg, 65%). $^1$HNMR (CDCl$_3$, 400 MHz) δ 1.26-1.28 (d, 6H), 1.89-1.91 (m, 2H), 2.02-2.05 (m, 2H), 3.08 (s, 3H), 3.49-3.54 (m, 2H), 3.69 (s, 3H), 3.71-3.77 (m, 2H), 4.78-4.79 (m, 1H), 4.93-4.96 (m, 1H), 6.76-6.77 (m, 1H), 7.61-7.63 (m, 1H), 7.69-7.73 (m, 2H), 7.91-7.92 (m, 1H) 9.70 (s, 1H). Exact mass calculated for $C_{22}H_{28}FN_3O_6S$ 481.17 found 482.3 (MH$^+$).

Example 9.8

Preparation of 4-{5-methoxy-6-[6-(2-methoxy-ethylamino)-2-methyl-pyridin-3-ylamino]-pyrimidin-4-yloxy}-piperidine-1-carboxylic acid isopropyl ester (Compound 31)

Step A: Preparation of (2-methoxy-ethyl)-(6-methyl-5-nitro-pyridin-2-yl)-amine

A mixture of 2-fluoro-5-nitro-6-picoline (656 mg, 4.2 mmol) and 2-methoxyethylamine (365 μl, 4.2 mmol) was stirred at 0° C. After 10 min, crude (2-methoxy-ethyl)-(6-methyl-5-nitro-pyridin-2-yl)-amine (957 mg) was obtained as a solid. $^1$HNMR (CDCl$_3$, 400 MHz) δ 2.77 (s, 3H), 2.85 (s, 2H), 3.40 (s, 3H), 3.57-3.60 (m, 2H), 5.51 (s br, 1H), 6.26-6.29 (m, 1H), 8.18-8.20 (m, 1H). Exact mass calculated for $C_9H_{13}N_3O_3$ 211.10. found 212.2 (MH$^+$).

Step B: Preparation of N2-(2-methoxy-ethyl)-6-methyl-pyridine-2,5-diamine

To a suspension of (2-methoxy-ethyl)-(6-methyl-5-nitro-pyridin-2-yl)-amine (421 mg, 2 mmol) and 5 ml of acetic acid, Zn dust (781 mg, 12 mmol) was added at 0° C. The mixture was stirred at 60° C. for 1 hour. Zn dust was filtered through celite and the residue was purified by HPLC to provide N$^2$-(2-Methoxy-ethyl)-6-methyl-pyridine-2,5-diamine as an oil (140 mg, 39%). Exact mass calculated for C9H$_{15}$N$_3$O 181.12 found 182.2 (MH$^+$).

Step C: Preparation of 4-{5-methoxy-6-[6-(2-methoxy-ethylamino)-2-methyl-pyridin-3-ylamino]-pyrimidin-4-yloxy}-piperidine-1-carboxylic acid isopropyl ester (Compound 31)

Compound 31 was obtained in a similar manner as described in Example 9.5 as an oil (HCl salt, 170 mg, 88%). $^1$HNMR (MeOD-$d_4$, 400 MHz) δ 1.16-1.18 (d, 6H), 1.71-1.74 (m, 2H), 1.94-1.98 (m, 2H), 2.36 (s, 3H), 3.21-3.22 (m, 6H), 3.33 (s, 3H), 3.33-3.36 (m, 2H), 3.66-3.70 (m, 2H), 3.88 (s, 3H), 4.80-4.82 (m, 1H), 5.34-5.35 (m, 1H), 6.95-6.97 (m, 1H), 7.73-7.76 (m, 1H), 8.00 (s, 1H). Exact mass calculated for $C_{23}H_{34}N_6O_5$ 474.26. found 475.2 (MH$^+$).

Example 9.9

Preparation of 4-{6-[6-(2-hydroxy-ethylamino)-2-methyl-pyridin-3-ylamino]-5-methoxy-pyrimidin-4-yloxy}-piperidine-1-carboxylic acid isopropyl ester (Compound 78)

To a solution of 4-{5-methoxy-6-[6-(2-methoxy-ethylamino)-2-methyl-pyridin-3-ylamino]-pyrimidin-4-yloxy}- piperidine-1-carboxylic acid isopropyl ester (HCl salt, 101 mg, 0.2 mmol) in 10 mL of $CH_2Cl_2$, iodotrimethylsilane (142 μl, 1 mmol) was added at room temperature. The mixture was stirred at the same temperature. After 2 hr, the mixture was purified by HPLC and converted to HCl salt by adding 2 mL of 4M HCl in dioxane solution and concentrated to give 4-{6-[6-(2-hydroxy-ethylamino)-2-methyl-pyridin-3-ylamino]-5-methoxy-pyrimidin-4-yloxy}-piperidine-1-carboxylic acid isopropyl ester (Compound 78) (HCl salt, 37 mg, 37%). $^1$HNMR ($CD_3CN$-$d_3$, 400 MHz) δ 1.12-1.14 (d, 6H), 1.66-1.68 (m, 2H), 1.84-1.89 (m, 2H), 2.35 (s, 3H), 3.27-3.32 (m, 2H), 3.41 (s, 2H), 3.61 (s, 4H), 3.82 (s, 3H), 4.72-4.78 (m, 1H), 5.28 (m, 1H), 6.88-6.90 (m, 1H), 6.69-7.71 (m, 1H), 7.99 (s, 1H) 8.18 (s br, 1H), 8.42 (s br, 1H). Exact mass calculated for $C_{22}H_{32}N_6O_5$ 460.24. found 461.5 (MH$^+$).

Example 9.10

4-{6-[6-(2-Hydroxy-ethylsulfanyl)-2-methyl-pyridin-3-ylamino]-1-methoxy-pyrimidin-4-yloxy}-piperidine-1-carboxylic acid isopropyl ester (Compound 79)

Step A: Preparation of 2-(6-methyl-5-nitro-pyridin-2-ylsulfanyl)-ethanol

To a solution of 2-fluoro-5-nitro-6-picoline (5.0 g, 32 mmol) and 2-mercaptoethanol (4.5 ml, 64 mmol), KOH (2 g, 36 mmol) was added at 0° C. The mixture was stirred at the same temperature for 15 minutes. The crude mixture was extracted with AcOEt and brine. Organic phase was dried over $MgSO_4$, filtered, and concentrated to provide the crude 2-(6-methyl-5-nitro-pyridin-2-ylsulfanyl)-ethanol as an oil (7.238 g). $^1$HNMR (DMSO-$d_4$, 400 MHz) δ 2.75 (s, 3H), 3.30-3.33 (m, 2H), 3.63-3.67 (m, 2H), 4.65-4.68 (m, 1H), 7.40-7.43 (m, 1H), 8.24-8.26 (m, 1H). Exact mass calculated for $C_8H_{10}N_2O_3S$ 214.04 found 215.1 (MH$^+$).

Step B: Preparation of 2-(5-amino-6-methyl-pyridin-2-ylsulfanyl)-ethanol

To a suspension of 2-(6-methyl-5-nitro-pyridin-2-ylsulfanyl)-ethanol (323 mg, 1.5 mmol) and 7 ml of acetic acid, zinc dust (220 mg, 3.4 mmol) was added at 0° C. The mixture was stirred at room temperature for 2 hr. Zinc dust was filtered through celite and the residue was purified by HPLC to provide 2-(5-amino-6-methyl-pyridin-2-ylsulfanyl)-ethanol as an oil (93 mg, 33%). $^1$HNMR (DMSO-$d_4$, 400 MHz) δ 1.91 (s, 1H), 2.38 (s, 3H), 2.50-2.51 (m, 2H), 3.12-3.15 (m, 2H), 3.57-3.61 (m, 2H), 7.26-7.28 (m, 1H), 734-7.36 (m, 1H). Exact mass calculated for $C_8H_{12}N_2OS$ 184.07 found 184.9 (MH$^+$).

Step C: Preparation of 4-{6-[6-(2-hydroxy-ethylsulfanyl)-2-methyl-pyridin-3-ylamino]-5-methoxy-pyrimidin-4-yloxy}-piperidine-1-carboxylic acid isopropyl ester (Compound 79)

4-{6-[6-(2-Hydroxy-ethylsulfanyl)-2-methyl-pyridin-3-ylamino]-5-methoxy-pyrimidin-4-yloxy}-piperidine-1-carboxylic acid isopropyl ester (Compound 79) was obtained in a similar manner as described in Example 9.5 as a solid (TFA salt, 30.6 mg, 10%). $^1$HNMR (CDCl$_3$, 400 MHz) δ 1.25-1.27 (d, 6H), 1.75-1.83 (m, 2H), 1.97-2.02 (m, 2H), 2.57 (s, 3H), 3.34-3.39 (m, 2H), 3.41-3.46 (m, 2H), 3.76 (s, 3H), 3.78-3.82 (m, 2H), 4.57-4.60 (m, 2H), 4.90-4.96 (m, 1H), 5.29-5.33 (m, 1H), 7.40-7.42 (m, 1H), 7.55-7.57 (m, 1H), 8.07 (s, 1H). Exact mass calculated for $C_{22}H_{31}N_5O_5S$ 477.2 found 477.7 (MH$^+$).

Example 9.11

Preparation of 4-{6-[6-(2-hydroxy-ethylsulfanyl)-pyridin-3-ylamino]-5-methoxy-pyrimidin-4-yloxy}-piperidine-1-carboxylic acid isopropyl ester (Compound 80)

Step A: Preparation of 2-(5-nitro-pyridin-2-ylsulfanyl)-ethanol 2-(5-Nitro-pyridin-2-ylsulfanyl)-ethanol was obtained in a similar manner as described in Example 9.9/Step A as crude product (835 mg). Exact mass calculated for $C_7H_8N_2O_3S$ 200.03 found 201.2 (MH$^+$).

Step B: Preparation of 2-(5-amino-pyridin-2-ylsulfanyl)-ethanol 2-(5-Amino-pyridin-2-ylsulfanyl)-ethanol was obtained in a similar manner as described in Example 9.9/Step B as an oil (277 mg, 39%). $^1$HNMR (CDCl$_3$, 400 MHz) δ 3.20-3.22 (m, 2H), 3.92-3.95 (m, 2H), 4.07 (s br, 3H), 6.91-6.93 (m, 1H), 7.13-7.15 (m, 1H), 7.92-7.93 (s, 1H). Exact mass calculated for $C_7H_{10}N_2OS$ 170.05 found 171.1 (MH$^+$).

Step C: Preparation of 4-{6-[6-(2-hydroxy-ethylsulfanyl)-pyridin-3-ylamino]-5-methoxy-pyrimidin-4-yloxy}-piperidine-1-carboxylic acid isopropyl ester (Compound 80)

4-{6-[6-(2-Hydroxy-ethylsulfanyl)-pyridin-3-ylamino]-5-methoxy-pyrimidin-4-yloxy}-piperidine-1-carboxylic acid isopropyl ester was obtained in a similar manner as described in Example 9.5 as a solid (HCl salt, 25 mg, 15.5%). $^1$HNMR (CDCl$_3$, 400 MHz) δ 1.26-1.27 (d, 6H), 1.83-1.84 (m, 2H), 2.03-2.04 (m, 2H), 3.40-3.45 (m, 2H), 3.46-3.51 (m, 2H), 3.64-3.644 (m, 1H), 3.75-3.79 (m, 2H), 4.00 (s, 3H), 4.08 (m, 2H), 4.92-4.96 (m, 1H), 5.39 (s br, 1H), 7.58-7.64 (m, 1H), 8.17-8.20 (m, 1H), 8.88 (s br, 1H), 9.49 (s br, 1H). Exact mass calculated for $C_{21}H_{29}N_5O_5S$ 463.19 found 464.4 (MH$^+$).

Example 9.12

Preparation of 4-{6-[6-(2-methanesulfonyl-ethylamino)-2-methyl-pyridin-3-ylamino]-5-methoxy-pyrimidin-4-yloxy}-piperidine-1-carboxylic acid isopropyl ester (Compound 81)

Step A: Preparation of 2-(5-nitro-pyridin-2-ylsulfanyl)-ethanol

To a solution of 2-fluoro-5-nitro-6-picoline (300.3 mg, 1.92 mmol) and 2-aminoethylmethylsulfone hydrochloride (HCl salt, 309 mg, 1.93 mmol) in 5 ml of THF, $K_2CO_3$ (798 mg, 5.77 mmol) was added at room temperature. The mixture was stirred at 60° C. for 100 hours. The crude mixture was purified by HPLC to provide (2-methanesulfonyl-ethyl)-(6-methyl-5-nitro-pyridin-2-yl)-amine as an oil (TFA salt, 562 mg, 78%). Exact mass calculated for $C_9H_{13}N_3O_4S$ 259.06 found 259.8 (MH$^+$).

Step B: Preparation of N²-(2-methanesulfonyl-ethyl)-6-methyl-pyridine-2,5-diamine N²-(2-Methanesulfonyl-ethyl)-6-methyl-pyridine-2,5-diamine was obtained in a similar manner as described in Example 9.9/Step B as an oil (184 mg, 56%). Exact mass calculated for $C_9H_{15}N_3O_2S$ 229.09 found 230.3 (MH⁺).

Step C: Preparation of 4-{6-[6-(2-methanesulfonyl-ethylamino)-2-methyl-pyridin-3-ylamino]-5-methoxy-pyrimidin-4-yloxy}-piperidine-1-carboxylic acid isopropyl ester (Compound 81)

4-{6-[6-(2-Methanesulfonyl-ethylamino)-2-methyl-pyridin-3-ylamino]-5-methoxy-pyrimidin-4-yloxy}-piperidine-1-carboxylic acid isopropyl ester was obtained in a similar manner as described in Example 9.5 as an oil (TFA salt, 41 mg, 16%). ¹HNMR (CDCl₃, 400 MHz) δ 1.25-1.29 (d, 6H), 1.80-1.82 (m, 2H), 2.01-2.02 (m, 2H), 2.48 (s, 3H), 3.02 (s, 3H), 3.37-3.41 (m, 2H), 3.42-3.47 (m, 2H), 3.78-3.79 (m, 2H), 3.83-3.84 (m, 2H), 3.94 (s, 3H), 4.92-4.95 (m, 1H), 5.35-5.37 (m, 1H), 6.75-6.80 (m, 1H), 8.01 (s, 1H), 8.05-8.08 (m, 1H). Exact mass calculated for $C_{23}H_{34}N_6O_6S$ 522.23 found 523.5 (MH⁺).

Example 9.13

Preparation of 4-{2-[2-fluoro-4-(2-methoxy-ethoxy)-phenylamino]-3-methoxy-pyridin-4-yloxy}-piperidine-1-carboxylic acid isopropyl ester (Compound 82)

Step A: Preparation of 2-fluoro-4-(2-methoxy-ethoxy)-phenylamine

A mixture of 2-fluoro-4-iodo-phenylamine (2.3672 g, 10 mmol), 2-methoxyethanol (13 ml, 164 mmol), copper(I)iodide (190 mg, 1 mmol), 1,10-phenanthridine (360 mg, 2 mmol), and cesium carbonate (4.55 g mg, 14 mmol) was sealed and heated at 110° C. After 17 hours, the crude mixture was extracted with CH₂Cl₂ and brine. Organic phase was dried over MgSO₄, filtered, and concentrated. The residue was purified by column chromatography on silica gel with hexane/ethyl acetate (1:1 v/v) twice to give 2-fluoro-4-(2-methoxy-ethoxy)-phenylamine as an oil (761 mg, 41%). Exact mass calculated for $C_9H_{12}FNO_2$ 185.09. found 186.0 (MH⁺).

Step B: Preparation of 4-{2-[2-fluoro-4-(2-methoxy-ethoxy)-phenylamino]-3-methoxy-pyridin-4-yloxy}-piperidine-1-carboxylic acid isopropyl ester 4-{2-[2-Fluoro-4-(2-methoxy-ethoxy)-phenylamino]-3-methoxy-pyridin-4-yloxy}-piperidine-1-carboxylic acid isopropyl ester was obtained in a similar manner as described in Example 9.7 as an oil (TFA salt, 173 mg, 84%). ¹HNMR (CDCl₃, 500 MHz) δ 1.25-1.28 (d, 6H), 1.88-1.90 (m, 2H), 2.02 (s, 1H), 2.04-2.05 (m, 2H), 3.48 (s, 3H), 3.49-3.54 (m, 2H), 3.73-3.76 (m, 2H), 3.77-3.80 (m, 2H), 3.93 (s, 3H), 4.11-4.13 (m, 2H), 4.77-4.78 (m, 1H), 4.94-4.96 (m, 1H), 6.64-6.65 (m, 1H), 6.77-6.80 (m, 2H) 7.57 (s, 1H), 7.70-7.71 (m, 1H). Exact mass calculated for $C_{24}H_{32}FN_3O_6$ 477.23. found 478.3 (MH⁺).

Example 9.14

Preparation of 4-[6-(6-dimethylcarbamoylmethyl-2-methyl-pyridin-3-ylamino)-5-methoxy-pyrimidin-4-yloxy]-piperidine-1-carboxylic acid isopropyl ester (Compound 47)

Step A: Preparation of 4-[6-(6-bromo-2-methyl-pyridin-3-ylamino)-5-methoxy-pyrimidin-4-yloxy]-piperidine-1-carboxylic acid isopropyl ester

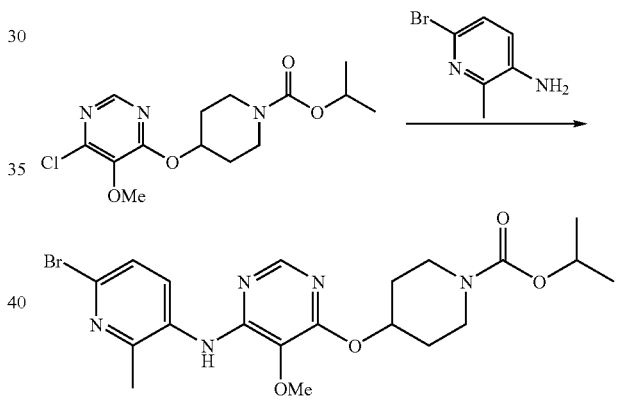

A mixture of 4-(6-chloro-5-methoxy-pyrimidin-4-yloxy)-piperidine-1-carboxylic acid isopropyl ester (3.3 g, 10.0 mmol), 6-bromo-2-methyl-pyridin-3-ylamine (1.88 g, 10.0 mmol), palladium acetate (118 mg, 0.53 mmol), 2-(di-t-butylphosphino) biphenyl (157 mg, 0.53 mmol) and LiN (TMS)₂ (1M in THF, 15 mL, 15 mmol) in 75 mL of dioxane was stirred under reflux. After 4.5 h, more palladium acetate (111 mg, 0.50 mmol) was added and mixture was stirred under reflux for another hour and then at room temperature for 3 days. The mixture was concentrated and residue was extracted with brine and AcOEt. Organic phases were dried over MgSO₄, filtered, and concentrated. The residue was purified by column chromatography (hexane/AcOEt 2:1→1:1) to give 4-[6-(6-bromo-2-methyl-pyridin-3-ylamino)-5-methoxy-pyrimidin-4-yloxy]-piperidine-1-carboxylic acid isopropyl ester as a solid (2.09 g, 44%). ¹HNMR (CDCl₃, 400 MHz) a 1.27-1.28 (d, 6H), 1.84-1.87 (m, 2H), 2.02-2.08 (m, 2H), 2.58 (s, 3H), 3.40-3.47 (m, 2H), 3.73 (s, 3H), 3.77-3.82 (m, 2H), 4.93-4.97 (m, 1H), 5.41-5.43 (m, 1H), 7.44-7.46 (m, 1H), 7.91-7.93 (m, 1H), 8.24 (s, 1H), 8.70 (s br, 1H). Exact mass calculated for $C_{20}H_{26}BrN_5O_4$ 479.12. found 482.0 (MH⁺).

Step B: Preparation of 4-{6-[(6-bromo-2-methyl-pyridin-3-yl)-tert-butoxycarbonyl-amino]-5-methoxy-pyrimidin-4-yloxy}-piperidine-1-carboxylic acid isopropyl ester

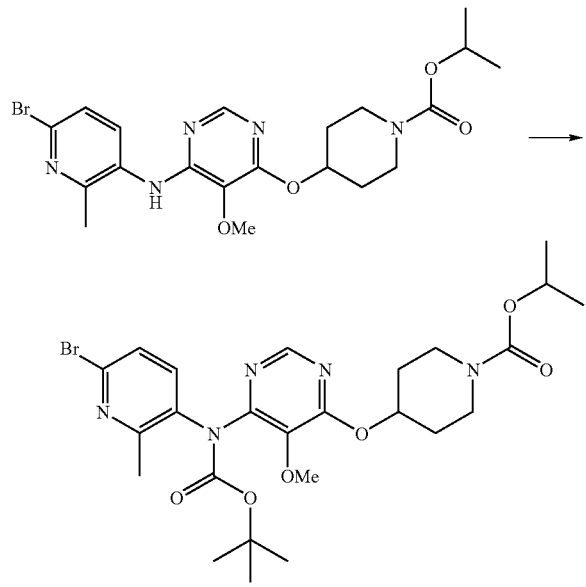

To a solution of 4-[6-(6-bromo-2-methyl-pyridin-3-ylamino)-5-methoxy-pyrimidin-4-yloxy]-piperidine-1-carboxylic acid isopropyl ester in 2 mL THF, Boc anhydride (62 mg, 0.28 mmol) and N,N-dimethylpyridin-4-amine (27 mg, 0.22 mmol) were added. After stirring for 30 min at room temperature, mixture was purified by column chromatography (hexane/AcOEt 2:1) to give 4-{6-[(6-bromo-2-methyl-pyridin-3-yl)-tert-butoxycarbonyl-amino]-5-methoxy-pyrimidin-4-yloxy}-piperidine-1-carboxylic acid isopropyl ester as a white solid (118 mg, 92%). $^1$HNMR (CDCl$_3$, 400 MHz) δ 1.25-1.27 (d, J=6.2 Hz, 6H), 1.42 (s, 9H), 1.79-1.84 (m, 2H), 1.99-2.05 (m, 2H), 2.52 (s, 3H), 3.39-3.47 (m, 2H), 3.71-3.77 (m, 2H), 3.90 (s, 3H), 4.90-4.97 (m, 1H), 5.37-5.42 (m, 1H), 7.30-7.32 (d, J=8.3 Hz, 1H), 7.41-7.43 (d, J=8.3 Hz, 1H), 8.24 (s, 1H). Exact mass calculated for C$_{25}$H$_{34}$BrN$_5$O$_6$ 579.17. found 580.1 (MH$^+$).

Step C: Preparation of 4-[6-(6-carboxymethyl-2-methyl-pyridin-3-ylamino)-5-methoxy-pyrimidin-4-yloxy]-piperidine-1-carboxylic acid isopropyl ester

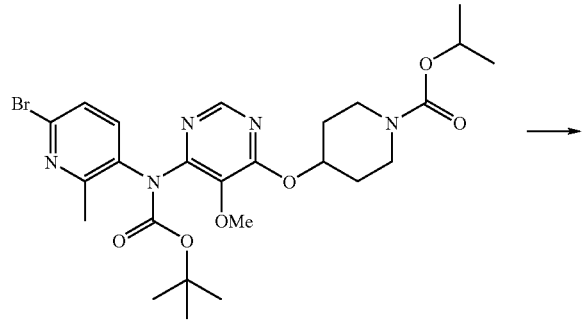

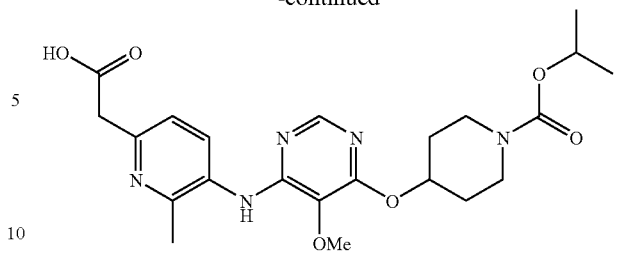

A mixture of 4-{6-[(6-bromo-2-methyl-pyridin-3-yl)-tert-butoxycarbonyl-amino]-5-methoxy-pyrimidin-4-yloxy}-piperidine-1-carboxylic acid isopropyl ester (1.5 g, 2.58 mmol), 2-tert-butoxy-2-oxoethylzinc chloride (0.5 M in Et$_2$O, 20 mL, 10 mmol), and palladium [tetrakis(triphenylphosphine)] (304 mg, 0.263 mmol) were stirred under reflux. After 22 h, mixture was cooled in an ice water bath and ca. 5 nL 4M HCl in dioxane was added. After 1 h, mixture was concentrated and residue was extracted with 2M HCl and methylene chloride. The combined organic phases were concentrated and residue was purified by HPLC to give 4-[6-(6-carboxymethyl-2-methyl-pyridin-3-ylamino)-5-methoxy-pyrimidin-4-yloxy]-piperidine-1-carboxylic acid isopropyl ester as a white solid (TFA salt, 525 mg, 35%). $^1$HNMR (MeOH-d$_4$, 400 MHz) δ 1.06-1.07 (d, J=6.2 Hz, 6H), 1.72-1.78 (m, 2H), 2.00-2.05 (m, 2H), 2.78 (s, 3H), 3.37-3.43 (m, 2H), 3.70-3.75 (m, 2H), 3.92 (s, 3H), 4.08 (s, 2H), 4.81-4.86 (m, 1H), 5.34-5.39 (m, 1H), 7.76-7.78 (d, J=8.5 Hz, 1H), 7.98 (s, 1H), 8.65-8.67 (d, J=8.5 Hz, 1H). Exact mass calculated for C$_{22}$H$_{29}$BrN$_5$O$_6$ 459.21. found 460.5 (MH$^+$).

Step D: Preparation of 4-[6-(6-dimethylcarbamoylmethyl-2-methyl-pyridin-3-ylamino)-5-methoxy-pyrimidin-4-yloxy]-piperidine-1-carboxylic acid isopropyl ester (Compound 47)

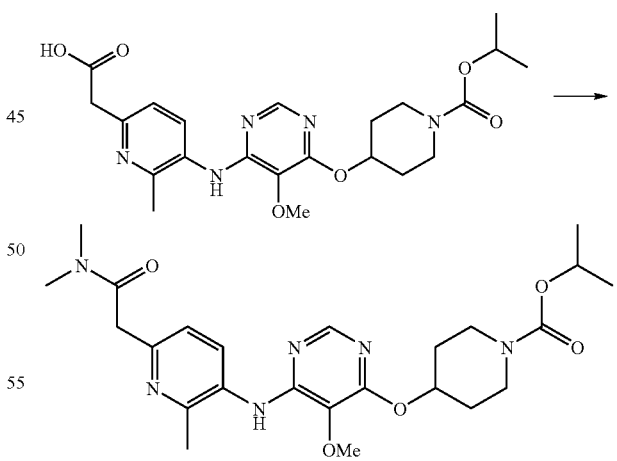

To a solution of 4-[6-(6-carboxymethyl-2-methyl-pyridin-3-ylamino)-5-methoxy-pyrimidin-4-yloxy]-piperidine-1-carboxylic acid isopropyl ester (74 mg, 0.129 mmol), triethylamine (89.9 µl, 0.645 mmol), and HATU (196 mg, 0.516 mmol) in 4 mL THF/DMF 1:1, diethylamine (2M in THF, 323 µl, 0.645 mmol) was added. After stirring for 10 min at room temperature, mixture was purified by HPLC to give 4-[6-(6-dimethylcarbamoylmethyl-2-methyl-pyridin-3-ylamino)-5- methoxy-pyrimidin-4-yloxy]-piperidine-1-carboxylic acid isopropyl ester as a white solid (TFA salt, 45.6 mg, 68%). ¹HNMR (DMSO-d₆, 400 MHz) δ 1.19-1.21 (d, J=6.3 Hz, 6H), 1.65-1.70 (m, 2H), 1.92-1.97 (m, 2H), 2.65 (s, 3H), 2.89 (s, 3H), 3.11 (s, 3H), 3.30-3.35 (m, 2H), 3.64-3.69 (m, 2H), 3.85 (s, 3H), 4.26 (s, 2H), 4.76-4.81 (m, 1H), 5.26-5.31 (m, 1H), 7.70-7.72 (d, J=8.5 Hz, 1H), 8.03 (s, 1H), 8.44-8.46 (d, J=8.5 Hz, 1H), 9.09 (s, 1H). Exact mass calculated for $C_{24}H_{34}N_6O_5$ 486.26. found 487.3 (MH⁺).

Example 9.15

Preparation of 4-{6-[6-(2-hydroxy-ethyl)-2-methyl-pyridin-3-ylamino]-5-methoxy-pyrimidin-4-yloxy}-piperidine-1-carboxylic acid isopropyl ester (Compound 27)

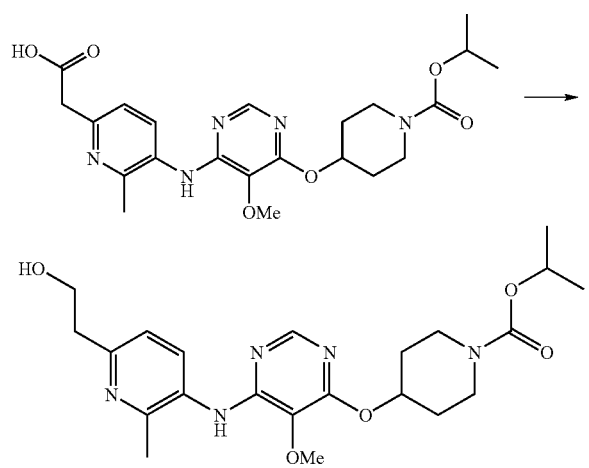

A solution of 4-[6-(6-carboxymethyl-2-methyl-pyridin-3-ylamino)-5-methoxy-pyrimidin-4-yloxy]-piperidine-1-carboxylic acid isopropyl ester (TFA salt, 582 mg, 1.01 mmol) in 4 mL THF was cooled in an ice-water bath and lithium aluminum hydride (ca 190 mg, 5 mmol) was added in small portions. After 2 h, mixture was quenched with ice-water; solids were filtered off, and washed with THF. Filtrate was concentrated and purified by HPLC. Fractions containing product were partly concentrated and residue was extracted with 1 M NaOH and methylene chloride. Organic phases were dried over MgSO₄, filtered, and concentrated to give 4-{6-[6-(2-hydroxy-ethyl)-2-methyl-pyridin-3-ylamino]-5-methoxy-pyrimidin-4-yloxy}-piperidine-1-carboxylic acid isopropyl ester as a white solid (85.0 mg, 19%). ¹HNMR (CDCl₃, 400 MHz) δ 1.25-1.27 (d, J=6.2 Hz, 6H), 1.80-1.86 (m, 2H), 2.00-2.05 (m, 2H), 2.72 (s, 3H), 3.16-3.19 (t, J=5.6 Hz, 2H), 3.38-3.44 (m, 2H), 3.76-3.82 (m, 2H), 3.96-3.99 (t, J=5.6 Hz, 2H), 4.00 (s, 3H), 4.91-4.97 (m, 1H), 5.37-5.41 (m, 1H), 5.30 (s, 1H), 5.37-5.41 (m, 1H), 7.03 (s, 1H), 7.36-7.38 (d, J=8.5 Hz, 1H), 8.13 (s, 1H), 8.85 (s, 1H). Exact mass calculated for $C_{22}H_{31}N_5O_5$ 445.23. found 446.1 (MH⁺).

Example 9.16

Preparation of 4-{5-methoxy-6-[2-methyl-6-(2-methylsulfanyl-ethyl)-pyridin-3-ylamino]-pyrimidin-4-yloxy}-piperidine-1-carboxylic acid isopropyl ester

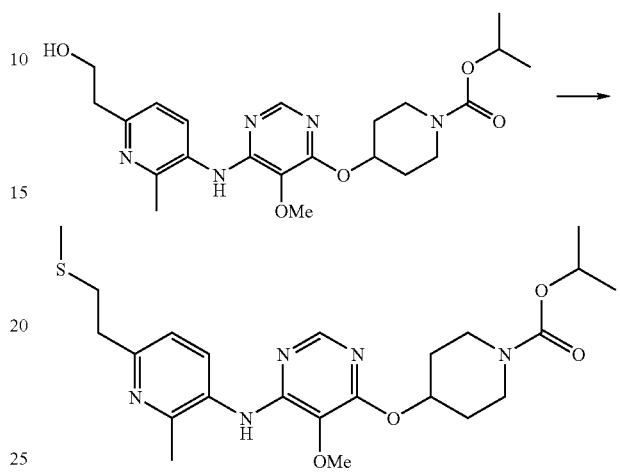

To an ice-cooled solution of 4-{6-[6-(2-hydroxy-ethyl)-2-methyl-pyridin-3-ylamino]-5-methoxy-pyrimidin-4-yloxy}-piperidine-1-carboxylic acid isopropyl ester (40.2 mg, 90.2 μmol) and triphenylphosphine (31 mg, 118 pmol) in 2 mL methylene chloride, perbromomethane (77.0 mg, 232 μmol) were added and solution was stirred at room temperature. After 18 h, the mixture was concentrated, re-dissolved in 1.5 mL MeOH, and added to a well stirred mixture of sodium hydroxide (120 mg, 3.0 mmol) and 2-methyl-2-thiopseudourea sulfate (208 mg, 0.70 mmol) in 2 mL MeOH. After stirring at room temperature for 17 h, mixture was concentrated and extracted with water and methylene chloride. Organic phases were concentrated and purified by HPLC to give 4-{5-methoxy-6-[2-methyl-6-(2-methylsulfanyl-ethyl)-pyrdin-3-ylamino]-pyrimidin-4-yloxy}-piperidine-1-carboxylic acid isopropyl ester (TFA salt, 10.0 mg, 19%) as a white solid. ¹HNMR (MeOH-d₄, 400 MHz) δ 1.21-1.23 (d, J=6.2 Hz, 6H), 1.72-1.78 (m, 2H), 1.94-2.01 (m, 2H), 2.12 (s, 3H), 2.65 (s, 3H), 2.90-2.93 (t, J=7.2 Hz, 2H), 3.24-3.27 (t, J=7.2 Hz, 2H), 3.39-3.46 (m, 2H), 3.69-3.76 (m, 2H), 3.91 (s, 3H), 4.80-4.86 (m, 2H), 5.32-5.38 (m, 1H), 7.75-7.77 (d, J=8.6 Hz, 1H), 7.96 (s, 1H), 8.57-5.59 (d, J=8.6 Hz, 1H). Exact mass calculated for $C_{23}H_{33}N_5O_4S$ 475.23 found 476.2 (MH⁺).

Example 9.17

Preparation of 4-{6-[6-(2-methanesulfonyl-ethyl)-2-methyl-pyridin-3-ylamino]-5-methoxy-pyrimidin-4-yloxy}-piperidine-1-carboxylic acid isopropyl ester (Compound 30)

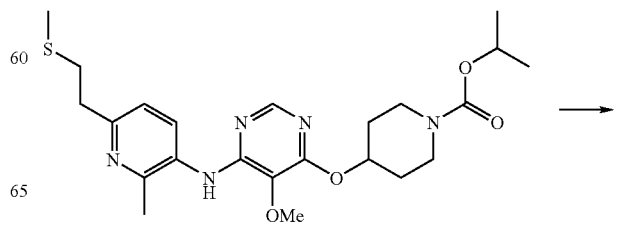

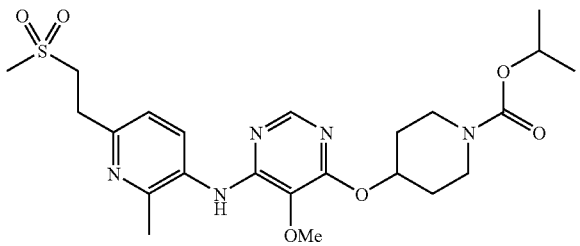

To a solution of 4-{5-methoxy-6-[2-methyl-6-(2-methyl-sulfanyl-ethyl)-pyridin-3-ylamino]-pyrimidin-4-yloxy}-piperidine-1-carboxylic acid isopropyl ester (8.6 mg, 15 μmol) in 2 mL methylene chloride, MCPBA (ca. 77% pure, 7.1 mg, ca. 32 μmol) was added and stirred at room temperature. After 3 h, solution was concentrated and residue was purified by HPLC to give 4-{6-[6-(2-methanesulfonyl-ethyl)-2-methyl-pyridin-3-ylamino]-5-methoxy-pyrimidin-4-yloxy}-piperidine-1-carboxylic acid isopropyl ester (TFA salt, 9.1 mg, 47%). $^1$HNMR (MeOH-$d_4$, 400 MHz) δ 1.24-1.25 (d, J=6.2 Hz, 6H), 1.73-1.79 (m, 2H), 1.99-2.06 (m, 2H), 2.64 (s, 3H), 3.15 (s, 3H), 3.40-3.46 (m, 2H), 3.48-3.51 (t, J=7.9 Hz, 2H), 3.64-3.67 (t, J=7.9 Hz, 2H), 3.74-3.80 (m, 2H), 3.94 (s, 3H), 4.82-4.88 (m, 1H), 3.35-3.40 (m, 1H), 7.78-7.80 (d, J=8.6, 1H), 7.99 (s, 1H), 8.59-8.60 (d, J=8.6, 1H). Exact mass calculated for $C_{23}H_{33}N_5O_6S$ 507.22 found 508.5 (MH$^+$).

Example 9.18

Preparation of 4-[6-(2,6-dimethyl-pyridin-3-ylamino)-5-methoxy-pyrimidin-4-yloxy]-piperidine-1-carboxylic acid isopropyl ester (Compound 83)

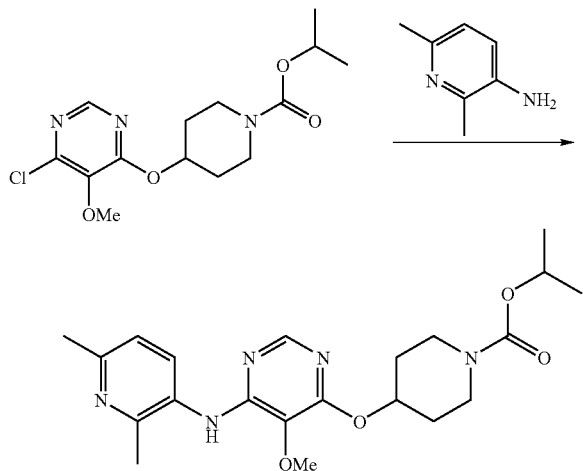

A mixture of 4-(6-chloro-5-methoxy-pyrimidin-4-yloxy)-piperidine-1-carboxylic acid isopropyl ester (1.52 g, 4.60 mmol), 2,6-dimethylpyridin-3-amine (0.562 g, 4.60 mmol), palladium acetate (0.0584 g, 0.260 mmol), and sodium 2-methylpropan-2-olate (0.663 g, 6.90 mmol) in 50 mL dioxane was stirred under reflux for 18 h. Mixture was concentrated and extracted with brine and CH$_2$Cl$_2$. Organic phases were dried over MgSO$_4$, filtered, and concentrated. Residue was purified by column chromatography (AcOEt/hexane 5:1→AcOEt→AcOEt/MeOH 10:1). Fractions containing pure product were concentrated, residue was treated with 4M HCl in dioxane, and concentrated to give 4-[6-(2,6-dimethyl-pyridin-3-ylamino)-5-methoxy-pyrimidin-4-yloxy]-piperidine-1-carboxylic acid isopropyl ester as a white (0.285 g, 15%). Fractions containing product contaminated with 2,6-dimethylpyridin-3-amine was concentrated to give 0.30 g of ca 80% pure product. $^1$HNMR (CDCl$_3$, 400 MHz) δ 1.24-1.25 (d, J=6.2 Hz, 6H), 1.78-1.84 (m, 2H), 2.00-2.05 (m, 2H), 2.52 (2s, 6H), 3.37-3.44 (m, 2H), 3.76-3.81 (m, 2H), 4.03 (s, 3H), 4.91-4.97 (m, 1H), 5.33-5.38 (m, 1H), 6.81 (s, 1H), 7.04-7.06 (d, J=8.2 Hz, 1H), 8.09 (s, 1H), 8.11-8.13 (d, J=8.2 Hz, 1H). Exact mass calculated for $C_{21}H_{29}N_5O_4$ 415.22. found 416.5 (MH$^+$).

Example 9.19

Preparation of 4-[6-(6-methanesulfonyl-2-methyl-pyridin-3-ylamino)-5-methoxy-pyrimidin-4-yloxy]-piperidine-1-carboxylic acid isopropyl ester (Compound 84)

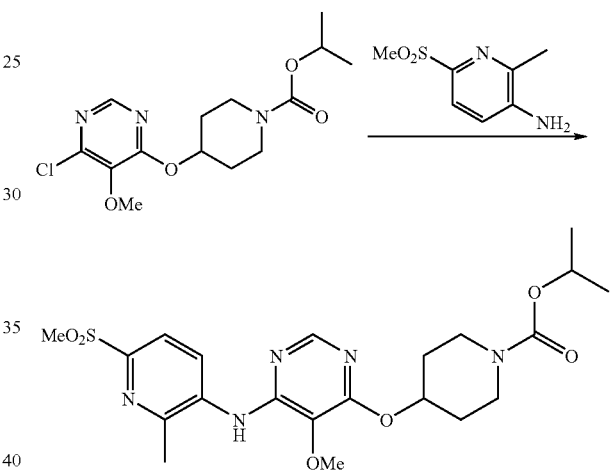

A mixture of 4-(6-chloro-5-methoxy-pyrimidin-4-yloxy)-piperidine-1-carboxylic acid isopropyl ester (611 mg, 1.85 mmol), 2-methyl-6-(methylsulfonyl)pyridin-3-amine (345 mg, 1.85 mmol), palladium acetate (37.2 mg, 0.166 mmol), 2,8,9-triisobutyl-2,5,8,9-tetraaza-1-phospha-bicyclo[3.3.3]undecane (118 μl, 0.332 mmol), and sodium 2-methylpropan-2-olate (267 mg, 2.78 mmol) in 15 mL dioxane was heated under microwave irradiation at 120° C. After 2 h, mixture was purified by HPLC; fractions containing product were collected and concentrated. Residue was extracted with 1M NaOH and CH$_2$Cl$_2$. Organic phases were dried over MgSO$_4$, filtered, and concentrated. Residue was re-purified by column chromatography (AcOEt/hexane 5:1). Fractions containing product were concentrated, treated with 4M HCl and concentrated to give 4-[6-(6-methanesulfonyl-2-methyl-pyridin-3-ylamino)-5-methoxy-pyrimidin-4-yloxy]-piperidine-1-carboxylic acid isopropyl ester as a white solid (HCl salt, 326 mg, 34%). $^1$HNMR (MeOH-$d_4$, 400 MHz) δ 1.23-1.24 (d, J=6.2 Hz, 6H), 1.77-1.85 (m, 2H), 2.01-2.07 (m, 2H), 2.59 (s, 3H), 3.20 (s, 3H), 3.40-3.46 (m, 2H), 3.71-3.77 (m, 2H), 3.98 (s, 3H), 4.83-4.89 (m, 1H), 5.41-5.46 (m, 1H), 7.97-7.99 (d, J=8.3 Hz, 1H), 8.11 (s, 1H), 8.29-8.31 (d, J=8.3 Hz, 1H). Exact mass calculated for $C_{21}H_{29}N_5O_6S$ 479.18 found 480.2 (MH$^+$).

Example 9.20

Preparation of 4-[6-(6-methanesulfonyl-4-methyl-pyridin-3-ylamino)-5-methoxy-pyrimidin-4-yloxy]-piperidine-1-carboxylic acid isopropyl ester (Compound 85)

Step A: Preparation of 6-methanesulfonyl-4-methyl-pyridin-3-ylamine

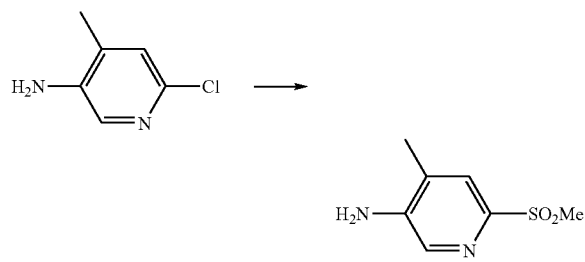

A mixture of 6-chloro-4-methyl-pyridin-3-ylamine (1.53 g, 11 mmol), sodium methanesulfinate (1.60 g, 16 mmol), copper catalyst (0.50 g, 0.99 mmol), and $N^1,N^2$-dimethyl-ethane-1,2-diamine (0.214 mL, 2.0 mmol) in 20 mL DMSO was heated under microwave irradiation at 150° C. After 2 h, mixture was poured into ca. 200 mL water and extracted five times with ca. 200 mL AcOEt. Organic phases were dried over MgSO$_4$, filtered, and concentrated. Residue was purified by column chromatography (AcOEt/hexane 5:1→AcOEt) to give 6-methanesulfonyl-4-methyl-pyridin-3-ylamine as a white solid (0.534 g, 27%). $^1$HNMR (DMSO-d$_6$, 400 MHz) 32.4 (s, 3H), 3.08 (s, 3H), 6.08 (s, 2H), 7.59 (s, 1H), 7.97 (s, 1H). Exact mass calculated for $C_7H_{10}N_2O_2S$ 186.05 found 187.0 (MH$^+$).

Step B: Preparation of 4-[6-(6-methanesulfonyl-4-methyl-pyridin-3-ylamino)-5-methoxy-pyrimidin-4-yloxy]-piperidine-1-carboxylic acid isopropyl ester (Compound 85)

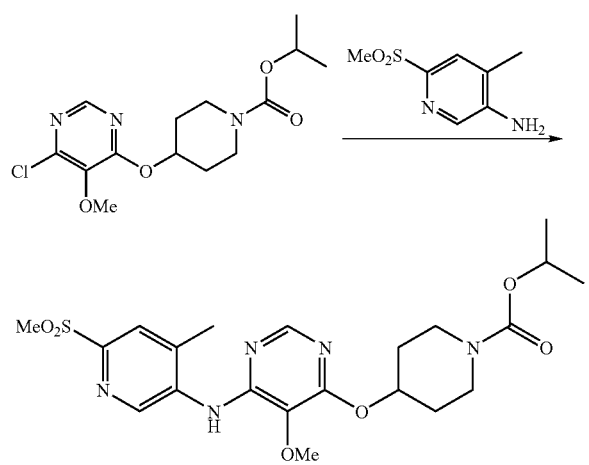

A mixture of 4-(6-chloro-5-methoxy-pyrimidin-4-yloxy)-piperidine-1-carboxylic acid isopropyl ester (570 mg, 1.73 mmol), 6-methanesulfonyl-4-methyl-pyridin-3-ylamine (272 mg, 1.46 mmol), palladium acetate (27.3 mg, 0.122 mmol), 2,8,9-triisobutyl-2,5,8,9-tetraaza-1-phospha-bicyclo[3.3.3]undecane (87 µl, 0.245 mmol), and sodium 2-methyl-propan-2-olate (249 mg, 2.59 mmol) in 4.5 mL dioxane was heated under microwave irradiation at 120° C. After 4 h, mixture was purified by HPLC; fractions containing pure product were collected and concentrated. Residue was treated with 4M HCl in dioxane, concentrated, and dried under high vacuum to give 4-[6-(6-methanesulfonyl-4-methyl-pyridin-3-ylamino)-5-methoxy-pyrimidin-4-yloxy]-piperidine-1-carboxylic acid isopropyl ester as a white solid (HCl salt, 261 mg, 29%). $^1$HNMR (MeOH-d$_4$, 400 MHz) δ 1.23-1.24 (d, J=6.2 Hz, 6H), 1.75-1.81 (m, 2H), 1.97-2.04 (m, 2H), 2.40 (s, 3H), 3.17 (s, 3H), 3.39-3.46 (m, 2H), 3.71-3.77 (m, 2H), 3.92 (s, 3H), 4.82-4.88 (m, 1H), 5.35-5.40 (m, 1H), 7.99 (s, 1H), 7.99 (s, 1H), 8.96 (s, 1H). Exact mass calculated for $C_{21}H_{29}N_5O_6S$ 479.18 found 480.4 (MH$^+$).

Example 9.21

Preparation of 4-[5-methoxy-6-(2-methyl-6-propyl-sulfanyl-pyridin-3-ylamino)-pyrimidin-4-yloxy]-piperidine-1-carboxylic acid isopropyl ester (Compound 86)

Step A: Preparation of 2-methyl-6-propylsulfanyl-pyridin-3-ylamine

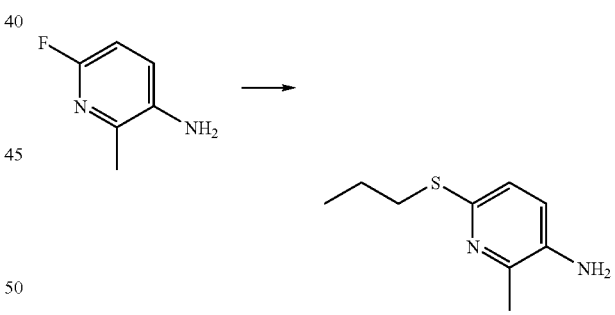

A mixture of 6-fluoro-2-methyl-pyridin-3-ylamine (2.01 g, 16 mmol), propane-1-thiol (3.0 mL, 33 mmol), and potassium hydroxide (1.8 g, 32 mmol) in 3 mL EtOH were heated under microwave irradiation at 100° C. for 1 h and then at 150° C. for 2 h. Mixture was extracted with CH$_2$Cl$_2$ and brine. Organic phases were dried over MgSO$_4$, filtered, and concentrated. Residue was purified by column chromatography (hexane/AcOEt 2:1) to give 2-methyl-6-propylsulfanyl-pyridin-3-ylamine (2.18 g, 75% yield) as a colorless oil. $^1$HNMR (CDCl$_3$, 400 MHz) δ 0.99-1.03 (t, J=7.3 Hz, 3H), 1.64-1.73 (m, 2H), 2.39 (s, 3H), 3.02-3.05 (t, J=7.3 Hz, 2H), 3.48 (s, 2H), 6.82-6.84 (d, J=8.2 Hz, 1H), 6.93-6.95 (d, J=8.2 Hz, 1H). Exact mass calculated for $C_9H_{14}N_2S$ 182.09 found 183.0 (MH$^+$).

Step B: Preparation of 4-[5-methoxy-6-(2-methyl-6-propylsulfanyl-pyridin-3-ylamino)-pyrimidin-4-yloxy]-piperidine-1-carboxylic acid isopropyl ester (Compound 86)

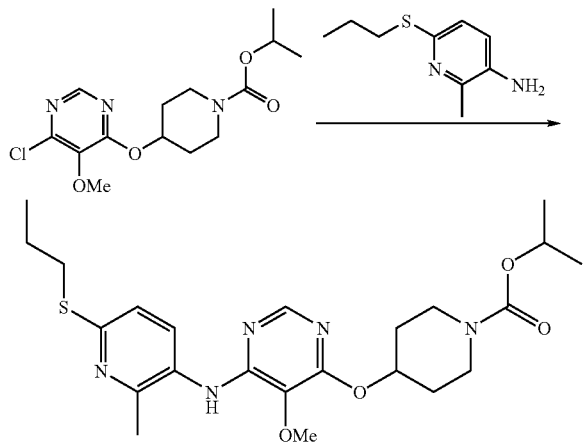

A mixture of 4-(6-chloro-5-methoxy-pyrimidin-4-yloxy)-piperidine-1-carboxylic acid isopropyl ester (0.966 g, 2.93 mmol), 2-methyl-6-propylsulfanyl-pyridin-3-ylamine (0.545 g, 2.99 mmol), palladium acetate (0.0375 g, 0.167 mmol), 2,8,9-triisobutyl-2,5,8,9-tetraaza-1-phospha-bicyclo[3.3.3]undecane (0.119 mL, 0.335 mmol), and sodium 2-methylpropan-2-olate (0.422 g, 4.39 mmol) in 15 mL dioxane was heated under microwave irradiation at 120° C. After 2 h, mixture was purified by HPLC; fractions containing pure product were collected, partly concentrated, and residue was extracted with CH$_2$Cl$_2$ and 1M NaOH. Organic phases were dried over MgSO$_4$, filtered, and concentrated to give 4-[5-methoxy-6-(2-methyl-6-propylsulfanyl-pyridin-3-ylamino)-pyrimidin-4-yloxy]-piperidine-1-carboxylic acid isopropyl ester as a thick oil (0.509 g, 36%). $^1$HNMR (MeOH-d$_4$, 400 MHz) δ 1.00-1.04 (t, J=7.3 Hz, 3H), 1.23-1.24 (d, J=6.2 Hz, 6H), 1.66-1.78 (m, 4H), 1.96-2.02 (m, 2H), 2.37 (s, 3H), 3.06-3.10 (t, J=7.3 Hz, 2H), 3.36-3.42 (m, 2H), 3.71-3.77 (m, 2H), 3.88 (s, 3H), 4.81-4.87 (m, 1H), 5.28-5.34 (m, 1H), 7.09-7.11 (d, J=8.3 Hz, 1H), 7.57-7.59 (d, J=8.3 Hz, 1H), 7.84 (s, 1H). Exact mass calculated for C$_{23}$H$_{33}$N$_5$O$_4$S 475.23 found 476.1 (MH$^+$).

Example 9.22

Preparation of 4-{5-methoxy-6-[2-methyl-6-(propane-1-sulfonyl)-pyridin-3-ylamino]-pyrimidin-4-yloxy}-piperidine-1-carboxylic acid isopropyl ester (Compound 87)

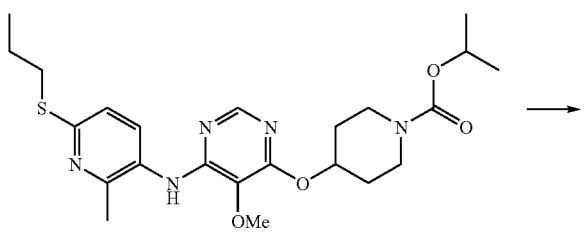

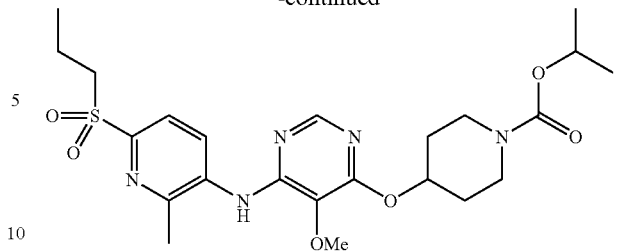

A solution of 4-[5-methoxy-6-(2-methyl-6-propylsulfanyl-pyridin-3-ylamino)-pyrimidin-4-yloxy]-piperidine-1-carboxylic acid isopropyl ester (498 mg, 1.05 mmol) in 25 mL CH$_2$Cl$_2$ was cooled in an ice-bath and mCPBA (max. 77% pure, 364 mg, 2.10 mmol) was added. After stirring under ice cooling for 1 h, more MCPBA (99 mg, 0.44 mmol) was added. After 3 h, solution was transferred into a sepratory funnel and extracted with 1M NaOH and CH$_2$Cl$_2$. Organic phases were dried over MgSO$_4$, filtered, and concentrated. Residue was purified by column chromatography (hexane/AcOEt 1:1); fractions containing product were collected, 4M HCl in dioxane was added, and concentrated to give 4-{5-methoxy-6-[2-methyl-6-(propane-1-sulfonyl)-pyridin-3-ylamino]-pyrimidin-4-yloxy}-piperidine-1-carboxylic acid isopropyl ester a white solid (HCl salt, 489 mg, 86%). $^1$HNMR (MeOH-d$_4$, 400 MHz) δ 0.98-1.00 (t, J=7.4 Hz, 3H), 1.23-1.25 (d, J=6.2 Hz, 6H), 1.66-1.80 (m, 4H), 1.99-2.05 (m, 2H), 2.58 (s, 3H), 3.28-3.34 (m, 2H), 3.40-3.45 (m, 2H), 3.69-3.75 (m, 2H), 3.95 (s, 3H), 4.82-4.86 (m, 1H), 5.35-5.40 (m, 1H), 7.90-7.92 (d, J=8.4 Hz, 1H), 8.03 (s, 1H), 8.48-8.50 (d, J=8.4 Hz, 1H). Exact mass calculated for C$_{23}$H$_{33}$N$_5$O$_4$S 475.23 found 508.4 (MH$^+$).

Example 9.23

Preparation of 4-[6-(6-ethylsulfanyl-2-methyl-pyridin-3-ylamino)-5-methoxy-pyrimidin-4-yloxy]-piperidine-1-carboxylic acid isopropyl ester (Compound 88)

Step A: Preparation of 6-ethylsulfanyl-2-methyl-pyridin-3-ylamine

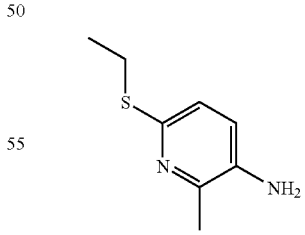

6-Ethylsulfanyl-2-methyl-pyridin-3-ylamine was prepared in similar manner as described in Example 9.21, Step A, to afford a yellow oil (0.99 g, 37%). $^1$HNMR (MeOH-d$_4$, 400 MHz) δ 1.30-1.34 (t, J=7.3 Hz, 3H), 2.39 (s, 3H), 3.04-3.10 (q, J=7.3 Hz, 2H), 3.49 (s, 2H), 6.83-6.85 (d, J=8.2 Hz, 1H), 6.94-6.96 (d, J=8.2 Hz, 1H). Exact mass calculated for C$_8$H$_{12}$N$_2$S 168.07 found 169.2 (MH$^+$).

Step B: Preparation of 4-[6-(6-ethylsulfanyl-2-methyl-pyridin-3-ylamino)-5-methoxy-pyrimidin-4-yloxy]-piperidine-1-carboxylic acid isopropyl ester (Compound 88)

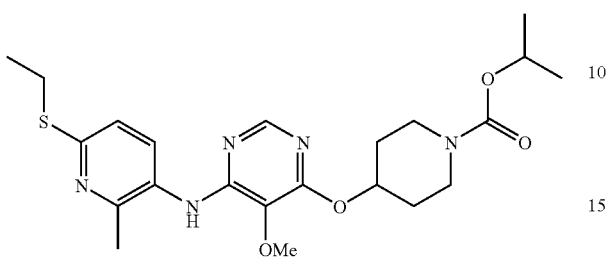

4-[6-(6-Ethylsulfanyl-2-methyl-pyridin-3-ylamino)-5-methoxy-pyrimidin-4-yloxy]-piperidine-1-carboxylic acid isopropyl ester was prepared in similar manner as described in Example 9.21, Step B, to afford a colorless oil (461 mg, 33%). $^1$HNMR (CDCl$_3$, 400 MHz) δ 1.24-1.25 (d, J=6.3 Hz, 6H), 1.35-1.39 (t, J=7.4 Hz, 3H), 1.78-1.85 (m, 2H), 2.00-2.05 (m, 2H), 2.50 (s, 3H), 3.11-3.17 (q, J=7.4 Hz, 2H), 3.37-3.44 (m, 2H), 3.75-3.81 (m, 2H), 3.95 (s, 3H), 4.91-4.97 (m, 1H), 5.33-5.38 (m, 1H), 6.79 (s, 1H), 7.06-7.09 (d, J=8.5 Hz, 1H), 8.08-8.11 (d, J=8.5 Hz, 1H), 8.10 (s, 1H). Exact mass calculated for C$_{22}$H$_{31}$N$_5$O$_4$S 461.21 found 462.5 (MH$^+$).

Example 9.24

Preparation of 4-[6-(6-ethanesulfonyl-2-methyl-pyridin-3-ylamino)-5-methoxy-pyrimidin-4-yloxy]-piperidine-1-carboxylic acid isopropyl ester (Compound 89)

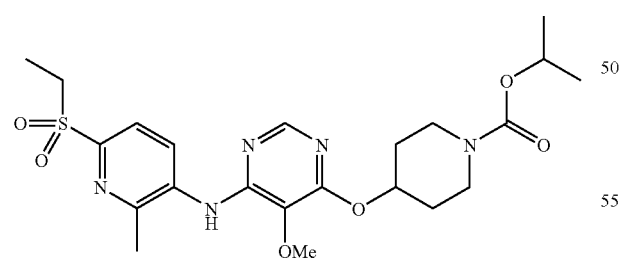

4-[6-(6-Ethanesulfonyl-2-methyl-pyridin-3-ylamino)-5-methoxy-pyrimidin-4-yloxy]-piperidine-1-carboxylic acid isopropyl ester was prepared in a similar manner as described in Example 9.22 to afford a white solid (HCl salt, 459 mg, 89%). $^1$HNMR (CDCl$_3$, 400 MHz) δ 1.26-1.32 (m, 9H), 1.80-1.87 (m, 2H), 2.02-2.07 (m, 2H), 2.66 (s, 3H), 3.34-3.45 (m, 4H), 3.75-3.81 (m, 2H), 4.00 (s, 3H), 4.91-4.97 (m, 1H), 5.37-5.43 (m, 1H), 7.35 (s, 1H), 7.96-7.98 (d, J=8.6 Hz, 1H), 8.21 (s, 1H) 9.00-9.02 (d, J=8.6 Hz, 1H). Exact mass, calculated for C$_{22}$H$_{31}$N$_5$O$_6$S 493.2 found 494.5 (MH$^+$).

Example 9.25

Preparation of 4-[6-(6-isopropylsulfanyl-2-methyl-pyridin-3-ylamino)-5-methoxy-pyrimidin-4-yloxy]-piperidine-1-carboxylic acid isopropyl ester (Compound 90)

Step A: Preparation of 6-isopropylsulfanyl-2-methyl-pyridin-3-ylamine

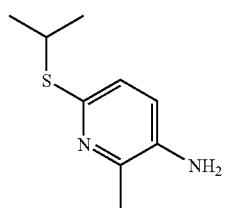

6-Isopropylsulfanyl-2-methyl-pyridin-3-ylamine was prepared in similar manner as described in Example 9.21, Step A, to afford a yellow oil (1.76 g, 38%). $^1$HNMR (CDCl$_3$, 400 MHz) δ 1.31-1.33 (d, J=6.7 Hz, 6H), 2.40 (s, 3H), 3.52 (s, 2H), 3.66-3.73 (m, 1H), 6.81-6.83 (d, J=8.1 Hz, 1H), 6.99-7.01 (d, J=8.1 Hz, 1H). Exact mass calculated for C$_9$H$_{14}$N$_2$S 182.09 found 183.1 (MH$^+$).

Step B: Preparation of 4-[6-(6-isopropylsulfanyl-2-methyl-pyridin-3-ylamino)-5-methoxy-pyrimidin-4-yloxy]-piperidine-1-carboxylic acid isopropyl ester

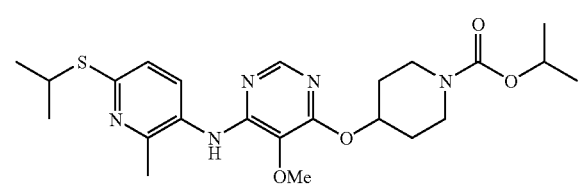 [SMILES: COc1c(Nc2ccc(SC(C)C)nc2C)ncnc1OC1CCN(C(=O)OC(C)C)CC1]

4-[6-(6-isopropylsulfanyl-2-methyl-pyridin-3-ylamino)-5-methoxy-pyrimidin-4-yloxy]-piperidine-1-carboxylic acid isopropyl ester was prepared in similar manner as described in Example 9.21, Step B, to afford a colorless oil (445 mg, 29%). $^1$HNMR (CDCl$_3$, 400 MHz) δ 1.25-1.27 (d, J=6.2 Hz, 6H), 1.37-1.39 (d, J=6.8 Hz, 6H), 1.79-1.85 (m, 2H), 1.99-2.05 (m, 2H), 2.50 (s, 3H), 3.37-3.44 (m, 2H), 3.75-3.92 (m, 3H), 3.95 (s, 3H), 4.91-4.97 (m, 1H), 5.34-5.38 (m, 1H), 6.81

(s, 1H), 7.09 (d, J=8.5 Hz, 1H), 8.09 (s, 1H), 8.13-8.15 (d, J=8.5 Hz, 1H). Exact mass calculated for C₂₃H₃₃N₅O₄S 475.23 found 476.2 (MH⁺).

Example 9.26

Preparation of 4-{5-methoxy-6-[2-methyl-6-(propane-2-sulfonyl)-pyridin-3-ylamino]-pyrimidin-4-yloxy}-piperidine-1-carboxylic acid isopropyl ester (Compound 91)

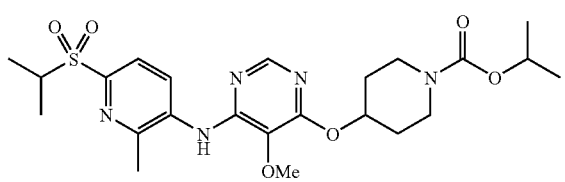 [SMILES: COc1c(Nc2ccc(S(=O)(=O)C(C)C)nc2C)ncnc1OC1CCN(C(=O)OC(C)C)CC1]

4-{5-Methoxy-6-[2-methyl-6-(propane-2-sulfonyl)-pyridin-3-ylamino]-pyrimidin-4-yloxy}-piperidine-1-carboxylic acid isopropyl ester was prepared in a similar manner as described in Example 9.22 to afford a white solid (HCl salt, 410 mg, 82%). ¹HNMR (MeOH-d₄, 400 MHz) δ 1.25-1.26 (d, J=6.2 Hz, 6H), 1.28-1.30 (d, J=6.8 Hz, 6H), 1.76-1.82 (m, 2H), 2.01-2.07 (m, 2H), 2.61 (s, 3H), 3.29-3.36 (m, 2H), 3.65-3.81 (m, 3H), 3.97 (s, 3H), 4.83-4.89 (m, 1H), 4.90-4.95 (m, 1H), 7.92-7.94 (d, J=8.4 Hz, 1H), 8.07 (s, 1H), 8.51-8.53 (d, J=8.4 Hz, 1H). Exact mass calculated for C₂₃H₃₃BrN₅O₆S 507.22 found 508.5 (MH⁺).

Example 9.27

Preparation of 4-{6-[6-(2-hydroxy-ethylsulfanyl)-2-methyl-pyridin-3-ylamino]-5-methoxy-pyrimidin-4-yloxy}-piperidine-1-carboxylic acid isopropyl ester (Compound 79)

Step A: Preparation of 2-(6-methyl-5-nitro-pyridin-2-ylsulfanyl)-ethanol

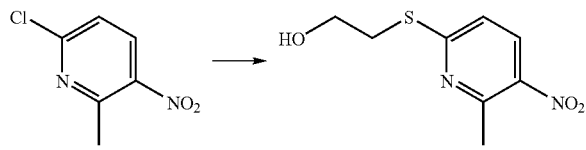

To an ice-cooled solution of 6-chloro-2-methyl-3-nitropyridine (2.17 g, 13 mmol) in 2-mercaptoethanol (5 mL, 71 mmol), potassium hydroxide (1.52 g, 27 mmol) was added. Mixture was stirred at room temperature for 2 h and then extracted with NaOH solution and CH₂Cl₂. Organic phases were dried over MgSO₄, filtered, and concentrated to give 2-(6-methyl-5-nitro-pyridin-2-ylsulfanyl)-ethanol as a brown oil (60% pure, 3.25 g, 72%). ¹HNMR (CDCl₃, 400 MHz) δ 2.87-2.90 (m, 6H), 3.43-3.46 (t, J=5.6 Hz, 2H), 7.22-7.24 (d, J=8.7 Hz, 1H), 8.15-8.17 (d, J=8.7 Hz, 1H). Exact mass calculated for C8H₁₀N₂O₃S 214.04 found 215.1 (MH⁺).

Step B: Preparation of 6-[2-(tert-butyl-dimethyl-silanyloxy)-ethylsulfanyl]-2-methyl-3-nitro-pyridine

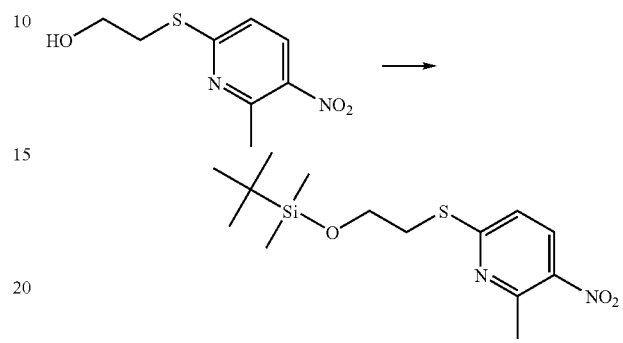

A mixture of 2-(6-methyl-5-nitro-pyridin-2-ylsulfanyl)-ethanol (60% pure, 3.25 g, 9.1 mmol), 1H-imidazole (1.24 g, 18.2 mmol), and tert-butylchlorodimethylsilane (2.75 g, 18.2 mmol) in 20 mL DMF was stirred at room temperature for 4 h. Solution was concentrated and residue was extracted with water and CH₂Cl₂. Organic phases were dried over MgSO₄, filtered, and concentrated. Residue was purified by column chromatography (hexane/AcOEt 30:1) to give 6-[2-(tert-butyl-dimethyl-silanyloxy)-ethylsulfanyl]-2-methyl-3-nitro-pyridine as a yellow oil (2.39 g, 48%). ¹HNMR (CDCl₃, 400 MHz) δ 0.8 (s, 6H), 0.90 (s, 9H), 2.85 (s, 3H), 3.39-3.42 (t, J=6.7 Hz, 2H), 3.85-3.89 (t, J=6.7 Hz, 2H), 7.13-7.15 (d, J=8.7 Hz, 1H), 8.10-8.13 (d, 1H). Exact mass calculated for C₁₄H₂₄N₂O₃SSi 328.13 found 329.1 (MH⁺).

Step C: Preparation of 6-[2-(tert-butyl-dimethyl-silanyloxy)-ethylsulfanyl]-2-methyl-pyridin-3-ylamine

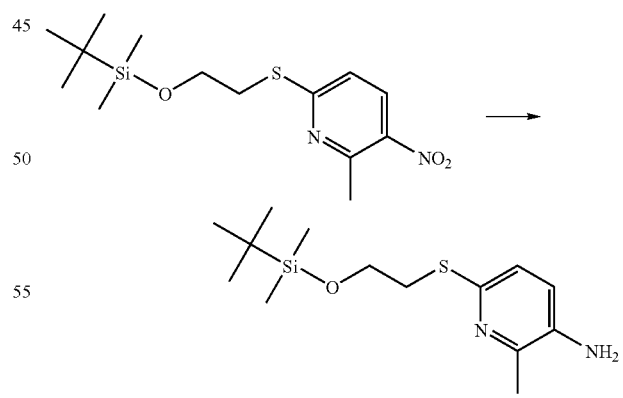

To a solution of 6-[2-(tert-butyl-dimethyl-silanyloxy)-ethylsulfanyl]-2-methyl-3-nitro-pyridine (80, 2.67 g, 8.1 mmol) in 15 mL THF, zinc dust (1.6 g, 24 mmol) followed by 8.2 mL (8.2 mmol) 1M NH₄Cl solution was added. After stirring at room temperature for 3 h, more zinc dust (0.77 g, 8.13 mmol) and NH₄Cl (0.43 g, 8.31 mmol) was added. After stirring for 4 h at mixture was filtered through celite and filtrate was extracted with CH₂Cl₂ and 1M NaOH. Organic phases were dried over MgSO₄, filtered, and concentrated. Residue was purified by column chromatography (Hexane/AcOEt 3:1→2:1) to give 6-[2-(tert-butyl-dimethyl-silanyloxy)-ethylsulfanyl]-2-methyl-pyridin-3-ylamine as a yellowish oil (1.3 g, 54%). Exact mass calculated for C₂₅H₃₄BrN₅O₅ 563.17. found 564.3 (MH⁺).

Step C: Preparation of 4-{6-[6-(2-hydroxy-ethylsulfanyl)-2-methyl-pyridin-3-ylamino]-5-methoxy-pyrimidin-4-yloxy}-piperidine-1-carboxylic acid isopropyl ester (Compound 79)

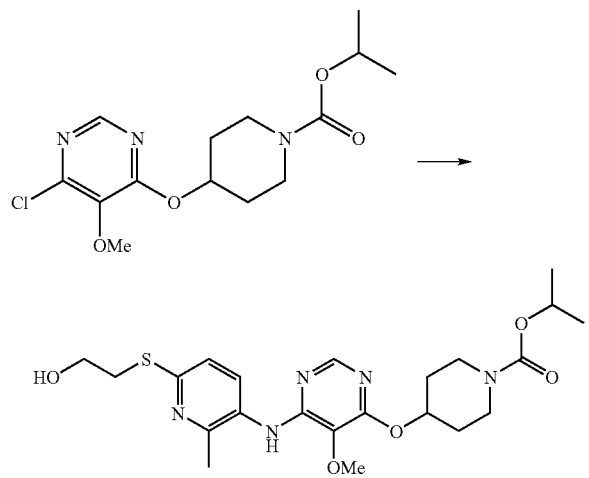

A mixture of 4-(6-chloro-5-methoxy-pyrimidin-4-yloxy)-piperidine-1-carboxylic acid isopropyl ester (1.00 g, 3.03 mmol), 6-[2-(tert-butyl-dimethyl-silanyloxy)-ethylsulfanyl]-2-methyl-pyridin-3-ylamine (0.85 g, 2.85 μmol), palladium acetate (0.0379 g, 0.169 mmol), 2,8,9-triisobutyl-2,5,8,9-tetraaza-1-phospha-bicyclo[3.3.3]undecane (0.120 mL, 0.338 mmol), and sodium 2-methylpropan-2-olate (0.437 g, 4.55 mmol) in 20 mL dioxane were heated at 80° C. for 14 h. Mixture was transferred into a separatory funnel and extracted with CH₂Cl₂ and brine. Organic phases were dried over MgSO₄, filtered, and concentrated. To the residue, 4M HCl in dioxane (ca. 10 mL) was added and stirred at room temperature for 1 h. Mixture was purified by HPLC; fractions containing pure product were collected, ammonium hydroxide was added (ca 5 mL), and partly concentrated. Residue was extracted with 1M NaOH and CH₂Cl₂. Organic phases were dried over MgSO₄, filtered, and concentrated to give 4-{6-[6-(2-hydroxy-ethylsulfanyl)-2-methyl-pyridin-3-ylamino]-5-methoxy-pyrimidin-4-yloxy}-piperidine-1-carboxylic acid isopropyl ester as a yellowish solid (HCl salt, 219 mg, 15%). ¹HNMR (CDCl₃, 400 MHz) δ 1.25-1.27 (d, J=6.3 Hz, 6H), 1.76-1.83 (m, 2H), 1.99-2.05 (m, 2H), 2.50 (s, 3H), 3.27-3.29 (m, 2H), 3.37-3.44 (m, 2H), 3.76-3.82 (m, 2H), 3.95 (s, 3H), 3.95-4.01 (m, 2H), 4.91-4.97 (m, 1H), 5.33-5.38 (m, 1H), 5.66-5.68 (m, 1H), 6.82 (s, 1H), 5.33-5.38 (m, 1H), 5.66-5.68 (m, 1H), 6.82 (s, 1H), 7.21-7.23 (d, J=8.5 Hz, 1H), 8.08 (s, 1H), 8.17-8.19 (d, J=8.5 Hz, 1H). Exact mass calculated for C₂₂H₃₁N₅O₅S 477.2 found 478.4 (MH⁺).

Example 9.28

Preparation of 4-{6-[6-(2-hydroxy-ethanesulfonyl)-2-methyl-pyridin-3-ylamino]-5-methoxy-pyrimidin yloxy}-piperidine-1-carboxylic acid isopropyl ester (Compound 92)

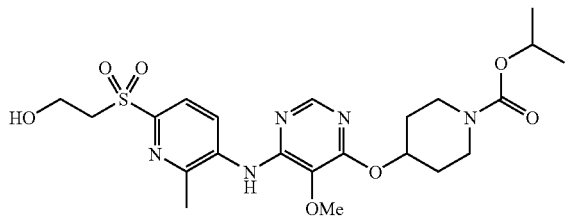 [SMILES: COc1c(Nc2ccc(S(=O)(=O)CCO)nc2C)ncnc1OC1CCN(C(=O)OC(C)C)CC1]

4-{6-[6-(2-Hydroxy-ethanesulfonyl)-2-methyl-pyridin-3-ylamino]-5-methoxy-pyrimidin-4-yloxy}-piperidine-1-carboxylic acid isopropyl ester was prepared in a similar manner as described in Example 9.22 to afford a white solid (HCl salt, 250 mg, 92%). ¹HNMR (MeOH-d₄, 400 MHz) a 1.24-1.26 (d, J=6.2 Hz, 6H), 1.78-1.84 (m, 2H), 2.01-2.07 (m, 2H), 2.60 (s, 3H), 3.41-3.46 (m, 2H), 3.42-3.46 (t, J=8.8 Hz, 2H), 3.58-3.64 (m, 2H), 2.74-3.77 (t, J=8.8 Hz, 2H), 3.97 (s, 3H), 4.82-4.87 (m, 1H), 5.40-5.45 (m, 1H), 5.48 (s, 1H), 7.94-7.96 (d, J=8.4, 1H), 8.09 (s, 1H), 8.42-8.44 (d, J=8.4 Hz, 1H). Exact mass calculated for C₂₂H₃₁N₅O₇S 509.19 found 510.4 (MH⁺).

Example 9.29

Preparation of 4-[5-hydroxy-6-(6-methanesulfonyl-2-methyl-pyridin-3-ylamino)-pyrimidin-4-yloxy]-piperidine-1-carboxylic acid isopropyl ester (Compound 93)

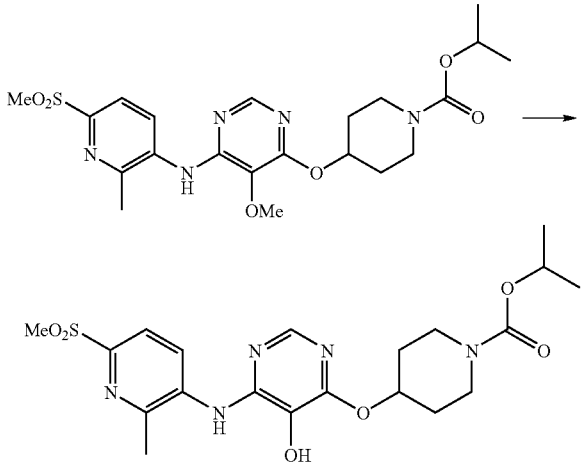

To an ice-cooled solution of 4-[6-(6-methanesulfonyl-2-methyl-pyridin-3-ylamino)-5-methoxy-pyrimidin-4-yloxy]-piperidine-1-carboxylic acid isopropyl ester (59 mg, 123 μmol) in 2 mL CH₂Cl₂, BBr₃ (1M in CH₂Cl₂ 0.123 mL, 0.123 mmol) was added. After stirring for 1 h under ice-cooling, more BBr₃ (0.246 mL, 0.246 mmol) was added. After 1 h, mixture was quenched with NH₄OH solution, concentrated, and purified by HPLC to give 4-[5-hydroxy-6-(6-methanesulfonyl-2-methyl-pyridin-3-ylamino)-pyrimidin-4-yloxy]-piperidine-1-carboxylic acid isopropyl ester as a white solid (TFA salt, 17 mg, 24%). ¹HNMR (MeOH-d₄, 400 MHz) a 1.22-1.23 (d, J=6.3 Hz, 6H), 1.70-1.78 (m, 2H), 1.97-2.02 (m, 2H), 2.59 (s, 3H), 3.15 (s, 3H), 3.26-3.32 (m, 2H), 3.82-3.88 (m, 2H), 4.81-4.87 (m, 1H), 5.27-5.32 (m, 1H), 7.88-7.90 (d, J=8.5 Hz, 1H), 7.95 (s, 1H), 8.67-8.69 (d, J=8.5 Hz, 1H). Exact mass calculated for $C_{20}H_{27}N_5O_6S$ 465.17 found 466.2 (MH⁺).

Example 9.30

Preparation of 4-[5-ethoxy-6-(6-methanesulfonyl-2-methyl-pyridin-3-ylamino)-pyrimidin-4-yloxy]-piperidine-1-carboxylic acid isopropyl ester (Compound 94)

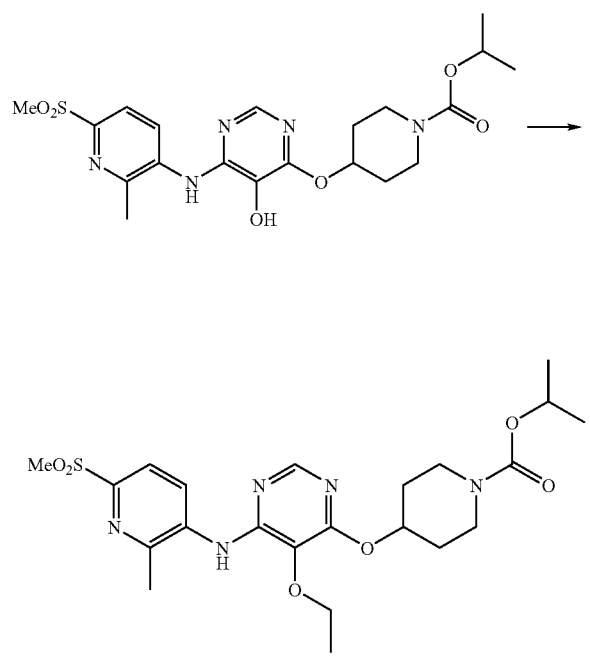

A mixture of 4-[5-hydroxy-6-(6-methanesulfonyl-2-methyl-pyridin-3-ylamino)-pyrimidin-4-yloxy]-piperidine-1-carboxylic acid isopropyl ester (40.4 mg, 87 μmol) potassium carbonate (24 mg, 174 μmol), and iodoethane (7.7 μl, 95 μmol) in 1 mL CH₃CN was stirred at 60° C. After 20 h, mixture was purified by HPLC; fractions containing product were partly concentrated and residue was extracted with CH₂Cl₂ and 1M NaOH. Organic phases were dried over MgSO₄, filtered, 4M HCl in dioxane (ca 0.5 mL) was added, and concentrated to give 4-[5-ethoxy-6-(6-methanesulfonyl-2-methyl-pyridin-3-ylamino)-pyrimidin-4-yloxy]-piperidine-1-carboxylic acid isopropyl ester as a white solid (HCl salt, 24.3 mg, 53%). ¹HNMR (MeOH-d₄, 400 MHz) a 1.25-1.27 (d, J=6.2 Hz, 6H), 1.41-1.44 (t, J=5.5 Hz, 3H), 1.74-1.80 (m, 2H), 2.01-2.06 (m, 2H), 2.62 (s, 3H), 3.21 (s, 3H), 3.30-3.35 (m, 2H), 3.72-3.77 (m, 2H), 4.22-4.28 (q, J=5.5 Hz, 2H), 4.83-4.88 (m, 1H), 5.38-5.43 (m, 1H), 7.93-7.96 (d, J=8.4 Hz, 1H), 8.09 (s, 1H), 8.57-8.59 (d, J=8.4 Hz, 1H). Exact mass calculated for $C_{22}H_{31}N_5O_6S$ 493.2 found 494.5 (MH⁺).

Example 9.31

Preparation of 4-[5-isopropoxy-6-(6-methanesulfonyl-2-methyl-pyridin-3-ylamino)-pyrimidin-4-yloxy]-piperidine-1-carboxylic acid isopropyl ester (Compound 95)

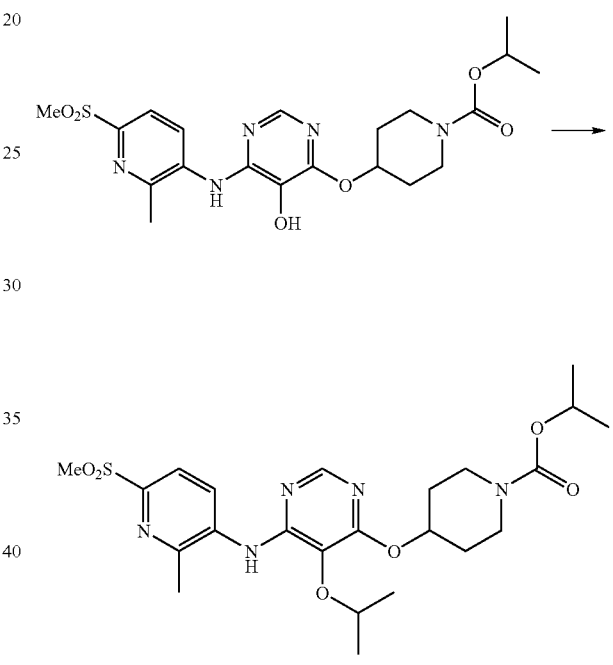

To a mixture of 4-[5-hydroxy-6-(6-methanesulfonyl-2-methyl-pyridin-3-ylamino)-pyrimidin-4-yloxy]-piperidine-1-carboxylic acid isopropyl ester (41.1 mg, 88 μmol), triphenylphosphine (34.7 mg, 132 μmol), propan-2-ol (6.4 mg, 106 μmol) in 1 mL THF, DIAD (21 μl, 106 μmol) was added. After stirring for 2 h at room temperature, the same amount of reagent was added again. After stirring for 16 h, mixture was purified by HPLC; fractions containing product were collected, partly concentrated, and extracted with 1M NaOH and CH₂Cl₂. Organic phases were dried, filtered, 4M HCl in dioxane (ca 0.5 mL) was added, and concentrated to give 4-[5-isopropoxy-6-(6-methanesulfonyl-2-methyl-pyridin-3-ylamino)-pyrimidin-4-yloxy]-piperidine-1-carboxylic acid isopropyl ester as a white solid (HCl salt, 9.7 mg, 20%). ¹HNMR (MeOH-d₄, 400 MHz) δ 1.25-1.27 (d, J=6.3 Hz, 6H), 1.37-1.39 (d, J=6.1 Hz, 6H), 1.75-1.81 (m, 2H), 2.01-2.07 (m, 2H), 2.62 (s, 3H), 3.20 (s, 3H), 3.42-3.47 (m, 2H), 3.70-3.76 (m, 2H), 4.68-4.74 (m, 1H), 4.83-4.89 (m, 1H), 5.37-5.42 (m, 1H), 7.91-7.94 (d, J=8.4 Hz, 1H), 8.09 (s, 1H), 8.70-8.71 (d, J=8.4 Hz, 1H). Exact mass calculated for $C_{23}H_{33}N_5O_6S$ 507.22 found 508.5 (MH⁺).

Example 9.32

Preparation of 4-[6-(6-methanesulfonyl-2-methyl-pyridin-3-ylamino)-5-propoxy-pyrimidin-4-yloxy]-piperidine-1-carboxylic acid isopropyl ester (Compound 96)

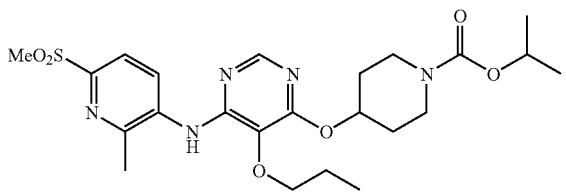 [SMILES: CCCOc1c(Nc2ccc(S(C)(=O)=O)nc2C)ncnc1OC1CCN(C(=O)OC(C)C)CC1]

4-[6-(6-Methanesulfonyl-2-methyl-pyridin-3-ylamino)-5-propoxy-pyrimidin-4-yloxy]-piperidine-1-carboxylic acid isopropyl ester was obtained in a similar manner as described in Example 30 to afford a white solid (HCl salt, 38.2 mg, 81%). $^1$HNMR (MeOH-d$_4$, 400 MHz) δ 1.02-1.06 (t, J=7.4 Hz, 3H), 1.22-1.24 (d, J=6.2 Hz, 6H), 1.75-1.84 (m, 4H), 2.00-2.05 (m, 2H), 2.59 (s, 3H), 3.19 (s, 3H), 3.40-3.45 (m, 2H), 3.71-3.76 (m, 2H), 4.10-4.13 (t, J=6.6 Hz, 2H), 4.82-4.88 (m, 1H), 4.36-4.41 (m, 1H), 7.92-7.95 (d, J=8.5 Hz, 1H), 8.09 (s, 1H), 8.51-8.53 (d, J=8.5 Hz, 1H). Exact mass calculated for $C_{23}H_{33}N_5O_6S$ 507.22 found 508.4 (MH$^+$).

Example 9.33

Preparation of 4-[6-(6-Methanesulfonyl-2-methyl-pyridin-3-ylamino)-5-methoxy-pyrimidin-4-yloxy]-piperidine-1-carboxylic acid 1-ethyl-propyl ester (Compound 97)

Step A: Preparation of 4-(6-Chloro-5-methoxy-pyrimidin-4-yloxy)-piperidine-1-carboxylic acid tert-butyl ester A solution of 4,6-dichloro-5-methoxy-pyrimidine (5.62 g, 27.9 mmol) and 4-hydroxy-piperidine-1-carboxylic acid tert-butyl ester (5.02 g, 27.9 mmol) in 200 mL THF was chilled to 0° C. A 1.0 M solution of potassium t-butoxide (30.7 mL, 30.7 mmol) was added drop-wise with stirring and the resulting mixture then was allowed to stir at 0° C. for one hour. Saturated ammonium chloride (100 mL) was added and the solution extracted with ethyl acetate. The organic phase was washed with brine and dried with magnesium sulfate, solvent removed to yield 9.10 g (94.8% yield). $^1$HNMR (CDCl$_3$, 400 MHz) a 1.48 (s, 2H), 1.79-1.83 (m, 2H), 1.99-2.04 (m, 2H), 3.33-3.39 (m, 2H), 3.72-3.77 (m, 2H), 3.91 (s, 3H), 5.30-5.38 (m, 1H), 8.26 (s, 1H). Exact mass calculated for $C_{15}H_{22}ClN_3O_4$: 343.13. found: 344.3 (MH$^+$).

Step B: Preparation of 4-Chloro-5-methoxy-6-(piperidin-4-yloxy)-pyrimidine 4-(6-Chloro-5-methoxy-pyrimidin-4-yloxy)-piperidine-1-carboxylic acid tert-butyl ester (5.0 g, 14.5 mmol) was taken up in 200 mL of 4N HCl in dioxane and 200 mL MeOH, stirred at 60° C. for 3 h. Solvent was removed to yield hydrochloride (3.9 g, 95.7% yield) a pale yellow solid, and the material used directly with out further purification. $^1$HNMR (CDCl$_3$, 400 MHz) δ 2.02-2.05 (m, 2H), 2.17-2.20 (m, 2H), 3.13-3.19 (m, 4H), 3.88 (s, 3H), 5.37-5.40 (m, 1H), 8.39 (s, 1H), 9.30 (bs, 2H). Exact mass calculated for $C_{10}H_{14}ClN_3O_2$: 243.08. found: 244.2 (MH$^+$).

Step C: Preparation of 4-(6-Chloro-5-methoxy-pyrimidin-4-yloxy)-piperidine-1-carboxylic acid 1-ethyl-propyl ester Pentan-3-ol (0.88 g, 9.99 mmol) and di-imidazol-1-yl-methanone (1.39, 8.57 mmol) were added to THF (10 mL) and stirred at 50° C. for one hour. DIPEA (1.38 g, 10.7 mmol) and 4-chloro-5-methoxy-6-(piperidin-4-yloxy)-pyrimidine HCl (2.00 g, 7.14 mmol) were added, the vessel sealed and heated by microwave at 150° C. for one hour. Upon cooling the reaction mixture was partitioned between water and Ethyl Acetate, the organic phase washed with brine and dried with Sodium Sulfate. The crude material was purified by column chromatograph (silica gel) with 10-30% EtOAc/Hexanes to yield 1.0 grams (39%) of the desired product, as a white solid. $^1$HNMR (CDCl$_3$, 400 MHz) δ 0.91 (t, J=7.83 Hz, 6H), 1.55-1.63 (m, 4H), 1.78-1.88 (m, 2H), 1.99-2.08 (m, 2H), 3.39-3.46 (m, 2H), 3.78-3.85 (m, 2H), 3.92 (s, 3H), 4.67 (m, 1H), 5.36-5.43 (m, 1H), 8.26 (s, 1H). Exact mass calculated for $C_{16}H_{24}ClN_3O_4$: 357.15. found: 358.3 (MH$^+$).

Step D: Preparation of 4-[6-(6-Methanesulfonyl-2-methyl-pyridin-3-ylamino)-5-methoxy-pyrimidin-4-yloxy]-piperidine-1-carboxylic acid 1-ethyl-propyl ester 4-(6-Chloro-5-methoxy-pyrimidin-4-yloxy)-piperidine-1-carboxylic acid 1-ethyl-propyl ester, (0.50 g, 1.40 mmol) and 6-methanesulfonyl-2-methyl-pyridin-3-ylamine (0.26 g, 1.40 mmol) and palladium acetate (0.062 g, 0.28 mmol) and 2,8,9-triisobutyl-2,5,8,9-tetraaza-1-phospha-bicyclo[3.3.3]undecane (0.191 g, 0.559 mmol) were combined in 50 mL dioxane, purged with nitrogen and a 1M solution of potassium t-butoxide in THF (2.79 mL, 2.79 mmol) added drop-wise. The reaction was heated to 100° C. and stirred for 2 hours, then was filtered, concentrated, acidified and purified by prep HPLC, the desired fractions partitioned between saturated sodium hydrogen carbonate and ethyl acetate, the organic phase washed with brine and dried with magnesium sulfate to yield (15 mg, 0.029 mmol, 2.11% yield) desired product, as a white solid. $^1$HNMR (CDCl$_3$, 400 MHz) δ 0.91 (t, J=7.33 Hz, 6H), 1.54-1.64 (m, 4H), 1.77-1.87 (m, 2H), 1.99-2.08 (m, 2H), 2.65 (s, 3H), 3.19 (s, 3H), 3.39-3.46 (m, 2H), 3.78-3.85 (m, 2H), 4.00 (s, 3H), 4.67 (pent, J=6.32 Hz, 1H), 5.36-5.43 (hept, J=3.79 Hz, 1H), 7.31 (bs, 1H), 7.96 (d, J=8.34 Hz, 1H), 8.20 (s, 1H), 9.02 (d, J=8.59 Hz, 1H). Exact mass calculated for $C_{23}H_{33}N_5O_6S$: 507.22 found: 508.5 (MH$^+$).

Example 9.34

Preparation of (R)-4-[6-(6-Methanesulfonyl-2-methyl-pyridin-3-ylamino)-5-methoxy-pyrimidin-4-yloxy]-piperidine-1-carboxylic acid sec-butyl ester (Compound 98 as the R-enantiomer)

The title compound was prepared in a similar manner as described in Example 9.33 (55 mg, 0.11 mmol, 19.2% yield). $^1$HNMR (CDCl$_3$, 400 MHz) δ 0.93 (t, J=7.07 Hz, 3H), (d, J=6.32 Hz, 3H), 1.52-1.63 (m, 2H), 1.77-1.87 (m, 2H), 1.99-2.08 (m, 2H), 2.65 (s, 3H), 3.19 (s, 3H), 3.39-3.46 (m, 2H), 3.76-3.85 (m, 2H), 4.01 (s, 3H), 4.73-4.81 (m, 1H), 5.37-5.43 (m, 1H), 7.33 (bs, 1H), 7.95 (d, J=8.59 Hz, 1H), 8.20 (s, 11H), 9.00 (d, J=8.59 Hz, 1H). Exact mass calculated for $C_{22}H_{31}N_5O_6S$: 493.20 found: 494.4 (MH$^+$).

Example 9.35

Preparation of (S)-4-[6-(6-Methanesulfonyl-2-methyl-pyridin-3-ylamino)-5-methoxy-pyrimidin-4-yloxy]-piperidine-1-carboxylic acid sec-butyl ester. (Compound 98 as the S-enantiomer)

The title compound was prepared in a similar manner as described in Example 9.33 (15 mg, 0.029 mmol, 2.11% yield). $^1$HNMR (CDCl$_3$, 400 MHz) δ 0.87-0.95 (m, 3H), 1.18-1.28 (m, 3H), 1.52-1.67 (m, 2H), 1.77-1.87 (m, 2H), 1.99-2.08 (m, 211), 2.65 (s, 3H), 3.19 (s, 3H), 3.42 (m, 2H), 3.82 (m, 2H), 4.00 (s, 3H), 4.67-4.78 (m, 1H), 5.36-5.43 (m, 1H), 7.31 (bs, 1H), 7.96 (d, J=8.54 Hz, 1H), 8.20 (s, 1H), 9.02 (d, J=9.60 Hz, 1H). Exact mass calculated for $C_{22}H_{31}N_5O_6S$: 493.20 found: 494.4 (MH$^+$).

Example 9.36

Preparation of 4-[6-(6-Methanesulfonyl-2-methyl-pyridin-3-ylamino)-5-methoxy-pyrimidin-4-yloxy]-piperidine-1-carboxylic acid cyclopentyl ester (Compound 99)

The title compound was prepared in a similar manner as described in Example 9.33 (60 mg, 0.12 mmol, 21.1% yield). $^1$HNMR (CDCl$_3$, 400 MHz) δ 1.55-1.65 (m, 2H), 1.67-1.76 (m, 4H), 1.79-1.91 (m, 4H), 1.99-2.09 (m, 2H), 2.65 (s, 3H), 3.19 (s, 3H), 3.39-3.46 (m, 2H), 3.76-3.85 (m, 2H), 4.01 (s, 3H), 5.11-5.13 (m, 1H), 5.40 (m, 1H), 7.33 (bs, 1H), 7.95 (d, J=8.34 Hz, 1H), 8.20 (s, 1H), 9.00 (d, J=8.59 Hz, 1H). Exact mass calculated for $C_{23}H_{31}N_5O_6S$: 505.20 found: 506.4 (MH$^+$).

Example 9.37

Preparation of 4-[6-(6-Hydroxymethyl-4-methyl-pyridin-3-ylamino)-5-methoxy-pyrimidin-4-yloxy]-piperidine-1-carboxylic acid isopropyl ester (Compound 100)

Step A: Preparation of (4-methyl-5-nitropyridin-2-yl)methanol

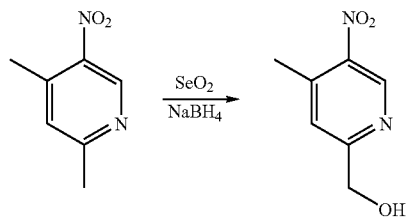

To a solution of the mixture of 2,4-dimethyl-5-nitropyridine (3.0 g, 20 mmol) in 30 ml of dioxane, was selenium oxide (2.8 g, 25 mmol) added at an ambient temperature. The reaction was refluxed for 10 hrs. The reaction was cooled to room temperature and concentrated under vacuum. The residue was poured into water and extracted with ethyl acetate. The organic layer was dried over MgSO$_4$ and concentrated under vacuum. The crude mixture of the aldehyde was diluted in methanol (30 mL) and sodium borohydride (0.74 g, 20 mmol) was added portionwise at 0° C. After stirred for 1 hr, the reaction was quenched with water (20 mL) and concentrated under vacuum. The reaction was extracted with ethyl acetate and dried over MgSO$_4$. The ethyl acetate was dried under vacuum and purified under SiO$_2$ with 50% ethyl acetate in hexane to afford (4-methyl-5-nitropyridin-2-yl)methanol in 83% (2.7 g). $^1$HNMR (CDCl$_3$, 400 MHz) δ 2.65 (s, 1H), 4.60 (d, J=8.1, 2H), 5.81 (t, J=8.1, 1H), 7.67 (s, 1H), 9.21 (s, 1H).

Step B: Preparation of 2-((tert-butyldiphenylsilyloxy)methyl)-4-methyl-5-nitropyridine

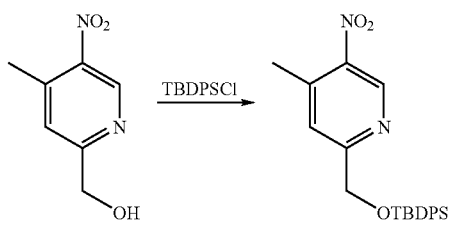

To a solution of (4-methyl-5-nitropyridin-2-yl)methanol (1.2 g, 7.1 mmol) in 5 mL of CH$_2$Cl$_2$, were added tert-butylchlorodiphenylsilane (2.0 g, 7.1 mmol) and imidazole (0.049 g, 0.71 mmol) at an ambient temperature. The reaction was stirred at 25° C. for 2 hrs. The reaction was poured into H$_2$O, extracted with ethyl acetate, and dried over MgSO$_4$. The ethyl acetate was concentrated under vacuum and purified over SiO$_2$ to afford the desired compound 2-((tert-butyldiphenylsilyloxy)methyl)-4-methyl-5-nitropyridine in 90% (2.6 g). $^1$HNMR (CDCl$_3$, 400 MHz) δ 1.12 (s, 9H), 2.78 (s, 3H), 4.85 (s, 2H), 7.21 (s, 1H), 7.24~7.89 (m, 10H), 9.15 (s, 1H).

Step C: Preparation of 6-((tert-butyldiphenylsilyloxy)methyl)-4-methylpyridin-3-amine

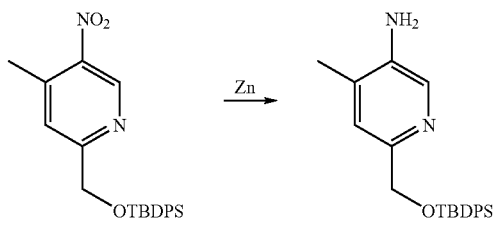

To a solution of 2-((tert-butyldiphenylsilyloxy)methyl)-4-methyl-5-nitropyridine (1.5 g, 3.7 mmol) in 20 ml of sat. NH$_4$Cl, were added zinc (1.7 g, 26 mmol) portionwise at 0° C. for 10 min. The reaction was stirred at the same temperature for 1 hr. The reaction was added with ethyl acetate (20 mL) and stirred for additional 1 hr. The organic layer was taken up, washed with H$_2$O, and dried over MgSO$_4$. The ethyl acetate was concentrated under vacuum to afford 6-((tert-butyldiphenylsilyloxy)methyl)-4-methylpyridin-3-amine in 72% (1.0 g). The compound was used for the next step without further purification. $^1$HNMR (CDCl$_3$, 400 MHz) δ 1.10 (s, 9H), 2.21 (s, 3H), 4.64 (s, 2H), 5.01~5.13 (b, 2H), 7.12 (s, 1H), 7.31~7.71 (m, 10H), 7.89 (s, 1H). Exact mass calculated for $C_{23}H_{28}N_2OSi$ 376.57 found 377.4 (MH$^+$).

Step D: Preparation of 4-[6-(6-Hydroxymethyl-4-methyl-pyridin-3-ylamino)-5-methoxy-pyrimidin-4-yloxy]-piperidine-1-carboxylic acid isopropyl ester (Compound 100)

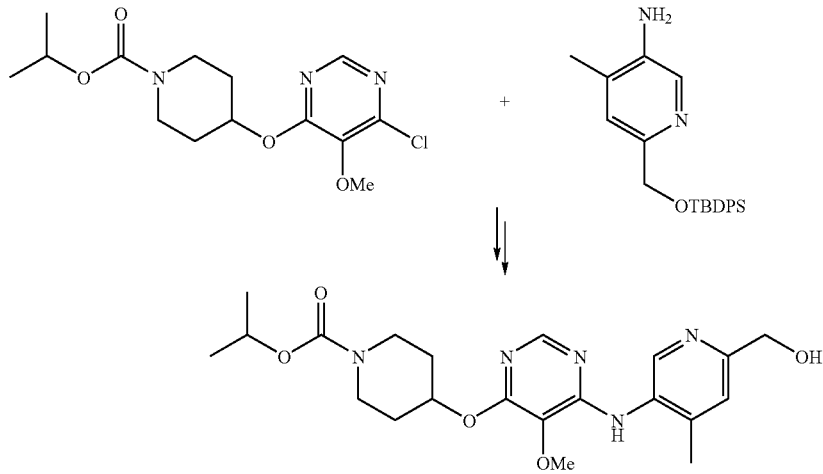

To a solution of isopropyl 4-(6-chloro-5-methoxypyrimidin-4-yloxy)piperidine-1-carboxylate (1.5 g, 4.548 mmol) in 100 mL of THF, were added 6-((tert-butyldiphenylsilyloxy)methyl)-4-methylpyridin-3-amine (1.713 g, 4.5 mmol), 2,8,9-triisobutyl-2,5,8,9-tetraaza-1-phospha-bicyclo[3.3.3]undecane (0.1558 g, 0.4548 mmol), Pd(OAc)$_2$ (0.05106 g, 0.2274 mmol), and Na-t-OBu (1.049 g, 10.92 mmol) at an ambient temperature. The reaction was stirred at 75° C. for 2 hrs. The reaction was cooled to room temperature and poured into H$_2$O. The organics were extracted with ethyl acetate and dried over MgSO$_4$. The ethyl acetate was concentrated under vacuum and dissolved in THF (10 mL). The solution was treated with 1.0 M TBAF at room temperature. After stirring for 2 hrs, the reaction was concentrated under vacuum and poured into H$_2$O. The organic compound was extracted with ethyl acetate and dried over MgSO$_4$. The organic layer was concentrated under vacuum and purified over SiO$_2$ to afford isopropyl 4-(6-(6-(hydroxymethyl)-3-methylpyridin-2-ylamino)-4-methoxypyrimidin-4-yloxy)piperidine-1-carboxylate in 33.1% (650 mg). $^1$HNMR (CDCl$_3$, 400 MHz) a 1.21 (d, 6H), 1.62-1.69 (m, 2H), 1.84-1.86 (m, 2H), 2.41 (s, 3H), 2.52 (s, 3H), 3.21-3.65 (m, 2H), 3.64~3.72 (m, 2H), 3.82 (s, 2H), 4.80-4.91 (m, 1H), 5.31~5.43 (m, 1H), 7.80 (s, 1H), 8.01 (s, 1H), 8.89 (s, 1H) Exact mass calculated for C$_{21}$H$_{29}$N$_5$O$_6$ 431.49. found 432.4 (MH$^+$).

Example 9.37

Preparation of 4-[6-(6Cyano-4-methyl-pyridin-3-ylamino)-5-methoxy-pyrimidin-4-yloxy]-piperidine-1-carboxylic acid isopropyl ester (Compound 99)

Step A: Preparation of 4-methyl-5-nitropicolinonitrile

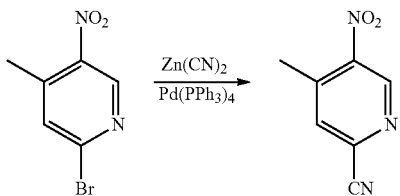

To a solution of 2-bromo-4-methyl-5-nitropyridine (5.0 g, 23 mmol) in 20 ml of THF, were added Zn(CN)$_2$ (6.8 g, 58 mmol), and Pd(PPh$_3$)$_4$ (2.7 g, 2.3 mmol) at an ambient temperature. The reaction was stirred at 130° C. for 2 hrs. The reaction was cooled to room temperature and poured into H$_2$O. The reaction was extracted with ethyl acetate and dried over MgSO$_4$. The organic layer was concentrated under vacuum to afford 4-methyl-5-nitropicolinonitrile 82% (3.1 g) which was used for the next step without further purification. $^1$HNMR (CDCl$_3$, 400 MHz) δ 8.90 (s, 1H), 7.12 (s, 1H), 2.54 (s, 3H).

Step B: Preparation of 5-amino-4-methylpicolinonitrile

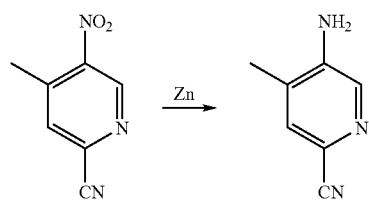

4-methyl-5-nitropicolinonitrile (7.0 g, 43 mmol) was suspended in aq. NH$_4$Cl (200 mL) and cooled to 0° C. Zinc was added portionwise for 30 min and stirred for 1 hr. The reaction was added with ethyl acetate (200 mL) and stirred for 2 hrs. The reaction was filtered and the organic layer was taken up, dried over MgSO$_4$, and concentrated over vacuum. The solid was triturated with 50% ethyl acetate in hexane to give 5-amino-4-methylpicolinonitrile in 67% (4.56 g). $^1$HNMR (CDCl$_3$, 400 MHz) δ 7.98 (s, 1H), 7.21 (s, 1H), 5.42~5.48 (b, 2H), 2.54 (s, 3H). Exact mass calculated for C$_7$H$_7$N$_3$ 133.15. found 134.21 (MH$^+$).

Step C: Preparation of 4-[6-(6-Cyano-4-methyl-pyridin-3-ylamino)-5-methoxy-pyrimidin-4-yloxy]-piperidine-1-carboxylic acid isopropyl ester (Compound 99)

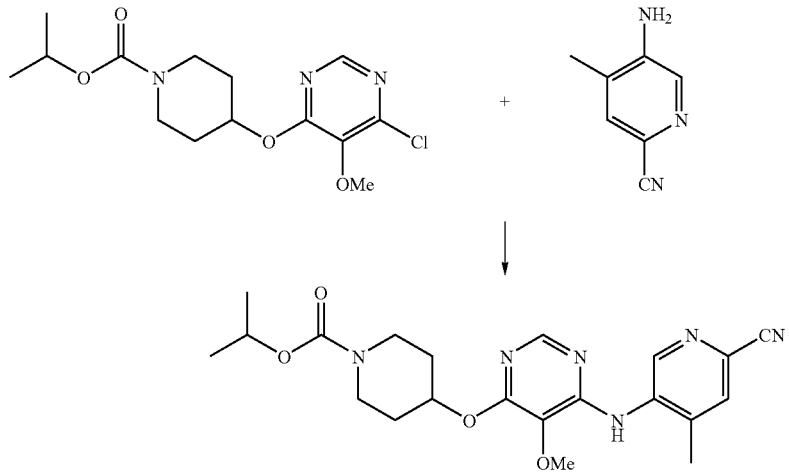

To a solution of isopropyl 4-(6-chloro-5-methoxypyrimidin-4-yloxy)piperidine-1-carboxylate (0.3 g, 0.91 mmol) in dioxane (3 mL), were added 5-amino-4-methylpicolinonitrile (0.12 g, 0.91 mmol), 2,8,9-triisobutyl-2,5,8,9-tetraaza-1-phospha-bicyclo[3.3.3]undecane (0.031 g, 0.091 mmol), Pd(OAc)$_2$ (0.10 g, 0.45 mmol), and NaO-t-Bu (0.21 g, 2.2 mmol) at an ambient temperature. The reaction was warmed to 75° C. and stirred for 2 hrs. After cooling to room temperature, the reaction was poured into H$_2$O and extracted with ethyl acetate. The organic layer was dried over MgSO$_4$ and concentrated under vacuum. The residue was purified over SiO$_2$ to afford isopropyl 4-(6-(6-cyano-4-methylpyridin-3-ylamino)-5-methoxypyrimidin-4-yloxy)piperidine-1-carboxylate in 31% (102 mg). $^1$HNMR (CDCl$_3$, 400 MHz) δ 1.21 (d, J=4.71, 6H), 1.71-1.75 (m, 2H), 1.95-2.01 (m, 2H), 2.31 (s, 3H), 2.62 (s, 3H), 3.32-3.41 (m, 2H), 3.64-3.71 (m, 2H), 4.85-4.90 (m, 1H), 5.35~5.41 (m, 1H), 7.81 (s, 1H), 8.10 (s, 1H), 8.82 (d, J=4.71 Hz, 1H). Exact mass calculated for C$_{21}$H$_{26}$N$_6$O$_4$ 426.47. found 427.51 (MH$^+$).

Example 9.38

Preparation of {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine (Compound 101)

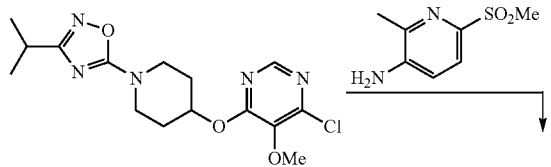

-continued

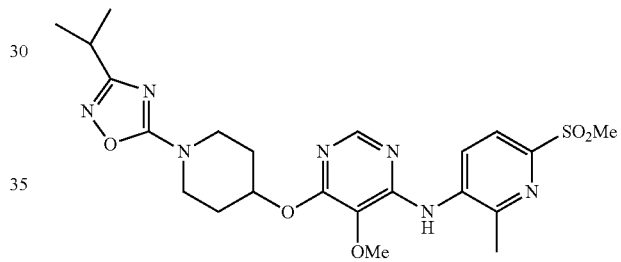

A mixture of 4-chloro-6-[1-(3-isopropyl-[1,2,4]oxadiazol-5-yl)-piperidin-4-yloxy]-5-methoxy-pyrimidine (1.78 g, 5.03 mmol), 6-Methanesulfonyl-2-methyl-pyridin-3-ylamine (1.12 g, 6.04 mmol), palladium acetate (102 mg, 0.45 mmol), 2,8,9-triisobutyl-2,5,8,9-tetraaza-1-phospha-bicyclo[3.3.3]undecane (322 μl, 0.91 mmol) and sodium tert-butoxide (725 mg, 7.54 mmol) in 30 mL of dioxane was heated under microwave irradiation at 150° C. for 1 hr. Additional 40 mL of dioxane were added and the mixture was refluxed under 130° C. After 65 hr, mixture was purified by HPLC. Fractions with product were collected, concentrated, and recrystalized with hot ethanol. 4N HCl in dioxane (ca 1 mL) and acetonitrile (ca 3 mL) were added and concentrated to give {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine as white solid (HCl salt, 360 mg, 13.3%). $^1$HNMR (DMSO-d$_6$, 400 MHz) δ 1.19-1.21 (d, J=6.82 Hz, 6H), 1.83-1.85 (m, 2H), 2.06-2.08 (m, 2H), 2.51 (s, 3H), 2.81-2.84 (sept, J=6.82 Hz, 1H), 3.57-3.59 (m, 2H), 3.75-3.77 (m, 2H), 3.87 (s, 1H), 5.31-3.39 (m, 1H), 7.89-7.91 (d, J=8.34 Hz, 1H), 8.07 (s, 1H), 8.23-8.25 (d, J=8.34 Hz, 1H) 8.69 (s, 1H). Exact mass calculated for C$_{22}$H$_{29}$N$_7$O$_5$S 503.2 found 504.2 (MH$^+$).

Example 9.39

Preparation of isopropyl 4-(6-(2,4-dimethyl-6-(methylsulfonyl)pyridin-3-ylamino)-5-methoxypyrimidin-4-yloxy)piperidine-1-carboxylate (Compound 102)

Step A: Preparation of 2,4-dimethylpyridin-3-amine

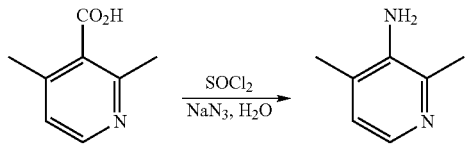

2,4-dimethylnicotinic acid (3.0 g, 20 mmol) was added in SOCl2 (20 mL) at 0° C. and warmed to 60° C. After stirring for 1 hr, the reaction was concentrated under vacuum. The residue was dissolved in acetone (20 mL) and NaN$_3$ (1.9 g, 30 mmol) followed by H$_2$O (20 mL). The reaction was warmed to 70° C. and stirred for 1 hr at the same temperature. The reaction was cooled to room temperature and concentrated under vacuum to a half volume and poured into H$_2$O (50 mL) and extracted with ethyl acetate (50 mL×5) and dried over MgSO$_4$. The ethyl acetate was concentrated under vacuum to afford the crude compound. The compound was used for the next step without further purification. $^1$HNMR (CDCl$_3$, 400 MHz) δ 2.10 (s, 3H), 2.30 (s, 3H), 4.65-4.70 (b, 2H), 6.85 (d, J=4.78 Hz, 1H), 7.75 (d, J=4.78 Hz, 1H). Exact mass calculated for C$_7$H$_{10}$N$_2$ 122.08. found 123.1 (MH$^+$).

Step B: Preparation of 6-bromo-2,4-dimethylpyridin-3-amine

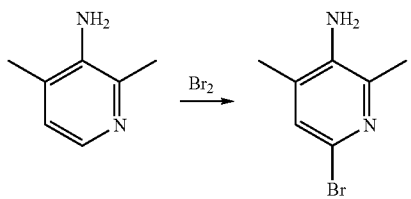

To a solution of 2,4-dimethylpyridin-3-amine (2.0 g, 16 mmol) in CH$_2$Cl$_2$ (20 mL), was added a solution of bromine (3.16 g; 20 mmol) in CH$_2$Cl$_2$ (5 mL) at 0° C. for 5 min. The reaction was concentrated under vacuum. The reaction was poured into H$_2$O (50 mL), extracted with CH$_2$Cl$_2$, washed with Na$_2$SO$_3$ solution, and dried over MgSO$_4$. The CH$_2$Cl$_2$ was concentrated under vacuum to afford the crude compound. The crude was purified over SiO$_2$ to afford to give 6-bromo-2,4-dimethylpyridin-3-amine. $^1$HNMR (CDCl$_3$, 400 MHz) δ 2.10 (s, 3H), 2.31 (s, 3H), 4.85-5.10 (b, 2H), 7.05 (s, 1H). Exact mass calculated for C$_7$H$_9$BrN$_2$ 201.06. found 202.3 (MH$^+$).

Step C: Preparation isopropyl 4-(6-(6-bromo-2,4-dimethylpyridin-3-ylamino)-5-methoxy pyrimidin-4-yloxy)piperidine-1-carboxylate

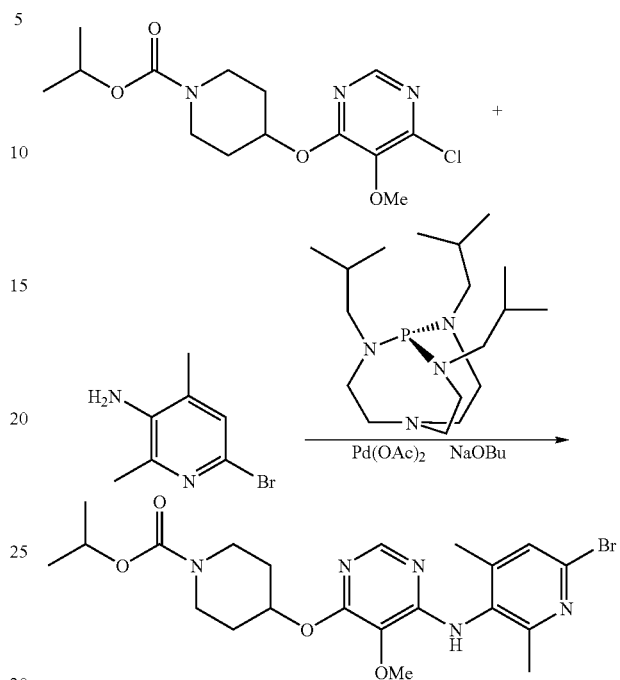

To a solution of isopropyl 4-(6-chloro-5-methoxypyrimidin-4-yloxy)piperidine-1-carboxylate (2.0 g, 6.1 mmol) in 10 ml of dioxane, were added 6-bromo-2,4-dimethylpyridin-3-amine (1.0 g, 5.1 mmol), 2,8,9-triisobutyl-2,5,8,9-tetraaza-1-phospha-bicyclo[3.3.3]undecane (0.35 g, 1.0 mmol), Pd(OAc)$_2$ (0.11 g, 0.51 mmol), and NaO-t-Bu (1.2 g, 12 mmol) at an ambient temperature. The reaction was heated to 150° C. for 3 hrs. The reaction was cooled to room temperature and poured into H$_2$O. The organics were extracted with ethyl acetate and dried over MgSO$_4$. The ethyl acetate was concentrated under vacuum and purified over SiO$_2$ to give isopropyl 4-(6-(6-bromo-2,4-dimethylpyridin-3-ylamino)-5-methoxy pyrimidin-4-yloxy)piperidine-1-carboxylate. $^1$HNMR (CDCl$_3$, 400 MHz) δ 1.24-1.25 (d, J=6.2 Hz, 6H), 1.72-1.77 (m, 2H), 1.95-2.01 (m, 2H), 2.22 (s, 3H), 2.52 (s, 3H), 3.37-3.44 (m, 2H), 3.73-3.79 (m, 2H), 4.91-4.97 (m, 1H), 5.30-5.35 (m, 1H), 6.01 (s, 1H), 7.34-7.36 (d, J=8.5 Hz, 1H), 8.14-8.16 (d, J=8.5 Hz, 1H), 8.37 (s, 1H). Exact mass calculated for C$_{21}$H$_{28}$BrN$_5$O$_4$ 494.31. found 495.2 (MH$^+$).

Step D: Preparation of isopropyl 4-(6-(2,4-dimethyl-6-(methylsulfonyl)pyridin-3-ylamino)-5-methoxypyrimidin-4-yloxy)piperidine-1-carboxylate (Compound 102)

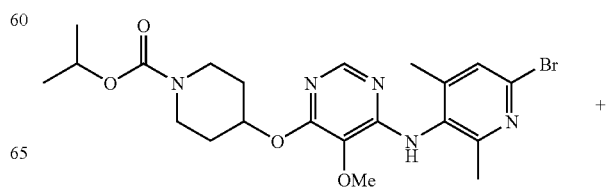

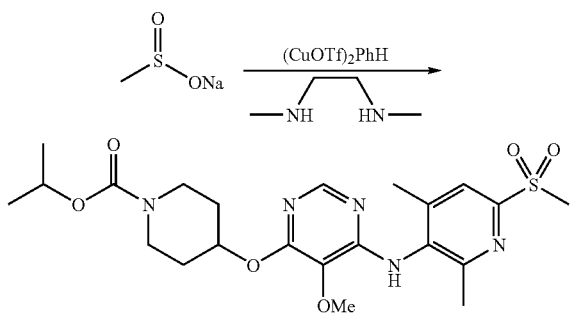

To a solution of isopropyl 4-(6-(6-bromo-2,4-dimethylpyridin-3-ylamino)-5-methoxypyrimidin-4-yloxy)piperidine-1-carboxylate (500 mg, 1.0 mmol) in 10 ml of DMSO, were added sodium sulfinate (0.36 g, 3.5 mmol), (CuOTf)$_2$PhH (0.051 g, 0.10 mmol), and N,N'-dimethylethylamine (0.018 g, 0.20 mmol) at an ambient temperature. The reaction was heated to 150° C. for 8 hrs. The reaction was cooled to room temperature and poured into H$_2$O. The organics were extracted with ethyl acetate and dried over MgSO$_4$. The ethyl acetate was concentrated under vacuum and purified over SiO$_2$ to afford isopropyl 4-(6-(2,4-dimethyl-6-(methylsulfonyl)pyridin-3-ylamino)-5-methoxypyrimidin-4-yloxy)piperidine-1-carboxy-late. $^1$HNMR (CDCl$_3$, 400 MHz) δ 1.24 (d, J=1.6 Hz, 6H), 1.75-1.81 (m, 2H), 1.98-2.02 (m, 2H), 2.25 (s, 3H), 2.65 (s, 3H), 3.21 (s, 3H), 3.52-3.65 (m, 2H), 3.65-3.75 (m, 1H), 3.84 (s, 3H), 5.21-5.35 (m, 1H), 7.78 (s, 1H), 7.79 (s, 1H), 8.89 (s, 1H). Exact mass calculated for C$_{22}$H$_{31}$N$_5$O$_6$S 493.58 found 494.5 (MH$^+$).

Example 9.40

Preparation of 4-{6-[6-(1-Methanesulfonyl-1-methyl-ethyl)-2-methyl-pyridin-3-ylamino]-5-methoxy-pyrimidin-4-yloxy}-piperidine-1-carboxylic acid isopropyl ester (Compound 103)

Step A: Preparation of 6-methyl-5-nitropicolinaldehyde

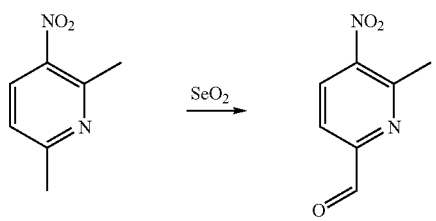

A solution of 2,6-dimethyl-3-nitropyridine (50 g, 329 mmol) and SeO$_2$ (5.02 g, 27.9 mmol) in dioxane (500 mL) was heated at reflux for 16 hours. The solution was filtered, the solvent removed and the residue purified by column chromatography directly (20% EtOAc/hexanes). The material was recrystalized from ethyl acetate to give 41 g of 6-methyl-5-nitropicolinaldehyde (41 g, 75%), a pale yellow solid; $^1$HNMR (CDCl$_3$, 400 MHz) δ 2.94 (s, 3H), 7.98 (d, J=8.34, 1H), 8.41 (d, J=8.34, 1H), 10.09 (s, 1H). Exact mass calculated for C$_7$H$_6$N$_2$O$_3$: 166.04. found: 167.12 MS m/z (MH$^+$).

Step B: Preparation of (6-methyl-5-nitropyridin-2-yl)methanol

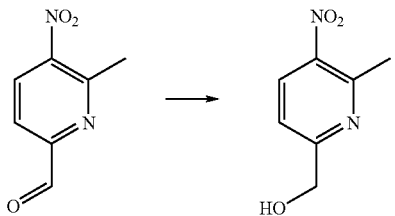

A solution of 6-methyl-5-nitropicolinaldehyde (50 g, 329 mmol) in ethanol (200 mL) was cooled to 10° C. and sodium borohydride (5.9 g, 157 mmol) was added portion-wise. The solution was allowed to stir for one half hour, the ethanol was removed and the residue partitioned between ethyl Acetate and water, the organic phase washed with brine, and dried with magnesium sulfate and stripped. The residue was purified by column chromatography (10-40% ethyl acetate/hexanes) to give (6-methyl-5-nitropyridin-2-yl)methanol (12 g, 91%), a pale white solid. $^1$HNMR (CDCl$_3$, 400 MHz) δ 2.89 (s, 3H), 3.55 (t, J=5.05, 1H), 4.83 (d, J=4.55, 2H), 7.31 (d, J=8.34, 1H), 8.31 (d, J=8.34, 1H); Exact mass calculated for C$_7$H$_8$N$_2$O$_3$: 168.05. found: 169.10 MS m/z (MH$^+$).

Step C: Preparation of (6-methyl-5-nitropyridin-2-yl)methyl methanesulfonate

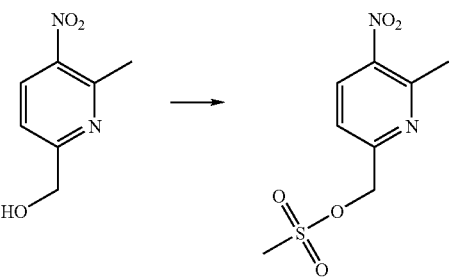

(6-Methyl-5-nitropyridin-2-yl)methanol (12 g, 71 mmol), and triethylamine (9.4 g, 93 mmol) in THF (300 mL) was chilled in an ice bath to 10° C. and methanesulfonyl chloride (9.0 g, 79 mmol) was added dropwise and the solution was stirred for one hour, then filtered to remove triethylamine HCl, and the solvent was removed under reduced pressure on the rotovap (with the bath temperature at 35° C.) and (6-methyl-5-nitropyridin-2-yl)methyl methanesulfonate (17 g, 97%), a brown oil which was directly used as such. $^1$HNMR (CDCl$_3$, 400 MHz) δ 2.87 (s, 3H), 3.16 (s, 3H), 5.83 (s, 2H), 7.55 (d, J=8.34, 1H), 8.38 (d, J=8.34, 1H); Exact mass calculated for C$_8$H$_{10}$N$_2$O$_5$: 246.03. found: 247.10 MS m/z (MH$^+$).

Step D: Preparation of 2-methyl-6-(methylsulfonylmethyl)-3-nitropyridine

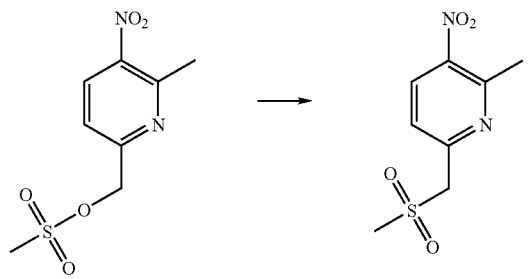

(6-Methyl-5-nitropyridin-2-yl)methyl methanesulfonate (17.48 g, 71 mmol) was taken up in dmso (100 mL), and NaSO$_2$Me (25.37 g, 248.5 mmol) was added portion wise, the solution heated to 120° C. and stirred for 15 minutes, cooled and partitioned between EtOAc and water, the organic phase washed with brine and dried with Magnesium Sulfate and the solvent removed. The residue was washed with 50 mL EtOAc and filtered to yield the 2-methyl-6-(methylsulfonyl-methyl)-3-nitropyridine (11.45 g, 70.04% yield), which is of sufficient purity for further use. $^1$HNMR (CDCl$_3$, 400 MHz) δ 2.87 (s, 3H), 2.99 (s, 3H), 4.48 (s, 2H), 7.53 (d, J=8.34, 11H), 8.4 (d, J=8.34, 1H); Exact mass calculated for C$_8$H$_{10}$N$_2$O$_4$S: 230.04 found: 231.12 MS m/z (MH$^+$).

Step E: Preparation of 2-methyl-6-(2-(methylsulfonyl)propan-2-yl)-3-nitropyridine

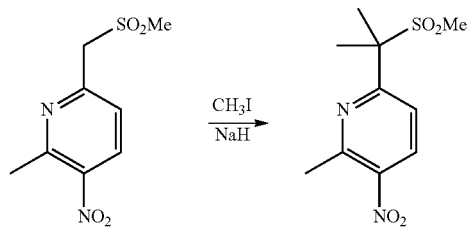

To a solution of 2-methyl-6-(methylsulfonylmethyl)-3-nitropyridine (1.54 g, 6.689 mmol) in 200 mL THF, iodomethane (1.252 mL, 20.07 mmol) and sodium hydride (60% dispersion, 1.1 g, 27.6 mmol) were added. Dark red mixture was stirred at room temperature for 30 minutes and then, quenched with ice-water, partly concentrated, and extracted with CH$_2$Cl$_2$ and water. Organic phases were dried over MgSO$_4$, filtered, and concentrated. Residue was purified by CC(hexane/AcOEt 2:1→1:1) to give 2-methyl-6-(2-(methylsulfonyl)propan-2-yl)-3-nitropyridine (1.374 g, 80%) as a white solid. $^1$HNMR (CDCl$_3$, 400 MHz) δ 1.92 (s, 6H), 2.85 (s, 3H), 2.88 (s, 3H), 7.69-7.71 (d, J=8.6 Hz, 1H), 8.32-8.34 (d, J=8.6 Hz, 1H). Exact mass calculated for C$_{10}$H$_{14}$N$_2$O$_4$S 258.07 found 259.2 (MH$^+$).

Step F: Preparation of 2-methyl-6-(2-(methylsulfonyl)propan-2-yl)pyridin-3-amine

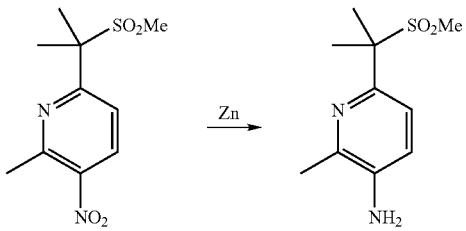

To a solution of 2-methyl-6-(2-(methylsulfonyl)propan-2-yl)-3-nitropyridine (1.27 g, 4.92 mmol) in 50 mL acetic acid, zinc dust (1.6 g, 24.5 mmol) was added in small portions under ice-cooling. After 1 h, more zinc dust (ca. 2 g, 31 mmol) was added in small portions and mixture was stirred at room temperature for another hour. Solids were filtered off, washed with CH$_3$CN, and filtrate was concentrated. Residue was purified by CC(CH$_2$Cl$_2$/MeOH 20:1+1% NEt$_3$). Fractions containing product were concentrated and re-purified by HPLC. Fractions containing product were partly concentrated and residue was extracted with 1M NaHCO$_3$ and CH$_2$Cl$_2$. Organic phases were dried over MgSO$_4$, filtered and concentrated to give 2-methyl-6-(2-(methylsulfonyl)propan-2-yl)pyridin-3-amine (0.664 g, 59% yield) as a white solid. $^1$HNMR (CDCl$_3$, 400 MHz) δ 1.84 (s, 6H), 2.39 (s, 3H), 2.76 (s, 3H), 3.68 (s, 2H), 6.92-6.94 (d, J=8.3 Hz, 1H), 7.29-7.31 (d, J=8.3 Hz, 1H). Exact mass calculated for C$_{10}$H$_{16}$N$_2$O$_2$S 228.09 found 229.2 (MH$^+$).

Step G: Preparation of 4-{6-[6-(1-Methanesulfonyl-1-methyl-ethyl)-2-methyl-pyridin-3-ylamino]-5-methoxy-pyrimidin-4-yloxy}-piperidine-1-carboxylic acid isopropyl ester (Compound 103)

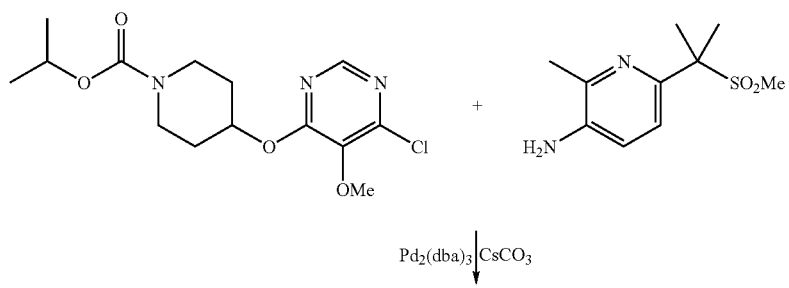

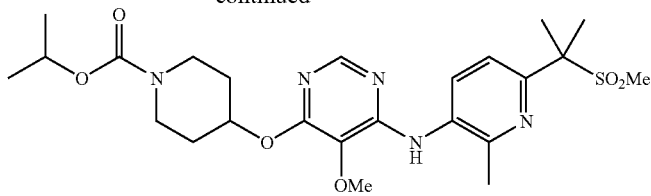

A mixture of isopropyl 4-(6-chloro-5-methoxypyrimidin-4-yloxy)piperidine-1-carboxylate (78.5 mg, 0.238 mmol), 2-methyl-6-(2-(methylsulfonyl)propan-2-yl)pyridin-3-amine (54.3 mg, 0.238 mmol), $Pd_2(dba)_3$ (20.0 mg, 0.0218 mmol), biphenyl-2-yl-di-tert-butyl-phosphane (3.0 mg, 0.0101 µmol), and cesium carbonate (160 mg, 0.491 mmol) in 4M dioxane were heated under microwave irradiation at 100° C. Mixture was purified by HPLC; fractions containing product were partly concentrated, and residue was extracted with $CH_2Cl_2$ and 1M $NaHCO_3$. Organic phases were dried over $MgSO_4$, filtered, and concentrated to give isopropyl 4-(5-methoxy-6-(2-methyl-6-(2-(methylsulfonyl)propan-2-yl)pyridin-3-ylamino)pyrimidin-4-yloxy)piperidine-1-carboxylate (4.6 mg, 4%) as a white solid. $^1$HNMR ($CDCl_3$, 400 MHz) δ 1.16-1.17 (d, J=6.3 Hz, 6H), 1.80-1.86 (m, 2H), 1.87 (s, 6H), 2.01-2.06 (m, 2H), 2.56 (s, 3H), 2.81 (s, 3H), 3.38-3.44 (m, 2H), 3.77-3.82 (m, 2H), 3.96 (s, 3H), 4.91-4.97 (m, 1H), 5.35-5.39 (m, 1H), 6.98 (s, 1H), 7.51-7.53 (d, J=8.6 Hz, 1H), 8.13 (s, 1H), 8.51-8.53 (d, J=8.6 Hz, 1H). Exact mass calculated for $C_{24}H_{35}N_5O_6S$ 521.23 found 522.5 ($MH^+$).

Example 9.41

Preparation of 4-[6-(6-Methanesulfonyl-2-methyl-pyridin-3-ylamino)-5-methoxy-pyrimidin-4-yloxy]-piperidine-1-carboxylic Acid Isopropyl Ester (Compound 84)

Step A: Preparation of 5-Methoxypyrimidine-4,6-diol

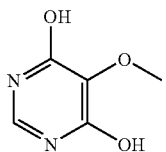

A 2-liter, three-necked, round-bottomed flask equipped with a mechanical stirrer and a reflux condenser was dried at 100° C. and cooled to 25° C. under $N_2$. Methanol (260 mL) was added, followed by a solution of sodium methoxide in methanol (25% by weight, 670 mL, 3.10 mol). The resulting solution was cooled to 0° C. Dimethyl methoxymalonate (151 g, 0.930 mol) was added in one portion, followed by formamidine acetate (100 g, 0.96 mol). The temperature was kept below 10° C. The resulting suspension was then stirred at 0° C. for 30 min, and refluxed for 1 h. The resulting suspension was cooled to 0° C. and quenched with concentrated HCl (250 mL) over 30 min, during which time the temperature was kept below 10° C. Stirring was continued at 5° C. for 30 min. The suspension was then filtered. The filter cake was re-suspended in water (1000 mL) and refluxed until a nearly clear solution was obtained. The solution was filtered while hot. The filtrate was cooled to 0-5° C. and stirred for 1 h. The solid precipitate was collected by filtration, washed with cold methanol (500 mL), and dried in a vacuum oven at 50° C. for 1 h to give the title compound (96.2 g, 73% yield) as a white solid. Exact Mass calculated for $C_5H_6N_2O_3$: 142.0, LCMS m/z=143.2 ($M+H^+$); $^1$H NMR (400 MHz, DMSO-$d_6$) δ 3.63 (s, 3H), 7.81 (s, 1H), 11.75 (br s, 2H).

Step B: Preparation of 4,6-Dichloro-5-methoxypyrimidine

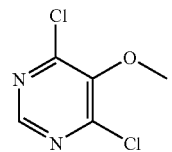

A suspension of 5-methoxypyrimidine-4,6-diol (96.0 g, 676 mmol) and triethylamine (95.0 mL, 680 mmol) in anhydrous toluene (1.2 L) was heated to 100-105° C. and a solution of $POCl_3$ (140 mL, 1.5 mol) in anhydrous toluene (200 mL) was added over 30 min. The mixture was refluxed for 1 h and cooled to ambient temperature. The toluene layer was decanted and ice was added. The dark, heavier layer was separated, more ice was added, and the mixture was extracted with toluene (2×200 mL). The toluene extracts were combined, and the aqueous layer was discarded. The organic extract was then washed with saturated $NaHCO_3$ (2×300 mL), brine (400 mL), dried over $MgSO_4$, and concentrated to give the title compound (103.4 g, 86% yield) as a white solid. $^1$H NMR ($CDCl_3$) δ 4.00 (s, 3H), 8.55 (s, 1H).

Step C: Preparation of 4-Hydroxy-piperidine-1-carboxylic Acid Isopropyl Ester

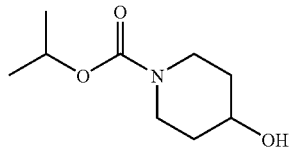

A magnetically stirred solution of 4-hydroxypiperidine (70.3 g, 695 mmol) and N,N-diisopropylethylamine (105 mL, 600 mmol) in dichloromethane (1.0 L) was cooled to 10° C. under $N_2$. A solution of isopropyl chloroformate (1.0 M in toluene, 580 mL, 580 mmol) was added dropwise over 2 h, maintaining a temperature of 10-15° C. The reaction mixture was stirred for an additional 2 h and then extracted with 1 N HCl (1.2 L). The organic extract was dried over $MgSO_4$, and the solvent was removed under reduced pressure to give the title compound (90.3 g, 83%) as a pale, straw-colored oil. Exact Mass calculated for $C_9H_{17}NO_3$: 187.1. Found: LCMS m/z=188.2 (M+H$^+$), 210.3 (M+Na$^+$); $^1$H NMR (400 MHz, CDCl$_3$) δ 1.24 (d, J=6.3 Hz, 6H), 1.47 (m, 2H), 1.86 (m, 2H), 3.08 (m, 2H), 3.86 (m, 3H), 4.90 (m, 1H).

Step D: Preparation of 4-(6-Chloro-5-methoxy-pyrimidin-4-yloxy)-piperidine-1-carboxylic Acid Isopropyl Ester

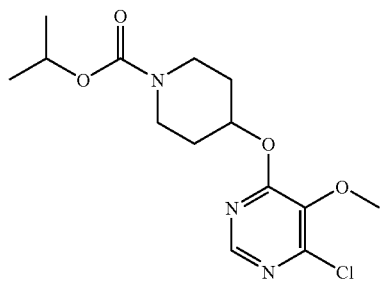 [SMILES: COc1c(Cl)ncnc1OC1CCN(C(=O)OC(C)C)CC1]

A solution of 4-hydroxy-piperidine-1-carboxylic acid isopropyl ester (71.0 g, 380 mmol) and 4,6-dichloro-5-methoxypyrimidine (71.6 g, 400 mmol) in anhydrous THF (1 L) was cooled to 5° C. under N$_2$. A solution of potassium t-butoxide (1.0 M in THF, 380 mL, 380 mmol) was added dropwise over 1 h. The reaction temperature was kept under 10° C. during addition. The reaction mixture was stirred at 5-10° C. for 1 h, quenched with saturated NH$_4$Cl (200 mL), and diluted with ether (1 L) and water (1 L). The aqueous phase was separated and discarded. The organic extract was washed with brine (800 mL), dried over MgSO$_4$, and then concentrated. The residue was dissolved in hexane (400 mL) and filtered over Celite™ to remove a small amount of brown solid. The solvent was removed from the filtrate to afford a pale amber oil which gradually crystallized to give the title compound (130 g, 98.6% yield) as a pale amber solid. Exact Mass calculated for $C_{14}H_{20}ClN_3O_4$: 329.1. Found: LCMS m/z=330.2 (M+H$^+$); $^1$H NMR (400 MHz, CDCl$_3$) δ 1.25 (d, J=6.2 Hz, 6H), 1.82 (m, 2H), 2.02 (m, 2H), 3.40 (m, 2H), 3.80 (m, 2H), 3.91 (s, 3H), 4.95 (m, 1H), 5.39 (m, 1H), 8.27 (s, 1H).

Step E1: Preparation of 2-Methyl-6-(methylsulfonyl)pyridin-3-amine (Method 1)

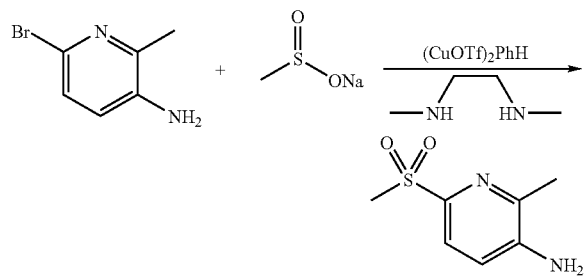

A mixture of 6-bromo-2-methylpyridin-3-amine (40.0 g, 214 mmol), sodium methanesulfinate (87.3 g, 855 mmol), copper(I)trifluoromethanesulfonate-benzene complex (10.8 g, 21.4 mmol), and N$^1$,N$^2$-dimethylethane-1,2-diamine(10.8 g, 21.4 mmol) in DMSO (300 mL) was heated at 150° C. for four hours, cooled, and H$_2$O (100 mL) was added. The dark brown solution was extracted with ethyl acetate (6×30 mL). The organic layer was washed with H$_2$O (100 mL) to remove DMSO. The aqueous layer was back extracted three times with ethyl acetate. The organic layers were combined, washed with brine, dried over Na$_2$SO$_4$, and filtered. After the volume of the filtrate was reduced to about 200 mL under reduced pressure, a solid product was precipitated and collected by filtration to give the title compound (24.0 g, 60%) as a brown powder. Exact mass calculated for $C_7H_{10}N_2O_2S$: 186.1. Found: LCMS m/z=187.1 (M+H$^+$); $^1$H NMR (400 MHz, CDCl$_3$) δ 2.44 (s, 3H), 3.13 (s, 3H), 4.66 (bs, 2H), 7.01 (d, J=8.34 Hz, 1H), 7.71 (d, J=8.34 Hz, 1H).

Step E2: Preparation of 2-Methyl-6-(methylsulfonyl)pyridin-3-amine (Method 2)

Step 1: Preparation of 2-Methyl-6-(methylsulfonyl)-3-nitropyridine

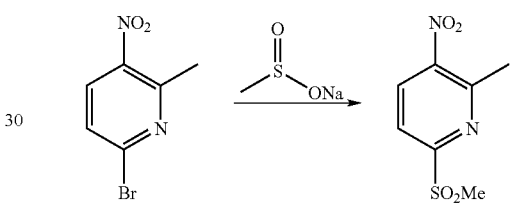

A mixture of 6-bromo-2-methyl-3-nitropyridine (100 g, 461 mmol) and sodium methanesulfinate (47.0 g, 461 mmol) in DMSO (300 mL) was stirred at room temperature for 1.5 h. The reaction mixture was poured into ice-water (1 L) and stirred until all the ice had melted. The ice-cold solution was filtered, and a dark purple solid was collected. The solid collected was dissolved in ethyl acetate (1 L). The solution was treated with activated charcoal, filtered through Celite™. The Celite™ cake was washed with ethyl acetate, and the filtrate was collected. The solvent was evaporated from the filtrate under reduced pressure to give the title compound (87.0 g, 87%) as a yellow solid. Exact mass calculated for $C_7H_8N_2O_4S$: 216.0. Found: LCMS m/z=217.2 (M+H$^+$).

Step 2: Preparation of 2-Methyl-6-(methylsulfonyl)pyridin-3-amine

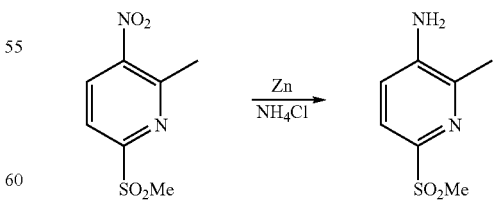

To a suspension of zinc dust (146 g, 2.01 mol) and aqueous ammonium chloride solution (3 M, 800 ml) was added dropwise a solution of 2-methyl-6-(methylsulfonyl)-3-nitropyridine (87.0 g, 401 mmol) in ethyl acetate (500 mL) via an addition funnel at 0° C. The mixture was stirred at room temperature for 17 h and filtered through Celite™. The filtrate was then extracted with ethyl acetate. The organic phase was separated, dried over MgSO$_4$, filtered, and concentrated. The residue was recrystallized from ethanol to give the title compound (34.7 g, 46%) as a solid. Exact mass calculated for C$_7$H$_{10}$N$_2$O$_2$S: 186.1. Found: LCMS m/z=187.2 (M+H$^+$).

Step F: Preparation of 4-[6-(6-Methanesulfonyl-2-methyl-pyridin-3-ylamino)-5-methoxy-pyrimidin-4-yloxy]-piperidine-1-carboxylic Acid Isopropyl Ester (Compound 84)

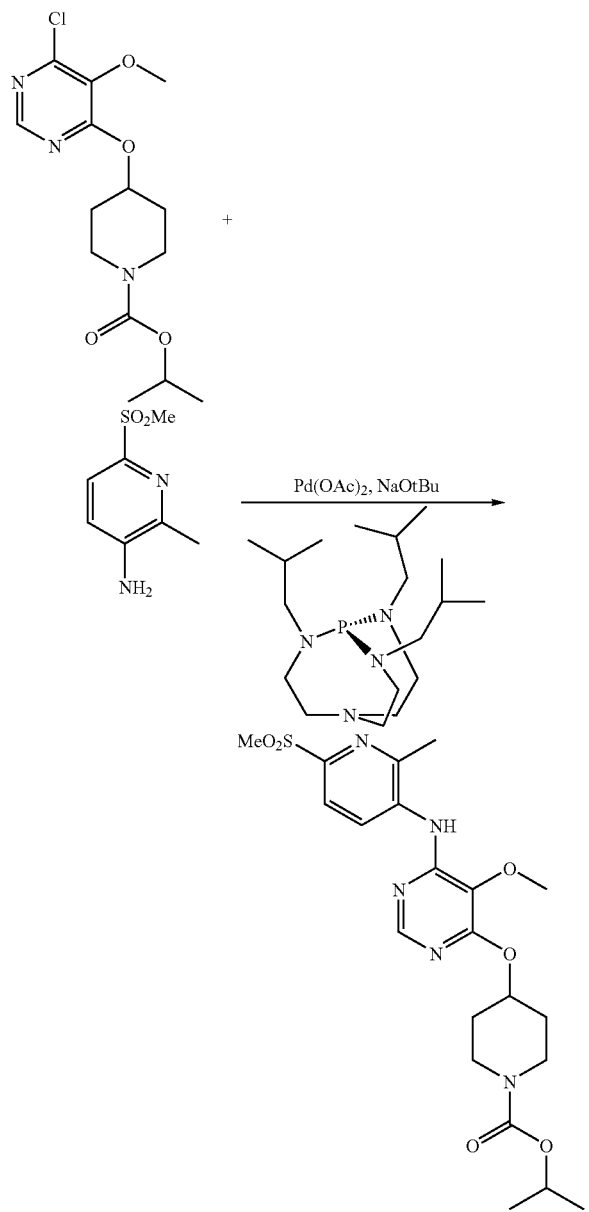

A mixture of 4-(6-chloro-5-methoxy-pyrimidin-4-yloxy)-piperidine-1-carboxylic acid isopropyl ester (14.7 g, 44.6 mmol), 2-methyl-6-(methylsulfonyl)pyridin-3-amine (8.20 g, 44.0 mmol), palladium acetate (0.50 g, 2.23 mmol), 2,8,9-triisobutyl-2,5,8,9-tetraaza-1-phospha-bicyclo[3.3.3]undecane (1.65 ml, 4.64 mmol), and sodium 2-methylpropan-2-olate (6.50 g, 67.6 mmol) in dioxane (300 mL) were stirred at 90° C. for 1 h and then at 60° C. overnight. The reaction mixture was cooled and filtered. The solid was washed with ethyl acetate. The filtrate was concentrated and the residue was purified by silica gel column chromatography using hexane/ethyl acetate (1:2). The fractions containing only the product were collected, and concentrated to give the title compound (4.6 g, 22%) that was crystallized from ethyl acetate/hexane as a white solid. The fractions containing the product contaminated with impurities were concentrated and the residue was further purified by recrystallization from ethanol to give the title compound (2.5 g, 12%) as a white solid. The two combined to give 7.1 g of the title compound in 34% yield. Exact mass calculated for C$_{21}$H$_{29}$N$_5$O$_6$S: 479.2. Found: LCMS m/z=480.4 (M+H$^+$); $^1$H NMR (400 MHz, CDCl$_3$) δ 1.27 (d, J=6.3 Hz, 6H), 1.80-1.85 (m, 2H), 2.02-2.07 (m, 2H), 2.66 (s, 3H), 3.19 (s, 3H), 3.38-3.45 (m, 2H), 3.78-3.83 (m, 2H), 4.01 (s, 3H), 4.91-4.97 (m, 1H), 5.38-5.42 (m, 1H), 7.30 (s, 1H), 7.97 (d, J=8.6 Hz, 1H), 8.20 (s, 1H), 9.01-9.04 (d, J=8.6 Hz, 1H).

Example 10

Protocol for RUP3 Dose Responses in Melanophores

Melanophores are maintained in culture as reported by Potenza, M. N. and Lerner, M. R., in Pigment Cell Research, Vol. 5, 372-378, 1992 and transfected with the RUP3 expression vector (pCMV) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate and compounds that stimulate RUP3 produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

The compounds in the above examples were screened using the melanophore dispersion assay, as described above. Representative compounds of the present invention and their corresponding observed EC$_{50}$ values are shown in Table 3 below. Certain other compounds illustrated in the Examples showed EC$_{50}$ activities in the melanophore dispersion assay of less than about 10 μL.

TABLE 3

| Compound | RUP3 (EC$_{50}$) (nM) |
|---|---|
| 10 | 26 |
| 24 | 0.49 |
| 76 | 2.51 |
| 84 | 3.55 |

Compounds of the present invention have unexpected aqueous solubilities. For example, Compound 77 has an aqueous solubility of 0.19 mg/mL (pH=5) and 1.12 mg/mL (pH=2); and Compound 78 has an aqueous solubility of 0.38 mg/mL (pH=5) and 1.45 mg/mL (pH=2).

Each of the embodiments of the present invention may in the alternative be limited to relate to those compounds that demonstrate about 100 fold or greater binding to RUP3 compared to the corticotrophin-releasing factor-1 (CRF-1) receptor; a recent review of CRF-1 compounds can be found in Expert Opin. Ther. Patents 2002, 12(11), 1619-1630, incorporated herein by reference in its entirety.

Example 11

Rat Dose-Range PK Study for 4-[6-(6-Methanesulfonyl-2-methyl-pyridin-3-ylamino)-5-methoxy-pyrimidin-4-yloxy]-piperidine-1-carboxylic acid isopropyl ester Animal, Compound Formulation, Dosing, and Blood Sample Collection:

Male SD rats (250-300 g) were purchased from Charles River Laboratory; upon reciept, animals were placed under light-dark cycle (6:30 am-6:30 pm lights on). They were allowed ad libitum access to water and 4 pieces of food daily (Purina Meals Rodent Diet, Product Number 5001).

Compound formulations were prepared as following: The IV injection formulation was prepared in 20% hydroxypropyl-beta-cyclodextrin with concentration of 0.667 mg/nL. The PO formulations were prepared in 0.5% hydroxypropyl methylcellulose with concentrations of 0.3, 3, and 30 mg/Kg. The dosing volume for IV injection was 3 mL/Kg and for PO administration was 10 mL/Kg. Four rats were used for each dose group. The dose of IV injection was 2 mg/kg and the dose of PO was 3, 30, or 300 mg/Kg, respectively.

All rats (4 rats per group, housed individually) were fasted overnight prior to in-life phase. On the next morning, rats were received an IV (via tail vein injection) injection or gavage dose of compound starting at 8 am (IV) and 9 am (PO). Next, each rat were orbital bled at 0.085, 0.25, 0.5, 1, 2, 4, 6, 8, and 24 hr (IV) or 0.5, 1, 2, 4, 6, 8, and 24 hr (PO) to collect blood samples for PK analysis.

The blood samples were collected via orbital bleeding into tubes containing EDTA, 0.25 mL blood each time. These samples were put on ice and within 2 hours plasma was prepared by centrifugation at 3,000 rpm for 30 min at 4° C. 100 µl of plasma were transferred into a 96-tube box for PK analysis.

Sample Analysis:

Plasma samples were prepared as follows. Two hundred microliters of acetonitrile containing internal standard was added to 100 µL of plasma to precipitate proteins. Samples were centrifuged at 3000 g for 5 minutes and supernatant removed for analysis by LC-MS-MS. Calibration standards and quality control samples were prepared by adding a known volume of standard stock solution (50% methanol, 50% $H_2O$) directly into blank plasma and treated identically to collected plasma samples. Calibration standards were typically prepared in the range of 2.0 ng/mL to 10 µg/mL with linear regression for quantitation. These sample preparation steps were automated using a liquid handling workstation (Tomtec Quadra 96) in the 96-well format. Reversed phase LC-MS-MS analysis was performed using either multiple reaction or selected ion monitoring for detection of characteristic ions for each drug candidate and the internal standard used was propranolol for positive ions or chloramphenicol for negative ions.

Data Interpretation:

Results were calculated by noncompartmental analysis using WinNonlin Pro version 3.1 based on plasma concentration—time profiles for individual animals. Plasma levels were determined as described above and the oral and intravenous area under the concentration vs. time curve (AUC was calculated using the linear trapezoidal rule up to the last measurable concentration and was then extrapolated to infinity) were compared to determine the % bioavailability (% F) by the following formula: Dose (IV)*AUC (oral)/Dose (oral) *AUC (IV).

There may be significant variation within the individual animals and the analytical method and that variation was evidenced by the % CV. AUMC was the first statistical moment of the AUC and was used to calculate the mean residence time (MRT=AUMC/AUC), which was the average time the compound was in the animal. The $C_{max}$ represented the maximum concentration observed, the $T_{max}$ was the time to reach that maximum concentration and the $T_{1/2}$ was the calculated terminal half-life of the compound in plasma using the slope of a log concentration vs time plot if there were sufficient elimination phase data points (at least three data points in the terminal phase excluding the Cmax). Systemic clearance (CL=Dose(IV)/AUC(IV)) was the volume of fluid (containing compound) from which compound was removed completely per unit time. Volume of distribution at steady state (Vss=CL*MRT) was the extent of distribution of a drug from the plasma to the tissues at steady state.

Figure 5:
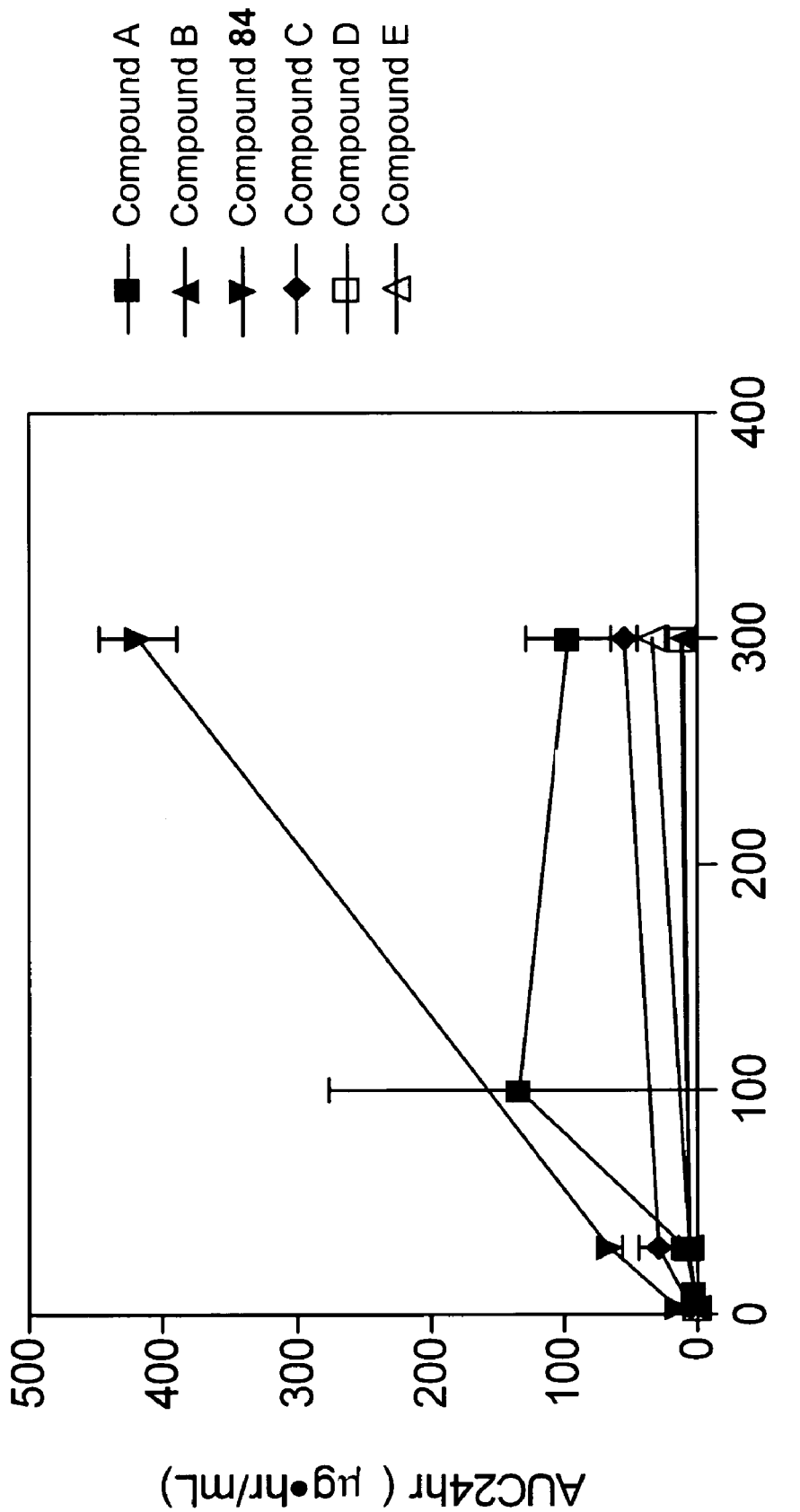
FIG. 5 shows dose escalation pharmacokinetics AUC vs dose for 4-[6-(6-Methanesulfonyl-2-methyl-pyridin-3-ylamino)-5-methoxy-pyrimidin-4-yloxy]-piperidine-1-carboxylic acid isopropyl ester (i.e., Compound 84) compared to different RUP3 compounds, see Example 11 for details.

The RUP3 agonist, 4-[6-(6-Methanesulfonyl-2-methyl-pyridin-3-ylamino)-5-methoxy-pyrimidin-4-yloxy]-piperidine-1-carboxylic acid isopropyl ester, showed essentially linear dose escalation pharmacokinetics, see FIG. 5.

Also shown in FIG. 5 is Compound A [i.e., 4-[1-(2-Fluoro-4-methanesulfonyl-phenyl)-1H-pyrazolo[3,4-d]pyrimidin-4-yloxy]-piperidine-1-carboxylic acid isopropyl ester] that is described in the genus found in PCT/US2004/022417; Compound B [i.e., (2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine] that is described in the genus found in PCT/US2004/022327; Compound C [i.e., 4-[6-(6-Methanesulfonyl-4-methyl-pyridin-3-ylamino)-5-methoxy-pyrimidin-4-yloxy]-piperidine-1-carboxylic acid isopropyl ester] that is described in the genus found in PCT/US2006/000567; Compound D that is described in the genus found in PCT/US2004/001267; and Compound E [i.e., {6-[1-(3-Isopropyl-[1,2,4]oxadiazol-5-yl)-piperidin-4-yloxy]-5-methoxy-pyrimidin-4-yl}-(6-methanesulfonyl-2-methyl-pyridin-3-yl)-amine] that is described in the genus found in PCT/US2006/000567.

The numerical data associated with each of the compounds shown in FIG. 5 can be found in the table below.

Dose Escalation Pharmacokinetics AUC vs. Dose

| Compound | AUC 24 hr (hr · μg/mL) | | | | | |
|---|---|---|---|---|---|---|
| | 3 mg | 10 mg | 30 mg | 100 mg | 300 mg | 1000 mg |
| A | — | 2.59 | 9.93 | 133.37 | 96.97 | 377.45 |
| B | 2.12 | — | 5.99 | — | 11.03 | — |
| 84 | 14.91 | — | 65.91 | — | 418.53 | — |
| C | 5.6 | — | 29.38 | — | 54.69 | — |
| D | 0.51 | — | 6.77 | — | 12.19 | — |
| E | 1.66 | — | 6.47 | — | 33.85 | — |

While RUP3 agonists can be useful as therapeutics in the treatment of a number of metabolic-related disorders as described herein, compounds that exhibit linear dose escalation pharmacokinetic properties, such as 4-[6-(6-Methanesulfonyl-2-methyl-pyridin-3-ylamino)-5-methoxy-pyrimidin-4-yloxy]-piperidine-1-carboxylic acid isopropyl ester, are particularly beneficial for a variety of reasons. For example, compounds with linear exposure vs. dose relationship have the following benefits:

The pharmacokinetic parameters are more predictable when different doses are administered or when the drug is given through different routes of administration or as single or multiple doses. Patients are less likely to be overdosed when doses are slightly increased.

These compounds have better absorption and may have enhanced oral bioavailability. Drug with nonlinearity may have decreased oral bioavailability due to several possible reasons including drug concentration approaching the drug's solubility limit in the GI tract, or a saturable transport system for absorption.

During preclinical drug development, these compounds will be able to achieve high exposure when dosed at higher doses.

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

We claim:

1. A compound that is 4-[6-(6-Methanesulfonyl-2-methyl-pyridin-3-ylamino)-5-methoxy-pyrimidin-4-yloxy]-piperidine-1-carboxylic acid isopropyl ester; or a pharmaceutically acceptable salt thereof.

* * * * *